US011447790B2

(12) United States Patent
Payyavula et al.

(10) Patent No.: US 11,447,790 B2
(45) Date of Patent: Sep. 20, 2022

(54) COMPOSITIONS AND METHODS FOR PRODUCING TOBACCO PLANTS AND PRODUCTS HAVING REDUCED OR ELIMINATED SUCKERS

(71) Applicant: ALTRIA CLIENT SERVICES LLC, Richmond, VA (US)

(72) Inventors: Raja S. Payyavula, Henrico, VA (US); Yanxin Shen, Henrico, VA (US); Chengalrayan Kudithipudi, Midlothian, VA (US); Rajanikanth Govindarajulu, Henrico, VA (US)

(73) Assignee: Altria Client Services LLC, Richmond, VA (US)

( * ) Notice: Subject to any disclaimer, the term of this patent is extended or adjusted under 35 U.S.C. 154(b) by 0 days.

(21) Appl. No.: 16/886,118

(22) Filed: May 28, 2020

(65) Prior Publication Data

US 2020/0377904 A1 Dec. 3, 2020

Related U.S. Application Data

(60) Provisional application No. 62/854,139, filed on May 29, 2019.

(51) Int. Cl.
*C12N 15/82* (2006.01)

(52) U.S. Cl.
CPC .............. *C12N 15/8262* (2013.01)

(58) Field of Classification Search
None
See application file for complete search history.

(56) References Cited

U.S. PATENT DOCUMENTS

| | | |
|---|---|---|
| 4,516,590 A | 5/1985 | Teng |
| 4,528,993 A | 7/1985 | Sensabaugh, Jr. et al. |
| 4,660,577 A | 4/1987 | Sensabaugh et al. |
| 4,848,373 A | 7/1989 | Lenkey |
| 4,897,355 A | 1/1990 | Eppstein et al. |
| 4,946,787 A | 8/1990 | Eppstein et al. |
| 4,987,907 A | 1/1991 | Townend |
| 5,049,386 A | 9/1991 | Eppstein et al. |
| 5,159,135 A | 10/1992 | Umbeck |
| 5,188,958 A | 2/1993 | Moloney et al. |
| 5,372,149 A | 12/1994 | Roth et al. |
| 5,463,174 A | 10/1995 | Moloney et al. |
| 5,538,880 A | 7/1996 | Lundquist et al. |
| 5,550,318 A | 8/1996 | Adams et al. |
| 5,591,616 A | 1/1997 | Hiei et al. |
| 5,750,871 A | 5/1998 | Moloney et al. |
| 5,824,877 A | 10/1998 | Hinchee et al. |
| 6,153,812 A | 11/2000 | Fry et al. |
| 6,160,208 A | 12/2000 | Lundquist et al. |
| 6,194,636 B1 | 2/2001 | McElroy et al. |
| 6,232,526 B1 | 5/2001 | McElroy et al. |
| 6,384,301 B1 | 5/2002 | Martinell et al. |
| 6,399,861 B1 | 6/2002 | Anderson et al. |
| 2004/0118422 A1 | 6/2004 | Lundin et al. |
| 2004/0216189 A1 | 10/2004 | Houmard et al. |
| 2005/0178398 A1 | 8/2005 | Breslin et al. |
| 2006/0191548 A1 | 8/2006 | Strickland et al. |
| 2006/0200878 A1 | 9/2006 | Lutfiyya et al. |
| 2016/0281100 A1 | 9/2016 | Kudithipudi et al. |
| 2017/0260535 A1 | 9/2017 | Xu et al. |

FOREIGN PATENT DOCUMENTS

| | | |
|---|---|---|
| EP | 3 437 465 A1 | 2/2019 |
| WO | WO 91/16024 A1 | 10/1991 |
| WO | WO 91/17424 A1 | 11/1991 |
| WO | WO 2016/057515 A2 | 4/2016 |
| WO | WO 2017/121776 A1 | 7/2017 |

OTHER PUBLICATIONS

Altschul, "Basic local alignment search tool," *Journal of Molecular Biology*, 215:403-410 (1990).
Altschul et al., "Gapped BLAST and PSI-BLAST: a new generation of protein database search programs," *Nucleic Acids Research*, 25:3389-3402 (1997).
Ambawat et al., "MYB transcription factor genes as regulators for plant responses: an overview," *Physiology and Molecular Biology of Plants*, 19:307-321 (2013).
Chenna et al., "Multiple sequence alignment with the Clustal series of programs," *Nucleic Acids Research*, 31: 3497-3500 (2003).
Davis et al., "Tobacco, Production, Chemistry and Technology," Blackwell Publishing, pp. 70-103 (1999).
Fisher et al., "Topping, Managing Suckers, and Using Ethephon," *2016 Flue-Cured Tobacco Information*, pp. 96-117 (2016).
Goldman et al., "Female sterile tobacco plants are produced by stigma-specific cell ablation," *EMBO Journal*, 13:2976-2984 (1994).
Griffiths-Jones et al., "Rfam: an RNA family database," *Nucleic Acids Research*, 31:439-441 (2003).
Horsch et al., "A simple and general method for transferring genes into plants," *Science*, 227:1229-1231 (1985).
Katoh et al., "Specific residues at every third position of siRNA shape its efficient RNAi activity;" *Nucleic Acids Research*, 3 5:e27 (2007).
Khvorova et al., "Functional siRNAs and miRNAs exhibit strand bias," *Cell*, 114:209-216(2003).
Kumar et al., "Why do plants need so many cyclin-dependent kinase inhibitors?," *Plant Signaling & Behavior*, 12:e1282021 (2017).
Larkin et al., "Clustal W and Clustal X version 2.0," *Bioinformatics*, 23:2947-2948 (2007).
Mayo et al., "Genetic transformation of tobacco NT1 cells with agrobacterium tumefaciens," *Nature Protocols*, 1:1105-11 (2006)
Menges et al., "Genomic Organization and Evolutionary Conservation of Plant D-Type Cyclins," *Plant Physiology*, 145:1558-1576 (2007).
Mironov et al., "Cyclin-Dependent Kinases and Cell Division in Plants—The Nexus," *The Plant Cell*, 11:509-521 (1999).

(Continued)

*Primary Examiner* — Elizabeth F McElwain
(74) *Attorney, Agent, or Firm* — Arnold & Porter Kaye Scholer

(57) ABSTRACT

The present disclosure provides methods and compositions for controlling sucker growth in tobacco by altering the expression of different target genes.

20 Claims, 6 Drawing Sheets

Specification includes a Sequence Listing.

(56) References Cited

OTHER PUBLICATIONS

Reynolds et al., "Rational siRNA design for RNA interference," *Nature Biotechnology*, 22:326-330 (2004).
Robinson et al., "A scaling normalization method for differential expression analysis of RNA-seq data," *Genome Biology*, 11:R25 (2010).
Robinson et al., "edgeR: a Bioconductor package for differential expression analysis of digital gene expression data," *Bioinformatics*, 26:139-140 (2010).
Thompson et al.,"Clustal W: Improving the sensitivity of progressive multiple sequence alignment through sequence weighting, position-specific gap penalties and weight matrix choice," *Nucleic Acids Research*, 22: 4673-4680 (1994).
Wernsman et al., "Principles of Cultivar Development: Crop Species," Chapter Seventeen, pp. 669-698 (1987).
Zeng et al., "Both natural and designed micro RNAs can inhibit the expression of cognate mRNAs when expressed in human cells," *Molecular Cell*, 9:1327-1333 (2002).
International Search Report and Written Opinion issued in International Application No. PCT/US2020/034884 dated Nov. 16, 2020.
Rushton et al., "WRKY transcription factors," *Trends in Plant Science*, 15:247-258 (2010).
Sun et al., "Inhibition of tobacco axillary bud differentiation by silencing Cup-shaped Cotyledon 3," *African Journal of Biotechnology*, 11(16):3919-3927 (2012) <http://www.academicjournals.org/AJB>.
Yang et al., "Regulation of Axillary Meristem Initiation by Transcription Factors and Plan Hormones" Frontiers in Plan Science; 7(183) Feb. 18, 2016.

COMPOSITIONS AND METHODS FOR PRODUCING TOBACCO PLANTS AND PRODUCTS HAVING REDUCED OR ELIMINATED SUCKERS

CROSS-REFERENCE TO RELATED APPLICATIONS

This application claims benefit of U.S. Provisional Application No. 62/854,139, which was filed on May 29, 2019. The entire content of this application is incorporated herein by reference.

FIELD

The present disclosure provides methods and compositions for refining the expression of nucleic acids and proteins useful for the reduction or elimination of suckers in plants.

INCORPORATION OF SEQUENCE LISTING

The instant application contains a Sequence Listing which has been submitted electronically in ASCII format and is hereby incorporated by reference in its entirety. Said ASCII copy, created on May 21, 2020, is named P34703US01_SL.txt and is 380,539 bytes in size.

BACKGROUND

Tobacco is a plant species that exhibits exceptionally strong apical dominance. Molecular signals from the shoot apical meristem (SAM) mediate a hormonal signal that effectively inhibits axillary bud growth. Upon removal of the SAM (also known as "topping"), physiological and molecular changes occur, enabling the growth of new shoots (or "suckers") from axillary meristems (buds). Sucker growth results in loss of yield and leaf quality. Suckers have been controlled by manual removal and through the application of chemicals. Maleic hydrazide and flumetralin are routinely used on topped plants to inhibit axillary bud growth ("suckering"). However, labor and chemical agents to control suckers are very expensive. Control of suckering in tobacco through conventional breeding, mutation breeding, and transgenic approaches have been a major objective for several decades but, to date, successful inhibition or elimination of suckering has not been achieved through these approaches. Recent molecular work has produced transgenic plants with reduced or eliminated suckers, but leaky expression of axillary bud-degrading genes can result in the death of seeds and embryos and prevents the production of successive generations of transgenic plants. Therefore, development of methods and compositions to prevent axillary bud-degrading genes from being expressed in non-desired tissues and/or organs would result in a reduction of the use of chemical agents and would reduce costs and labor associated with tobacco production.

SUMMARY

In one aspect, this disclosure provides a modified tobacco plant comprising a mutation in an endogenous gene encoding a polypeptide selected from the group consisting of a cyclin, a cyclin-dependent kinase (CDK), a CDK inhibitor, a MYB, and a WRKY transcription factor, where the mutation is not present in the endogenous gene in a control tobacco plant of the same variety, and where the modified tobacco plant comprises no suckers or reduced suckers after topping as compared to the control tobacco plant when grown under comparable growth conditions.

In one aspect, this disclosure provides a modified tobacco plant comprising a mutation in an endogenous gene encoding a polypeptide selected from the group consisting of a cyclin, a cyclin-dependent kinase (CDK), a CDK inhibitor, a MYB, and a WRKY transcription factor, where the mutation is not present in the endogenous gene in a control tobacco plant of the same variety.

In one aspect, this disclosure provides a modified tobacco plant comprising a polynucleotide sequence encoding a polypeptide selected from the group consisting of a cyclin, a cyclin-dependent kinase (CDK), a CDK inhibitor, a MYB, and a WRKY transcription factor operably linked to a heterologous promoter, where the modified tobacco plant comprises no suckers or reduced suckers after topping as compared to a control tobacco plant when grown under comparable growth conditions.

In one aspect, this disclosure provides a modified tobacco plant comprising a polynucleotide sequence encoding a polypeptide selected from the group consisting of a cyclin, a cyclin-dependent kinase (CDK), a CDK inhibitor, a MYB, and a WRKY transcription factor operably linked to a heterologous promoter.

In one aspect, this disclosure provides a modified tobacco plant comprising a recombinant DNA construct comprising a heterologous promoter operably linked to a nucleic acid encoding at least one small RNA molecule capable of reducing the expression of an endogenous mRNA that encodes a polypeptide selected from the group consisting of a cyclin, a cyclin-dependent kinase (CDK), a CDK inhibitor, a MYB, and a WRKY transcription factor, where the modified tobacco plant comprises no suckers or reduced suckers after topping as compared to a control tobacco plant when grown under comparable growth conditions.

In one aspect, this disclosure provides a modified tobacco plant comprising a recombinant DNA construct comprising a heterologous promoter operably linked to a nucleic acid encoding at least one small RNA molecule capable of reducing the expression of an endogenous mRNA that encodes a polypeptide selected from the group consisting of a cyclin, a cyclin-dependent kinase (CDK), a CDK inhibitor, a MYB, and a WRKY transcription factor.

In one aspect, this disclosure provides a tobacco product comprising cured tobacco material from a modified tobacco plant comprising a mutation in an endogenous gene encoding a polypeptide selected from the group consisting of a cyclin, a cyclin-dependent kinase (CDK), a CDK inhibitor, a MYB, and a WRKY transcription factor, where the mutation is not present in the endogenous gene in a control tobacco plant of the same variety, and where the modified tobacco plant comprises no suckers or reduced suckers after topping as compared to the control tobacco plant when grown under comparable growth conditions.

In one aspect, this disclosure provides a tobacco product comprising cured tobacco material from a modified tobacco plant comprising a mutation in an endogenous gene encoding a polypeptide selected from the group consisting of a cyclin, a cyclin-dependent kinase (CDK), a CDK inhibitor, a MYB, and a WRKY transcription factor, where the mutation is not present in the endogenous gene in a control tobacco plant of the same variety.

In one aspect, this disclosure provides a tobacco product comprising cured tobacco material from a modified tobacco plant comprising a polynucleotide sequence encoding a polypeptide selected from the group consisting of a cyclin, a cyclin-dependent kinase (CDK), a CDK inhibitor, a MYB, and a WRKY transcription factor operably linked to a heterologous promoter, and where the modified tobacco plant comprises no suckers or reduced suckers after topping as compared to a control tobacco plant when grown under comparable growth conditions.

In one aspect, this disclosure provides a tobacco product comprising cured tobacco material from a modified tobacco plant comprising a polynucleotide sequence encoding a polypeptide selected from the group consisting of a cyclin, a cyclin-dependent kinase (CDK), a CDK inhibitor, a MYB, and a WRKY transcription factor operably linked to a heterologous promoter.

In one aspect, this disclosure provides a tobacco product comprising cured tobacco material from a modified tobacco plant comprising a recombinant DNA construct comprising a heterologous promoter operably linked to a nucleic acid encoding at least one small RNA molecule capable of reducing the expression of an endogenous mRNA that encodes a polypeptide selected from the group consisting of a cyclin, a cyclin-dependent kinase (CDK), a CDK inhibitor, a MYB, and a WRKY transcription factor, where the modified tobacco plant comprises no suckers or reduced suckers after topping as compared to a control tobacco plant when grown under comparable growth conditions.

In one aspect, this disclosure provides a tobacco product comprising cured tobacco material from a modified tobacco plant comprising a recombinant DNA construct comprising a heterologous promoter operably linked to a nucleic acid encoding at least one small RNA molecule capable of reducing the expression of an endogenous mRNA that encodes a polypeptide selected from the group consisting of a cyclin, a cyclin-dependent kinase (CDK), a CDK inhibitor, a MYB, and a WRKY transcription factor.

In one aspect, this disclosure provides a method for producing a modified tobacco plant comprising: (a) inducing a mutation in at least one tobacco cell at a genomic locus encoding a polypeptide selected from the group consisting of a cyclin, a cyclin-dependent kinase (CDK), a CDK inhibitor, a MYB, and a WRKY transcription factor; (b) selecting at least one tobacco cell comprising the mutation from step (a); and (c) regenerating a modified tobacco plant from the at least one tobacco cell selected in step (b), where the modified tobacco plant comprises no suckers or reduced suckers after topping as compared to a control tobacco plant lacking the mutation when grown under comparable growth conditions.

In one aspect, this disclosure provides a method for producing a modified tobacco plant comprising: (a) introducing a recombinant DNA construct to at least one tobacco cell, where the recombinant DNA construct comprises a heterologous promoter operably linked to a nucleic acid encoding a polypeptide selected from the group consisting of a cyclin, a cyclin-dependent kinase (CDK), a CDK inhibitor, a MYB, and a WRKY transcription factor; (b) selecting at least one tobacco cell comprising the recombinant DNA construct; and (c) regenerating a modified tobacco plant from the at least one tobacco cell selected in step (b), where the modified tobacco plant comprises no suckers or reduced suckers after topping as compared to a control tobacco plant lacking the recombinant DNA construct when grown under comparable growth conditions.

In one aspect, this disclosure provides a method for producing a modified tobacco plant comprising: (a) introducing a recombinant DNA construct to at least one tobacco cell, where the recombinant DNA construct comprises a heterologous promoter operably linked to a nucleic acid encoding at least one small RNA molecule capable of reducing the expression of an endogenous mRNA that encodes a polypeptide selected from the group consisting of a cyclin, a cyclin-dependent kinase (CDK), a CDK inhibitor, a MYB, and a WRKY transcription factor; (b) selecting at least one tobacco cell comprising the recombinant DNA construct; and (c) regenerating a modified tobacco plant from the at least one tobacco cell selected in step (b), where the modified tobacco plant comprises no suckers or reduced suckers after topping as compared to a control tobacco plant lacking the recombinant DNA construct when grown under comparable growth conditions.

In one aspect, this disclosure provides a method comprising preparing a tobacco product using cured tobacco material from a modified tobacco plant comprising a mutation in an endogenous gene encoding a polypeptide selected from the group consisting of a cyclin, a cyclin-dependent kinase (CDK), a CDK inhibitor, a MYB, and a WRKY transcription factor, where the mutation is not present in the endogenous gene in a control tobacco plant of the same variety, and where the modified tobacco plant comprises no suckers or reduced suckers after topping as compared to a control tobacco plant when grown under comparable growth conditions.

In one aspect, this disclosure provides a method comprising preparing a tobacco product using cured tobacco material from a modified tobacco plant comprising a polynucleotide sequence encoding a polypeptide selected from the group consisting of a cyclin, a cyclin-dependent kinase (CDK), a CDK inhibitor, a MYB, and a WRKY transcription factor operably linked to a heterologous promoter, and where the modified tobacco plant comprises no suckers or reduced suckers after topping as compared to a control tobacco plant when grown under comparable growth conditions.

In one aspect, this disclosure provides a method comprising preparing a tobacco product using cured tobacco material from a modified tobacco plant comprising a polynucleotide sequence encoding a polypeptide selected from the group consisting of a cyclin, a cyclin-dependent kinase (CDK), a CDK inhibitor, a MYB, and a WRKY transcription factor operably linked to a heterologous promoter, and wherein said modified tobacco plant comprises no suckers or reduced suckers after topping as compared to a control tobacco plant when grown under comparable growth conditions.

In one aspect, this disclosure provides a method comprising preparing a tobacco product using cured tobacco material from a modified tobacco plant comprising a polynucleotide sequence encoding a polypeptide selected from the group consisting of a cyclin, a cyclin-dependent kinase (CDK), a CDK inhibitor, a MYB, and a WRKY transcription factor operably linked to a heterologous promoter, wherein said modified tobacco plant comprises no suckers or reduced suckers after topping as compared to a control tobacco plant when grown under comparable growth conditions.

In one aspect, this disclosure provides a method comprising preparing a tobacco product using cured tobacco material from a modified tobacco plant comprising a polynucleotide sequence encoding a polypeptide selected from the group consisting of a cyclin, a cyclin-dependent kinase (CDK), a CDK inhibitor, a MYB, and a WRKY transcription factor operably linked to a heterologous promoter.

In one aspect, this disclosure provides a method comprising preparing a tobacco product using cured tobacco material from a modified tobacco plant comprising a recombinant DNA construct comprising a heterologous promoter operably linked to a nucleic acid encoding at least one small RNA molecule capable of reducing the expression of an endogenous mRNA that encodes a polypeptide selected from the group consisting of a cyclin, a cyclin-dependent kinase (CDK), a CDK inhibitor, a MYB, and a WRKY transcription factor, wherein said modified tobacco plant comprises no suckers or reduced suckers after topping as compared to a control tobacco plant when grown under comparable growth conditions.

In one aspect, this disclosure provides a method comprising preparing a tobacco product using cured tobacco material from a modified tobacco plant comprising a recombinant DNA construct comprising a heterologous promoter operably linked to a nucleic acid encoding at least one small RNA molecule capable of reducing the expression of an endogenous mRNA that encodes a polypeptide selected from the group consisting of a cyclin, a cyclin-dependent kinase (CDK), a CDK inhibitor, a MYB, and a WRKY transcription factor.

In one aspect, this disclosure provides a method comprising transforming a tobacco cell with a recombinant DNA construct comprising a heterologous promoter operably linked to a nucleic acid encoding a polypeptide selected from the group consisting of a cyclin, a cyclin-dependent kinase (CDK), a CDK inhibitor, a MYB, and a WRKY transcription factor.

In one aspect, this disclosure provides a method comprising transforming a tobacco cell with a recombinant DNA construct comprising a heterologous promoter operably linked to a nucleic acid encoding at least one small RNA molecule capable of reducing the expression of an endogenous mRNA that encodes a polypeptide selected from the group consisting of a cyclin, a cyclin-dependent kinase (CDK), a CDK inhibitor, a MYB, and a WRKY transcription factor.

In one aspect, this disclosure provides a method for producing a modified tobacco plant comprising: (a) crossing at least one tobacco plant of a first tobacco variety with at least one tobacco plant of a second tobacco variety, where the at least one tobacco plant of the first tobacco variety comprises a mutation in an endogenous gene encoding a polypeptide selected from the group consisting of a cyclin, a cyclin-dependent kinase (CDK), a CDK inhibitor, a MYB, and a WRKY transcription factor, where the mutation is not present in the endogenous gene in a control tobacco plant of the same variety, and where the at least one tobacco plant comprises no suckers or reduced suckers after topping as compared to the control tobacco plant when grown under comparable growth conditions; and (b) selecting for progeny tobacco plants that exhibit no suckers or reduced suckers after topping compared to a control tobacco plant of the same cross grown under comparable growth conditions.

In one aspect, this disclosure provides a method for producing a modified tobacco plant comprising: (a) crossing at least one tobacco plant of a first tobacco variety with at least one tobacco plant of a second tobacco variety, where the at least one tobacco plant of the first tobacco variety comprises a recombinant DNA construct comprising a heterologous promoter operably linked to a nucleic acid encoding a polypeptide selected from the group consisting of a cyclin, a cyclin-dependent kinase (CDK), a CDK inhibitor, a MYB, and a WRKY transcription factor, where the at least one tobacco plant comprises no suckers or reduced suckers after topping as compared to a control tobacco plant when grown under comparable growth conditions; and (b) selecting for progeny tobacco plants that exhibit no suckers or reduced suckers after topping compared to a control tobacco plant of the same cross grown under comparable growth conditions.

In one aspect, this disclosure provides a method for producing a modified tobacco plant comprising: (a) crossing at least one tobacco plant of a first tobacco variety with at least one tobacco plant of a second tobacco variety, where the at least one tobacco plant of the first tobacco variety comprises a recombinant DNA construct comprising a heterologous promoter operably linked to a nucleic acid encoding at least one small RNA molecule capable of reducing the expression of an endogenous genomic locus that encodes a polypeptide selected from the group consisting of a cyclin, a cyclin-dependent kinase (CDK), a CDK inhibitor, a MYB, and a WRKY transcription factor, where the at least one tobacco plant comprises no suckers or reduced suckers after topping as compared to a control tobacco plant when grown under comparable growth conditions; and (b) selecting for progeny tobacco plants that exhibit no suckers or reduced suckers after topping compared to a control tobacco plant of the same cross grown under comparable growth conditions.

BRIEF DESCRIPTION OF THE SEQUENCES

SEQ ID NOs: 1-44, 89-113, and 118-126 are nucleic acid sequences.

SEQ ID NOs: 45-88 and 114-117 are amino acid sequences.

Additional descriptions of the SEQ ID NOs provided herein can be found below in Table 1.

TABLE 1

Description of sequences

| SEQ ID NO | Sequence Type | Sequence Description |
| --- | --- | --- |
| 1 | Nucleic acid | Cyclin-dependent kinase |
| 2 | Nucleic acid | Cyclin-dependent kinase |
| 3 | Nucleic acid | Cyclin-dependent kinase |
| 4 | Nucleic acid | Cyclin-dependent kinase |
| 5 | Nucleic acid | Cyclin-dependent kinase inhibitor |
| 6 | Nucleic acid | Cyclin |
| 7 | Nucleic acid | Cyclin |
| 8 | Nucleic acid | Cyclin |
| 9 | Nucleic acid | Cyclin |
| 10 | Nucleic acid | Cyclin |
| 11 | Nucleic acid | Cyclin |
| 12 | Nucleic acid | Cyclin |
| 13 | Nucleic acid | Cyclin |
| 14 | Nucleic acid | Cyclin |
| 15 | Nucleic acid | Cyclin |
| 16 | Nucleic acid | Cyclin |
| 17 | Nucleic acid | Cyclin |
| 18 | Nucleic acid | Cyclin |
| 19 | Nucleic acid | Cyclin |
| 20 | Nucleic acid | Cyclin |
| 21 | Nucleic acid | Cyclin |
| 22 | Nucleic acid | Cyclin |
| 23 | Nucleic acid | Cyclin |
| 24 | Nucleic acid | Cyclin |
| 25 | Nucleic acid | Cyclin |
| 26 | Nucleic acid | Cyclin |
| 27 | Nucleic acid | Cyclin |
| 28 | Nucleic acid | Cyclin |
| 29 | Nucleic acid | Cyclin |
| 30 | Nucleic acid | Cyclin |
| 31 | Nucleic acid | Cyclin |
| 32 | Nucleic acid | Cyclin |
| 33 | Nucleic acid | MYB |
| 34 | Nucleic acid | MYB |
| 35 | Nucleic acid | MYB |
| 36 | Nucleic acid | MYB |
| 37 | Nucleic acid | MYB |

TABLE 1-continued

Description of sequences

| SEQ ID NO | Sequence Type | Sequence Description |
|---|---|---|
| 38 | Nucleic acid | MYB |
| 39 | Nucleic acid | MYB |
| 40 | Nucleic acid | MYB |
| 41 | Nucleic acid | MYB |
| 42 | Nucleic acid | MYB |
| 43 | Nucleic acid | MYB |
| 44 | Nucleic acid | MYB |
| 45 | Amino acid | Cyclin-dependent kinase |
| 46 | Amino acid | Cyclin-dependent kinase |
| 47 | Amino acid | Cyclin-dependent kinase |
| 48 | Amino acid | Cyclin-dependent kinase |
| 49 | Amino acid | Cyclin-dependent kinase inhibitor |
| 50 | Amino acid | Cyclin |
| 51 | Amino acid | Cyclin |
| 52 | Amino acid | Cyclin |
| 53 | Amino acid | Cyclin |
| 54 | Amino acid | Cyclin |
| 55 | Amino acid | Cyclin |
| 56 | Amino acid | Cyclin |
| 57 | Amino acid | Cyclin |
| 58 | Amino acid | Cyclin |
| 59 | Amino acid | Cyclin |
| 60 | Amino acid | Cyclin |
| 61 | Amino acid | Cyclin |
| 62 | Amino acid | Cyclin |
| 63 | Amino acid | Cyclin |
| 64 | Amino acid | Cyclin |
| 65 | Amino acid | Cyclin |
| 66 | Amino acid | Cyclin |
| 67 | Amino acid | Cyclin |
| 68 | Amino acid | Cyclin |
| 69 | Amino acid | Cyclin |
| 70 | Amino acid | Cyclin |
| 71 | Amino acid | Cyclin |
| 72 | Amino acid | Cyclin |
| 73 | Amino acid | Cyclin |
| 74 | Amino acid | Cyclin |
| 75 | Amino acid | Cyclin |
| 76 | Amino acid | Cyclin |
| 77 | Amino acid | MYB |
| 78 | Amino acid | MYB |
| 79 | Amino acid | MYB |
| 80 | Amino acid | MYB |
| 81 | Amino acid | MYB |
| 82 | Amino acid | MYB |
| 83 | Amino acid | MYB |
| 84 | Amino acid | MYB |
| 85 | Amino acid | MYB |
| 86 | Amino acid | MYB |
| 87 | Amino acid | MYB |
| 88 | Amino acid | MYB |
| 89 | Nucleic acid | Promoter |
| 90 | Nucleic acid | Promoter |
| 91 | Nucleic acid | Promoter |
| 92 | Nucleic acid | Promoter |
| 93 | Nucleic acid | Promoter |
| 94 | Nucleic acid | Promoter |
| 95 | Nucleic acid | Promoter |
| 96 | Nucleic acid | Promoter |
| 97 | Nucleic acid | Promoter |
| 98 | Nucleic acid | Promoter |
| 99 | Nucleic acid | Promoter |
| 100 | Nucleic acid | Promoter |
| 101 | Nucleic acid | Promoter |
| 102 | Nucleic acid | Promoter |
| 103 | Nucleic acid | Promoter |
| 104 | Nucleic acid | Promoter |
| 105 | Nucleic acid | Promoter |
| 106 | Nucleic acid | Promoter |
| 107 | Nucleic acid | Promoter |
| 108 | Nucleic acid | Promoter |
| 109 | Nucleic acid | Promoter |
| 110 | Nucleic acid | WRKY core domain |
| 111 | Nucleic acid | WRKY core domain variant |
| 112 | Nucleic acid | WRKY domain motif |
| 113 | Nucleic acid | WRKY transcription factor |
| 114 | Amino acid | WRKY transcription factor |
| 115 | Amino acid | WRKY transcription factor zinc finger region |
| 116 | Amino acid | WRKY transcription factor zinc finger region |
| 117 | Amino acid | WRKY domain |
| 118 | Nucleic acid | Artificial miRNA precursor |
| 119 | Nucleic acid | Artificial miRNA precursor |
| 120 | Nucleic acid | Artificial miRNA precursor |
| 121 | Nucleic acid | Mature artificial miRNA |
| 122 | Nucleic acid | Mature artificial miRNA |
| 123 | Nucleic acid | Mature artificial miRNA |
| 124 | Nucleic acid | Artificial miRNA* |
| 125 | Nucleic acid | Artificial miRNA* |
| 126 | Nucleic acid | Artificial miRNA* |

DETAILED DESCRIPTION

Figure 1:
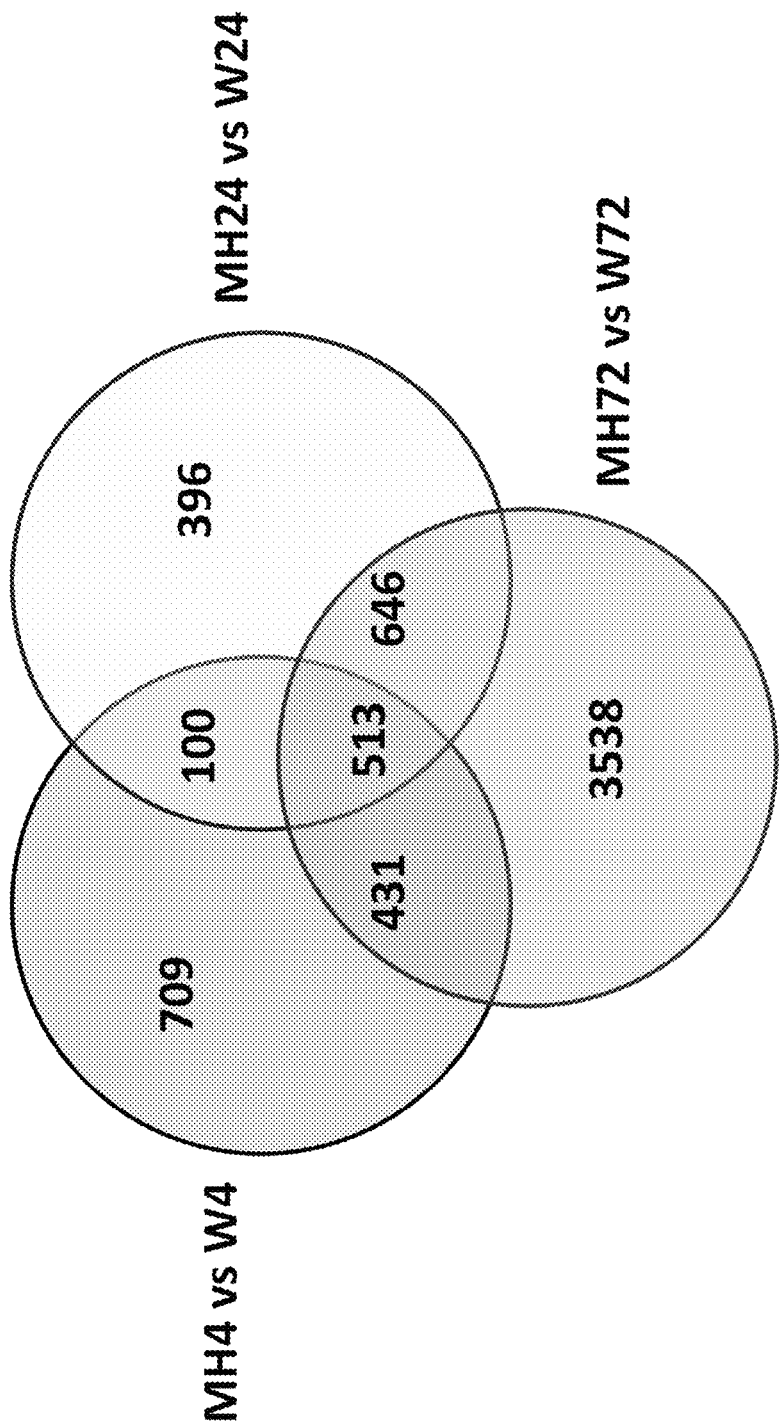
FIG. 1 is a Venn diagram depicting the overlap of differentially expressed genes in axillary buds between 4-hour, 24-hour, and 72-hour post-topping pairwise comparisons of water-treated and maleic hydrazine-treated tobacco plants. MH4 refers 4-hours after maleic hydrazide treatment; W4 refers to 4-hours after water treatment; MH24 refers to 24-hours after maleic hydrazide treatment; W24 refers to 24-hours after water treatment; MH72 refers to 72-hours after maleic hydrazide treatment; W72 refers to 72-hours after water treatment.

Unless defined otherwise, all technical and scientific terms used have the same meaning as commonly understood by one of ordinary skill in the art to which this disclosure belongs. Where a term is provided in the singular, the inventors also contemplate aspects of the disclosure described by the plural of that term. Where there are discrepancies in terms and definitions used in references that are incorporated by reference, the terms used in this application shall have the definitions given herein. Other technical terms used have their ordinary meaning in the art in which they are used, as exemplified by various art-specific dictionaries, for example, "The American Heritage® Science Dictionary" (Editors of the American Heritage Dictionaries, 2011, Houghton Mifflin Harcourt, Boston and New York), the "McGraw-Hill Dictionary of Scientific and Technical Terms" (6th edition, 2002, McGraw-Hill, New York), or the "Oxford Dictionary of Biology" (6th edition, 2008, Oxford University Press, Oxford and New York).

Any references cited herein, including, e.g., all patents, published patent applications, and non-patent publications, are incorporated herein by reference in their entirety.

When a grouping of alternatives is presented, any and all combinations of the members that make up that grouping of alternatives is specifically envisioned. For example, if an item is selected from a group consisting of A, B, C, and D, the inventors specifically envision each alternative individually (e.g., A alone, B alone, etc.), as well as combinations such as A, B, and D; A and C; B and C; etc. The term "and/or" when used in a list of two or more items means any one of the listed items by itself or in combination with any one or more of the other listed items. For example, the expression "A and/or B" is intended to mean either or both of A and B—i.e., A alone, B alone, or A and B in combination. The expression "A, B and/or C" is intended to mean A alone, B alone, C alone, A and B in combination, A and C in combination, B and C in combination, or A, B, and C in combination.

When a range of numbers is provided herein, the range is understood to inclusive of the edges of the range as well as any number between the defined edges of the range. For example, "between 1 and 10" includes any number between 1 and 10, as well as the number 1 and the number 10.

As used herein, the singular form "a," "an," and "the" include plural references unless the context clearly dictates otherwise. For example, the term "a compound" or "at least one compound" may include a plurality of compounds, including mixtures thereof.

In an aspect, a modified tobacco plant provided herein comprises reduced suckering or no suckering after topping as compared to a control tobacco plant when grown under comparable conditions.

As used herein, "suckering" refers to the development and/or growth of axillary (or lateral) buds ("suckers") from axillary meristems that grow between a leaf and the stalk. An axillary bud is an embryonic shoot that comprises an axillary meristem, surrounding leaf tissue, and surrounding stem tissue. See, for example, U.S. Patent Application Publication Nos. 2016/0281100; and 2017/0260535, which are incorporated by reference herein in their entireties.

As used herein, "topping" refers to the removal of the stalk apex, including the shoot apical meristem, flowers, and up to several adjacent leaves, when a plant is near maturity. Topping a tobacco plant results in the loss of apical dominance. Prior to topping, suckering is largely kept dormant by hormonal signals emanating from the shoot-apical meristem; topping removes the hormonal signals and can allow the outgrowth of suckers ("topping-induced suckering"). Provided suckering is sufficiently controlled, topping increases yield, increases value-per-acre, and results in desirable modifications to physical and chemical properties of tobacco leaves.

As used herein, "comparable growth conditions" refers to similar environmental conditions and/or agronomic practices for growing and making meaningful comparisons between two or more plant genotypes so that neither environmental conditions nor agronomic practices would contribute to, or explain, any differences observed between the two or more plant genotypes. Environmental conditions include, for example, light, temperature, water, humidity, and nutrition (e.g., nitrogen and phosphorus). Agronomic practices include, for example, seeding, clipping, undercutting, transplanting, topping, and suckering. See Chapters 4B and 4C of Tobacco, Production, Chemistry and Technology, Davis & Nielsen, eds., Blackwell Publishing, Oxford (1999), pp. 70-103. It is appreciated in the art that "comparable growth conditions" does not require identical growth conditions.

As used herein, "modified" refers to plants, seeds, plant parts, plant cells, and plant genomes that have been subjected to mutagenesis, genome editing, genetic transformation, or a combination thereof.

In an aspect, this disclosure provides a modified tobacco plant that comprise no suckers or reduced suckers after topping as compared to a control tobacco plant when grown under comparable conditions. As used herein, a "reduction" in the number of suckers, the size of suckers, and/or the impact suckers have on agronomic performance refers to a statistically significant reduction. As used herein, "statistically significant" refers to a p-value of less than 0.05 when using an appropriate measure of statistical significance (e.g., a one-tailed two sample t-test).

In one aspect, a modified plant or method provided herein requires reduced management for controlling suckering compared to a control plant when grown under comparable conditions. As used herein, "management" refers to manually removing suckers, application of chemicals (e.g., maleic hydrazide, flumetralin) to inhibit or remove suckers, or both. In one aspect, a modified plant or method provided herein requires reduced frequency of manual sucker removal, reduced frequency of chemical application, reduced quantities of chemical application, or a combination thereof, as compared to a control plant grown under comparable conditions. See, for example, Fisher et al. "Topping, Managing Suckers, and Using Ethephon," pages 96-117 In: 2016 Flue-Cured Tobacco Information, North Carolina State University, which is herein incorporated by reference in its entirety.

In an aspect, a modified plant or method provided herein requires reduced frequency of maleic hydrazide application to reduce or eliminate suckers. In an aspect, a modified plant or method provided herein requires reduced quantities of maleic hydrazide application to reduce or eliminate suckers. In an aspect, a modified plant or method provided herein requires reduced frequency of flumetralin application to reduce or eliminate suckers. In an aspect, a modified plant or method provided herein requires reduced quantities of flumetralin application to reduce or eliminate suckers.

In one aspect, a modified plant or method provided herein requires manual removal of suckers 1% as frequently as a control plant when grown under comparable conditions. In one aspect, a modified plant or method provided herein requires manual removal of suckers 5% as frequently as a control plant when grown under comparable conditions. In one aspect, a modified plant or method provided herein requires manual removal of suckers 10% as frequently as a control plant when grown under comparable conditions. In one aspect, a modified plant or method provided herein requires manual removal of suckers 20% as frequently as a control plant when grown under comparable conditions. In one aspect, a modified plant or method provided herein requires manual removal of suckers 30% as frequently as a control plant when grown under comparable conditions. In one aspect, a modified plant or method provided herein requires manual removal of suckers 40% as frequently as a control plant when grown under comparable conditions. In one aspect, a modified plant or method provided herein requires manual removal of suckers 50% as frequently as a control plant when grown under comparable conditions. In one aspect, a modified plant or method provided herein requires manual removal of suckers 60% as frequently as a control plant when grown under comparable conditions. In one aspect, a modified plant or method provided herein requires manual removal of suckers 70% as frequently as a control plant when grown under comparable conditions. In one aspect, a modified plant or method provided herein requires manual removal of suckers 80% as frequently as a control plant when grown under comparable conditions. In one aspect, a modified plant or method provided herein requires manual removal of suckers 90% as frequently as a control plant when grown under comparable conditions. In one aspect, a modified plant or method provided herein requires manual removal of suckers 95% as frequently as a control plant when grown under comparable conditions.

In one aspect, a modified plant or method provided herein requires manual removal of suckers less than 1% as frequently as a control plant when grown under comparable conditions. In one aspect, a modified plant or method provided herein requires manual removal of suckers less than 5% as frequently as a control plant when grown under comparable conditions. In one aspect, a modified plant or method provided herein requires manual removal of suckers less than 10% as frequently as a control plant when grown under comparable conditions. In one aspect, a modified plant or method provided herein requires manual removal of suckers less than 20% as frequently as a control plant when grown under comparable conditions. In one aspect, a modified plant or method provided herein requires manual removal of suckers less than 30% as frequently as a control plant when grown under comparable conditions. In one aspect, a modified plant or method provided herein requires manual removal of suckers less than 40% as frequently as a control plant when grown under comparable conditions. In one aspect, a modified plant or method provided herein requires manual removal of suckers less than 50% as frequently as a control plant when grown under comparable conditions. In one aspect, a modified plant or method provided herein requires manual removal of suckers less than 60% as frequently as a control plant when grown under comparable conditions. In one aspect, a modified plant or method provided herein requires manual removal of suckers less than 70% as frequently as a control plant when grown under comparable conditions. In one aspect, a modified plant or method provided herein requires manual removal of suckers less than 80% as frequently as a control plant when grown under comparable conditions. In one aspect, a modified plant or method provided herein requires manual removal of suckers less than 90% as frequently as a control plant when grown under comparable conditions. In one aspect, a modified plant or method provided herein requires manual removal of suckers less than 95% as frequently as a control plant when grown under comparable conditions.

In one aspect, a modified plant provided herein requires manual removal of suckers between 10% and 95% as frequently as a control plant when grown under comparable conditions. In one aspect, a modified plant provided herein requires manual removal of suckers between 20% and 95% as frequently as a control plant when grown under comparable conditions. In one aspect, a modified plant provided herein requires manual removal of suckers between 30% and 95% as frequently as a control plant when grown under comparable conditions. In one aspect, a modified plant provided herein requires manual removal of suckers between 40% and 95% as frequently as a control plant when grown under comparable conditions. In one aspect, a modified plant provided herein requires manual removal of suckers between 50% and 95% as a control plant when grown under comparable conditions. In one aspect, a modified plant provided herein requires manual removal of suckers between 60% and 95% as frequently as a control plant when grown under comparable conditions. In one aspect, a modified plant provided herein requires manual removal of suckers between 70% and 95% as frequently as a control plant when grown under comparable conditions. In one aspect, a modified plant provided herein requires manual removal of suckers between 80% and 95% as frequently as a control plant when grown under comparable conditions. In one aspect, a modified plant provided herein requires manual removal of suckers between 90% and 95% as frequently as a control plant when grown under comparable conditions. In one aspect, a modified plant provided herein requires manual removal of suckers between 10% and 75% as frequently as a control plant when grown under comparable conditions. In one aspect, a modified plant provided herein requires manual removal of suckers between 10% and 50% as frequently as a control plant when grown under comparable conditions. In one aspect, a modified plant provided herein requires manual removal of suckers between 10% and 25% as frequently as a control plant when grown under comparable conditions. In one aspect, a modified plant provided herein requires manual removal of suckers between 50% and 75% as frequently as a control plant when grown under comparable conditions. In one aspect, a modified plant provided herein requires manual removal of suckers between 25% and 75% as frequently as a control plant when grown under comparable conditions. In one aspect, a modified plant provided herein requires manual removal of suckers between 25% and 50% as frequently as a control plant when grown under comparable conditions. In one aspect, a modified plant provided herein requires manual removal of suckers between 1% and 50% as frequently as a control plant when grown under comparable conditions. In one aspect, a modified plant provided herein requires manual removal of suckers between 1% and 25% as frequently as a control plant when grown under comparable conditions. In one aspect, a modified plant provided herein requires manual removal of suckers between 1% and 10% as frequently as a control plant when grown under comparable conditions.

In one aspect, a modified plant provided herein requires chemical application to control suckering 1% as frequently as a control plant when grown under comparable conditions. In one aspect, a modified plant provided herein requires chemical application to control suckering 5% as frequently as a control plant when grown under comparable conditions. In one aspect, a modified plant provided herein requires chemical application to control suckering 10% as frequently as a control plant when grown under comparable conditions. In one aspect, a modified plant provided herein requires chemical application to control suckering 20% as frequently as a control plant when grown under comparable conditions. In one aspect, a modified plant provided herein requires chemical application to control suckering 30% as frequently as a control plant when grown under comparable conditions. In one aspect, a modified plant provided herein requires chemical application to control suckering 40% as frequently as a control plant when grown under comparable conditions. In one aspect, a modified plant provided herein requires chemical application to control suckering 50% as frequently as a control plant when grown under comparable conditions. In one aspect, a modified plant provided herein requires chemical application to control suckering 60% as frequently as a control plant when grown under comparable conditions. In one aspect, a modified plant provided herein requires chemical application to control suckering 70% as frequently as a control plant when grown under comparable conditions.

In one aspect, a modified plant provided herein requires chemical application to control suckering 80% as frequently as a control plant when grown under comparable conditions. In one aspect, a modified plant provided herein requires chemical application to control suckering 90% as frequently as a control plant when grown under comparable conditions. In one aspect, a modified plant provided herein requires chemical application to control suckering 95% as frequently as a control plant when grown under comparable conditions.

In one aspect, a modified plant provided herein requires chemical application to control suckering less than 1% as frequently as a control plant when grown under comparable conditions. In one aspect, a modified plant provided herein requires chemical application to control suckering less than 5% as frequently as a control plant when grown under comparable conditions. In one aspect, a modified plant provided herein requires chemical application to control suckering less than 10% as frequently as a control plant when grown under comparable conditions. In one aspect, a modified plant provided herein requires chemical application to control suckering less than 20% as frequently as a control plant when grown under comparable conditions. In one aspect, a modified plant provided herein requires chemical application to control suckering less than 30% as frequently as a control plant when grown under comparable conditions. In one aspect, a modified plant provided herein requires chemical application to control suckering less than 40% as frequently as a control plant when grown under comparable conditions. In one aspect, a modified plant provided herein requires chemical application to control suckering less than 50% as frequently as a control plant when grown under comparable conditions. In one aspect, a modified plant provided herein requires chemical application to control suckering less than 60% as frequently as a control plant when grown under comparable conditions. In one aspect, a modified plant provided herein requires chemical application to control suckering less than 70% as frequently as a control plant when grown under comparable conditions. In one aspect, a modified plant provided herein requires chemical application to control suckering less than 80% as frequently as a control plant when grown under comparable conditions. In one aspect, a modified plant provided herein requires chemical application to control suckering less than 90% as frequently as a control plant when grown under comparable conditions. In one aspect, a modified plant provided herein requires chemical application to control suckering less than 95% as frequently as a control plant when grown under comparable conditions.

In one aspect, a modified plant provided herein requires chemical application to control suckering between 10% and 95% as frequently as a control plant when grown under comparable conditions. In one aspect, a modified plant provided herein requires chemical application to control suckering between 20% and 95% as frequently as a control plant when grown under comparable conditions. In one aspect, a modified plant provided herein requires chemical application to control suckering between 30% and 95% as frequently as a control plant when grown under comparable conditions. In one aspect, a modified plant provided herein requires chemical application to control suckering between 40% and 95% as frequently as a control plant when grown under comparable conditions. In one aspect, a modified plant provided herein requires chemical application to control suckering between 50% and 95% as frequently as a control plant when grown under comparable conditions. In one aspect, a modified plant provided herein requires chemical application to control suckering between 60% and 95% as frequently as a control plant when grown under comparable conditions. In one aspect, a modified plant provided herein requires chemical application to control suckering between 70% and 95% as frequently as a control plant when grown under comparable conditions. In one aspect, a modified plant provided herein requires chemical application to control suckering between 80% and 95% as frequently as a control plant when grown under comparable conditions. In one aspect, a modified plant provided herein requires chemical application to control suckering between 90% and 95% as frequently as a control plant when grown under comparable conditions. In one aspect, a modified plant provided herein requires chemical application to control suckering between 10% and 75% as frequently as a control plant when grown under comparable conditions. In one aspect, a modified plant provided herein requires chemical application to control suckering between 10% and 50% as frequently as a control plant when grown under comparable conditions. In one aspect, a modified plant provided herein requires chemical application to control suckering between 10% and 25% as frequently as a control plant when grown under comparable conditions. In one aspect, a modified plant provided herein requires chemical application to control suckering between 50% and 75% as frequently as a control plant when grown under comparable conditions. In one aspect, a modified plant provided herein requires chemical application to control suckering between 25% and 50% as frequently as a control plant when grown under comparable conditions. In one aspect, a modified plant provided herein requires chemical application to control suckering between 25% and 75% as frequently as a control plant when grown under comparable conditions. In one aspect, a modified plant provided herein requires chemical application to control suckering between 1% and 50% as frequently as a control plant when grown under comparable conditions. In one aspect, a modified plant provided herein requires chemical application to control suckering between 1% and 25% as frequently as a control plant when grown under comparable conditions. In one aspect, a modified plant provided herein requires chemical application to control suckering between 1% and 10% as frequently as a control plant when grown under comparable conditions.

In one aspect, a modified plant provided herein requires a chemical spray volume of 1% of the volume used to control suckering of a control plant when grown under comparable conditions. In one aspect, a modified plant provided herein requires a chemical spray volume of 5% of the volume used to control suckering of a control plant when grown under comparable conditions. In one aspect, a modified plant provided herein requires a chemical spray volume of 10% of the volume used to control suckering of a control plant when grown under comparable conditions. In one aspect, a modified plant provided herein requires a chemical spray volume of 20% of the volume used to control suckering of a control plant when grown under comparable conditions. In one aspect, a modified plant provided herein requires a chemical spray volume of 30% of the volume used to control suckering of a control plant when grown under comparable conditions. In one aspect, a modified plant provided herein requires a chemical spray volume of 40% of the volume used to control suckering of a control plant when grown under comparable conditions. In one aspect, a modified plant provided herein requires a chemical spray volume of 50% of the volume used to control suckering of a control plant when grown under comparable conditions. In one aspect, a modified plant provided herein requires a chemical spray volume of 60% of the volume used to control suckering of a control plant when grown under comparable conditions. In one aspect, a modified plant provided herein requires a chemical spray volume of 70% of the volume used to control suckering of a control plant when grown under comparable conditions. In one aspect, a modified plant provided herein requires a chemical spray volume of 80% of the volume used to control suckering of a control plant when grown under comparable conditions. In one aspect, a modified plant provided herein requires a chemical spray volume of 90% of the volume used to control suckering of a control plant when grown under comparable conditions. In one aspect, a modified plant provided herein requires a chemical spray volume of 95% of the volume used to control suckering of a control plant when grown under comparable conditions.

In one aspect, a modified plant provided herein requires a chemical spray volume of less than 1% of the volume used to control suckering of a control plant when grown under comparable conditions. In one aspect, a modified plant provided herein requires a chemical spray volume of less than 5% of the volume used to control suckering of a control plant when grown under comparable conditions. In one aspect, a modified plant provided herein requires a chemical spray volume of less than 10% of the volume used to control suckering of a control plant when grown under comparable conditions. In one aspect, a modified plant provided herein requires a chemical spray volume of less than 20% of the volume used to control suckering of a control plant when grown under comparable conditions. In one aspect, a modified plant provided herein requires a chemical spray volume of less than 30% of the volume used to control suckering of a control plant when grown under comparable conditions. In one aspect, a modified plant provided herein requires a chemical spray volume of less than 40% of the volume used to control suckering of a control plant when grown under comparable conditions. In one aspect, a modified plant provided herein requires a chemical spray volume of less than 50% of the volume used to control suckering of a control plant when grown under comparable conditions. In one aspect, a modified plant provided herein requires a chemical spray volume of less than 60% of the volume used to control suckering of a control plant when grown under comparable conditions. In one aspect, a modified plant provided herein requires a chemical spray volume of less than 70% of the volume used to control suckering of a control plant when grown under comparable conditions. In one aspect, a modified plant provided herein requires a chemical spray volume of less than 80% of the volume used to control suckering of a control plant when grown under comparable conditions. In one aspect, a modified plant provided herein requires a chemical spray volume of less than 90% of the volume used to control suckering of a control plant when grown under comparable conditions. In one aspect, a modified plant provided herein requires a chemical spray volume of less than 95% of the volume used to control suckering of a control plant when grown under comparable conditions.

In one aspect, a modified plant provided herein requires a chemical spray volume between 10% and 95% less than a control plant when grown under comparable conditions. In one aspect, a modified plant provided herein requires a chemical spray volume between 20% and 95% less than a control plant when grown under comparable conditions. In one aspect, a modified plant provided herein requires a chemical spray volume between 30% and 95% less than a control plant when grown under comparable conditions. In one aspect, a modified plant provided herein requires a chemical spray volume between 40% and 95% less than a control plant when grown under comparable conditions. In one aspect, a modified plant provided herein requires a chemical spray volume between 50% and 95% less than a control plant when grown under comparable conditions. In one aspect, a modified plant provided herein requires a chemical spray volume between 60% and 95% less than a control plant when grown under comparable conditions. In one aspect, a modified plant provided herein requires a chemical spray volume between 70% and 95% less than a control plant when grown under comparable conditions. In one aspect, a modified plant provided herein requires a chemical spray volume between 80% and 95% less than a control plant when grown under comparable conditions. In one aspect, a modified plant provided herein requires a chemical spray volume between 90% and 95% less than a control plant when grown under comparable conditions. In one aspect, a modified plant provided herein requires a chemical spray volume between 10% and 75% less than a control plant when grown under comparable conditions. In one aspect, a modified plant provided herein requires a chemical spray volume between 10% and 50% less than a control plant when grown under comparable conditions. In one aspect, a modified plant provided herein requires a chemical spray volume between 10% and 25% less than a control plant when grown under comparable conditions. In one aspect, a modified plant provided herein requires a chemical spray volume between 25% and 50% less than a control plant when grown under comparable conditions. In one aspect, a modified plant provided herein requires a chemical spray volume between 25% and 75% less than a control plant when grown under comparable conditions. In one aspect, a modified plant provided herein requires a chemical spray volume between 50% and 75% less than a control plant when grown under comparable conditions. In one aspect, a modified plant provided herein requires a chemical spray volume between 1% and 50% less than a control plant when grown under comparable conditions. In one aspect, a modified plant provided herein requires a chemical spray volume between 1% and 25% less than a control plant when grown under comparable conditions. In one aspect, a modified plant provided herein requires a chemical spray volume between 1% and 10% less than a control plant when grown under comparable conditions.

In an aspect, reduced suckers comprises fewer total suckers, smaller average sucker size, or both, as compared to a control tobacco plant when grown under comparable conditions. In another aspect, smaller average sucker size comprises a measurement selected from the group consisting of reduced average mass, reduced average length, reduced average diameter, or any combination thereof, as compared to suckers of a control tobacco plant when grown under comparable growth conditions. In another aspect, smaller average sucker size comprises reduced average mass of suckers. In a further aspect, smaller average sucker size comprises reduced average length of suckers. In a still further aspect, smaller average sucker size comprises reduced average diameter of suckers.

In an aspect, a modified tobacco plant comprises fewer total suckers as compared to a control tobacco plant when grown under comparable conditions. In an aspect, a modified tobacco plant comprises a smaller average sucker size as compared to a control tobacco plant when grown under comparable conditions. In an aspect, a modified tobacco plant comprises a shorter average sucker length as compared to a control tobacco plant when grown under comparable conditions. In an aspect, a modified tobacco plant comprises a lower average sucker mass as compared to a control tobacco plant when grown under comparable conditions. In an aspect, a modified tobacco plant comprises a shorter average sucker diameter as compared to a control tobacco plant when grown under comparable conditions.

In an aspect, a modified tobacco plant comprises at least 1 fewer sucker as compared to a control tobacco plant when grown under comparable conditions. In an aspect, a modified tobacco plant comprises at least 2 fewer suckers as compared to a control tobacco plant when grown under comparable conditions. In an aspect, a modified tobacco plant comprises at least 3 fewer suckers as compared to a control tobacco plant when grown under comparable conditions. In an aspect, a modified tobacco plant comprises at least 4 fewer suckers as compared to a control tobacco plant when grown under comparable conditions. In an aspect, a modified tobacco plant comprises at least 5 fewer suckers as compared to a control tobacco plant when grown under comparable conditions. In an aspect, a modified tobacco plant comprises at least 7 fewer suckers as compared to a control tobacco plant when grown under comparable conditions. In an aspect, a modified tobacco plant comprises at least 10 fewer suckers as compared to a control tobacco plant when grown under comparable conditions. In an aspect, a modified tobacco plant comprises at least 15 fewer suckers as compared to a control tobacco plant when grown under comparable conditions. In an aspect, a modified tobacco plant comprises at least 20 fewer suckers as compared to a control tobacco plant when grown under comparable conditions. In an aspect, a modified tobacco plant comprises at least 25 fewer suckers as compared to a control tobacco plant when grown under comparable conditions. In an aspect, a modified tobacco plant comprises at least 30 fewer suckers as compared to a control tobacco plant when grown under comparable conditions.

In an aspect, a modified tobacco plant comprises at least 5% fewer suckers as compared to a control tobacco plant when grown under comparable conditions. In an aspect, a modified tobacco plant comprises at least 10% fewer suckers as compared to a control tobacco plant when grown under comparable conditions. In an aspect, a modified tobacco plant comprises at least 15% fewer suckers as compared to a control tobacco plant when grown under comparable conditions. In an aspect, a modified tobacco plant comprises at least 20% fewer suckers as compared to a control tobacco plant when grown under comparable conditions. In an aspect, a modified tobacco plant comprises at least 25% fewer suckers as compared to a control tobacco plant when grown under comparable conditions. In an aspect, a modified tobacco plant comprises at least 30% fewer suckers as compared to a control tobacco plant when grown under comparable conditions. In an aspect, a modified tobacco plant comprises at least 40% fewer suckers as compared to a control tobacco plant when grown under comparable conditions. In an aspect, a modified tobacco plant comprises at least 50% fewer suckers as compared to a control tobacco plant when grown under comparable conditions. In an aspect, a modified tobacco plant comprises at least 60% fewer suckers as compared to a control tobacco plant when grown under comparable conditions. In an aspect, a modified tobacco plant comprises at least 70% fewer suckers as compared to a control tobacco plant when grown under comparable conditions. In an aspect, a modified tobacco plant comprises at least 80% fewer suckers as compared to a control tobacco plant when grown under comparable conditions. In an aspect, a modified tobacco plant comprises at least 90% fewer suckers as compared to a control tobacco plant when grown under comparable conditions. In an aspect, a modified tobacco plant comprises at least 95% fewer suckers as compared to a control tobacco plant when grown under comparable conditions.

In an aspect, average sucker mass is measured using fresh sucker weight. In another aspect, average sucker mass is measured using dry sucker weight.

In an aspect, a modified tobacco plant comprises an average sucker mass at least 5% lower as compared to the average sucker mass of a control tobacco plant when grown under comparable conditions. In an aspect, a modified tobacco plant comprises an average sucker mass at least 10% lower as compared to the average sucker mass of a control tobacco plant when grown under comparable conditions. In an aspect, a modified tobacco plant comprises an average sucker mass at least 15% lower as compared to the average sucker mass of a control tobacco plant when grown under comparable conditions. In an aspect, a modified tobacco plant comprises an average sucker mass at least 20% lower as compared to the average sucker mass of a control tobacco plant when grown under comparable conditions. In an aspect, a modified tobacco plant comprises an average sucker mass at least 25% lower as compared to the average sucker mass of a control tobacco plant when grown under comparable conditions. In an aspect, a modified tobacco plant comprises an average sucker mass at least 30% lower as compared to the average sucker mass of a control tobacco plant when grown under comparable conditions. In an aspect, a modified tobacco plant comprises an average sucker mass at least 40% lower as compared to the average sucker mass of a control tobacco plant when grown under comparable conditions. In an aspect, a modified tobacco plant comprises an average sucker mass at least 50% lower as compared to the average sucker mass of a control tobacco plant when grown under comparable conditions. In an aspect, a modified tobacco plant comprises an average sucker mass at least 60% lower as compared to the average sucker mass of a control tobacco plant when grown under comparable conditions. In an aspect, a modified tobacco plant comprises an average sucker mass at least 70% lower as compared to the average sucker mass of a control tobacco plant when grown under comparable conditions. In an aspect, a modified tobacco plant comprises an average sucker mass at least 80% lower as compared to the average sucker mass of a control tobacco plant when grown under comparable conditions. In an aspect, a modified tobacco plant comprises an average sucker mass at least 90% lower as compared to the average sucker mass of a control tobacco plant when grown under comparable conditions. In an aspect, a modified tobacco plant comprises an average sucker mass at least 95% lower as compared to the average sucker mass of a control tobacco plant when grown under comparable conditions.

In an aspect, average sucker length is measured from the base of the sucker where it joins the main tobacco stem to the distal tip of the sucker stem.

In an aspect, a modified tobacco plant comprises an average sucker length at least 1 centimeter shorter as compared to the average sucker length of a control tobacco plant when grown under comparable conditions. In an aspect, a modified tobacco plant comprises an average sucker length at least 2 centimeters shorter as compared to the average sucker length of a control tobacco plant when grown under comparable conditions. In an aspect, a modified tobacco plant comprises an average sucker length at least 3 centimeters shorter as compared to the average sucker length of a control tobacco plant when grown under comparable conditions. In an aspect, a modified tobacco plant comprises an average sucker length at least 4 centimeters shorter as compared to the average sucker length of a control tobacco plant when grown under comparable conditions. In an aspect, a modified tobacco plant comprises an average sucker length at least 5 centimeters shorter as compared to the average sucker length of a control tobacco plant when grown under comparable conditions. In an aspect, a modified tobacco plant comprises an average sucker length at least 10 centimeters shorter as compared to the average sucker length of a control tobacco plant when grown under comparable conditions. In an aspect, a modified tobacco plant comprises an average sucker length at least 15 centimeters shorter as compared to the average sucker length of a control tobacco plant when grown under comparable conditions. In an aspect, a modified tobacco plant comprises an average sucker length at least 20 centimeters shorter as compared to the average sucker length of a control tobacco plant when grown under comparable conditions.

In an aspect, a modified tobacco plant comprises an average sucker length between 0.5 centimeters and 30 centimeters shorter as compared to the average sucker length of a control tobacco plant when grown under comparable conditions. In an aspect, a modified tobacco plant comprises an average sucker length between 0.5 centimeters and 25 centimeters shorter as compared to the average sucker length of a control tobacco plant when grown under comparable conditions. In an aspect, a modified tobacco plant comprises an average sucker length between 0.5 centimeters and 20 centimeters shorter as compared to the average sucker length of a control tobacco plant when grown under comparable conditions. In an aspect, a modified tobacco plant comprises an average sucker length between 0.5 centimeters and 15 centimeters shorter as compared to the average sucker length of a control tobacco plant when grown under comparable conditions. In an aspect, a modified tobacco plant comprises an average sucker length between 0.5 centimeters and 10 centimeters shorter as compared to the average sucker length of a control tobacco plant when grown under comparable conditions. In an aspect, a modified tobacco plant comprises an average sucker length between 0.5 centimeters and 5 centimeters shorter as compared to the average sucker length of a control tobacco plant when grown under comparable conditions. In an aspect, a modified tobacco plant comprises an average sucker length between 1 centimeter and 30 centimeters shorter as compared to the average sucker length of a control tobacco plant when grown under comparable conditions. In an aspect, a modified tobacco plant comprises an average sucker length between 1 centimeter and 20 centimeters shorter as compared to the average sucker length of a control tobacco plant when grown under comparable conditions. In an aspect, a modified tobacco plant comprises an average sucker length between 1 centimeter and 10 centimeters shorter as compared to the average sucker length of a control tobacco plant when grown under comparable conditions.

In an aspect, a modified tobacco plant comprises an average sucker length at least 5% shorter as compared to the average sucker length of a control tobacco plant when grown under comparable conditions. In an aspect, a modified tobacco plant comprises an average sucker length at least 10% shorter as compared to the average sucker length of a control tobacco plant when grown under comparable conditions. In an aspect, a modified tobacco plant comprises an average sucker length at least 15% shorter as compared to the average sucker length of a control tobacco plant when grown under comparable conditions. In an aspect, a modified tobacco plant comprises an average sucker length at least 20% shorter as compared to the average sucker length of a control tobacco plant when grown under comparable conditions. In an aspect, a modified tobacco plant comprises an average sucker length at least 25% shorter as compared to the average sucker length of a control tobacco plant when grown under comparable conditions. In an aspect, a modified tobacco plant comprises an average sucker length at least 30% shorter as compared to the average sucker length of a control tobacco plant when grown under comparable conditions. In an aspect, a modified tobacco plant comprises an average sucker length at least 40% shorter as compared to the average sucker length of a control tobacco plant when grown under comparable conditions. In an aspect, a modified tobacco plant comprises an average sucker length at least 50% shorter as compared to the average sucker length of a control tobacco plant when grown under comparable conditions. In an aspect, a modified tobacco plant comprises an average sucker length at least 60% shorter as compared to the average sucker length of a control tobacco plant when grown under comparable conditions. In an aspect, a modified tobacco plant comprises an average sucker length at least 70% shorter as compared to the average sucker length of a control tobacco plant when grown under comparable conditions. In an aspect, a modified tobacco plant comprises an average sucker length at least 80% shorter as compared to the average sucker length of a control tobacco plant when grown under comparable conditions. In an aspect, a modified tobacco plant comprises an average sucker length at least 90% shorter as compared to the average sucker length of a control tobacco plant when grown under comparable conditions. In an aspect, a modified tobacco plant comprises an average sucker length at least 95% shorter as compared to the average sucker length of a control tobacco plant when grown under comparable conditions.

In an aspect, sucker diameter is measured at the base of the sucker where it adjoins the main stem of the plant.

In an aspect, a modified tobacco plant comprises an average sucker diameter at least 5% shorter as compared to the average sucker diameter of a control tobacco plant when grown under comparable conditions. In an aspect, a modified tobacco plant comprises an average sucker diameter at least 10% shorter as compared to the average sucker diameter of a control tobacco plant when grown under comparable conditions. In an aspect, a modified tobacco plant comprises an average sucker diameter at least 15% shorter as compared to the average sucker diameter of a control tobacco plant when grown under comparable conditions. In an aspect, a modified tobacco plant comprises an average sucker diameter at least 20% shorter as compared to the average sucker diameter of a control tobacco plant when grown under comparable conditions. In an aspect, a modified tobacco plant comprises an average sucker diameter at least 25% shorter as compared to the average sucker diameter of a control tobacco plant when grown under comparable conditions. In an aspect, a modified tobacco plant comprises an average sucker diameter at least 30% shorter as compared to the average sucker diameter of a control tobacco plant when grown under comparable conditions. In an aspect, a modified tobacco plant comprises an average sucker diameter at least 40% shorter as compared to the average sucker diameter of a control tobacco plant when grown under comparable conditions. In an aspect, a modified tobacco plant comprises an average sucker diameter at least 50% shorter as compared to the average sucker diameter of a control tobacco plant when grown under comparable conditions. In an aspect, a modified tobacco plant comprises an average sucker diameter at least 60% shorter as compared to the average sucker diameter of a control tobacco plant when grown under comparable conditions. In an aspect, a modified tobacco plant comprises an average sucker diameter at least 70% shorter as compared to the average sucker diameter of a control tobacco plant when grown under comparable conditions. In an aspect, a modified tobacco plant comprises an average sucker diameter at least 80% shorter as compared to the average sucker diameter of a control tobacco plant when grown under comparable conditions. In an aspect, a modified tobacco plant comprises an average sucker diameter at least 90% shorter as compared to the average sucker diameter of a control tobacco plant when grown under comparable conditions. In an aspect, a modified tobacco plant comprises an average sucker diameter at least 95% shorter as compared to the average sucker diameter of a control tobacco plant when grown under comparable conditions.

In an aspect, a modified tobacco plant comprises an average sucker diameter at least 1 millimeter shorter as compared to the average sucker diameter of a control tobacco plant when grown under comparable conditions. In an aspect, a modified tobacco plant comprises an average sucker diameter at least 2 millimeters shorter as compared to the average sucker diameter of a control tobacco plant when grown under comparable conditions. In an aspect, a modified tobacco plant comprises an average sucker diameter at least 3 millimeters shorter as compared to the average sucker diameter of a control tobacco plant when grown under comparable conditions. In an aspect, a modified tobacco plant comprises an average sucker diameter at least 4 millimeters shorter as compared to the average sucker diameter of a control tobacco plant when grown under comparable conditions. In an aspect, a modified tobacco plant comprises an average sucker diameter at least 5 millimeters shorter as compared to the average sucker diameter of a control tobacco plant when grown under comparable conditions. In an aspect, a modified tobacco plant comprises an average sucker diameter at least 6 millimeters shorter as compared to the average sucker diameter of a control tobacco plant when grown under comparable conditions. In an aspect, a modified tobacco plant comprises an average sucker diameter at least 7 millimeters shorter as compared to the average sucker diameter of a control tobacco plant when grown under comparable conditions. In an aspect, a modified tobacco plant comprises an average sucker diameter at least 8 millimeters shorter as compared to the average sucker diameter of a control tobacco plant when grown under comparable conditions. In an aspect, a modified tobacco plant comprises an average sucker diameter at least 9 millimeters shorter as compared to the average sucker diameter of a control tobacco plant when grown under comparable conditions. In an aspect, a modified tobacco plant comprises an average sucker diameter at least 1 centimeter shorter as compared to the average sucker diameter of a control tobacco plant when grown under comparable conditions. In an aspect, a modified tobacco plant comprises an average sucker diameter at least 1.5 centimeters shorter as compared to the average sucker diameter of a control tobacco plant when grown under comparable conditions. In an aspect, a modified tobacco plant comprises an average sucker diameter at least 2 centimeters shorter as compared to the average sucker diameter of a control tobacco plant when grown under comparable conditions. In an aspect, a modified tobacco plant comprises an average sucker diameter at least 3 centimeters shorter as compared to the average sucker diameter of a control tobacco plant when grown under comparable conditions. In an aspect, a modified tobacco plant comprises an average sucker diameter at least 4 centimeters shorter as compared to the average sucker diameter of a control tobacco plant when grown under comparable conditions. In an aspect, a modified tobacco plant comprises an average sucker diameter at least 5 centimeters shorter as compared to the average sucker diameter of a control tobacco plant when grown under comparable conditions.

Any nucleic acid molecule, protein, or polypeptide provided herein is envisioned for use with any method provided herein. Any nucleic acid molecule, protein, or polypeptide provided herein is envisioned for use with any plant, plant part, cell, or seed provided herein. Any nucleic acid molecule, protein, or polypeptide provided herein is envisioned for use with any tobacco plant, tobacco plant part, tobacco cell, or tobacco seed provided herein.

The use of the term "polynucleotide" or "nucleic acid molecule" is not intended to limit the present disclosure to polynucleotides comprising deoxyribonucleic acid (DNA). For example, ribonucleic acid (RNA) molecules are also envisioned. Those of ordinary skill in the art will recognize that polynucleotides and nucleic acid molecules can comprise ribonucleotides and combinations of ribonucleotides and deoxyribonucleotides. Such deoxyribonucleotides and ribonucleotides include both naturally occurring molecules and synthetic analogues. The polynucleotides of the present disclosure also encompass all forms of sequences including, but not limited to, single-stranded forms, double-stranded forms, hairpins, stem-and-loop structures, and the like. In an aspect, a nucleic acid molecule provided herein is a DNA molecule. In another aspect, a nucleic acid molecule provided herein is an RNA molecule. In an aspect, a nucleic acid molecule provided herein is single-stranded. In another aspect, a nucleic acid molecule provided herein is double-stranded. A nucleic acid molecule can encode a polypeptide or a small RNA.

Nucleic acids can be isolated using techniques routine in the art. For example, nucleic acids can be isolated using any method including, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides. Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

In one aspect, this disclosure provides methods of detecting recombinant nucleic acids and polypeptides in plant cells. Without being limiting, nucleic acids also can be detected using hybridization. Hybridization between nucleic acids is discussed in detail in Sambrook et al. (1989, Molecular Cloning: A Laboratory Manual, 2nd Ed., Cold Spring Harbor Laboratory Press, Cold Spring Harbor, N.Y.).

In an aspect, an endogenous gene provided herein comprises a polynucleotide sequence at least 80% identical to a sequence selected from the group consisting of SEQ ID NOs: 1-44 and 113. In an aspect, an endogenous gene provided herein comprises a polynucleotide sequence at least 85% identical to a sequence selected from the group consisting of SEQ ID NOs: 1-44 and 113. In an aspect, an endogenous gene provided herein comprises a polynucleotide sequence at least 90% identical to a sequence selected from the group consisting of SEQ ID NOs: 1-44 and 113. In an aspect, an endogenous gene provided herein comprises a polynucleotide sequence at least 95% identical to a sequence selected from the group consisting of SEQ ID NOs: 1-44 and 113. In an aspect, an endogenous gene provided herein comprises a polynucleotide sequence at least 96% identical to a sequence selected from the group consisting of SEQ ID NOs: 1-44 and 113. In an aspect, an endogenous gene provided herein comprises a polynucleotide sequence at least 97% identical to a sequence selected from the group consisting of SEQ ID NOs: 1-44 and 113. In an aspect, an endogenous gene provided herein comprises a polynucleotide sequence at least 98% identical to a sequence selected from the group consisting of SEQ ID NOs: 1-44 and 113. In an aspect, an endogenous gene provided herein comprises a polynucleotide sequence at least 99% identical to a sequence selected from the group consisting of SEQ ID NOs: 1-44 and 113. In an aspect, an endogenous gene provided herein comprises a polynucleotide sequence 100% identical to a sequence selected from the group consisting of SEQ ID NOs: 1-44 and 113.

As used herein, the term "polypeptide" refers to a chain of at least two covalently linked amino acids. Polypeptides can be encoded by polynucleotides provided herein. Proteins provided herein can be encoded by nucleic acid molecules provided herein. Proteins can comprise polypeptides provided herein. As used herein, a "protein" refers to a chain of amino acid residues that is capable of providing structure or enzymatic activity to a cell.

Polypeptides can be detected using antibodies. Techniques for detecting polypeptides using antibodies include enzyme linked immunosorbent assays (ELISAs), Western blots, immunoprecipitations and immunofluorescence. An antibody provided herein can be a polyclonal antibody or a monoclonal antibody. An antibody having specific binding affinity for a polypeptide provided herein can be generated using methods well known in the art. An antibody provided herein can be attached to a solid support such as a microtiter plate using methods known in the art.

Detection (e.g., of an amplification product, of a hybridization complex, of a polypeptide) can be accomplished using detectable labels. The term "label" is intended to encompass the use of direct labels as well as indirect labels. Detectable labels include enzymes, prosthetic groups, fluorescent materials, luminescent materials, bioluminescent materials, and radioactive materials.

In an aspect, an endogenous gene provided herein encodes a polypeptide comprising an amino acid sequence at least 70% identical or similar to an amino acid sequence selected from the group consisting of SEQ ID NOs: 45-88 and 114. In an aspect, an endogenous gene provided herein encodes a polypeptide comprising an amino acid sequence at least 75% identical or similar to an amino acid sequence selected from the group consisting of SEQ ID NOs: 45-88 and 114. In an aspect, an endogenous gene provided herein encodes a polypeptide comprising an amino acid sequence at least 80% identical or similar to an amino acid sequence selected from the group consisting of SEQ ID NOs: 45-88 and 114. In an aspect, an endogenous gene provided herein encodes a polypeptide comprising an amino acid sequence at least 85% identical or similar to an amino acid sequence selected from the group consisting of SEQ ID NOs: 45-88 and 114. In an aspect, an endogenous gene provided herein encodes a polypeptide comprising an amino acid sequence at least 90% identical or similar to an amino acid sequence selected from the group consisting of SEQ ID NOs: 45-88 and 114. In an aspect, an endogenous gene provided herein encodes a polypeptide comprising an amino acid sequence at least 95% identical or similar to an amino acid sequence selected from the group consisting of SEQ ID NOs: 45-88 and 114. In an aspect, an endogenous gene provided herein encodes a polypeptide comprising an amino acid sequence at least 96% identical or similar to an amino acid sequence selected from the group consisting of SEQ ID NOs: 45-88 and 114. In an aspect, an endogenous gene provided herein encodes a polypeptide comprising an amino acid sequence at least 97% identical or similar to an amino acid sequence selected from the group consisting of SEQ ID NOs: 45-88 and 114. In an aspect, an endogenous gene provided herein encodes a polypeptide comprising an amino acid sequence at least 98% identical or similar to an amino acid sequence selected from the group consisting of SEQ ID NOs: 45-88 and 114. In an aspect, an endogenous gene provided herein encodes a polypeptide comprising an amino acid sequence at least 99% identical or similar to an amino acid sequence selected from the group consisting of SEQ ID NOs: 45-88 and 114. In an aspect, an endogenous gene provided herein encodes a polypeptide comprising an amino acid sequence 100% identical or similar to an amino acid sequence selected from the group consisting of SEQ ID NOs: 45-88 and 114.

The terms "percent identity" or "percent identical" as used herein in reference to two or more nucleotide or amino acid sequences is calculated by (i) comparing two optimally aligned sequences (nucleotide or amino acid) over a window of comparison (the "alignable" region or regions), (ii) determining the number of positions at which the identical nucleic acid base (for nucleotide sequences) or amino acid residue (for proteins and polypeptides) occurs in both sequences to yield the number of matched positions, (iii) dividing the number of matched positions by the total number of positions in the window of comparison, and then (iv) multiplying this quotient by 100% to yield the percent identity. If the "percent identity" is being calculated in relation to a reference sequence without a particular comparison window being specified, then the percent identity is determined by dividing the number of matched positions over the region of alignment by the total length of the reference sequence. Accordingly, for purposes of the present application, when two sequences (query and subject) are optimally aligned (with allowance for gaps in their alignment), the "percent identity" for the query sequence is equal to the number of identical positions between the two sequences divided by the total number of positions in the query sequence over its length (or a comparison window), which is then multiplied by 100%.

When percentage of sequence identity is used in reference to amino acids it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity can be adjusted upwards to correct for the conservative nature of the substitution. Sequences that differ by such conservative substitutions are said to have "sequence similarity" or "similarity."

For optimal alignment of sequences to calculate their percent identity, various pair-wise or multiple sequence alignment algorithms and programs are known in the art, such as ClustalW or Basic Local Alignment Search Tool® (BLAST™), etc., that can be used to compare the sequence identity or similarity between two or more nucleotide or amino acid sequences. Although other alignment and comparison methods are known in the art, the alignment and percent identity between two sequences (including the percent identity ranges described above) can be as determined by the ClustalW algorithm, see, e.g., Chenna et al., "Multiple sequence alignment with the Clustal series of programs," *Nucleic Acids Research* 31: 3497-3500 (2003); Thompson et al., "Clustal W: Improving the sensitivity of progressive multiple sequence alignment through sequence weighting, position-specific gap penalties and weight matrix choice," *Nucleic Acids Research* 22: 4673-4680 (1994); Larkin M A et al., "*Clustal W and Clustal X version 2.0,*" *Bioinformatics* 23: 2947-48 (2007); and Altschul et al. "Basic local alignment search tool." *J. Mol. Biol.* 215:403-410 (1990), the entire contents and disclosures of which are incorporated herein by reference.

The terms "percent complementarity" or "percent complementarity" as used herein in reference to two nucleotide sequences is similar to the concept of percent identity but refers to the percentage of nucleotides of a query sequence that optimally base-pair or hybridize to nucleotides a subject sequence when the query and subject sequences are linearly arranged and optimally base paired without secondary folding structures, such as loops, stems or hairpins. Such a percent complementarity can be between two DNA strands, two RNA strands, or a DNA strand and a RNA strand. The "percent complementarity" can be calculated by (i) optimally base-pairing or hybridizing the two nucleotide sequences in a linear and fully extended arrangement (i.e., without folding or secondary structures) over a window of comparison, (ii) determining the number of positions that base-pair between the two sequences over the window of comparison to yield the number of complementary positions, (iii) dividing the number of complementary positions by the total number of positions in the window of comparison, and (iv) multiplying this quotient by 100% to yield the percent complementarity of the two sequences. Optimal base pairing of two sequences can be determined based on the known pairings of nucleotide bases, such as G-C, A-T, and A-U, through hydrogen binding. If the "percent complementarity" is being calculated in relation to a reference sequence without specifying a particular comparison window, then the percent identity is determined by dividing the number of complementary positions between the two linear sequences by the total length of the reference sequence. Thus, for purposes of the present application, when two sequences (query and subject) are optimally base-paired (with allowance for mismatches or non-base-paired nucleotides), the "percent complementarity" for the query sequence is equal to the number of base-paired positions between the two sequences divided by the total number of positions in the query sequence over its length, which is then multiplied by 100%.

In one aspect, this disclosure provides a modified tobacco plant comprising a mutation in an endogenous gene encoding a polypeptide selected from the group consisting of a cyclin, a cyclin-dependent kinase (CDK), a CDK inhibitor, a MYB, and a WRKY transcription factor, where the mutation is not present in the endogenous gene in a control tobacco plant of the same variety, and where the modified tobacco plant comprises no suckers or reduced suckers after topping as compared to the control tobacco plant when grown under comparable growth conditions.

In another aspect, this disclosure provides a modified tobacco plant comprising a mutation in an endogenous gene encoding a polypeptide selected from the group consisting of a cyclin, a cyclin-dependent kinase (CDK), a CDK inhibitor, a MYB, and a WRKY transcription factor, where the mutation is not present in the endogenous gene in a control tobacco plant of the same variety.

In a further aspect, this disclosure provides a method for producing a modified tobacco plant comprising: (a) inducing a mutation in at least one tobacco cell at a genomic locus encoding a polypeptide selected from the group consisting of a cyclin, a cyclin-dependent kinase (CDK), a CDK inhibitor, a MYB, and a WRKY transcription factor; (b) selecting at least one tobacco cell comprising the mutation from step (a); and (c) regenerating a modified tobacco plant from the at least one tobacco cell selected in step (b), where the modified tobacco plant comprises no suckers or reduced suckers after topping as compared to a control tobacco plant lacking the mutation when grown under comparable growth conditions. In an aspect, this method further comprises (d) growing the modified tobacco plant regenerated in step (c). In another aspect, this method further comprises (e) crossing the modified tobacco plant grown in step (d) with a second tobacco plant; and (f) obtaining at least one seed from the crossing in step (e).

In an aspect, a modified tobacco plant, tobacco plant part, tobacco seed, tobacco cell, or tobacco genome provided herein comprises one or more mutations in an endogenous gene encoding a cyclin. In an aspect, a modified tobacco plant, tobacco plant part, tobacco seed, tobacco cell, or tobacco genome provided herein comprises one or more mutations in an endogenous gene encoding a cyclin-dependent kinase. In an aspect, a modified tobacco plant, tobacco plant part, tobacco seed, tobacco cell, or tobacco genome provided herein comprises one or more mutations in an endogenous gene encoding a cyclin-dependent kinase inhibitor. In an aspect, a modified tobacco plant, tobacco plant part, tobacco seed, tobacco cell, or tobacco genome provided herein comprises one or more mutations in an endogenous gene encoding a MYB. In an aspect, a modified tobacco plant, tobacco plant part, tobacco seed, tobacco cell, or tobacco genome provided herein comprises one or more mutations in an endogenous gene encoding a WRKY transcription factor.

Cyclins control the progression of cells through the cell cycle. They often play a role in the activation of CDKs. Cyclins are characterized as having a conserved cyclin box domain. Cyclin box domains typically comprise about 150 amino acids, which are organized into five alpha-helical regions. Cyclin box domains are important for binding other proteins, such as CDKs. See, for example, Noble et al., "The cyclin box fold: protein recognition in cell-cycle and transcription control," *Trends Biochem. Sci.* 22:482-487 (1997); and Menges et al., "Genomic Organization and Evolutionary Conservation of Plant D-Type Cyclins," *Plant Physiology*, 145:1558-1576 (2007), which are incorporated herein by reference in their entireties.

$G_1$ (Gap 1 phase) is the first part of interphase during the cell cycle in eukaryotic cells. Cells synthesize mRNA and proteins during $G_1$ phase, which ends with the transition into S phase. S phase (Synthesis phase) is the second part of interphase during the cell cycle, in which DNA is replicated. S phase ends with the transition into $G_2$ phase. $G_2$ (Gap 2 phase) typically involves rapid cellular growth as the cell prepares for transition to M phase (Mitosis phase). Cyclins and CDKs are important regulators at the checkpoints between the transition from $G_1$ to S phase and from $G_2$ to M phase, as well as during $G_1$ phase, S phase, $G_2$ phase, and M phase.

There are two main groups of cyclins: $G_1$/S cyclins, which are required for control of the cell cycle through the $G_1$/S transition, and $G_2$/M cyclins, which are required for control of the cell cycle through the $G_2$/M transition. If the required cyclins or CDKs are unable to function correctly, the cell cycle can arrest at the $G_1$/S transition or the $G_2$/M transition and prevent the formation of daughter cells. In an aspect, a cyclin provided herein is a G/S cyclin. In another aspect, a cyclin provided herein is a $G_2$/M cyclin.

In an aspect, this disclosure provides a polynucleotide that encodes a cyclin. In another aspect, this disclosure provides a cyclin.

In an aspect, this disclosure provides a mutated polynucleotide comprising a mutation in an endogenous gene, where the mutated polynucleotide encodes a mutated cyclin as compared to a cyclin encoded by the endogenous gene lacking the mutation. In an aspect, this disclosure provides a mutated polynucleotide comprising a mutation in an endogenous gene, where the mutated polynucleotide encodes a truncated cyclin as compared to a cyclin encoded by the endogenous gene lacking the mutation. In another aspect, this disclosure provides a non-naturally occurring truncated cyclin. In an aspect, this disclosure provides a polynucleotide encoding a mutated mRNA of an endogenous gene comprising a premature stop codon, where the mutated mRNA encodes a truncated cyclin as compared to an mRNA of the endogenous gene lacking the premature stop codon.

In an aspect, this disclosure provides a polynucleotide comprising a non-naturally occurring mutation in a sequence encoding a cyclin box domain. In an aspect, this disclosure provides a mutated polynucleotide comprising a mutation in an endogenous gene encoding a cyclin, where the mutated polynucleotide encodes a cyclin lacking a cyclin box domain. In another aspect, this disclosure provides a mutated polynucleotide comprising a mutation in an endogenous gene encoding a cyclin, where the mutated polynucleotide encodes a cyclin comprising a truncated cyclin box domain as compared to a cyclin encoded by the endogenous gene lacking the mutation. In an aspect, this disclosure provides a mutated polynucleotide comprising a mutation in an endogenous gene encoding a cyclin, where the mutated polynucleotide encodes a cyclin that is incapable of binding a CDK. In an aspect, this disclosure provides a mutated polynucleotide comprising a mutation in an endogenous gene encoding a cyclin, where the mutated polynucleotide encodes a cyclin that exhibits reduced binding affinity for at least one CDK as compared to a cyclin encoded by the endogenous gene lacking the mutation.

In an aspect, a mutated polynucleotide encodes a dominant negative allele of a cyclin. In another aspect, a mutated polynucleotide encodes a dominant positive allele of a cyclin. In a further aspect, a mutated polynucleotide encodes a constitutively active cyclin. In another aspect, a mutated polynucleotide encodes an inactive cyclin.

In an aspect, an endogenous gene encoding a cyclin comprises a polynucleotide sequence at least 80% identical to a sequence selected from the group consisting of SEQ ID NOs: 6-32. In an aspect, an endogenous gene encoding a cyclin comprises a polynucleotide sequence at least 85% identical to a sequence selected from the group consisting of SEQ ID NOs: 6-32. In an aspect, an endogenous gene encoding a cyclin comprises a polynucleotide sequence at least 90% identical to a sequence selected from the group consisting of SEQ ID NOs: 6-32. In an aspect, an endogenous gene encoding a cyclin comprises a polynucleotide sequence at least 95% identical to a sequence selected from the group consisting of SEQ ID NOs: 6-32. In an aspect, an endogenous gene encoding a cyclin comprises a polynucleotide sequence at least 96% identical to a sequence selected from the group consisting of SEQ ID NOs: 6-32. In an aspect, an endogenous gene encoding a cyclin comprises a polynucleotide sequence at least 97% identical to a sequence selected from the group consisting of SEQ ID NOs: 6-32. In an aspect, an endogenous gene encoding a cyclin comprises a polynucleotide sequence at least 98% identical to a sequence selected from the group consisting of SEQ ID NOs: 6-32. In an aspect, an endogenous gene encoding a cyclin comprises a polynucleotide sequence at least 99% identical to a sequence selected from the group consisting of SEQ ID NOs: 6-32. In an aspect, an endogenous gene encoding a cyclin comprises a polynucleotide sequence 100% identical to a sequence selected from the group consisting of SEQ ID NOs: 6-32.

In an aspect, an endogenous cyclin comprises an amino acid sequence at least 70% identical to a sequence selected from the group consisting of SEQ ID NOs: 50-76. In an aspect, an endogenous cyclin comprises an amino acid sequence at least 75% identical to a sequence selected from the group consisting of SEQ ID NOs: 50-76. In an aspect, an endogenous cyclin comprises an amino acid sequence at least 80% identical to a sequence selected from the group consisting of SEQ ID NOs: 50-76. In an aspect, an endogenous cyclin comprises an amino acid sequence at least 85% identical to a sequence selected from the group consisting of SEQ ID NOs: 50-76. In an aspect, an endogenous cyclin comprises an amino acid sequence at least 90% identical to a sequence selected from the group consisting of SEQ ID NOs: 50-76. In an aspect, an endogenous cyclin comprises an amino acid sequence at least 95% identical to a sequence selected from the group consisting of SEQ ID NOs: 50-76. In an aspect, an endogenous cyclin comprises an amino acid sequence at least 96% identical to a sequence selected from the group consisting of SEQ ID NOs: 50-76. In an aspect, an endogenous cyclin comprises an amino acid sequence at least 97% identical to a sequence selected from the group consisting of SEQ ID NOs: 50-76. In an aspect, an endogenous cyclin comprises an amino acid sequence at least 98% identical to a sequence selected from the group consisting of SEQ ID NOs: 50-76. In an aspect, an endogenous cyclin comprises an amino acid sequence at least 99% identical to a sequence selected from the group consisting of SEQ ID NOs: 50-76. In an aspect, a cyclin comprises an amino acid sequence 100% identical to a sequence selected from the group consisting of SEQ ID NOs: 50-76.

In an aspect, an endogenous cyclin comprises an amino acid sequence at least 70% similar to a sequence selected from the group consisting of SEQ ID NOs: 50-76. In an aspect, an endogenous cyclin comprises an amino acid sequence at least 75% similar to a sequence selected from the group consisting of SEQ ID NOs: 50-76. In an aspect, an endogenous cyclin comprises an amino acid sequence at least 80% similar to a sequence selected from the group consisting of SEQ ID NOs: 50-76. In an aspect, an endogenous cyclin comprises an amino acid sequence at least 85% similar to a sequence selected from the group consisting of SEQ ID NOs: 50-76. In an aspect, an endogenous cyclin comprises an amino acid sequence at least 90% similar to a sequence selected from the group consisting of SEQ ID NOs: 50-76. In an aspect, an endogenous cyclin comprises an amino acid sequence at least 95% similar to a sequence selected from the group consisting of SEQ ID NOs: 50-76. In an aspect, an endogenous cyclin comprises an amino acid sequence at least 96% similar to a sequence selected from the group consisting of SEQ ID NOs: 50-76. In an aspect, an endogenous cyclin comprises an amino acid sequence at least 97% similar to a sequence selected from the group consisting of SEQ ID NOs: 50-76. In an aspect, an endogenous cyclin comprises an amino acid sequence at least 98% similar to a sequence selected from the group consisting of SEQ ID NOs: 50-76. In an aspect, an endogenous cyclin comprises an amino acid sequence at least 99% similar to a sequence selected from the group consisting of SEQ ID NOs: 50-76. In an aspect, a cyclin comprises an amino acid sequence 100% similar to a sequence selected from the group consisting of SEQ ID NOs: 50-76.

Cyclin dependent kinases (CDKs) are a family of protein kinases that are involved in regulating the cell cycle, regulating transcription, and regulating mRNA processing. CDKs are recognized as belonging to the Enzyme Commission class 2.7.11.22. CDKs comprise a kinase domain, and they interact with, or bind to, cyclins. CDKs phosphorylate substrates on serine and threonine, so they can also be referred to as serine-threonine kinases. CDKs, in conjunction with cyclins, are required for cells to progress through the cell cycle. See, for example, Mironov et al., "Cyclin-Dependent Kinases and Cell Division in Plants—The Nexus," Plant Cell, 11:509-521 (1999), which is herein incorporated by reference in its entirety.

In an aspect, this disclosure provides a polynucleotide that encodes a CDK. In another aspect, this disclosure provides a CDK.

In an aspect, this disclosure provides a mutated polynucleotide comprising a mutation in an endogenous gene, where the mutated polynucleotide encodes a mutated CDK as compared to a CDK encoded by the endogenous gene lacking the mutation. In an aspect, this disclosure provides a mutated polynucleotide comprising a mutation in an endogenous gene, where the mutated polynucleotide encodes a truncated CDK as compared to a CDK encoded by the endogenous gene lacking the mutation. In another aspect, this disclosure provides a non-naturally occurring truncated CDK. In an aspect, this disclosure provides a polynucleotide encoding a mutated mRNA of an endogenous gene comprising a premature stop codon, where the mutated mRNA encodes a truncated CDK as compared to an mRNA of the endogenous gene lacking the premature stop codon.

In an aspect, this disclosure provides a polynucleotide comprising a non-naturally occurring mutation in a sequence encoding a kinase domain. In an aspect, this disclosure provides a mutated polynucleotide comprising a mutation in an endogenous gene encoding a CDK, where the mutated polynucleotide encodes a CDK lacking a kinase domain. In another aspect, this disclosure provides a mutated polynucleotide comprising a mutation in an endogenous gene encoding a CDK, where the mutated polynucleotide encodes a CDK comprising a truncated kinase domain as compared to a CDK encoded by the endogenous gene lacking the mutation. In an aspect, this disclosure provides a mutated polynucleotide comprising a mutation in an endogenous gene encoding a CDK, where the mutated polynucleotide encodes a CDK that is incapable of binding a cyclin. In an aspect, this disclosure provides a mutated polynucleotide comprising a mutation in an endogenous gene encoding a CDK that exhibits reduced binding affinity for at least one cyclin as compared to a CDK encoded by the endogenous gene lacking the mutation.

In an aspect, a mutated polynucleotide encodes a dominant negative allele of a CDK. In another aspect, a mutated polynucleotide encodes a dominant positive allele of a CDK. In a further aspect, a mutated polynucleotide encodes a constitutively active CDK. In another aspect, a mutated polynucleotide encodes an inactive CDK.

In an aspect, an endogenous gene encoding a CDK comprises a polynucleotide sequence at least 80% identical to a sequence selected from the group consisting of SEQ ID NOs: 1-4. In an aspect, an endogenous gene encoding a CDK comprises a polynucleotide sequence at least 85% identical to a sequence selected from the group consisting of SEQ ID NOs: 1-4. In an aspect, an endogenous gene encoding a CDK comprises a polynucleotide sequence at least 90% identical to a sequence selected from the group consisting of SEQ ID NOs: 1-4. In an aspect, an endogenous gene encoding a CDK comprises a polynucleotide sequence at least 95% identical to a sequence selected from the group consisting of SEQ ID NOs: 1-4. In an aspect, an endogenous gene encoding a CDK comprises a polynucleotide sequence at least 96% identical to a sequence selected from the group consisting of SEQ ID NOs: 1-4. In an aspect, an endogenous gene encoding a CDK comprises a polynucleotide sequence at least 97% identical to a sequence selected from the group consisting of SEQ ID NOs: 1-4. In an aspect, an endogenous gene encoding a CDK comprises a polynucleotide sequence at least 98% identical to a sequence selected from the group consisting of SEQ ID NOs: 1-4. In an aspect, an endogenous gene encoding a CDK comprises a polynucleotide sequence at least 99% identical to a sequence selected from the group consisting of SEQ ID NOs: 1-4. In an aspect, an endogenous gene encoding a CDK comprises a polynucleotide sequence 100% identical to a sequence selected from the group consisting of SEQ ID NOs: 1-4.

In an aspect, an endogenous CDK comprises an amino acid sequence at least 70% identical to a sequence selected from the group consisting of SEQ ID NOs: 45-48. In an aspect, an endogenous CDK comprises an amino acid sequence at least 75% identical to a sequence selected from the group consisting of SEQ ID NOs: 45-48. In an aspect, an endogenous CDK comprises an amino acid sequence at least 80% identical to a sequence selected from the group consisting of SEQ ID NOs: 45-48. In an aspect, an endogenous CDK comprises an amino acid sequence at least 85% identical to a sequence selected from the group consisting of SEQ ID NOs: 45-48. In an aspect, an endogenous CDK comprises an amino acid sequence at least 90% identical to a sequence selected from the group consisting of SEQ ID NOs: 45-48. In an aspect, an endogenous CDK comprises an amino acid sequence at least 95% identical to a sequence selected from the group consisting of SEQ ID NOs: 45-48. In an aspect, an endogenous CDK comprises an amino acid sequence at least 96% identical to a sequence selected from the group consisting of SEQ ID NOs: 45-48. In an aspect, an endogenous CDK comprises an amino acid sequence at least 97% identical to a sequence selected from the group consisting of SEQ ID NOs: 45-48. In an aspect, an endogenous CDK comprises an amino acid sequence at least 98% identical to a sequence selected from the group consisting of SEQ ID NOs: 45-48. In an aspect, an endogenous CDK comprises an amino acid sequence at least 99% identical to a sequence selected from the group consisting of SEQ ID NOs: 45-48. In an aspect, a CDK comprises an amino acid sequence 100% identical to a sequence selected from the group consisting of SEQ ID NOs: 45-48.

In an aspect, an endogenous CDK comprises an amino acid sequence at least 70% similar to a sequence selected from the group consisting of SEQ ID NOs: 45-48. In an aspect, an endogenous CDK comprises an amino acid sequence at least 75% similar to a sequence selected from the group consisting of SEQ ID NOs: 45-48. In an aspect, an endogenous CDK comprises an amino acid sequence at least 80% similar to a sequence selected from the group consisting of SEQ ID NOs: 45-48. In an aspect, an endogenous CDK comprises an amino acid sequence at least 85% similar to a sequence selected from the group consisting of SEQ ID NOs: 45-48. In an aspect, an endogenous CDK comprises an amino acid sequence at least 90% similar to a sequence selected from the group consisting of SEQ ID NOs: 45-48. In an aspect, an endogenous CDK comprises an amino acid sequence at least 95% similar to a sequence selected from the group consisting of SEQ ID NOs: 45-48. In an aspect, an endogenous CDK comprises an amino acid sequence at least 96% similar to a sequence selected from the group consisting of SEQ ID NOs: 45-48. In an aspect, an endogenous CDK comprises an amino acid sequence at least 97% similar to a sequence selected from the group consisting of SEQ ID NOs: 45-48. In an aspect, an endogenous CDK comprises an amino acid sequence at least 98% similar to a sequence selected from the group consisting of SEQ ID NOs: 45-48. In an aspect, an endogenous CDK comprises an amino acid sequence at least 99% similar to a sequence selected from the group consisting of SEQ ID NOs: 45-48. In an aspect, a CDK comprises an amino acid sequence 100% similar to a sequence selected from the group consisting of SEQ ID NOs: 45-48.

Cyclin-dependent kinase inhibitors (CDKIs) are proteins that inhibit CDKs. CDKIs can bind to CDKs to prevent CDKs from binding to cyclins, thereby negatively regulating the cell cycle in eukaryotes. In plants, CDKIs are categorized into two families: KIP-RELATED PROTEINS (KRPs) and SIAMESE-RELATED PROTEINS (SMRs). See, for example, Kumar and Larkin, "Why do plants need so many cyclin-dependent kinase inhibitors?," Plant Signaling & Behavior, 12:e1282021 (2017), which is herein incorporated by reference in its entirety.

In an aspect, this disclosure provides a polynucleotide that encodes a CDKI. In another aspect, this disclosure provides a CDKI. In an aspect, a CDKI provided herein is a KRP. In another aspect, a CDKI provided herein is an SMR.

In an aspect, this disclosure provides a mutated polynucleotide comprising a mutation in an endogenous gene, where the mutated polynucleotide encodes a mutated CDKI as compared to a CDKI encoded by the endogenous gene lacking the mutation. In an aspect, this disclosure provides a mutated polynucleotide comprising a mutation in an endogenous gene, where the mutated polynucleotide encodes a truncated CDKI as compared to a CDKI encoded by the endogenous gene lacking the mutation. In another aspect, this disclosure provides a non-naturally occurring truncated CDKI. In an aspect, this disclosure provides a polynucleotide encoding a mutated mRNA of an endogenous gene comprising a premature stop codon, where the mutated mRNA encodes a truncated CDKI as compared to an mRNA of the endogenous gene lacking the premature stop codon.

In an aspect, this disclosure provides a mutated polynucleotide comprising a mutation in an endogenous gene encoding a CDKI, where the mutated polynucleotide encodes a CDKI that is incapable of binding a CDK. In an aspect, this disclosure provides a mutated polynucleotide comprising a mutation in an endogenous gene encoding a CDKI, where the mutated polynucleotide encodes a CDKI that exhibits reduced binding affinity for at least one CDK as compared to a CDKI encoded by the endogenous gene lacking the mutation.

In an aspect, a mutated polynucleotide encodes a dominant negative allele of a CDKI. In another aspect, a mutated polynucleotide encodes a dominant positive allele of a CDKI. In a further aspect, a mutated polynucleotide encodes a constitutively active CDKI. In another aspect, a mutated polynucleotide encodes an inactive CDKI.

In an aspect, an endogenous gene encoding a CDKI comprises a polynucleotide sequence at least 80% identical to SEQ ID NO: 5. In an aspect, an endogenous gene encoding a CDKI comprises a polynucleotide sequence at least 85% identical to SEQ ID NO: 5. In an aspect, an endogenous gene encoding a CDKI comprises a polynucleotide sequence at least 90% identical to SEQ ID NO: 5. In an aspect, an endogenous gene encoding a CDKI comprises a polynucleotide sequence at least 95% identical to SEQ ID NO: 5. In an aspect, an endogenous gene encoding a CDKI comprises a polynucleotide sequence at least 96% identical to SEQ ID NO: 5. In an aspect, an endogenous gene encoding a CDKI comprises a polynucleotide sequence at least 97% identical to SEQ ID NO: 5. In an aspect, an endogenous gene encoding a CDKI comprises a polynucleotide sequence at least 98% identical to SEQ ID NO: 5. In an aspect, an endogenous gene encoding a CDKI comprises a polynucleotide sequence at least 99% identical to SEQ ID NO: 5. In an aspect, an endogenous gene encoding a CDKI comprises a polynucleotide sequence 100% identical to SEQ ID NO: 5.

In an aspect, an endogenous CDKI comprises an amino acid sequence at least 70% identical to SEQ ID NO: 49. In an aspect, an endogenous CDKI comprises an amino acid sequence at least 75% identical to SEQ ID NO: 49. In an aspect, an endogenous CDKI comprises an amino acid sequence at least 80% identical to SEQ ID NO: 49. In an aspect, an endogenous CDKI comprises an amino acid sequence at least 85% identical to SEQ ID NO: 49. In an aspect, an endogenous CDKI comprises an amino acid sequence at least 90% identical to SEQ ID NO: 49. In an aspect, an endogenous CDKI comprises an amino acid sequence at least 95% identical to SEQ ID NO: 49. In an aspect, an endogenous CDKI comprises an amino acid sequence at least 96% identical to SEQ ID NO: 49. In an aspect, an endogenous CDKI comprises an amino acid sequence at least 97% identical to SEQ ID NO: 49. In an aspect, an endogenous CDKI comprises an amino acid sequence at least 98% identical to SEQ ID NO: 49. In an aspect, an endogenous CDKI comprises an amino acid sequence at least 99% identical to SEQ ID NO: 49. In an aspect, a CDKI comprises an amino acid sequence 100% identical to SEQ ID NO: 49.

In an aspect, an endogenous CDKI comprises an amino acid sequence at least 70% similar to SEQ ID NO: 49. In an aspect, an endogenous CDKI comprises an amino acid sequence at least 75% similar to SEQ ID NO: 49. In an aspect, an endogenous CDKI comprises an amino acid sequence at least 80% similar to SEQ ID NO: 49. In an aspect, an endogenous CDKI comprises an amino acid sequence at least 85% similar to SEQ ID NO: 49. In an aspect, an endogenous CDKI comprises an amino acid sequence at least 90 similar identical to SEQ ID NO: 49. In an aspect, an endogenous CDKI comprises an amino acid sequence at least 95% similar to SEQ ID NO: 49. In an aspect, an endogenous CDKI comprises an amino acid sequence at least 96% similar to SEQ ID NO: 49. In an aspect, an endogenous CDKI comprises an amino acid sequence at least 97% similar to SEQ ID NO: 49. In an aspect, an endogenous CDKI comprises an amino acid sequence at least 98% similar to SEQ ID NO: 49. In an aspect, an endogenous CDKI comprises an amino acid sequence at least 99% similar to SEQ ID NO: 49. In an aspect, a CDKI comprises an amino acid sequence 100% similar to SEQ ID NO: 49.

MYB proteins (MYBs) are part of a family of transcription factors. In plants, MYBs comprise a conserved MYB DNA-binding domain. The MYB DNA-binding domain contains up to three imperfect repeats of about 55 amino acids each, in a helix-turn-helix structure. These repeats are termed R1, R2, and R3, and the R2/R3 repeats have been shown to bind directly to the major groove of DNA. A subfamily of plant-specific MYBs contains an R2R3-type MYB domain and are termed R2R3-type MYBs. Other subfamilies of MYBs include R1-type, 3R-type, and 4R-type MYBs. See, for example, Ambawat et al., "MYB transcription factor genes as regulators for plant responses: an overview," *Physiol. Mol. Biol. Plants,* 19:307-321 (2013), which is herein incorporated by reference in its entirety.

In an aspect, a MYB provided herein is an R1-type MYB. In another aspect, a MYB provided herein is an R2R3-type MYB. In another aspect, a MYB provided herein is a 3R-type MYB. In another aspect, a MYB provided herein is a 4R-type MYB.

In an aspect, this disclosure provides a polynucleotide that encodes a MYB. In another aspect, this disclosure provides a MYB.

In an aspect, this disclosure provides a mutated polynucleotide comprising a mutation in an endogenous gene, where the mutated polynucleotide encodes a mutated MYB as compared to a MYB encoded by the endogenous gene lacking the mutation. In an aspect, this disclosure provides a mutated polynucleotide comprising a mutation in an endogenous gene, where the mutated polynucleotide encodes a truncated MYB as compared to a MYB encoded by the endogenous gene lacking the mutation. In another aspect, this disclosure provides a non-naturally occurring truncated MYB. In an aspect, this disclosure provides a polynucleotide encoding a mutated mRNA of an endogenous gene comprising a premature stop codon, where the mutated mRNA encodes a truncated MYB as compared to an mRNA of the endogenous gene lacking the premature stop codon.

In an aspect, this disclosure provides a polynucleotide comprising a non-naturally occurring mutation in a sequence encoding a MYB DNA-binding domain. In an aspect, this disclosure provides a mutated polynucleotide comprising a mutation in an endogenous gene encoding a MYB, where the mutated polynucleotide encodes a MYB lacking a MYB DNA-binding domain. In another aspect, this disclosure provides a mutated polynucleotide comprising a mutation in an endogenous gene encoding a MYB, where the mutated polynucleotide encodes a MYB comprising a truncated MYB DNA-binding domain as compared to a MYB encoded by the endogenous gene lacking the mutation.

In an aspect, this disclosure provides a mutated polynucleotide comprising a mutation in an endogenous gene encoding a MYB, where the mutated polynucleotide encodes a MYB that is incapable of binding DNA. In an aspect, this disclosure provides a mutated polynucleotide comprising a mutation in an endogenous gene encoding a MYB, where the mutated polynucleotide encodes a MYB that exhibits reduced binding affinity for DNA as compared to a MYB encoded by the endogenous gene lacking the mutation.

In another aspect, this disclosure provides a mutated polynucleotide comprising a mutation in an endogenous gene encoding a MYB, where the mutated polynucleotide encodes a MYB comprising a truncated R2R3-type MYB domain as compared to a MYB encoded by the endogenous gene lacking the mutation. In another aspect, this disclosure provides a mutated polynucleotide comprising a mutation in an endogenous gene encoding a MYB, where the mutated polynucleotide encodes a MYB comprising a truncated R1-type MYB domain as compared to a MYB encoded by the endogenous gene lacking the mutation. In another aspect, this disclosure provides a mutated polynucleotide comprising a mutation in an endogenous gene encoding a MYB, where the mutated polynucleotide encodes a MYB comprising a truncated 3R-type MYB domain as compared to a MYB encoded by the endogenous gene lacking the mutation. In another aspect, this disclosure provides a mutated polynucleotide comprising a mutation in an endogenous gene encoding a MYB, where the mutated polynucleotide encodes a MYB comprising a truncated 4R-type MYB domain as compared to a MYB encoded by the endogenous gene lacking the mutation.

In an aspect, a mutated polynucleotide encodes a dominant negative allele of a MYB. In another aspect, a mutated polynucleotide encodes a dominant positive allele of a MYB. In a further aspect, a mutated polynucleotide encodes a constitutively active MYB. In another aspect, a mutated polynucleotide encodes an inactive MYB.

In an aspect, an endogenous gene encoding a MYB comprises a polynucleotide sequence at least 80% identical to a sequence selected from the group consisting of SEQ ID NOs: 33-44. In an aspect, an endogenous gene encoding a MYB comprises a polynucleotide sequence at least 85% identical to a sequence selected from the group consisting of SEQ ID NOs: 33-44. In an aspect, an endogenous gene encoding a MYB comprises a polynucleotide sequence at least 90% identical to a sequence selected from the group consisting of SEQ ID NOs: 33-44. In an aspect, an endogenous gene encoding a MYB comprises a polynucleotide sequence at least 95% identical to a sequence selected from the group consisting of SEQ ID NOs: 33-44. In an aspect, an endogenous gene encoding a MYB comprises a polynucleotide sequence at least 96% identical to a sequence selected from the group consisting of SEQ ID NOs: 33-44. In an aspect, an endogenous gene encoding a MYB comprises a polynucleotide sequence at least 97% identical to a sequence selected from the group consisting of SEQ ID NOs: 33-44. In an aspect, an endogenous gene encoding a MYB comprises a polynucleotide sequence at least 98% identical to a sequence selected from the group consisting of SEQ ID NOs: 33-44. In an aspect, an endogenous gene encoding a MYB comprises a polynucleotide sequence at least 99% identical to a sequence selected from the group consisting of SEQ ID NOs: 33-44. In an aspect, an endogenous gene encoding a MYB comprises a polynucleotide sequence 100% identical to a sequence selected from the group consisting of SEQ ID NOs: 33-44.

In an aspect, an endogenous MYB comprises an amino acid sequence at least 70% identical to a sequence selected from the group consisting of SEQ ID NOs: 77-88. In an aspect, an endogenous MYB comprises an amino acid sequence at least 75% identical to a sequence selected from the group consisting of SEQ ID NOs: 77-88. In an aspect, an endogenous MYB comprises an amino acid sequence at least 80% identical to a sequence selected from the group consisting of SEQ ID NOs: 77-88. In an aspect, an endogenous MYB comprises an amino acid sequence at least 85% identical to a sequence selected from the group consisting of SEQ ID NOs: 77-88. In an aspect, an endogenous MYB comprises an amino acid sequence at least 90% identical to a sequence selected from the group consisting of SEQ ID NOs: 77-88. In an aspect, an endogenous MYB comprises an amino acid sequence at least 95% identical to a sequence selected from the group consisting of SEQ ID NOs: 77-88. In an aspect, an endogenous MYB comprises an amino acid sequence at least 96% identical to a sequence selected from the group consisting of SEQ ID NOs: 77-88. In an aspect, an endogenous MYB comprises an amino acid sequence at least 97% identical to a sequence selected from the group consisting of SEQ ID NOs: 77-88. In an aspect, an endogenous MYB comprises an amino acid sequence at least 98% identical to a sequence selected from the group consisting of SEQ ID NOs: 77-88. In an aspect, an endogenous MYB comprises an amino acid sequence at least 99% identical to a sequence selected from the group consisting of SEQ ID NOs: 77-88. In an aspect, a MYB comprises an amino acid sequence 100% identical to a sequence selected from the group consisting of SEQ ID NOs: 77-88.

In an aspect, an endogenous MYB comprises an amino acid sequence at least 70% similar to a sequence selected from the group consisting of SEQ ID NOs: 77-88. In an aspect, an endogenous MYB comprises an amino acid sequence at least 75% similar to a sequence selected from the group consisting of SEQ ID NOs: 77-88. In an aspect, an endogenous MYB comprises an amino acid sequence at least 80% similar to a sequence selected from the group consisting of SEQ ID NOs: 77-88. In an aspect, an endogenous MYB comprises an amino acid sequence at least 85% similar to a sequence selected from the group consisting of SEQ ID NOs: 77-88. In an aspect, an endogenous MYB comprises an amino acid sequence at least 90% similar to a sequence selected from the group consisting of SEQ ID NOs: 77-88. In an aspect, an endogenous MYB comprises an amino acid sequence at least 95% similar to a sequence selected from the group consisting of SEQ ID NOs: 77-88. In an aspect, an endogenous MYB comprises an amino acid sequence at least 96% similar to a sequence selected from the group consisting of SEQ ID NOs: 77-88. In an aspect, an endogenous MYB comprises an amino acid sequence at least 97% similar to a sequence selected from the group consisting of SEQ ID NOs: 77-88. In an aspect, an endogenous MYB comprises an amino acid sequence at least 98% similar to a sequence selected from the group consisting of SEQ ID NOs: 77-88. In an aspect, an endogenous MYB comprises an amino acid sequence at least 99% similar to a sequence selected from the group consisting of SEQ ID NOs: 77-88. In an aspect, a MYB comprises an amino acid sequence 100% similar to a sequence selected from the group consisting of SEQ ID NOs: 77-88.

WRKY transcription factors are one of the largest families of transcriptional regulators known in plants. A WRKY transcription factor is a protein that comprises a "WRKY domain." A WRKY domain comprises about 60 to 70 amino acids, and is involved in DNA binding. The WRKY domain contains a highly conserved "WRKY core domain" having an amino acid motif of WRKYGQK (SEQ ID NO: 110). The conserved core of the WRKY domain can vary, and the amino acid motif WRKYGKK (SEQ ID NO: 111) is a commonly observed "WRKY core variant domain." WRKY domains comprise a globular shape composed of five antiparallel β-strands, and the conserved core is found on the second β-strand. The third β-strand also contains a highly conserved amino acid motif of PRSYY (SEQ ID NO: 112). In many WRKY transcription factors, the PR and SYY amino acids of the "PRSYY motif" (SEQ ID NO: 112) are encoded by different exons; the position of the intervening intron is highly conserved amongst WRKY transcription factors. WRKY domains also contain a "zinc finger region" comprising an amino acid motif of $CX_{4-5}CX_{22-23}HXH$ (SEQ ID NO: 115) or $CX_7CX_{23}HXC$ (SEQ ID NO: 116), where X can be any amino acid, C is a cysteine, and H is a histidine. WRKY domains also contain a "DWK salt bridge" motif, where the conserved tryptophan (W) of the WRKY core (SEQ ID NO: 117) forms a triad with an aspartic acid (D) four amino acids upstream of the W, and a lysine (K) twenty-nine amino acids downstream of the W. It is believed that the DWK salt bridge is important for stabilizing the WRKY domain. See, for example, Rushton et al., "WRKY transcription factors," *Trends in Plant Science*, 15:247-258 (2010), which is incorporated herein by reference in its entirety.

In an aspect, this disclosure provides a polynucleotide that encodes a WRKY transcription factor. In another aspect, this disclosure provides a WRKY transcription factor.

In an aspect, this disclosure provides a polynucleotide comprising a non-naturally occurring mutation, where the polynucleotide encodes a WRKY transcription factor. In an aspect, this disclosure provides a polynucleotide encoding a truncated WRKY transcription factor. In another aspect, this disclosure provides a non-naturally occurring truncated WRKY transcription factor. In an aspect, this disclosure provides a polynucleotide encoding an mRNA comprising a premature stop codon, where the mRNA encodes a truncated WRKY transcription factor.

In an aspect, this disclosure provides a mutated polynucleotide comprising a mutation in an endogenous gene, where the mutated polynucleotide encodes a mutated WRKY transcription factor as compared to a WRKY transcription factor encoded by the endogenous gene lacking the mutation. In an aspect, this disclosure provides a mutated polynucleotide comprising a mutation in an endogenous gene, where the mutated polynucleotide encodes a truncated WRKY transcription factor as compared to a WRKY transcription factor encoded by the endogenous gene lacking the mutation. In another aspect, this disclosure provides a non-naturally occurring truncated WRKY transcription factor. In an aspect, this disclosure provides a polynucleotide encoding a mutated mRNA of an endogenous gene comprising a premature stop codon, where the mutated mRNA encodes a truncated WRKY transcription factor as compared to an mRNA of the endogenous gene lacking the premature stop codon.

In an aspect, this disclosure provides a polynucleotide comprising a non-naturally occurring mutation in a sequence encoding a WRKY domain. In an aspect, this disclosure provides a mutated polynucleotide comprising a mutation in an endogenous gene encoding a WRKY transcription factor, where the mutated polynucleotide encodes a WRKY transcription factor lacking a WRKY domain. In another aspect, this disclosure provides a mutated polynucleotide comprising a mutation in an endogenous gene encoding a WRKY transcription factor, where the mutated polynucleotide encodes a WRKY transcription factor comprising a truncated WRKY domain as compared to a WRKY transcription factor encoded by the endogenous gene lacking the mutation.

In an aspect, this disclosure provides a polynucleotide comprising a non-naturally occurring mutation in a sequence encoding a WRKY core domain. In an aspect, this disclosure provides a mutated polynucleotide comprising a mutation in an endogenous gene encoding a WRKY transcription factor, where the mutated polynucleotide encodes a WRKY transcription factor lacking a WRKY core domain. In another aspect, this disclosure provides a mutated polynucleotide comprising a mutation in an endogenous gene encoding a WRKY transcription factor, where the mutated polynucleotide encodes a WRKY transcription factor comprising a truncated WRKY core domain as compared to a WRKY transcription factor encoded by the endogenous gene lacking the mutation.

In an aspect, this disclosure provides a polynucleotide comprising a non-naturally occurring mutation in a sequence encoding a WRKY core variant domain. In an aspect, this disclosure provides a mutated polynucleotide comprising a mutation in an endogenous gene encoding a WRKY transcription factor, where the mutated polynucleotide encodes a WRKY transcription factor lacking a WRKY core variant domain. In another aspect, this disclosure provides a mutated polynucleotide comprising a mutation in an endogenous gene encoding a WRKY transcription factor, where the mutated polynucleotide encodes a WRKY transcription factor comprising a truncated WRKY core variant domain as compared to a WRKY transcription factor encoded by the endogenous gene lacking the mutation.

In an aspect, this disclosure provides a polynucleotide comprising a non-naturally occurring mutation in a sequence encoding a PRSYY motif (SEQ ID NO: 112). In an aspect, this disclosure provides a mutated polynucleotide comprising a mutation in an endogenous gene encoding a WRKY transcription factor, where the mutated polynucleotide encodes a WRKY transcription factor lacking a PRSYY motif (SEQ ID NO: 112). In another aspect, this disclosure provides a mutated polynucleotide comprising a mutation in an endogenous gene encoding a WRKY transcription factor, where the mutated polynucleotide encodes a WRKY transcription factor comprising a truncated PRSYY motif (SEQ ID NO: 112) as compared to a WRKY transcription factor encoded by the endogenous gene lacking the mutation.

In an aspect, this disclosure provides a polynucleotide comprising a non-naturally occurring mutation in a sequence encoding a zinc finger region. In an aspect, this disclosure provides a mutated polynucleotide comprising a mutation in an endogenous gene encoding a WRKY transcription factor, where the mutated polynucleotide encodes a WRKY transcription factor lacking a zinc finger region. In another aspect, this disclosure provides a mutated polynucleotide comprising a mutation in an endogenous gene encoding a WRKY transcription factor, where the mutated polynucleotide encodes a WRKY transcription factor comprising a truncated zinc finger region as compared to a WRKY transcription factor encoded by the endogenous gene lacking the mutation.

In an aspect, this disclosure provides a polynucleotide comprising a non-naturally occurring mutation in a sequence encoding a DWK salt bridge motif. In an aspect, this disclosure provides a mutated polynucleotide comprising a mutation in an endogenous gene encoding a WRKY transcription factor, where the mutated polynucleotide encodes a WRKY transcription factor lacking a DWK salt bridge motif. In another aspect, this disclosure provides a mutated polynucleotide comprising a mutation in an endogenous gene encoding a WRKY transcription factor, where the mutated polynucleotide encodes a WRKY transcription factor comprising a truncated DWK salt bridge motif as compared to a WRKY transcription factor encoded by the endogenous gene lacking the mutation.

In an aspect, this disclosure provides a mutated polynucleotide comprising a mutation in an endogenous gene encoding a WRKY transcription factor, where the mutated polynucleotide encodes a WRKY transcription factor that is incapable of binding DNA. In an aspect, this disclosure provides a mutated polynucleotide comprising a mutation in an endogenous gene encoding a WRKY transcription factor, where the mutated polynucleotide encodes a WRKY transcription factor that exhibits reduced binding affinity for DNA as compared to a WRKY transcription factor encoded by the endogenous gene lacking the mutation.

In an aspect, a mutated polynucleotide encodes a dominant negative allele of a WRKY transcription factor. In another aspect, a mutated polynucleotide encodes a dominant positive allele of a WRKY transcription factor. In a further aspect, a mutated polynucleotide encodes a constitutively active WRKY transcription factor. In another aspect, a mutated polynucleotide encodes an inactive WRKY transcription factor.

In an aspect, an endogenous gene encoding a WRKY transcription factor comprises a polynucleotide sequence at least 80% identical to SEQ ID NO: 113. In an aspect, an endogenous gene encoding a WRKY transcription factor comprises a polynucleotide sequence at least 85% identical to SEQ ID NO: 113. In an aspect, an endogenous gene encoding a WRKY transcription factor comprises a polynucleotide sequence at least 90% identical to SEQ ID NO: 113. In an aspect, an endogenous gene encoding a WRKY transcription factor comprises a polynucleotide sequence at least 95% identical to SEQ ID NO: 113. In an aspect, an endogenous gene encoding a WRKY transcription factor comprises a polynucleotide sequence at least 96% identical to SEQ ID NO: 113. In an aspect, an endogenous gene encoding a WRKY transcription factor comprises a polynucleotide sequence at least 97% identical to SEQ ID NO: 113. In an aspect, an endogenous gene encoding a WRKY transcription factor comprises a polynucleotide sequence at least 98% identical to SEQ ID NO: 113. In an aspect, an endogenous gene encoding a WRKY transcription factor comprises a polynucleotide sequence at least 99% identical to SEQ ID NO: 113. In an aspect, an endogenous gene encoding a WRKY transcription factor comprises a polynucleotide sequence 100% identical to SEQ ID NO: 113.

In an aspect, an endogenous WRKY transcription factor comprises an amino acid sequence at least 70% identical to SEQ ID NO: 114. In an aspect, an endogenous WRKY transcription factor comprises an amino acid sequence at least 75% identical to SEQ ID NO: 114. In an aspect, an endogenous WRKY transcription factor comprises an amino acid sequence at least 80% identical to SEQ ID NO: 114. In an aspect, an endogenous WRKY transcription factor comprises an amino acid sequence at least 85% identical to SEQ ID NO: 114. In an aspect, an endogenous WRKY transcription factor comprises an amino acid sequence at least 90% identical to SEQ ID NO: 114. In an aspect, an endogenous WRKY transcription factor comprises an amino acid sequence at least 95% identical to SEQ ID NO: 114. In an aspect, an endogenous WRKY transcription factor comprises an amino acid sequence at least 96% identical to SEQ ID NO: 114. In an aspect, an endogenous WRKY transcription factor comprises an amino acid sequence at least 97% identical to SEQ ID NO: 114. In an aspect, an endogenous WRKY transcription factor comprises an amino acid sequence at least 98% identical to SEQ ID NO: 114. In an aspect, an endogenous WRKY transcription factor comprises an amino acid sequence at least 99% identical to SEQ ID NO: 114. In an aspect, a WRKY transcription factor comprises an amino acid sequence 100% identical to SEQ ID NO: 114.

In an aspect, an endogenous WRKY transcription factor comprises an amino acid sequence at least 70% similar to SEQ ID NO: 114. In an aspect, an endogenous WRKY transcription factor comprises an amino acid sequence at least 75% similar to SEQ ID NO: 114. In an aspect, an endogenous WRKY transcription factor comprises an amino acid sequence at least 80% similar to SEQ ID NO: 114. In an aspect, an endogenous WRKY transcription factor comprises an amino acid sequence at least 85% similar to SEQ ID NO: 114. In an aspect, an endogenous WRKY transcription factor comprises an amino acid sequence at least 90% similar to SEQ ID NO: 114. In an aspect, an endogenous WRKY transcription factor comprises an amino acid sequence at least 95% similar to SEQ ID NO: 114. In an aspect, an endogenous WRKY transcription factor comprises an amino acid sequence at least 96% similar to SEQ ID NO: 114. In an aspect, an endogenous WRKY transcription factor comprises an amino acid sequence at least 97% similar to SEQ ID NO: 114. In an aspect, an endogenous WRKY transcription factor comprises an amino acid sequence at least 98% similar to SEQ ID NO: 114. In an aspect, an endogenous WRKY transcription factor comprises an amino acid sequence at least 99% similar to SEQ ID NO: 114. In an aspect, a WRKY transcription factor comprises an amino acid sequence 100% similar to SEQ ID NO: 114.

In an aspect, a modified tobacco plant, tobacco plant part, tobacco seed, tobacco cell, or tobacco genome provided herein comprises one or more mutations. As used herein, a "mutation" refers to a non-naturally occurring alteration to DNA as compared to an endogenous reference DNA sequence. It will be appreciated that, when identifying a mutation, the endogenous reference DNA sequence should be from the same variety of tobacco. For example, if a modified tobacco plant comprising a mutation is from the variety TN90, then the endogenous reference sequence must be the endogenous TN90 sequence, not a homologous sequence from a different tobacco variety (e.g., K326). Similarly, if a modified tobacco cell comprising a mutation is a TN90 cell, then the endogenous reference sequence must be the endogenous TN90 sequence, not a homologous sequence from a tobacco cell from a different tobacco variety (e.g., K326).

In an aspect, a mutation provided herein creates a dominant allele of the mutated locus. Dominant alleles are alleles that mask the contribution of a second allele at the same locus. A dominant allele can be a "dominant negative allele" or a "dominant positive allele." Dominant negative alleles, or antimorphs, are alleles that act in opposition to normal allelic function. A dominant negative allele typically does not function normally and either directly inhibits the activity of a wild-type protein (e.g., through dimerization) or inhibits the activity of a second protein that is required for the normal function of the wild-type protein (e.g., an activator or a downstream component of a pathway). For example, a dominant negative allele abrogates or reduces the normal function of an allele in a heterozygous or homozygous state. Dominant positive alleles can increase normal gene function (e.g., a hypermorph) or provide new functions for a gene (e.g., a neomorph). A semi-dominant allele occurs when penetrance of a linked phenotype in individuals heterozygous for the allele is less than that which is observed in individuals homozygous for the allele.

In an aspect, a mutation provided herein creates a dominant negative allele of the mutated locus. In another aspect, a mutation provided herein creates a dominant positive allele of a mutated locus.

As used herein, "inducing" a mutation refers to generating a mutation in a polynucleotide sequence via human intervention. Many suitable methods for inducing mutations in tobacco are known in the art. Non-limiting examples of such methods include use of chemical mutagens, use of radiation, and use of nucleases. In an aspect, inducing a mutation comprises the use of an agent selected from the group consisting of a chemical mutagen, irradiation, a transposon, *Agrobacterium*, and a nuclease.

In an aspect, inducing a mutation comprises the use of a chemical mutagen. In an aspect, a chemical mutagen comprises ethyl methanesulfonate (EMS).

In another aspect, inducing a mutation comprises the use of irradiation. In an aspect, irradiation comprises gamma rays, X-rays, or ionizing radiation. In another aspect, irradiation comprises the use of fast neutrons.

In an aspect, inducing a mutation comprises the use of a transposon. In another aspect, inducing a mutation comprises the use of *Agrobacterium*.

In a further aspect, inducing a mutation comprises the use of a nuclease. In an aspect, a nuclease is selected from the group consisting of a meganuclease, a zinc-finger nuclease, a transcription activator-like effector nuclease, a CRISPR/Cas9 nuclease, a CRISPR/Cpf1 nuclease, a CRISPR/CasX nuclease, a CRISPR/CasY nuclease, and a Csm1 nuclease. In an aspect, inducing a mutation comprises the use of a CRISPR/Cas9 nuclease. In an aspect, inducing a mutation comprises the use of a CRISPR/Cpf1 nuclease. In an aspect, inducing a mutation comprises the use of a CRISPR/CasX nuclease. In an aspect, inducing a mutation comprises the use of a CRISPR/CasY nuclease. In an aspect, inducing a mutation comprises the use of a Csm1 nuclease.

Several types of mutations are known in the art. In an aspect, a mutation comprises an insertion. An "insertion" refers to the addition of one or more nucleotides or amino acids to a given polynucleotide or amino acid sequence, respectively, as compared to an endogenous reference polynucleotide or amino acid sequence. In another aspect, a mutation comprises a deletion. A "deletion" refers to the removal of one or more nucleotides or amino acids to a given polynucleotide or amino acid sequence, respectively, as compared to an endogenous reference polynucleotide or amino acid sequence. In another aspect, a mutation comprises a substitution. A "substitution" refers to the replacement of one or more nucleotides or amino acids to a given polynucleotide or amino acid sequence, respectively, as compared to an endogenous reference polynucleotide or amino acid sequence. In another aspect, a mutation comprises an inversion. An "inversion" refers to when a segment of a polynucleotide or amino acid sequence is reversed end-to-end. In an aspect, a mutation provided herein comprises a mutation selected from the group consisting of an insertion, a deletion, a substitution, and an inversion.

Mutations in coding regions of genes (e.g., exonic mutations) can result in a truncated protein or polypeptide when a mutated messenger RNA (mRNA) is translated into a protein or polypeptide. In an aspect, this disclosure provides a mutation that results in the truncation of a protein or polypeptide. As used herein, a "truncated" protein or polypeptide comprises at least one fewer amino acid as compared to an endogenous control protein or polypeptide. For example, if endogenous Protein A comprises 100 amino acids, a truncated version of Protein A can comprise between 1 and 99 amino acids.

Without being limited by any scientific theory, one way to cause a protein or polypeptide truncation is by the introduction of a premature stop codon in an mRNA transcript of an endogenous gene. In an aspect, this disclosure provides a mutation that results in a premature stop codon in an mRNA transcript of an endogenous gene. As used herein, a "stop codon" refers to a nucleotide triplet within an mRNA transcript that signals a termination of protein translation. A "premature stop codon" refers to a stop codon positioned earlier (e.g., on the 5'-side) than the normal stop codon position in an endogenous mRNA transcript. Without being limiting, several stop codons are known in the art, including "UAG," "UAA," "UGA," "TAG," "TAA," and "TGA."

In an aspect, a mutation provided herein comprises a null mutation. As used herein, a "null mutation" refers to a mutation that confers a complete loss-of-function for a protein encoded by a gene comprising the mutation, or, alternatively, a mutation that confers a complete loss-of-function for a small RNA encoded by a genomic locus. A null mutation can cause lack of mRNA transcript production, a lack of small RNA transcript production, a lack of protein function, or a combination thereof.

A mutation provided herein can be positioned in any part of an endogenous gene. In an aspect, a mutation provided herein is positioned within an exon of an endogenous gene. In another aspect, a mutation provided herein is positioned within an intron of an endogenous gene. In a further aspect, a mutation provided herein is positioned within a 5'-untranslated region of an endogenous gene. In still another aspect, a mutation provided herein is positioned within a 3'-untranslated region of an endogenous gene. In yet another aspect, a mutation provided herein is positioned within a promoter of an endogenous gene.

The screening and selection of mutagenized tobacco plants can be through any methodologies known to those having ordinary skill in the art. Examples of screening and selection methodologies include, but are not limited to, Southern analysis, PCR amplification for detection of a polynucleotide, Northern blots, RNase protection, primer-extension, RT-PCR amplification for detecting RNA transcripts, Sanger sequencing, Next Generation sequencing technologies (e.g., Illumina, PacBio, Ion Torrent, 454) enzymatic assays for detecting enzyme or ribozyme activity of polypeptides and polynucleotides, and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known.

In an aspect, a mutation in an endogenous gene results in a reduced level of expression as compared to the endogenous gene lacking the mutation. In another aspect, a mutation in an endogenous gene results in an increased level of expression as compared to the endogenous gene lacking the mutation. In a further aspect, a mutation in an endogenous gene results in a reduced level of activity by a protein or polypeptide encoded by the endogenous gene having the mutation as compared to a protein or polypeptide encoded by the endogenous gene lacking the mutation. In a further aspect, a mutation in an endogenous gene results in an increased level of activity by a protein or polypeptide encoded by the endogenous gene having the mutation as compared to a protein or polypeptide encoded by the endogenous gene lacking the mutation.

In an aspect, a mutation in a genomic locus results in a reduced level of expression as compared to the genomic locus lacking the mutation. In another aspect, a mutation in a genomic locus results in an increased level of expression as compared to the genomic locus lacking the mutation. In a further aspect, a mutation in a genomic locus results in a reduced level of activity by a protein or polypeptide encoded by the genomic locus having the mutation as compared to a protein or polypeptide encoded by the genomic locus lacking the mutation. In a further aspect, a mutation in a genomic locus results in an increased level of activity by a protein or polypeptide encoded by the genomic locus having the mutation as compared to a protein or polypeptide encoded by the genomic locus lacking the mutation.

Levels of gene expression are routinely investigated in the art. As non-limiting examples, gene expression can be measured using quantitative reverse transcriptase PCR (qRT-PCR), RNA sequencing, or Northern blots. In an aspect, gene expression is measured using qRT-PCR. In another aspect, gene expression is measured using a Northern blot. In another aspect, gene expression is measured using RNA sequencing.

Levels of protein activity are also routinely investigated in the art. For example, CDK activity can be measured using phosphorylation assays.

As used herein, the term "heterologous" refers to a combination of two or more DNA molecules or sequences, such as a promoter and an associated transcribable DNA sequence, coding sequence or gene, when such a combination is man-made and not normally found in nature.

In one aspect, the level of expression of an endogenous gene comprising a mutation is reduced by at least 1% as compared to the level of expression of the endogenous gene lacking the mutation. In one aspect, the level of expression of an endogenous gene comprising a mutation is reduced by at least 5% as compared to the level of expression of the endogenous gene lacking the mutation. In one aspect, the level of expression of an endogenous gene comprising a mutation is reduced by at least 10% as compared to the level of expression of the endogenous gene lacking the mutation. In one aspect, the level of expression of an endogenous gene comprising a mutation is reduced by at least 15% as compared to the level of expression of the endogenous gene lacking the mutation. In one aspect, the level of expression of an endogenous gene comprising a mutation is reduced by at least 20% as compared to the level of expression of the endogenous gene lacking the mutation. In one aspect, the level of expression of an endogenous gene comprising a mutation is reduced by at least 25% as compared to the level of expression of the endogenous gene lacking the mutation. In one aspect, the level of expression of an endogenous gene comprising a mutation is reduced by at least 50% as compared to the level of expression of the endogenous gene lacking the mutation. In one aspect, the level of expression of an endogenous gene comprising a mutation is reduced by at least 75% as compared to the level of expression of the endogenous gene lacking the mutation. In one aspect, the level of expression of an endogenous gene comprising a mutation is reduced by at least 90% as compared to the level of expression of the endogenous gene lacking the mutation. In one aspect, the level of expression of an endogenous gene comprising a mutation is reduced by at least 95% as compared to the level of expression of the endogenous gene lacking the mutation.

In one aspect, the level of expression of an endogenous gene comprising a mutation is reduced by between 1% and 99% as compared to the level of expression of the endogenous gene lacking the mutation. In one aspect, the level of expression of an endogenous gene comprising a mutation is reduced by between 1% and 90% as compared to the level of expression of the endogenous gene lacking the mutation. In one aspect, the level of expression of an endogenous gene comprising a mutation is reduced by between 1% and 75% as compared to the level of expression of the endogenous gene lacking the mutation. In one aspect, the level of expression of an endogenous gene comprising a mutation is reduced by between 1% and 50% as compared to the level of expression of the endogenous gene lacking the mutation. In one aspect, the level of expression of an endogenous gene comprising a mutation is reduced by between 1% and 25% as compared to the level of expression of the endogenous gene lacking the mutation. In one aspect, the level of expression of an endogenous gene comprising a mutation is reduced by between 1% and 10% as compared to the level of expression of the endogenous gene lacking the mutation. In one aspect, the level of expression of an endogenous gene comprising a mutation is reduced by between 75% and 99% as compared to the level of expression of the endogenous gene lacking the mutation. In one aspect, the level of expression of an endogenous gene comprising a mutation is reduced by between 50% and 99% as compared to the level of expression of the endogenous gene lacking the mutation. In one aspect, the level of expression of an endogenous gene comprising a mutation is reduced by between 25% and 99% as compared to the level of expression of the endogenous gene lacking the mutation. In one aspect, the level of expression of an endogenous gene comprising a mutation is reduced by between 10% and 99% as compared to the level of expression of the endogenous gene lacking the mutation. In one aspect, the level of expression of an endogenous gene comprising a mutation is reduced by between 50% and 75% as compared to the level of expression of the endogenous gene lacking the mutation. In one aspect, the level of expression of an endogenous gene comprising a mutation is reduced by between 25% and 75% as compared to the level of expression of the endogenous gene lacking the mutation. In one aspect, the level of expression of an endogenous gene comprising a mutation is reduced by between 10% and 50% as compared to the level of expression of the endogenous gene lacking the mutation.

In one aspect, the level of expression of an endogenous gene comprising a mutation is increased by at least 1% as compared to the level of expression of the endogenous gene lacking the mutation. In one aspect, the level of expression of an endogenous gene comprising a mutation is increased by at least 5% as compared to the level of expression of the endogenous gene lacking the mutation. In one aspect, the level of expression of an endogenous gene comprising a mutation is increased by at least 10% as compared to the level of expression of the endogenous gene lacking the mutation. In one aspect, the level of expression of an endogenous gene comprising a mutation is increased by at least 15% as compared to the level of expression of the endogenous gene lacking the mutation. In one aspect, the level of expression of an endogenous gene comprising a mutation is increased by at least 20% as compared to the level of expression of the endogenous gene lacking the mutation. In one aspect, the level of expression of an endogenous gene comprising a mutation is increased by at least 25% as compared to the level of expression of the endogenous gene lacking the mutation. In one aspect, the level of expression of an endogenous gene comprising a mutation is increased by at least 50% as compared to the level of expression of the endogenous gene lacking the mutation. In one aspect, the level of expression of an endogenous gene comprising a mutation is increased by at least 75% as compared to the level of expression of the endogenous gene lacking the mutation. In one aspect, the level of expression of an endogenous gene comprising a mutation is increased by at least 90% as compared to the level of expression of the endogenous gene lacking the mutation. In one aspect, the level of expression of an endogenous gene comprising a mutation is increased by at least 95% as compared to the level of expression of the endogenous gene lacking the mutation. In one aspect, the level of expression of an endogenous gene comprising a mutation is increased by at least 100% as compared to the level of expression of the endogenous gene lacking the mutation. In one aspect, the level of expression of an endogenous gene comprising a mutation is increased by at least 150% as compared to the level of expression of the endogenous gene lacking the mutation. In one aspect, the level of expression of an endogenous gene comprising a mutation is increased by at least 200% as compared to the level of expression of the endogenous gene lacking the mutation. In one aspect, the level of expression of an endogenous gene comprising a mutation is increased by at least 250% as compared to the level of expression of the endogenous gene lacking the mutation. In one aspect, the level of expression of an endogenous gene comprising a mutation is increased by at least 300% as compared to the level of expression of the endogenous gene lacking the mutation. In one aspect, the level of expression of an endogenous gene comprising a mutation is increased by at least 400% as compared to the level of expression of the endogenous gene lacking the mutation. In one aspect, the level of expression of an endogenous gene comprising a mutation is increased by at least 500% as compared to the level of expression of the endogenous gene lacking the mutation. In one aspect, the level of expression of an endogenous gene comprising a mutation is increased by at least 750% as compared to the level of expression of the endogenous gene lacking the mutation. In one aspect, the level of expression of an endogenous gene comprising a mutation is increased by at least 1000% as compared to the level of expression of the endogenous gene lacking the mutation.

In one aspect, the level of expression of an endogenous gene comprising a mutation is increased by between 1% and 1000% as compared to the level of expression of the endogenous gene lacking the mutation. In one aspect, the level of expression of an endogenous gene comprising a mutation is increased by between 1% and 750% as compared to the level of expression of the endogenous gene lacking the mutation. In one aspect, the level of expression of an endogenous gene comprising a mutation is increased by between 1% and 500% as compared to the level of expression of the endogenous gene lacking the mutation. In one aspect, the level of expression of an endogenous gene comprising a mutation is increased by between 1% and 400% as compared to the level of expression of the endogenous gene lacking the mutation. In one aspect, the level of expression of an endogenous gene comprising a mutation is increased by between 1% and 300% as compared to the level of expression of the endogenous gene lacking the mutation. In one aspect, the level of expression of an endogenous gene comprising a mutation is increased by between 1% and 200% as compared to the level of expression of the endogenous gene lacking the mutation. In one aspect, the level of expression of an endogenous gene comprising a mutation is increased by between 1% and 100% as compared to the level of expression of the endogenous gene lacking the mutation. In one aspect, the level of expression of an endogenous gene comprising a mutation is increased by between 1% and 75% as compared to the level of expression of the endogenous gene lacking the mutation. In one aspect, the level of expression of an endogenous gene comprising a mutation is increased by between 1% and 50% as compared to the level of expression of the endogenous gene lacking the mutation. In one aspect, the level of expression of an endogenous gene comprising a mutation is increased by between 1% and 25% as compared to the level of expression of the endogenous gene lacking the mutation. In one aspect, the level of expression of an endogenous gene comprising a mutation is increased by between 1% and 10% as compared to the level of expression of the endogenous gene lacking the mutation. In one aspect, the level of expression of an endogenous gene comprising a mutation is increased by between 100% and 1000% as compared to the level of expression of the endogenous gene lacking the mutation. In one aspect, the level of expression of an endogenous gene comprising a mutation is increased by between 100% and 750% as compared to the level of expression of the endogenous gene lacking the mutation. In one aspect, the level of expression of an endogenous gene comprising a mutation is increased by between 100% and 500% as compared to the level of expression of the endogenous gene lacking the mutation. In one aspect, the level of expression of an endogenous gene comprising a mutation is increased by between 100% and 250% as compared to the level of expression of the endogenous gene lacking the mutation. In one aspect, the level of expression of an endogenous gene comprising a mutation is increased by between 750% and 1000% as compared to the level of expression of the endogenous gene lacking the mutation. In one aspect, the level of expression of an endogenous gene comprising a mutation is increased by between 500% and 1000% as compared to the level of expression of the endogenous gene lacking the mutation. In one aspect, the level of expression of an endogenous gene comprising a mutation is increased by between 250% and 1000% as compared to the level of expression of the endogenous gene lacking the mutation. In one aspect, the level of expression of an endogenous gene comprising a mutation is increased by between 1% and 100% as compared to the level of expression of the endogenous gene lacking the mutation. In one aspect, the level of expression of an endogenous gene comprising a mutation is increased by between 50% and 100% as compared to the level of expression of the endogenous gene lacking the mutation.

As used herein, the term "endogenous gene" or "native gene" refers to a gene that originates within a tobacco genome. An "endogenous gene" is a gene that was not previously modified by human action. In an aspect, an endogenous gene is a nuclear gene. In another aspect, an endogenous gene is a mitochondrial gene. In a further aspect, an endogenous gene is a chloroplast gene.

As used herein, a "gene" refers to a polynucleotide that can produce a functional unit (e.g., without being limiting, for example, a protein, or a small RNA molecule). A gene can comprise a promoter, an enhancer sequence, a leader sequence, a transcriptional start site, a transcriptional stop site, a polyadenylation site, one or more exons, one or more introns, a 5'-untranslated region (UTR), a 3'-UTR, or any combination thereof. A "gene sequence" can comprise a polynucleotide sequence encoding a promoter, an enhancer sequence, a leader sequence, a transcriptional start site, a transcriptional stop site, a polyadenylation site, one or more exons, one or more introns, a 5'-UTR, a 3'-UTR, or any combination thereof. In one aspect, a gene encodes a small RNA molecule or a precursor thereof. In another aspect, a gene encodes a protein or polypeptide.

As used herein, a "genomic locus" refers to a fixed position on a chromosome. In an aspect, a genomic locus comprises a polynucleotide encoding a gene. In an aspect, a genomic locus comprises a polynucleotide encoding an endogenous gene. In another aspect, a genomic locus comprises a polynucleotide encoding a transgene. In an aspect, a genomic locus can be transcribed from DNA to RNA. In an aspect, a genomic locus encodes a messenger RNA. In another aspect, a genomic locus encodes a small RNA molecule.

As commonly understood in the art, the term "promoter" refers to a DNA sequence that contains an RNA polymerase binding site, transcription start site, and/or TATA box and assists or promotes the transcription and expression of an associated transcribable polynucleotide sequence and/or gene (or transgene). A promoter can be synthetically produced, varied, or derived from a known or naturally occurring promoter sequence or other promoter sequence. A promoter can also include a chimeric promoter comprising a combination of two or more heterologous sequences. A promoter of the present application can thus include variants of promoter sequences that are similar in composition, but not identical to, other promoter sequence(s) known or provided herein.

Promoters that drive expression in all or most tissues of the plant are referred to as "constitutive" promoters. Promoters that drive expression during certain periods or stages of development are referred to as "developmental" promoters. Promoters that drive enhanced expression in certain tissues of an organism relative to other tissues of the organism are referred to as "tissue-preferred" promoters. Thus, a "tissue-preferred" promoter causes relatively higher or preferential expression in a specific tissue(s) of a plant, but with lower levels of expression in other tissue(s) of the plant. As a non-limiting example, an "axillary bud-preferred promoter" causes relatively higher or preferential expression in axillary bud tissues, but can have lower levels of expression in other parts of a plant (e.g., roots, leaves, stem). Promoters that express within a specific tissue(s) of an organism, with little or no expression in other tissues, are referred to as "tissue-specific" promoters. As a non-limited example, an "axillary bud-specific promoter" drives expression in axillary bud tissues, with little to no detectable expression in other plant tissue types. An "inducible" promoter is a promoter that initiates transcription in response to an environmental stimulus such as heat, cold, drought, light, or other stimuli, such as wounding or chemical application.

In an aspect, a promoter provided herein is an axillary bud-specific promoter. In another aspect, a promoter provided herein is an axillary bud-preferred promoter. In an aspect, a promoter provided herein is a constitutive promoter. In another aspect, a promoter provided herein is an inducible promoter. In a further aspect, a promoter provided herein is a developmental promoter.

In an aspect, this disclosure provides a heterologous promoter. In another aspect, this disclosure provides a promoter that is operably linked to a heterologous polynucleotide. In another aspect, this disclosure provides a polynucleotide sequence that is operably linked to a heterologous promoter.

In an aspect, a heterologous promoter comprises an axillary bud-specific promoter. In another aspect, a heterologous promoter comprises an axillary bud-preferred promoter. In an aspect, a heterologous promoter comprises a constitutive promoter. In an aspect, a heterologous promoter comprises an inducible promoter. In an aspect, a heterologous promoter comprises a developmental promoter.

As used herein, "operably linked" refers to a functional linkage between two or more elements. For example, an operable linkage between a polynucleotide of interest and a regulatory sequence (e.g., a promoter) is a functional link that allows for expression of the polynucleotide of interest. Operably linked elements may be contiguous or non-contiguous. In an aspect, a promoter provided herein is operably linked to a heterologous nucleic acid molecule.

In an aspect, a heterologous promoter comprises a polynucleotide sequence at least 90% identical to a polynucleotide selected from the group consisting of SEQ ID NOs: 89-109. In an aspect, a heterologous promoter comprises a polynucleotide sequence at least 91% identical to a polynucleotide selected from the group consisting of SEQ ID NOs: 89-109. In an aspect, a heterologous promoter comprises a polynucleotide sequence at least 92% identical to a polynucleotide selected from the group consisting of SEQ ID NOs: 89-109. In an aspect, a heterologous promoter comprises a polynucleotide sequence at least 93% identical to a polynucleotide selected from the group consisting of SEQ ID NOs: 89-109. In an aspect, a heterologous promoter comprises a polynucleotide sequence at least 94% identical to a polynucleotide selected from the group consisting of SEQ ID NOs: 89-109. In an aspect, a heterologous promoter comprises a polynucleotide sequence at least 95% identical to a polynucleotide selected from the group consisting of SEQ ID NOs: 89-109. In an aspect, a heterologous promoter comprises a polynucleotide sequence at least 96% identical to a polynucleotide selected from the group consisting of SEQ ID NOs: 89-109. In an aspect, a heterologous promoter comprises a polynucleotide sequence at least 97% identical to a polynucleotide selected from the group consisting of SEQ ID NOs: 89-109. In an aspect, a heterologous promoter comprises a polynucleotide sequence at least 98% identical to a polynucleotide selected from the group consisting of SEQ ID NOs: 89-109. In an aspect, a heterologous promoter comprises a polynucleotide sequence at least 99% identical to a polynucleotide selected from the group consisting of SEQ ID NOs: 89-109. In an aspect, a heterologous promoter comprises a polynucleotide sequence 100% identical to a polynucleotide selected from the group consisting of SEQ ID NOs: 89-109.

In an aspect, an axillary bud-preferred promoter comprises a polynucleotide sequence at least 90% identical to a polynucleotide selected from the group consisting of SEQ ID NOs: 89-109. In an aspect, an axillary bud-preferred promoter comprises a polynucleotide sequence at least 95% identical to a polynucleotide selected from the group consisting of SEQ ID NOs: 89-109. In an aspect, an axillary bud-preferred promoter comprises a polynucleotide sequence at least 96% identical to a polynucleotide selected from the group consisting of SEQ ID NOs: 89-109. In an aspect, an axillary bud-preferred promoter comprises a polynucleotide sequence at least 97% identical to a polynucleotide selected from the group consisting of SEQ ID NOs: 89-109. In an aspect, an axillary bud-preferred promoter comprises a polynucleotide sequence at least 98% identical to a polynucleotide selected from the group consisting of SEQ ID NOs: 89-109. In an aspect, an axillary bud-preferred promoter comprises a polynucleotide sequence at least 99% identical to a polynucleotide selected from the group consisting of SEQ ID NOs: 89-109. In an aspect, an axillary bud-preferred promoter comprises a polynucleotide sequence 100% identical to a polynucleotide selected from the group consisting of SEQ ID NOs: 89-109.

In an aspect, an axillary bud-specific promoter comprises a polynucleotide sequence at least 90% identical to a polynucleotide selected from the group consisting of SEQ ID NOs: 89-109. In an aspect, an axillary bud-specific promoter comprises a polynucleotide sequence at least 95% identical to a polynucleotide selected from the group consisting of SEQ ID NOs: 89-109. In an aspect, an axillary bud-specific promoter comprises a polynucleotide sequence at least 96% identical to a polynucleotide selected from the group consisting of SEQ ID NOs: 89-109. In an aspect, an axillary bud-specific promoter comprises a polynucleotide sequence at least 97% identical to a polynucleotide selected from the group consisting of SEQ ID NOs: 89-109. In an aspect, an axillary bud-specific promoter comprises a polynucleotide sequence at least 98% identical to a polynucleotide selected from the group consisting of SEQ ID NOs: 89-109. In an aspect, an axillary bud-specific promoter comprises a polynucleotide sequence at least 99% identical to a polynucleotide selected from the group consisting of SEQ ID NOs: 89-109. In an aspect, an axillary bud-specific promoter comprises a polynucleotide sequence 100% identical to a polynucleotide selected from the group consisting of SEQ ID NOs: 89-109.

In one aspect, this disclosure provides a modified tobacco plant comprising a polynucleotide sequence encoding a polypeptide selected from the group consisting of a cyclin, a cyclin-dependent kinase (CDK), a CDK inhibitor, a MYB, and a WRKY transcription factor operably linked to a heterologous promoter, where the modified tobacco plant comprises no suckers or reduced suckers after topping as compared to a control tobacco plant when grown under comparable growth conditions.

In another aspect, this disclosure provides a modified tobacco plant comprising a polynucleotide sequence encoding a polypeptide selected from the group consisting of a cyclin, a cyclin-dependent kinase (CDK), a CDK inhibitor, a MYB, and a WRKY transcription factor operably linked to a heterologous promoter.

In a further aspect, this disclosure provides a method for producing a modified tobacco plant comprising: (a) introducing a recombinant DNA construct to at least one tobacco cell, where the recombinant DNA construct comprises a heterologous promoter operably linked to a nucleic acid encoding a polypeptide selected from the group consisting of a cyclin, a cyclin-dependent kinase (CDK), a CDK inhibitor, a MYB, and a WRKY transcription factor; (b) selecting at least one tobacco cell comprising the recombinant DNA construct; and (c) regenerating a modified tobacco plant from the at least one tobacco cell selected in step (b), where the modified tobacco plant comprises no suckers or reduced suckers after topping as compared to a control tobacco plant lacking the recombinant DNA construct when grown under comparable growth conditions. In an aspect, this method further comprises (d) growing the modified tobacco plant regenerated in step (c). In another aspect, this method further comprises (e) crossing the modified tobacco plant grown in step (d) with a second tobacco plant; and (f) obtaining at least one seed from the crossing in step (e).

In an aspect, this disclosure provides a method comprising transforming a tobacco cell with a recombinant DNA construct comprising a heterologous promoter operably linked to a nucleic acid encoding a polypeptide selected from the group consisting of a cyclin, a cyclin-dependent kinase (CDK), a CDK inhibitor, a MYB, and a WRKY transcription factor. In an aspect, this method further comprises regenerating a modified tobacco plant from said tobacco cell, wherein said modified tobacco plant comprises said recombinant DNA construct.

In one aspect, this disclosure provides recombinant DNA constructs comprising polynucleotides provided herein. As used herein, the term "recombinant DNA construct" refers to a construct formed by laboratory methods of genetic recombination, such as molecular cloning. In an aspect, a recombinant DNA construct is synthetically produced. In another aspect, a recombinant DNA construct comprises a promoter operably linked to a heterologous polynucleotide sequence. In an aspect, a recombinant DNA construct comprises a polynucleotide sequence that encodes an amino acid sequence. In another aspect, a recombinant DNA construct comprises a polynucleotide sequence encoding a small RNA or a prescursor thereof. In an aspect, a recombinant DNA construct comprises a plasmid. In another aspect, a recombinant DNA construct comprises a vector.

As used herein, the terms "vector" or "plasmid" are used interchangeably and refer to a circular, double-stranded DNA molecule that is physically separate from chromosomal DNA. In one aspect, a plasmid or vector used herein is capable of replication in vivo. A "transformation vector," as used herein, is a plasmid that is capable of transforming a plant cell. In an aspect, a plasmid provided herein is a bacterial plasmid. In another aspect, a plasmid provided herein is an *Agrobacterium* Ti plasmid or derived from an *Agrobacterium* Ti plasmid.

In an aspect, a vector provided herein comprises a promoter. In an aspect, a vector provided herein comprises an axillary bud-specific promoter. In an aspect, a vector provided herein comprises an axillary bud-preferred promoter. In another aspect, a vector provided herein comprises a small RNA. In another aspect, a vector provided herein comprises a small RNA precursor. In an aspect, a vector provided herein comprises an artificial miRNA. In another aspect, a vector provided herein comprises an artificial miRNA precursor. In another aspect, a vector provided herein comprises a sequence at least 80% identical to a sequence selected from the group consisting of SEQ ID NOs: 1-44 and 89-113, or fragments thereof. In another aspect, a vector provided herein comprises a sequence at least 85% identical to a sequence selected from the group consisting of SEQ ID NOs: 1-44 and 89-113, or fragments thereof. In another aspect, a vector provided herein comprises a sequence at least 90% identical to a sequence selected from the group consisting of SEQ ID NOs: 1-44 and 89-113, or fragments thereof. In another aspect, a vector provided herein comprises a sequence at least 95% identical to a sequence selected from the group consisting of SEQ ID NOs: 1-44 and 89-113, or fragments thereof. In another aspect, a vector provided herein comprises a sequence at least 96% identical to a sequence selected from the group consisting of SEQ ID NOs: 1-44 and 89-113, or fragments thereof. In another aspect, a vector provided herein comprises a sequence at least 97% identical to a sequence selected from the group consisting of SEQ ID NOs: 1-44 and 89-113, or fragments thereof. In another aspect, a vector provided herein comprises a sequence at least 98% identical to a sequence selected from the group consisting of SEQ ID NOs: 1-44 and 89-113, or fragments thereof. In another aspect, a vector provided herein comprises a sequence at least 99% identical to a sequence selected from the group consisting of SEQ ID NOs: 1-44 and 89-113, or fragments thereof. In another aspect, a vector provided herein comprises a sequence 100% identical to a sequence selected from the group consisting of SEQ ID NOs: 1-44 and 89-113, or fragments thereof.

As used herein, a "fragment" of a nucleic acid sequence or amino acid sequence comprises a contiguous segment of sequence comprising between 1% to 99.99% of the total length of a reference sequence. For example, if a nucleic acid sequence comprises 1000 nucleotides, a fragment of the nucleic acid sequence could comprise any number between 10 and 999 contiguous nucleotides of the reference sequence. This disclosure explicitly provides fragments of each of SEQ ID NOs: 1-114 where ever SEQ ID NOs 1-114 are referenced.

Numerous methods for introducing a recombinant DNA construct to a plant cell are known in the art, which can be used according to methods of the present application to produce a transgenic plant cell and plant. Any suitable method or technique for transformation of a plant cell known in the art can be used according to present methods. Effective methods for transformation of plants include bacterially mediated transformation, such as *Agrobacterium*-mediated or *Rhizobium*-mediated transformation and microprojectile bombardment-mediated transformation. A variety of methods are known in the art for transforming explants with a transformation vector via bacterially mediated transformation or microprojectile bombardment and then subsequently culturing, etc., those explants to regenerate or develop transgenic plants. Other methods for plant transformation, such as microinjection, electroporation, vacuum infiltration, pressure, sonication, silicon carbide fiber agitation, polyethylene glycol (PEG)-mediated transformation, etc., are also known in the art. Transgenic plants produced by these transformation methods can be chimeric or non-chimeric for the transformation event depending on the methods and explants used.

Methods of transforming plant cells are well known by persons of ordinary skill in the art. For instance, specific instructions for transforming plant cells by microprojectile bombardment with particles coated with recombinant DNA (e.g., biolistic transformation) are found in U.S. Pat. Nos. 5,550,318; 5,538,880 6,160,208; 6,399,861; and 6,153,812 and *Agrobacterium*-mediated transformation is described in U.S. Pat. Nos. 5,159,135; 5,824,877; 5,591,616; 6,384,301; 5,750,871; 5,463,174; and 5,188,958, all of which are incorporated herein by reference. Additional methods for transforming plants can be found in, for example, Compendium of Transgenic Crop Plants (2009) Blackwell Publishing. Any appropriate method known to those skilled in the art can be used to transform a tobacco cell with any of the nucleic acid molecules provided herein.

In an aspect, a method of providing a nucleic acid molecule to a tobacco cell comprises *Agrobacterium*-mediated transformation. In another aspect, a method of providing a nucleic acid molecule to a cell comprises PEG-mediated transformation. In another aspect, a method of providing a nucleic acid molecule to a cell comprises biolistic transformation. In another aspect, a method of providing a nucleic acid molecule to a cell comprises liposome-mediated transfection (lipofection). In another aspect, a method of providing a nucleic acid molecule to a cell comprises lentiviral transfection.

Lipofection is described in e.g., U.S. Pat. Nos. 5,049,386, 4,946,787; and 4,897,355) and lipofection reagents are sold commercially (e.g., Transfectam™ and Lipofectin™) Cationic and neutral lipids that are suitable for efficient receptor-recognition lipofection of polynucleotides include those of WO 91/17424 and WO 91/16024. Delivery can be to cells (e.g. in vitro or ex vivo administration) or target tissues (e.g. in vivo administration).

Any tobacco cell from which a fertile tobacco plant can be regenerated is contemplated as a useful recipient cell for practice of this disclosure. In an aspect, a recombinant DNA construct is introduced to a tobacco cell. In an aspect, a recombinant DNA construct is introduced to a tobacco protoplast cell. In another aspect, a recombinant DNA construct is introduced to a tobacco callus cell. In an aspect, a recombinant DNA construct is introduced to a tobacco cell selected from the group consisting of a seed cell, a fruit cell, a leaf cell, a cotyledon cell, a hypocotyl cell, a meristem cell, an embryo cell, an endosperm cell, a root cell, a shoot cell, a stem cell, a flower cell, an inflorescence cell, a stalk cell, a pedicel cell, a style cell, a stigma cell, a receptacle cell, a petal cell, a sepal cell, a pollen cell, an anther cell, a filament cell, an ovary cell, an ovule cell, a pericarp cell, and a phloem cell.

Callus can be initiated from various tissue sources, including, but not limited to, immature embryos or parts of embryos, seedling apical meristems, microspores, and the like. Those cells which are capable of proliferating as callus can serve as recipient cells for transformation. Practical transformation methods and materials for making transgenic plants of this disclosure (e.g., various media and recipient target cells, transformation of immature embryos, and subsequent regeneration of fertile transgenic plants) are disclosed, for example, in U.S. Pat. Nos. 6,194,636 and 6,232,526 and U.S. Patent Application Publication 2004/0216189, all of which are incorporated herein by reference.

In one aspect, this disclosure provides a modified tobacco plant comprising a recombinant DNA construct comprising a heterologous promoter operably linked to a nucleic acid encoding at least one small RNA molecule capable of reducing the expression of an endogenous mRNA that encodes a polypeptide selected from the group consisting of a cyclin, a cyclin-dependent kinase (CDK), a CDK inhibitor, a MYB, and a WRKY transcription factor, where the modified tobacco plant comprises no suckers or reduced suckers after topping as compared to a control tobacco plant when grown under comparable growth conditions.

In another aspect, this disclosure provides a modified tobacco plant comprising a recombinant DNA construct comprising a heterologous promoter operably linked to a nucleic acid encoding at least one small RNA molecule capable of reducing the expression of an endogenous mRNA that encodes a polypeptide selected from the group consisting of a cyclin, a cyclin-dependent kinase (CDK), a CDK inhibitor, a MYB, and a WRKY transcription factor.

In a further aspect, this disclosure provides a method for producing a modified tobacco plant comprising: (a) introducing a recombinant DNA construct to at least one tobacco cell, where the recombinant DNA construct comprises a heterologous promoter operably linked to a nucleic acid encoding at least one small RNA molecule capable of reducing the expression of an endogenous mRNA that encodes a polypeptide selected from the group consisting of a cyclin, a cyclin-dependent kinase (CDK), a CDK inhibitor, a MYB, and a WRKY transcription factor; (b) selecting at least one tobacco cell comprising the recombinant DNA construct; and (c) regenerating a modified tobacco plant from the at least one tobacco cell selected in step (b), where the modified tobacco plant comprises no suckers or reduced suckers after topping as compared to a control tobacco plant lacking the recombinant DNA construct when grown under comparable growth conditions. In an aspect, this method further comprises (d) growing the modified tobacco plant regenerated in step (c). In another aspect, this method further comprises (e) crossing the modified tobacco plant grown in step (d) with a second tobacco plant; and (f) obtaining at least one seed from the crossing in step (e).

In another aspect, this disclosure provides a method comprising transforming a tobacco cell with a recombinant DNA construct comprising a heterologous promoter operably linked to a nucleic acid encoding at least one small RNA molecule capable of reducing the expression of an endogenous mRNA that encodes a polypeptide selected from the group consisting of a cyclin, a cyclin-dependent kinase (CDK), a CDK inhibitor, a MYB, and a WRKY transcription factor. In an aspect, this method further comprises regenerating a modified tobacco plant from said tobacco cell, wherein said modified tobacco plant comprises said recombinant DNA construct.

As used herein, the term "small RNA molecule" refers to any non-coding RNA molecule. In addition to providing small RNA molecules, this disclosure also provides a small RNA precursor molecule for each small RNA molecule.

In an aspect, a small RNA molecule comprises between 18 nucleotides and 30 nucleotides in length. In another aspect, a small RNA molecule comprises between 18 nucleotides and 24 nucleotides in length. In another aspect, a small RNA molecule comprises between 18 nucleotides and 22 nucleotides in length.

In another aspect, a small RNA molecule is 18 nucleotides in length. In another aspect, a small RNA molecule is 19 nucleotides in length. In another aspect, a small RNA molecule is 20 nucleotides in length. In another aspect, a small RNA molecule is 21 nucleotides in length. In another aspect, a small RNA molecule is 22 nucleotides in length. In another aspect, a small RNA molecule is 23 nucleotides in length. In another aspect, a small RNA molecule is 24 nucleotides in length. In another aspect, a small RNA molecule is 25 nucleotides in length. In another aspect, a small RNA molecule is 26 nucleotides in length. In another aspect, a small RNA molecule is 27 nucleotides in length. In another aspect, a small RNA molecule is 28 nucleotides in length.

In another aspect, a small RNA molecule is at least 18 nucleotides in length. In another aspect, a small RNA molecule is at least 19 nucleotides in length. In another aspect, a small RNA molecule is at least 20 nucleotides in length. In another aspect, a small RNA molecule is at least 21 nucleotides in length. In another aspect, a small RNA molecule is at least 22 nucleotides in length. In another aspect, a small RNA molecule is at least 23 nucleotides in length. In another aspect, a small RNA molecule is at least 24 nucleotides in length. In another aspect, a small RNA molecule is at least 25 nucleotides in length. In another aspect, a small RNA molecule is at least 26 nucleotides in length. In another aspect, a small RNA molecule is at least 27 nucleotides in length. In another aspect, a small RNA molecule is at least 28 nucleotides in length.

In an aspect, a small RNA molecule comprises between 18 nucleotides and 30 nucleotides. In another aspect, a small RNA molecule comprises between 18 nucleotides and 24 nucleotides. In another aspect, a small RNA molecule comprises between 18 nucleotides and 21 nucleotides. In another aspect, a small RNA molecule comprises between 21 nucleotides and 24 nucleotides. In another aspect, a small RNA molecule comprises between 21 nucleotides and 30 nucleotides.

In an aspect, a small RNA molecule provided herein is a microRNA (miRNA). In an aspect, a small RNA molecule provided herein is an artificial miRNA. In another aspect, a small RNA molecule provided herein is a small interfering RNA (siRNA). In another aspect, a small RNA molecule provided herein is a heterochromatic siRNA (hc-siRNA). In another aspect, a small RNA molecule provided herein is a Piwi-interacting RNA (piRNA). In an aspect, a small RNA molecule provided herein is a double-stranded RNA (dsRNA). In another aspect, a small RNA molecule provided herein is a hairpin double-stranded RNA (hp-dsRNA). In another aspect, a small RNA molecule provided herein is a trans-acting siRNA (ta-siRNA). In another aspect, a small RNA molecule provided herein is a naturally occurring antisense siRNA (nat-siRNA). In another aspect, a small RNA molecule provided herein is a Cas9-guide RNA (gRNA). In another aspect, a small RNA molecule provided herein is a Cpf1-gRNA. In another aspect, a small RNA molecule provided herein is a CasX-gRNA. In another aspect, a small RNA molecule provided herein is a Csm1-gRNA.

In an aspect, a small RNA molecule is selected from the group consisting of a dsRNA, a siRNA, a ta-siRNA, and a miRNA. In another aspect, a small RNA molecule is selected from the group consisting of a miRNA, an siRNA, a hc-siRNA, a piRNA, a dsRNA, a hp-dsRNA, a ta-siRNA, a nat-siRNA, a Cas9-gRNA, a Cpf1-gRNA, a CasX-gRNA, and a Csm1-gRNA.

In an aspect, a small RNA molecule provided herein comprises a polynucleotide sequence having at least 90% identity or complementarity with an endogenous mRNA. In an aspect, a small RNA molecule provided herein comprises a polynucleotide sequence having at least 91% identity or complementarity with an endogenous mRNA. In an aspect, a small RNA molecule provided herein comprises a polynucleotide sequence having at least 92% identity or complementarity with an endogenous mRNA. In an aspect, a small RNA molecule provided herein comprises a polynucleotide sequence having at least 93% identity or complementarity with an endogenous mRNA. In an aspect, a small RNA molecule provided herein comprises a polynucleotide sequence having at least 94% identity or complementarity with an endogenous mRNA. In an aspect, a small RNA molecule provided herein comprises a polynucleotide sequence having at least 95% identity or complementarity with an endogenous mRNA. In an aspect, a small RNA molecule provided herein comprises a polynucleotide sequence having at least 96% identity or complementarity with an endogenous mRNA. In an aspect, a small RNA molecule provided herein comprises a polynucleotide sequence having at least 97% identity or complementarity with an endogenous mRNA. In an aspect, a small RNA molecule provided herein comprises a polynucleotide sequence having at least 98% identity or complementarity with an endogenous mRNA. In an aspect, a small RNA molecule provided herein comprises a polynucleotide sequence having at least 99% identity or complementarity with an endogenous mRNA. In an aspect, a small RNA molecule provided herein comprises a polynucleotide sequence having 100% identity or complementarity with an endogenous mRNA.

In an aspect, a small RNA molecule comprises a polynucleotide sequence having at least 85% identity or complementarity with a polynucleotide sequence selected from the group consisting of SEQ ID NOs: 1-44 and 113. In an aspect, a small RNA molecule comprises a polynucleotide sequence having at least 90% identity or complementarity with a polynucleotide sequence selected from the group consisting of SEQ ID NOs: 1-44 and 113. In an aspect, a small RNA molecule comprises a polynucleotide sequence having at least 91% identity or complementarity with a polynucleotide sequence selected from the group consisting of SEQ ID NOs: 1-44 and 113. In an aspect, a small RNA molecule comprises a polynucleotide sequence having at least 92% identity or complementarity with a polynucleotide sequence selected from the group consisting of SEQ ID NOs: 1-44 and 113. In an aspect, a small RNA molecule comprises a polynucleotide sequence having at least 93% identity or complementarity with a polynucleotide sequence selected from the group consisting of SEQ ID NOs: 1-44 and 113. In an aspect, a small RNA molecule comprises a polynucleotide sequence having at least 94% identity or complementarity with a polynucleotide sequence selected from the group consisting of SEQ ID NOs: 1-44 and 113. In an aspect, a small RNA molecule comprises a polynucleotide sequence having at least 95% identity or complementarity with a polynucleotide sequence selected from the group consisting of SEQ ID NOs: 1-44 and 113. In an aspect, a small RNA molecule comprises a polynucleotide sequence having at least 96% identity or complementarity with a polynucleotide sequence selected from the group consisting of SEQ ID NOs: 1-44 and 113. In an aspect, a small RNA molecule comprises a polynucleotide sequence having at least 97% identity or complementarity with a polynucleotide sequence selected from the group consisting of SEQ ID NOs: 1-44 and 113. In an aspect, a small RNA molecule comprises a polynucleotide sequence having at least 98% identity or complementarity with a polynucleotide sequence selected from the group consisting of SEQ ID NOs: 1-44 and 113. In an aspect, a small RNA molecule comprises a polynucleotide sequence having at least 99% identity or complementarity with a polynucleotide sequence selected from the group consisting of SEQ ID NOs: 1-44 and 113. In an aspect, a small RNA molecule comprises a polynucleotide sequence having 100% identity or complementarity with a polynucleotide sequence selected from the group consisting of SEQ ID NOs: 1-44 and 113.

In an aspect, a small RNA molecule comprises a polynucleotide sequence identical to, or complementary to, at least 16 contiguous nucleotides of a polynucleotide sequence selected from the group consisting of SEQ ID NOs: 1-44 and 113. In an aspect, a small RNA molecule comprises a polynucleotide sequence identical to, or complementary to, at least 17 contiguous nucleotides of a polynucleotide sequence selected from the group consisting of SEQ ID NOs: 1-44 and 113. In an aspect, a small RNA molecule comprises a polynucleotide sequence identical to, or complementary to, at least 18 contiguous nucleotides of a polynucleotide sequence selected from the group consisting of SEQ ID NOs: 1-44 and 113. In an aspect, a small RNA molecule comprises a polynucleotide sequence identical to, or complementary to, at least 19 contiguous nucleotides of a polynucleotide sequence selected from the group consisting of SEQ ID NOs: 1-44 and 113. In an aspect, a small RNA molecule comprises a polynucleotide sequence identical to, or complementary to, at least 20 contiguous nucleotides of a polynucleotide sequence selected from the group consisting of SEQ ID NOs: 1-44 and 113. In an aspect, a small RNA molecule comprises a polynucleotide sequence identical to, or complementary to, at least 21 contiguous nucleotides of a polynucleotide sequence selected from the group consisting of SEQ ID NOs: 1-44 and 113. In an aspect, a small RNA molecule comprises a polynucleotide sequence identical to, or complementary to, at least 22 contiguous nucleotides of a polynucleotide sequence selected from the group consisting of SEQ ID NOs: 1-44 and 113. In an aspect, a small RNA molecule comprises a polynucleotide sequence identical to, or complementary to, at least 23 contiguous nucleotides of a polynucleotide sequence selected from the group consisting of SEQ ID NOs: 1-44 and 113. In an aspect, a small RNA molecule comprises a polynucleotide sequence identical to, or complementary to, at least 24 contiguous nucleotides of a polynucleotide sequence selected from the group consisting of SEQ ID NOs: 1-44 and 113. In an aspect, a small RNA molecule comprises a polynucleotide sequence identical to, or complementary to, at least 25 contiguous nucleotides of a polynucleotide sequence selected from the group consisting of SEQ ID NOs: 1-44 and 113. In an aspect, a small RNA molecule comprises a polynucleotide sequence identical to, or complementary to, at least 26 contiguous nucleotides of a polynucleotide sequence selected from the group consisting of SEQ ID NOs: 1-44 and 113. In an aspect, a small RNA molecule comprises a polynucleotide sequence identical to, or complementary to, at least 27 contiguous nucleotides of a polynucleotide sequence selected from the group consisting of SEQ ID NOs: 1-44 and 113. In an aspect, a small RNA molecule comprises a polynucleotide sequence identical to, or complementary to, at least 28 contiguous nucleotides of a polynucleotide sequence selected from the group consisting of SEQ ID NOs: 1-44 and 113. In an aspect, a small RNA molecule comprises a polynucleotide sequence identical to, or complementary to, at least 29 contiguous nucleotides of a polynucleotide sequence selected from the group consisting of SEQ ID NOs: 1-44 and 113. In an aspect, a small RNA molecule comprises a polynucleotide sequence identical to, or complementary to, at least 30 contiguous nucleotides of a polynucleotide sequence selected from the group consisting of SEQ ID NOs: 1-44 and 113.

In an aspect, this disclosure provides a small RNA capable of reducing the expression of a polynucleotide encoding a cyclin. In an aspect, this disclosure provides a small RNA capable of reducing the translation of a polynucleotide encoding a cyclin. In an aspect, this disclosure provides a small RNA capable of reducing the expression of a polynucleotide encoding a CDK. In an aspect, this disclosure provides a small RNA capable of reducing the translation of a polynucleotide encoding a CDK. In an aspect, this disclosure provides a small RNA capable of reducing the expression of a polynucleotide encoding a CDKI. In an aspect, this disclosure provides a small RNA capable of reducing the translation of a polynucleotide encoding a CDKI. In an aspect, this disclosure provides a small RNA capable of reducing the expression of a polynucleotide encoding a MYB. In an aspect, this disclosure provides a small RNA capable of reducing the translation of a polynucleotide encoding a MYB. In an aspect, this disclosure provides a small RNA capable of reducing the expression of a polynucleotide encoding a WRKY transcription factor. In an aspect, this disclosure provides a small RNA capable of reducing the translation of a polynucleotide encoding a WRKY transcription factor.

MicroRNAs (miRNAs) are non-protein coding RNAs, generally of between about 19 to about 25 nucleotides (commonly about 20-24 nucleotides in plants), that guide cleavage in trans of target transcripts, negatively regulating the expression of genes involved in various regulation and development pathways. In some cases, miRNAs serve to guide in-phase processing of siRNA primary transcripts.

Many microRNA genes (MIR genes) have been identified and made publicly available in a database ("miRBase", available on line at microrna(dot)sanger(dot)ac(dot)uk/sequences; also see Griffiths-Jones et al. (2003) Nucleic Acids Res., 31:439-441). MIR genes have been reported to occur in intergenic regions, both isolated and in clusters in the genome, but can also be located entirely or partially within introns of other genes (both protein-coding and non-protein-coding). Transcription of MIR genes can be, at least in some cases, under promotional control of a MIR gene's own promoter. The primary transcript, termed a "pri-miRNA", can be quite large (several kilobases) and can be polycistronic, containing one or more pre-miRNAs (fold-back structures containing a stem-loop arrangement that is processed to the mature miRNA) as well as the usual 5' "cap" and polyadenylated tail of an mRNA.

Transgenic expression of miRNAs (whether a naturally occurring sequence or an artificial sequence) can be employed to regulate expression of the miRNA's target gene or genes. Inclusion of a miRNA recognition site in a transgenically expressed transcript is also useful in regulating expression of the transcript. Recognition sites of miRNAs have been validated in all regions of an mRNA, including the 5' untranslated region, coding region, and 3' untranslated region, indicating that the position of the miRNA target site relative to the coding sequence may not necessarily affect suppression.

Because miRNAs are important regulatory elements in eukaryotes, transgenic suppression of miRNAs is useful for manipulating biological pathways and responses. Various utilities of miRNAs, their precursors, their recognition sites, and their promoters are described in detail in U.S. Patent Application Publication 2006/0200878 A1, incorporated by reference herein. Non-limiting examples of these utilities include: (1) the expression of a native miRNA or miRNA precursor sequence to suppress a target gene; (2) the expression of an artificial miRNA or miRNA precursor sequence to suppress a target gene; (3) expression of a transgene with a miRNA recognition site, where the transgene is suppressed when the mature miRNA is expressed; (4) expression of a transgene driven by a miRNA promoter.

Designing an artificial miRNA sequence can be as simple as substituting sequence that is complementary to the intended target for nucleotides in the miRNA stem region of the miRNA precursor, as demonstrated by Zeng et al. (2002) Mol. Cell, 9:1327-1333. One non-limiting example of a general method for determining nucleotide changes in the native miRNA sequence to produce the engineered miRNA precursor includes the following steps: (a) Selecting a unique target sequence of at least 18 nucleotides specific to the target gene, e.g., by using sequence alignment tools such as BLAST (see, for example, Altschul et al. (1990) J. Mol. Biol., 215:403-410; Altschul et al. (1997) Nucleic Acids Res., 25:3389-3402), for example, of both tobacco cDNA and genomic DNA databases, to identify target transcript orthologues and any potential matches to unrelated genes, thereby avoiding unintentional silencing of non-target sequences; (b) Analyzing the target gene for undesirable sequences (e.g., matches to sequences from non-target species), and score each potential 19-mer segment for GC content, Reynolds score (see Reynolds et al. (2004) Nature Biotechnol., 22:326-330), and functional asymmetry characterized by a negative difference in free energy (".DELTA..DELTA.G" or "AAG") (see Khvorova et al. (2003) Cell, 114:209-216). Preferably 19-mers are selected that have all or most of the following characteristics: (1) a Reynolds score>4, (2) a GC content between about 40% to about 60%, (3) a negative AAG, (4) a terminal adenosine, (5) lack of a consecutive run of 4 or more of the same nucleotide; (6) a location near the 3' terminus of the target gene; (7) minimal differences from the miRNA precursor transcript. Positions at every third nucleotide in an siRNA have been reported to be especially important in influencing RNAi efficacy and an algorithm, "siExplorer" is publicly available at rna.chem.t.u-tokyo.ac.jp/siexplorer.htm (see Katoh and Suzuki (2007) Nucleic Acids Res., 10.1093/nar/gkl1120); (c) Determining the reverse complement of the selected 19-mers to use in making a modified mature miRNA. The additional nucleotide at position 20 is preferably matched to the selected target sequence, and the nucleotide at position 21 is preferably chosen to either be unpaired to prevent spreading of silencing on the target transcript or paired to the target sequence to promote spreading of silencing on the target transcript; and (d) transforming the artificial miRNA into a plant.

In one aspect, an artificial miRNA provided herein is complementary to at least 18 contiguous nucleotides of a nucleic acid sequence selected from the group consisting of SEQ ID NOs: 1-44 and 113. In one aspect, an artificial miRNA provided herein is complementary to at least 19 contiguous nucleotides of a nucleic acid sequence selected from the group consisting of SEQ ID NOs: 1-44 and 113. In one aspect, an artificial miRNA provided herein is complementary to at least 20 contiguous nucleotides of a nucleic acid sequence selected from the group consisting of SEQ ID NOs: 1-44 and 113. In one aspect, an artificial miRNA provided herein is complementary to at least 21 contiguous nucleotides of a nucleic acid sequence selected from the group consisting of SEQ ID NOs: 1-44 and 113. In one aspect, an artificial miRNA provided herein is complementary to at least 22 contiguous nucleotides of a nucleic acid sequence selected from the group consisting of SEQ ID NOs: 1-44 and 113. In one aspect, an artificial miRNA provided herein is complementary to at least 23 contiguous nucleotides of a nucleic acid sequence selected from the group consisting of SEQ ID NOs: 1-44 and 113. In one aspect, an artificial miRNA provided herein is complementary to at least 24 contiguous nucleotides of a nucleic acid sequence selected from the group consisting of SEQ ID NOs: 1-44 and 113. In one aspect, an artificial miRNA provided herein is complementary to at least 25 contiguous nucleotides of a nucleic acid sequence selected from the group consisting of SEQ ID NOs: 1-44 and 113. In one aspect, an artificial miRNA provided herein is complementary to at least 26 contiguous nucleotides of a nucleic acid sequence selected from the group consisting of SEQ ID NOs: 1-44 and 113.

In one aspect, an artificial miRNA provided herein is at least 75% complementary to a nucleic acid sequence selected from the group consisting of SEQ ID NOs: 1-44 and 113. In one aspect, an artificial miRNA provided herein is at least 80% complementary to a nucleic acid sequence selected from the group consisting of SEQ ID NOs: 1-44 and 113. In one aspect, an artificial miRNA provided herein is at least 85% complementary to a nucleic acid sequence selected from the group consisting of SEQ ID NOs: 1-44 and 113. In one aspect, an artificial miRNA provided herein is at least 90% complementary to a nucleic acid sequence selected from the group consisting of SEQ ID NOs: 1-44 and 113. In one aspect, an artificial miRNA provided herein is at least 91% complementary to a nucleic acid sequence selected from the group consisting of SEQ ID NOs: 1-44 and 113. In one aspect, an artificial miRNA provided herein is at least 92% complementary to a nucleic acid sequence selected from the group consisting of SEQ ID NOs: 1-44 and 113. In one aspect, an artificial miRNA provided herein is at least 93% complementary to a nucleic acid sequence selected from the group consisting of SEQ ID NOs: 1-44 and 113. In one aspect, an artificial miRNA provided herein is at least 94% complementary to a nucleic acid sequence selected from the group consisting of SEQ ID NOs: 1-44 and 113. In one aspect, an artificial miRNA provided herein is at least 95% complementary to a nucleic acid sequence selected from the group consisting of SEQ ID NOs: 1-44 and 113. In one aspect, an artificial miRNA provided herein is at least 96% complementary to a nucleic acid sequence selected from the group consisting of SEQ ID NOs: 1-44 and 113. In one aspect, an artificial miRNA provided herein is at least 97% complementary to a nucleic acid sequence selected from the group consisting of SEQ ID NOs: 1-44 and 113. In one aspect, an artificial miRNA provided herein is at least 98% complementary to a nucleic acid sequence selected from the group consisting of SEQ ID NOs: 1-44 and 113. In one aspect, an artificial miRNA provided herein is at least 99% complementary to a nucleic acid sequence selected from the group consisting of SEQ ID NOs: 1-44 and 113. In one aspect, an artificial miRNA provided herein is 100% complementary to a nucleic acid sequence selected from the group consisting of SEQ ID NOs: 1-44 and 113.

In one aspect, an artificial miRNA provided herein reduces or eliminates RNA transcription or protein translation of a target gene.

In one aspect, an artificial miRNA, or a precursor thereof, is operably linked to an axillary bud-specific promoter. In another aspect, an artificial miRNA, or a precursor thereof, is operably linked to an axillary bud-preferred promoter. In another aspect, an artificial miRNA, or a precursor thereof, is operably linked to a promoter comprising a sequence selected from the group consisting of SEQ ID NOs: 89-109 and fragments thereof.

Tobacco is known in the art as a plant from the family Solanaceae. As used herein, a tobacco plant can be from any plant from the *Nicotiana* genus including, but not limited to *Nicotiana tabacum, Nicotiana amplexicaulis* PI 271989; *Nicotiana benthamiana* PI 555478; *Nicotiana bigelovii* PI 555485; *Nicotiana debneyi; Nicotiana excelsior* PI 224063; *Nicotiana glutinosa* PI 555507; *Nicotiana goodspeedii* PI 241012; *Nicotiana gossei* PI 230953; *Nicotiana hesperis* PI 271991; *Nicotiana knightiana* PI 555527; *Nicotiana maritima* PI 555535; *Nicotiana megalosiphon* PI 555536; *Nicotiana nudicaulis* PI 555540; *Nicotiana paniculata* PI 555545; *Nicotiana plumbaginifolia* PI 555548; *Nicotiana repanda* PI 555552; *Nicotiana rustica; Nicotiana suaveolens* PI 230960; *Nicotiana sylvestris* PI 555569; *Nicotiana tomentosa* PI 266379; *Nicotiana tomentosiformis*; and *Nicotiana trigonophylla* PI 555572. In an aspect, a tobacco plant described here is a *Nicotiana tabacum* plant.

In one aspect, modified tobacco plants, seeds, cells, hybrids, varieties, or lines provided herein are essentially derived from or in the genetic background of BU 64, CC 101, CC 200, CC 13, CC27, CC33, CC35, CC37, CC65, CC67, CC301, CC400, CC500, CC600, CC700, CC 800, CC 900, CC 1063, Coker 176, Coker 319, Coker 371 Gold, Coker 48, CU 263, DF911, Galpão, GL 26H, GL 338, GL 350, GL 395, GL 600, GL 737, GL 939, GL 973, GF 157, GF 318, RJR 901, HB 04P, K 149, K 326, K 346, K 358, K394, K 399, K 730, NC 196, NC 37NF, NC 471, NC 55, NC 92, NC2326, NC 95, NC 925, PVH 1118, PVH 1452, PVH 2110, PVH 2254, PVH 2275, VA 116, VA 119, KDH 959, KT 200, KT204LC, KY 10, KY 14, KY 160, KY 17, KY 171, KY 907, KY 907LC, KTY14×L8 LC, Little Crittenden, McNair 373, McNair 944, male sterile KY 14×L8, Narrow Leaf Madole, MS KY171, Narrow Leaf Madole (phph), MS Narrow Leaf Madole, MS TND950, PD 7302LC, PD 7305LC, PD 7309LC, PD 7312LC, PD 7318LC, PD 7319LC, MSTKS 2002, TKF 2002, TKF 6400, TKF 4028, TKF 4024, KT206LC, KT209LC, KT210LC, KT212LC, NC 100, NC 102, NC 2000, NC 291, NC 297, NC 299, NC 3, NC 4, NC 5, NC 6, NC7, NC 606, NC 71, NC 72, *NC* 810, *NC BH* 129, *NC* 2002, Neal Smith Madole, OXFORD 207, 'Perique', PVH03, PVH9, PVH19, PVH50, PVH51, R610, R630, R7-11, R7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN90LC, TN 97, TN97LC, TN D94, TN D950, a TR (Tom Rosson) Madole, VA 309, VA 359, or any commercial tobacco variety according to standard tobacco breeding techniques known in the art.

In an aspect, a modified tobacco plant is selected from the group consisting of a BU 64 plant, a CC 101 plant, a CC 200 plant, a CC 13 plant, a CC 27 plant, a CC 33 plant, a CC 35 plant, a CC 37 plant, a CC 65 plant, a CC 67 plant, a CC 301 plant, a CC 400 plant, a CC 500 plant, CC 600 plant, a CC 700 plant, a CC 800 plant, a CC 900 plant, a CC 1063 plant, a Coker 176 plant, a Coker 319 plant, a Coker 371 Gold plant, a Coker 48 plant, a CU 263 plant, a DF911 plant, a Galpao plant, a GL 26H plant, a GL 338 plant, a GL 350 plant, a GL 395 plant, a GL 600 plant, a GL 737 plant, a GL 939 plant, a GL 973 plant, a GF 157 plant, a GF 318 plant, an RJR 901 plant, an HB 04P plant, a K 149 plant, a K 326 plant, a K 346 plant, a K 358 plant, a K394 plant, a K 399 plant, a K 730 plant, an NC 196 plant, an NC 37NF plant, an NC 471 plant, an NC 55 plant, an NC 92 plant, an NC2326 plant, an NC 95 plant, an NC 925 plant, a PVH 1118 plant, a PVH 1452 plant, a PVH 2110 plant, a PVH 2254 plant, a PVH 2275 plant, a VA 116 plant, a VA 119 plant, a KDH 959 plant, a KT 200 plant, a KT204LC plant, a KY 10 plant, a KY 14 plant, a KY 160 plant, a KY 17 plant, a KY 171 plant, a KY 907 plant, a KY 907LC plant, a KTY14×L8 LC plant, a Little Crittenden plant, a McNair 373 plant, a McNair 944 plant, a male sterile KY 14×L8 plant, a Narrow Leaf Madole plant, a MS KY171 plant, a Narrow Leaf Madole (phph) plant, a MS Narrow Leaf Madole plant, a MS TND950 plant, a PD 7302LC plant, a PD 7305LC plant, a PD 7309LC plant, a PD 7312LC plant, a PD 7318LC plant, a PD 7319LC plant, a MSTKS 2002 plant, a TKF 2002 plant, a TKF 6400 plant, a TKF 4028 plant, a TKF 4024 plant, a KT206LC plant, a KT209LC plant, a KT210LC plant, a KT212LC plant, an NC 100 plant, an NC 102 plant, an NC 2000 plant, an NC 291 plant, an NC 297 plant, an NC 299 plant, an NC 3 plant, an NC 4 plant, an NC 5 plant, an NC 6 plant, an NC7 plant, an NC 606 plant, an NC 71 plant, an NC 72 plant, an NC 810 plant, an NC BH 129 plant, an NC 2002 plant, a Neal Smith Madole plant, an OXFORD 207 plant, a 'Perique' plant, a PVH03 plant, a PVH09 plant, a PVH19 plant, a PVH50 plant, a PVH51 plant, an R 610 plant, an R 630 plant, an R 7-11 plant, an R 7-12 plant, an RG 17 plant, an RG 81 plant, an RG H51 plant, an RGH 4 plant, an RGH 51 plant, an RS 1410 plant, a Speight 168 plant, a Speight 172 plant, a Speight 179 plant, a Speight 210 plant, a Speight 220 plant, a Speight 225 plant, a Speight 227 plant, a Speight 234 plant, a Speight G-28 plant, a Speight G-70 plant, a Speight H-6 plant, a Speight H20 plant, a Speight NF3 plant, a TI 1406 plant, a TI 1269 plant, a TN 86 plant, a TN86LC plant, a TN 90 plant, a TN90LC plant, a TN 97 plant, a TN97LC plant, a TN D94 plant, a TN D950 plant, a TR (Tom Rosson) Madole plant, a VA 309 plant, and a VA 359 plant.

In another aspect, a modified tobacco cell is selected from the group consisting of a BU 64 cell, a CC 101 cell, a CC 200 cell, a CC 13 cell, a CC 27 cell, a CC 33 cell, a CC 35 cell, a CC 37 cell, a CC 65 cell, a CC 67 cell, a CC 301 cell, a CC 400 cell, a CC 500 cell, CC 600 cell, a CC 700 cell, a CC 800 cell, a CC 900 cell, a CC 1063 cell, a Coker 176 cell, a Coker 319 cell, a Coker 371 Gold cell, a Coker 48 cell, a CU 263 cell, a DF911 cell, a Galpao cell, a GL 26H cell, a GL 338 cell, a GL 350 cell, a GL 395 cell, a GL 600 cell, a GL 737 cell, a GL 939 cell, a GL 973 cell, a GF 157 cell, a GF 318 cell, an RJR 901 cell, an HB 04P cell, a K 149 cell, a K 326 cell, a K 346 cell, a K 358 cell, a K394 cell, a K 399 cell, a K 730 cell, an NC 196 cell, an NC 37NF cell, an NC 471 cell, an NC 55 cell, an NC 92 cell, an NC2326 cell, an NC 95 cell, an NC 925 cell, a PVH 1118 cell, a PVH 1452 cell, a PVH 2110 cell, a PVH 2254 cell, a PVH 2275 cell, a VA 116 cell, a VA 119 cell, a KDH 959 cell, a KT 200 cell, a KT204LC cell, a KY 10 cell, a KY 14 cell, a KY 160 cell, a KY 17 cell, a KY 171 cell, a KY 907 cell, a KY 907LC cell, a KTY14×L8 LC cell, a Little Crittenden cell, a McNair 373 cell, a McNair 944 cell, a male sterile KY 14×L8 cell, a Narrow Leaf Madole cell, a MS KY171 cell, a Narrow Leaf Madole (phph) cell, a MS Narrow Leaf Madole cell, a MS TND950 cell, a PD 7302LC cell, a PD 7305LC cell, a PD 7309LC cell, a PD 7312LC cell, a PD 7318LC cell, a PD 7319LC cell, a MSTKS 2002 cell, a TKF 2002 cell, a TKF 6400 cell, a TKF 4028 cell, a TKF 4024 cell, a KT206LC cell, a KT209LC cell, a KT210LC cell, a KT212LC cell, an NC 100 cell, an NC 102 cell, an NC 2000 cell, an NC 291 cell, an NC 297 cell, an NC 299 cell, an NC 3 cell, an NC 4 cell, an NC 5 cell, an NC 6 cell, an NC7 cell, an NC 606 cell, an NC 71 cell, an NC 72 cell, an NC 810 cell, an NC BH 129 cell, an NC 2002 cell, a Neal Smith Madole cell, an OXFORD 207 cell, a 'Perique' cell, a PVH03 cell, a PVH09 cell, a PVH19 cell, a PVH50 cell, a PVH51 cell, an R 610 cell, an R 630 cell, an R 7-11 cell, an R 7-12 cell, an RG 17 cell, an RG 81 cell, an RG H51 cell, an RGH 4 cell, an RGH 51 cell, an RS 1410 cell, a Speight 168 cell, a Speight 172 cell, a Speight 179 cell, a Speight 210 cell, a Speight 220 cell, a Speight 225 cell, a Speight 227 cell, a Speight 234 cell, a Speight G-28 cell, a Speight G-70 cell, a Speight H-6 cell, a Speight H20 cell, a Speight NF3 cell, a TI 1406 cell, a TI 1269 cell, a TN 86 cell, a TN86LC cell, a TN 90 cell, a TN90LC cell, a TN 97 cell, a TN97LC cell, a TN D94 cell, a TN D950 cell, a TR (Tom Rosson) Madole cell, a VA 309 cell, and a VA 359 cell.

In another aspect, a modified tobacco seed is selected from the group consisting of a BU 64 seed, a CC 101 seed, a CC 200 seed, a CC 13 seed, a CC 27 seed, a CC 33 seed, a CC 35 seed, a CC37 seed, a CC65 seed, a CC67 seed, a CC301 seed, a CC400 seed, a CC500 seed, CC600 seed, a CC700 seed, a CC 800 seed, a CC900 seed, a CC 1063 seed, a Coker 176 seed, a Coker 319 seed, a Coker 371 Gold seed, a Coker 48 seed, a CU 263 seed, a DF911 seed, a Galpao seed, a GL 26H seed, a GL 338 seed, a GL 350 seed, a GL 395 seed, a GL 600 seed, a GL 737 seed, a GL 939 seed, a GL 973 seed, a GF 157 seed, a GF 318 seed, an RJR 901 seed, an HB 04P seed, a K 149 seed, a K 326 seed, a K 346 seed, a K 358 seed, a K394 seed, a K 399 seed, a K 730 seed, an NC 196 seed, an NC 37NF seed, an NC 471 seed, an NC 55 seed, an NC 92 seed, an NC2326 seed, an NC 95 seed, an NC 925 seed, a PVH 1118 seed, a PVH 1452 seed, a PVH 2110 seed, a PVH 2254 seed, a PVH 2275 seed, a VA 116 seed, a VA 119 seed, a KDH 959 seed, a KT 200 seed, a KT204LC seed, a KY 10 seed, a KY 14 seed, a KY 160 seed, a KY 17 seed, a KY 171 seed, a KY 907 seed, a KY 907LC seed, a KTY14×L8 LC seed, a Little Crittenden seed, a McNair 373 seed, a McNair 944 seed, a male sterile KY 14×L8 seed, a Narrow Leaf Madole seed, a MS KY171 seed, a Narrow Leaf Madole (phph) seed, a MS Narrow Leaf Madole seed, a MS TND950 seed, a PD 7302LC seed, a PD 7305LC seed, a PD 7309LC seed, a PD 7312LC seed, a PD 7318LC seed, a PD 7319LC seed, a MSTKS 2002 seed, a TKF 2002 seed, a TKF 6400 seed, a TKF 4028 seed, a TKF 4024 seed, a KT206LC seed, a KT209LC seed, a KT210LC seed, a KT212LC seed, an NC 100 seed, an NC 102 seed, an NC 2000 seed, an NC 291 seed, an NC 297 seed, an NC 299 seed, an NC 3 seed, an NC 4 seed, an NC 5 seed, an NC 6 seed, an NC7 seed, an NC 606 seed, an NC 71 seed, an NC 72 seed, an NC 810 seed, an NC BH 129 seed, an NC 2002 seed, a Neal Smith Madole seed, an OXFORD 207 seed, a 'Perique' seed, a PVH03 seed, a PVH09 seed, a PVH19 seed, a PVH50 seed, a PVH51 seed, an R 610 seed, an R 630 seed, an R 7-11 seed, an R 7-12 seed, an RG 17 seed, an RG 81 seed, an RG H51 seed, an RGH 4 seed, an RGH 51 seed, an RS 1410 seed, a Speight 168 seed, a Speight 172 seed, a Speight 179 seed, a Speight 210 seed, a Speight 220 seed, a Speight 225 seed, a Speight 227 seed, a Speight 234 seed, a Speight G-28 seed, a Speight G-70 seed, a Speight H-6 seed, a Speight H20 seed, a Speight NF3 seed, a TI 1406 seed, a TI 1269 seed, a TN 86 seed, a TN86LC seed, a TN 90 seed, a TN90LC seed, a TN 97 seed, a TN97LC seed, a TN D94 seed, a TN D950 seed, a TR (Tom Rosson) Madole seed, a VA 309 seed, and a VA 359 seed.

As used herein, "tobacco plant" refers to a whole tobacco plant. A tobacco cell or tobacco tissue culture derived from a tobacco plant can comprise any tobacco plant parts or tobacco plant organs (e.g., leaves, stems, roots, etc.), tobacco plant tissues, tobacco seeds, tobacco plant cells, and/or progeny of the same. A progeny plant can be from any filial generation, e.g., $F_1, F_2, F_3, F_4, F_5, F_6, F_7$, etc. A tobacco plant cell is a biological cell of a tobacco plant, taken from a tobacco plant or derived through culture from a cell taken from a tobacco plant. As used herein, "seedling" refers to a tobacco plant that is equal to, or less than, 14 days post-germination.

In one aspect, a tobacco plant part provided herein includes, but is not limited to, a leaf, a stem, a root, a seed, a flower, pollen, an anther, an ovule, a pedicel, a fruit, a meristem, a cotyledon, a hypocotyl, a pod, an embryo, endosperm, an explant, a callus, a tissue culture, a shoot, a cell, and a protoplast. In further aspects, this disclosure provides tobacco plant cells, tissues, and organs that are not reproductive material and do not mediate the natural reproduction of the plant. In another aspect, this disclosure also provides tobacco plant cells, tissues, and organs that are reproductive material and mediate the natural reproduction of the plant. In another aspect, this disclosure provides tobacco plant cells, tissues, and organs that cannot maintain themselves via photosynthesis. In another aspect, this disclosure provides somatic plant cells. Somatic cells, contrary to germline cells, do not mediate plant reproduction.

Provided tobacco cells, tobacco tissues and tobacco organs can be from seed, fruit, leaf, cotyledon, hypocotyl, meristem, embryos, endosperm, root, shoot, stem, pod, flower, inflorescence, stalk, pedicel, style, stigma, receptacle, petal, sepal, pollen, anther, filament, ovary, ovule, pericarp, phloem, and vascular tissue. In another aspect, this disclosure provides a tobacco plant chloroplast. In a further aspect, this disclosure provides an epidermal cell, a stomata cell, a trichome cell, a root hair, or a storage root.

In an aspect, this disclosure provides a tobacco protoplast cell. In another aspect, this disclosure provides a tobacco callus cell. In another aspect, this disclosure provides a tobacco seed cell. In another aspect, this disclosure provides a tobacco fruit cell. In another aspect, this disclosure provides a tobacco leaf cell. In another aspect, this disclosure provides a tobacco cotyledon cell. In another aspect, this disclosure provides a tobacco hypocotyl cell. In another aspect, this disclosure provides a tobacco meristem cell. In another aspect, this disclosure provides a tobacco embryo cell. In another aspect, this disclosure provides a tobacco root cell. In another aspect, this disclosure provides a tobacco shoot cell. In another aspect, this disclosure provides a tobacco stem cell. In another aspect, this disclosure provides a tobacco flower cell. In another aspect, this disclosure provides a tobacco inflorescence cell. In another aspect, this disclosure provides a tobacco stalk cell. In another aspect, this disclosure provides a tobacco pedicel cell. In another aspect, this disclosure provides a tobacco style cell. In another aspect, this disclosure provides a tobacco stigma cell. In another aspect, this disclosure provides a tobacco receptacle cell. In another aspect, this disclosure provides a tobacco petal cell. In another aspect, this disclosure provides a tobacco sepal cell. In another aspect, this disclosure provides a tobacco pollen cell. In another aspect, this disclosure provides a tobacco anther cell. In another aspect, this disclosure provides a tobacco filament cell. In another aspect, this disclosure provides a tobacco ovary cell. In another aspect, this disclosure provides a tobacco ovule cell. In another aspect, this disclosure provides a tobacco pericarp cell. In another aspect, this disclosure provides a tobacco phloem cell.

This disclosure provides modified tobacco plants, modified tobacco plant parts, modified tobacco seeds, and modified tobacco cells and methods of making the same. In an aspect, this disclosure provides a tobacco leaf of a modified tobacco plant. In another aspect, this disclosure provides a tobacco seed of a modified tobacco plant. In another aspect, this disclosure provides a tobacco stem of a modified tobacco plant. In a further aspect, this disclosure provides a tobacco plant part of a modified tobacco plant. In another aspect, this disclosure provides a tobacco cell of a modified tobacco plant. In a further aspect, this disclosure provides a dried tobacco leaf of a modified tobacco plant. In still a further aspect, this disclosure provides a cured tobacco leaf of a modified tobacco plant. In yet another aspect, this disclosure provides a fermented tobacco leaf of a modified tobacco plant.

In another aspect, this disclosure provides an alkaloid extracted from a modified tobacco plant. In another aspect, this disclosure provides nicotine extracted from a modified tobacco plant. In another aspect, this disclosure provides anatabine extracted from a modified tobacco plant. In another aspect, this disclosure provides anabasine extracted from a modified tobacco plant. In another aspect, this disclosure provides nornicotine extracted from a modified tobacco plant.

In an aspect, a modified tobacco plant, plant part, seed, cell, or genome is cisgenic. As used herein, "cisgenic" refers to genetic modification of a plant, plant cell, or plant genome in which all parts (e.g., promoter, donor nucleic acid, selection gene) have only plant origins (i.e., no non-plant origin parts are used). Cisgenic plants, plant cells, and plant genomes provided herein can lead to ready-to-use tobacco lines. In another aspect, a modified tobacco plant provided herein comprises no non-tobacco genetic material or sequences.

In an aspect, a modified plant comprises an increased leaf yield mass as compared to a control tobacco plant when grown under comparable conditions. In an aspect, leaf yield is selected from the group consisting of fresh leaf yield mass, dry leaf yield mass, and cured leaf yield mass.

In an aspect, a modified plant comprises at least 0.5% increased leaf yield mass as compared to a control tobacco plant when grown under comparable conditions. In an aspect, a modified plant comprises at least 0.5% increased fresh leaf yield mass as compared to a control tobacco plant when grown under comparable conditions. In an aspect, a modified plant comprises at least 0.5% increased dry leaf yield mass as compared to a control tobacco plant when grown under comparable conditions. In an aspect, a modified plant comprises at least 0.5% increased cured leaf yield mass as compared to a control tobacco plant when grown under comparable conditions. In an aspect, a modified plant comprises at least 1% increased leaf yield mass as compared to a control tobacco plant when grown under comparable conditions. In an aspect, a modified plant comprises at least 1% increased fresh leaf yield mass as compared to a control tobacco plant when grown under comparable conditions. In an aspect, a modified plant comprises at least 1% increased dry leaf yield mass as compared to a control tobacco plant when grown under comparable conditions. In an aspect, a modified plant comprises at least 1% increased cured leaf yield mass as compared to a control tobacco plant when grown under comparable conditions. In an aspect, a modified plant comprises at least 2% increased leaf yield mass as compared to a control tobacco plant when grown under comparable conditions. In an aspect, a modified plant comprises at least 2% increased fresh leaf yield mass as compared to a control tobacco plant when grown under comparable conditions. In an aspect, a modified plant comprises at least 2% increased dry leaf yield mass as compared to a control tobacco plant when grown under comparable conditions. In an aspect, a modified plant comprises at least 2% increased cured leaf yield mass as compared to a control tobacco plant when grown under comparable conditions. In an aspect, a modified plant comprises at least 3% increased leaf yield mass as compared to a control tobacco plant when grown under comparable conditions. In an aspect, a modified plant comprises at least 3% increased fresh leaf yield mass as compared to a control tobacco plant when grown under comparable conditions. In an aspect, a modified plant comprises at least 3% increased dry leaf yield mass as compared to a control tobacco plant when grown under comparable conditions. In an aspect, a modified plant comprises at least 3% increased cured leaf yield mass as compared to a control tobacco plant when grown under comparable conditions. In an aspect, a modified plant comprises at least 4% increased leaf yield mass as compared to a control tobacco plant when grown under comparable conditions. In an aspect, a modified plant comprises at least 4% increased fresh leaf yield mass as compared to a control tobacco plant when grown under comparable conditions. In an aspect, a modified plant comprises at least 4% increased dry leaf yield mass as compared to a control tobacco plant when grown under comparable conditions. In an aspect, a modified plant comprises at least 4% increased cured leaf yield mass as compared to a control tobacco plant when grown under comparable conditions. In an aspect, a modified plant comprises at least 5% increased leaf yield mass as compared to a control tobacco plant when grown under comparable conditions. In an aspect, a modified plant comprises at least 5% increased fresh leaf yield mass as compared to a control tobacco plant when grown under comparable conditions. In an aspect, a modified plant comprises at least 5% increased dry leaf yield mass as compared to a control tobacco plant when grown under comparable conditions. In an aspect, a modified plant comprises at least 5% increased cured leaf yield mass as compared to a control tobacco plant when grown under comparable conditions. In an aspect, a modified plant comprises at least 250% increased leaf yield mass as compared to a control tobacco plant when grown under comparable conditions. In an aspect, a modified plant comprises at least 250% increased fresh leaf yield mass as compared to a control tobacco plant when grown under comparable conditions. In an aspect, a modified plant comprises at least 250% increased dry leaf yield mass as compared to a control tobacco plant when grown under comparable conditions. In an aspect, a modified plant comprises at least 250% increased cured leaf yield mass as compared to a control tobacco plant when grown under comparable conditions. In an aspect, a modified plant comprises at least 25% increased leaf yield mass as compared to a control tobacco plant when grown under comparable conditions. In an aspect, a modified plant comprises at least 25% increased fresh leaf yield mass as compared to a control tobacco plant when grown under comparable conditions. In an aspect, a modified plant comprises at least 25% increased dry leaf yield mass as compared to a control tobacco plant when grown under comparable conditions. In an aspect, a modified plant comprises at least 25% increased cured leaf yield mass as compared to a control tobacco plant when grown under comparable conditions. In an aspect, a modified plant comprises at least 50% increased leaf yield mass as compared to a control tobacco plant when grown under comparable conditions. In an aspect, a modified plant comprises at least 50% increased fresh leaf yield mass as compared to a control tobacco plant when grown under comparable conditions. In an aspect, a modified plant comprises at least 50% increased dry leaf yield mass as compared to a control tobacco plant when grown under comparable conditions. In an aspect, a modified plant comprises at least 50% increased cured leaf yield mass as compared to a control tobacco plant when grown under comparable conditions. In an aspect, a modified plant comprises at least 75% increased leaf yield mass as compared to a control tobacco plant when grown under comparable conditions. In an aspect, a modified plant comprises at least 75% increased fresh leaf yield mass as compared to a control tobacco plant when grown under comparable conditions. In an aspect, a modified plant comprises at least 75% increased dry leaf yield mass as compared to a control tobacco plant when grown under comparable conditions. In an aspect, a modified plant comprises at least 75% increased cured leaf yield mass as compared to a control tobacco plant when grown under comparable conditions. In an aspect, a modified plant comprises at least 100% increased leaf yield mass as compared to a control tobacco plant when grown under comparable conditions. In an aspect, a modified plant comprises at least 100% increased fresh leaf yield mass as compared to a control tobacco plant when grown under comparable conditions. In an aspect, a modified plant comprises at least 100% increased dry leaf yield mass as compared to a control tobacco plant when grown under comparable conditions. In an aspect, a modified plant comprises at least 100% increased cured leaf yield mass as compared to a control tobacco plant when grown under comparable conditions.

"Curing" is the aging process that reduces moisture and brings about the destruction of chlorophyll giving tobacco leaves a golden color and by which starch is converted to sugar. Cured tobacco therefore has a higher reducing sugar content and a lower starch content compared to harvested green leaf. In one aspect, tobacco plants or plant components provided herein can be cured using conventional means, e.g., flue-cured, barn-cured, fire-cured, air-cured or sun-cured. See, for example, Tso (1999, Chapter 1 in Tobacco, Production, Chemistry and Technology, Davis & Nielsen, eds., Blackwell Publishing, Oxford) for a description of different types of curing methods. Cured tobacco is usually aged in a wooden drum (e.g., a hogshead) or cardboard cartons in compressed conditions for several years (e.g., two to five years), at a moisture content ranging from 10% to about 25%. See, U.S. Pat. Nos. 4,516,590 and 5,372,149. Cured and aged tobacco then can be further processed. Further processing includes conditioning the tobacco under vacuum with or without the introduction of steam at various temperatures, pasteurization, and fermentation.

In an aspect, cured tobacco leaf provided herein is selected from the group consisting of air-cured tobacco leaf, fire-cured tobacco leaf, sun-cured tobacco leaf, and flue-cured tobacco leaf. In another aspect, cured tobacco material provided herein is selected from the group consisting of air-cured tobacco material, fire-cured tobacco material, sun-cured tobacco material, and flue-cured tobacco material. In an aspect, cured tobacco leaf is from a tobacco variety selected from the group consisting of a flue-cured variety, a bright variety, a Burley variety, a Virginia variety, a Maryland variety, a dark variety, an Oriental variety, and a Turkish variety. In another aspect, cured tobacco material is from a tobacco variety selected from the group consisting of a flue-cured variety, a bright variety, a Burley variety, a Virginia variety, a Maryland variety, a dark variety, an Oriental variety, and a Turkish variety.

Fermentation typically is characterized by high initial moisture content, heat generation, and a 10 to 20% loss of dry weight. See, for example, U.S. Pat. Nos. 4,528,993, 4,660,577, 4,848,373, 5,372,149; U.S. Publication No. 2005/0178398; and Tso (1999, Chapter 1 in Tobacco, Production, Chemistry and Technology, Davis & Nielsen, eds., Blackwell Publishing, Oxford). Cured, aged, and fermented tobacco can be further processed (e.g., cut, shredded, expanded, or blended). See, for example, U.S. Pat. Nos. 4,528,993; 4,660,577; and 4,987,907. In one aspect, the cured tobacco material of the present disclosure is flue-cured, sun-cured, air-cured, or fire-cured.

In one aspect, tobacco plants, seeds, plant parts, plant cells, and plant genomes provided herein are from a tobacco type selected from the group consisting of flue-cured tobacco, sun-cured tobacco, air-cured tobacco, dark air-cured tobacco, and dark fire-cured tobacco. In another aspect, tobacco plants, seeds, plant parts, plant cells, and plant genomes provided herein are from a tobacco type selected from the group consisting of Burley tobacco, Maryland tobacco, bright tobacco, Virginia tobacco, Oriental tobacco, Turkish tobacco, and Galpao tobacco.

In one aspect, a modified tobacco plant provided herein is of a tobacco variety selected from the group consisting of a flue-cured variety, a bright variety, a Burley variety, a Virginia variety, a Maryland variety, a Galpao variety, a dark variety, an Oriental variety, and a Turkish variety.

In one aspect, a modified tobacco plant provided herein is selected from the group consisting of a flue-cured variety tobacco plant, a bright variety tobacco plant, a Burley variety tobacco plant, a Virginia variety tobacco plant, a Maryland variety tobacco plant, a Galpao variety tobacco plant, a dark variety tobacco plant, an Oriental variety tobacco plant, and a Turkish variety tobacco plant. In one aspect, a modified tobacco cell provided herein is selected from the group consisting of a flue-cured variety tobacco cell, a bright variety tobacco cell, a Burley variety tobacco cell, a Virginia variety tobacco cell, a Maryland variety tobacco cell, a Galpao variety tobacco cell, a dark variety tobacco cell, an Oriental variety tobacco cell, and a Turkish variety tobacco cell. In one aspect, a modified tobacco plant part provided herein is selected from the group consisting of a flue-cured variety tobacco plant part, a bright variety tobacco plant part, a Burley variety tobacco plant part, a Virginia variety tobacco plant part, a Maryland variety tobacco plant part, a Galpao variety tobacco plant part, a dark variety tobacco plant part, an Oriental variety tobacco plant part, and a Turkish variety tobacco plant part. In one aspect, a modified tobacco seed provided herein is selected from the group consisting of a flue-cured variety tobacco seed, a bright variety tobacco seed, a Burley variety tobacco seed, a Virginia variety tobacco seed, a Maryland variety tobacco seed, a Galpao variety tobacco seed, a dark variety tobacco seed, an Oriental variety tobacco seed, and a Turkish variety tobacco seed.

As used herein, a "hybrid" is created by crossing two plants from different varieties or species, such that the progeny comprises genetic material from each parent. Skilled artisans recognize that higher order hybrids can be generated as well. For example, a first hybrid can be made by crossing Variety C with Variety D to create a C×D hybrid, and a second hybrid can be made by crossing Variety E with Variety F to create an E×F hybrid. The first and second hybrids can be further crossed to create the higher order hybrid (C×D)×(E×F) comprising genetic information from all four parent varieties. In an aspect, a modified tobacco plant provided herein is a hybrid tobacco plant. In another aspect, a modified tobacco seed provided herein is a hybrid tobacco seed.

As used herein, the term "crossing" refers to the deliberate mating of two plants. In an aspect, crossing comprises pollination and/or fertilization of a first tobacco plant by a second tobacco plant. The two tobacco plants being crossed can be distantly related, closely related, or identical. In an aspect, the two tobacco plants being crossed are both modified tobacco plants. In an aspect, the two tobacco plants being crossed are of the same tobacco variety. In an aspect, the two tobacco plants being crossed are of two different tobacco varieties. In an aspect, one of the two tobacco plants being crossed is male sterile. In an aspect, one of the two tobacco plants being crossed is female sterile. In an aspect, at least one of the two tobacco plants being crossed is a hybrid tobacco plant. In an aspect, at least one of the two tobacco plants being crossed is a modified tobacco plant.

In an aspect, this disclosure provides a method for producing a modified tobacco plant comprising: (a) crossing at least one tobacco plant of a first tobacco variety with at least one tobacco plant of a second tobacco variety, where the at least one tobacco plant of the first tobacco variety comprises a mutation in an endogenous gene encoding a polypeptide selected from the group consisting of a cyclin, a cyclin-dependent kinase (CDK), a CDK inhibitor, a MYB, and a WRKY transcription factor, where the mutation is not present in the endogenous gene in a control tobacco plant of the same variety, and where the at least one tobacco plant comprises no suckers or reduced suckers after topping as compared to the control tobacco plant when grown under comparable growth conditions; and (b) selecting for progeny tobacco plants that exhibit no suckers or reduced suckers after topping compared to a control tobacco plant of the same cross grown under comparable growth conditions.

In another aspect, this disclosure provides a method for producing a modified tobacco plant comprising: (a) crossing at least one tobacco plant of a first tobacco variety with at least one tobacco plant of a second tobacco variety, where the at least one tobacco plant of the first tobacco variety comprises a recombinant DNA construct comprising a heterologous promoter operably linked to a nucleic acid encoding a polypeptide selected from the group consisting of a cyclin, a cyclin-dependent kinase (CDK), a CDK inhibitor, a MYB, and a WRKY transcription factor, where the at least one tobacco plant comprises no suckers or reduced suckers after topping as compared to a control tobacco plant when grown under comparable growth conditions; and (b) selecting for progeny tobacco plants that exhibit no suckers or reduced suckers after topping compared to a control tobacco plant of the same cross grown under comparable growth conditions.

In a further aspect, this disclosure provides a method for producing a modified tobacco plant comprising: (a) crossing at least one tobacco plant of a first tobacco variety with at least one tobacco plant of a second tobacco variety, where the at least one tobacco plant of said first tobacco variety comprises a recombinant DNA construct comprising a heterologous promoter operably linked to a nucleic acid encoding at least one small RNA molecule capable of reducing the expression of an endogenous genomic locus that encodes a polypeptide selected from the group consisting of a cyclin, a cyclin-dependent kinase (CDK), a CDK inhibitor, a MYB, and a WRKY transcription factor, where the at least one tobacco plant comprises no suckers or reduced suckers after topping as compared to a control tobacco plant when grown under comparable growth conditions; and (b) selecting for progeny tobacco plants that exhibit no suckers or reduced suckers after topping compared to a control tobacco plant of the same cross grown under comparable growth conditions.

In one aspect, a tobacco variety provided herein is male sterile. In another aspect, a tobacco variety provided herein is cytoplasmic male sterile (CMS). In an aspect, a modified tobacco plant provided herein is male sterile. In another aspect, a modified tobacco plant provided herein is cytoplasmic male sterile. Male sterile tobacco plants can be produced by any method known in the art. Methods of producing male sterile tobacco are described in Wernsman, E. A., and Rufty, R. C. 1987. Chapter Seventeen. Tobacco. Pages 669-698 In: Cultivar Development. Crop Species. W. H. Fehr (ed.), MacMillan Publishing Go., Inc., New York, N.Y. 761 pp.

In another aspect, a tobacco variety provided herein is female sterile. As a non-limiting example, female sterile plants can be made by mutating the STIG1 gene. See, for example, Goldman et al. 1994, *EMBO Journal* 13:2976-2984. In an aspect, a modified tobacco plant provided herein is female sterile.

Flue-cured tobaccos (also called "Virginia" or "bright" tobaccos) amount to approximately 40% of world tobacco production. Flue-cured tobaccos are often also referred to as "bright tobacco" because of the golden-yellow to deep-orange color it reaches during curing. Flue-cured tobaccos have a light, bright aroma and taste. Flue-cured tobaccos are generally high in sugar and low in oils. Major flue-cured tobacco growing countries are Argentina, Brazil, China, India, Tanzania and the United States of America. In one aspect, modified tobacco plants or seeds provided herein are of a flue-cured tobacco variety selected from the group consisting of CC 13, CC 27, CC 33, CC35, CC 37, CC 65, CC 67, CC 700, GF 318, GL 338, GL 368, GL 939, K 346, K 399, K326, NC 102, NC 196, NC 291, NC 297, NC 299, NC 471, NC 55, NC 606, NC 71, NC 72, NC 92, PVH 1118, PVH 1452, PVH 2110, SPEIGHT 168, SPEIGHT 220, SPEIGHT 225, SPEIGHT 227, SPEIGHT 236, and any variety essentially derived from any one of the foregoing varieties. In another aspect, modified tobacco plants or seeds provided herein are in a flue-cured tobacco variety selected from the group consisting of Coker 48, Coker 176, Coker 371-Gold, Coker 319, Coker 347, GL 939, K 149, K326, K 340, K 346, K 358, K 394, K 399, K 730, NC 27NF, NC 37NF, NC 55, NC 60, NC 71, NC 72, NC 82, NC 95, NC 297, NC 606, NC 729, NC 2326, McNair 373, McNair 944, Ox 207, Ox 414 NF, Reams 126, Reams 713, Reams 744, RG 8, RG 11, RG 13, RG 17, RG 22, RG 81, RG H4, RG H51, Speight H-20, Speight G-28, Speight G-58, Speight G-70, Speight G-108, Speight G-111, Speight G-117, Speight 168, Speight 179, Speight NF-3, Va 116, Va 182, and any variety essentially derived from any one of the foregoing varieties. See WO 2004/041006 A1. In a further aspect, modified tobacco plants or seeds provided herein are in a flue-cured variety selected from the group consisting of K326, K346, and NC196.

Air-cured tobaccos include "Burley," "Maryland," and "dark" tobaccos. The common factor linking air-cured tobaccos is that curing occurs primarily without artificial sources of heat and humidity. Burley tobaccos are light to dark brown in color, high in oil, and low in sugar. Burley tobaccos are typically air-cured in barns. Major Burley growing countries include Argentina, Brazil, Italy, Malawi, and the United States of America.

Maryland tobaccos are extremely fluffy, have good burning properties, low nicotine and a neutral aroma. Major Maryland growing countries include the United States of America and Italy.

In one aspect, modified tobacco plants or seeds provided herein are of a Burley tobacco variety selected from the group consisting of Clay 402, Clay 403, Clay 502, Ky 14, Ky 907, Ky 910, Ky 8959, NC 2, NC 3, NC 4, NC 5, NC 2000, TN 86, TN 90, TN 97, R 610, R 630, R 711, R 712, NCBH 129, HB4488PLC, PD 7319LC, Bu 21×Ky 10, HB04P, Ky 14×L 8, Kt 200, Newton 98, Pedigo 561, Pf561 and Va 509. In a further aspect, modified tobacco plants or seeds provided herein are in a Burley variety selected from the group consisting of TN 90, KT 209, KT 206, KT212, and HB 4488. In another aspect, modified tobacco plants or seeds provided herein are of a Maryland tobacco variety selected from the group consisting of Md 10, Md 40, Md 201, Md 609, Md 872 and Md 341.

Dark air-cured tobaccos are distinguished from other tobacco types primarily by its curing process, which gives dark air-cured tobacco its medium-brown to dark-brown color and a distinct aroma. Dark air-cured tobaccos are mainly used in the production of chewing tobacco and snuff. In one aspect, modified tobacco plants or seeds provided herein are of a dark air-cured tobacco variety selected from the group consisting of Sumatra, Jatim, Dominican Cubano, Besuki, One sucker, Green River, Virginia sun-cured, and Paraguan Passado.

Dark fire-cured tobaccos are generally cured with low-burning wood fires on the floors of closed curing barns. Dark fire-cured tobaccos are typically used for making pipe blends, cigarettes, chewing tobacco, snuff, and strong-tasting cigars. Major growing regions for dark fire-cured tobaccos are Tennessee, Kentucky, and Virginia in the United States of America. In one aspect, modified tobacco plants or seeds provided herein are of a dark fire-cured tobacco variety selected from the group consisting of Narrow Leaf Madole, Improved Madole, Tom Rosson Madole, Newton's VH Madole, Little Crittenden, Green Wood, Little Wood, Small Stalk Black Mammoth, DT 508, DT 518, DT 592, KY 171, DF 911, DF 485, TN D94, TN D950, VA 309, and VA 359.

Oriental tobaccos are also referred to as Greek, aroma and Turkish tobaccos due to the fact that they are typically grown in eastern Mediterranean regions such as Turkey, Greece, Bulgaria, Macedonia, Syria, Lebanon, Italy, and Romania. The small plant size, small leaf size, and unique aroma properties of Oriental tobacco varieties are a result of their adaptation to the poor soil and stressful climatic conditions in which they have been developed. In one aspect, modified tobacco plants or seeds provided herein are of an Oriental tobacco variety selected from the group consisting of Izmir, Katerini, Samsun, Basma, Krumovgrad, Trabzon, Thesalian, Tasova, Sinop, Izmit, Hendek, Edirne, Semdinli, Adiyanman, Yayladag, Iskenderun, Duzce, Macedonian, Mavra, Prilep, Bafra, Bursa, Bucak, Bitlis, Balikesir, and any variety essentially derived from any one of the foregoing varieties.

The tobacco plants, plant parts, and tobacco material provided herein can be used in any tobacco product. As used herein, "tobacco product" is defined as any product made or derived from tobacco that is intended for human use or consumption. In an aspect, a tobacco product provided herein comprises cured components from a tobacco plant provided herein. In another aspect, a tobacco product provided herein comprises cured tobacco leaves from a tobacco plant provided herein. In an aspect, this disclosure provides a tobacco product comprising cured tobacco material from any tobacco plant provided herein.

In an aspect, this disclosure provides a tobacco product comprising cured tobacco material from a modified tobacco plant comprising a mutation in an endogenous gene encoding a polypeptide selected from the group consisting of a cyclin, a cyclin-dependent kinase (CDK), a CDK inhibitor, a MYB, and a WRKY transcription factor, where the mutation is not present in the endogenous gene in a control tobacco plant of the same variety, and where the modified tobacco plant comprises no suckers or reduced suckers after topping as compared to the control tobacco plant when grown under comparable growth conditions. In another aspect, this disclosure provides a tobacco product comprising cured tobacco material from a modified tobacco plant comprising a mutation in an endogenous gene encoding a polypeptide selected from the group consisting of a cyclin, a cyclin-dependent kinase (CDK), a CDK inhibitor, a MYB, and a WRKY transcription factor, where the mutation is not present in the endogenous gene in a control tobacco plant of the same variety.

In an aspect, this disclosure provides a method comprising preparing a tobacco product using cured tobacco material from a modified tobacco plant comprising a mutation in an endogenous gene encoding a polypeptide selected from the group consisting of a cyclin, a cyclin-dependent kinase (CDK), a CDK inhibitor, a MYB, and a WRKY transcription factor, wherein said mutation is not present in said endogenous gene in a control tobacco plant of the same variety, and wherein said modified tobacco plant comprises no suckers or reduced suckers after topping as compared to a control tobacco plant when grown under comparable growth conditions. In another aspect, this disclosure provides a method comprising preparing a tobacco product using cured tobacco material from a modified tobacco plant comprising a polynucleotide sequence encoding a polypeptide selected from the group consisting of a cyclin, a cyclin-dependent kinase (CDK), a CDK inhibitor, a MYB, and a WRKY transcription factor operably linked to a heterologous promoter, and wherein said modified tobacco plant comprises no suckers or reduced suckers after topping as compared to a control tobacco plant when grown under comparable growth conditions.

In an aspect, this disclosure provides a tobacco product comprising cured tobacco material from a modified tobacco plant comprising a polynucleotide sequence encoding a polypeptide selected from the group consisting of a cyclin, a cyclin-dependent kinase (CDK), a CDK inhibitor, a MYB, and a WRKY transcription factor operably linked to a heterologous promoter, and where the modified tobacco plant comprises no suckers or reduced suckers after topping as compared to a control tobacco plant when grown under comparable growth conditions. In another aspect, this disclosure provides a tobacco product comprising cured tobacco material from a modified tobacco plant comprising a polynucleotide sequence encoding a polypeptide selected from the group consisting of a cyclin, a cyclin-dependent kinase (CDK), a CDK inhibitor, a MYB, and a WRKY transcription factor operably linked to a heterologous promoter.

In an aspect, this disclosure provides a method comprising preparing a tobacco product using cured tobacco material from a modified tobacco plant comprising a polynucleotide sequence encoding a polypeptide selected from the group consisting of a cyclin, a cyclin-dependent kinase (CDK), a CDK inhibitor, a MYB, and a WRKY transcription factor operably linked to a heterologous promoter, wherein said modified tobacco plant comprises no suckers or reduced suckers after topping as compared to a control tobacco plant when grown under comparable growth conditions. In another aspect, this disclosure provides a method comprising preparing a tobacco product using cured tobacco material from a modified tobacco plant comprising a polynucleotide sequence encoding a polypeptide selected from the group consisting of a cyclin, a cyclin-dependent kinase (CDK), a CDK inhibitor, a MYB, and a WRKY transcription factor operably linked to a heterologous promoter.

In an aspect, this disclosure provides a tobacco product comprising cured tobacco material from a modified tobacco plant comprising a recombinant DNA construct comprising a heterologous promoter operably linked to a nucleic acid encoding at least one small RNA molecule capable of reducing the expression of an endogenous mRNA that encodes a polypeptide selected from the group consisting of a cyclin, a cyclin-dependent kinase (CDK), a CDK inhibitor, a MYB, and a WRKY transcription factor, where the modified tobacco plant comprises no suckers or reduced suckers after topping as compared to a control tobacco plant when grown under comparable growth conditions. In another aspect, this disclosure provides a tobacco product comprising cured tobacco material from a modified tobacco plant comprising a recombinant DNA construct comprising a heterologous promoter operably linked to a nucleic acid encoding at least one small RNA molecule capable of reducing the expression of an endogenous mRNA that encodes a polypeptide selected from the group consisting of a cyclin, a cyclin-dependent kinase (CDK), a CDK inhibitor, a MYB, and a WRKY transcription factor.

In an aspect, this disclosure provides a method comprising preparing a tobacco product using cured tobacco material from a modified tobacco plant comprising a recombinant DNA construct comprising a heterologous promoter operably linked to a nucleic acid encoding at least one small RNA molecule capable of reducing the expression of an endogenous mRNA that encodes a polypeptide selected from the group consisting of a cyclin, a cyclin-dependent kinase (CDK), a CDK inhibitor, a MYB, and a WRKY transcription factor, wherein said modified tobacco plant comprises no suckers or reduced suckers after topping as compared to a control tobacco plant when grown under comparable growth conditions. In another aspect, this disclosure provides a method comprising preparing a tobacco product using cured tobacco material from a modified tobacco plant comprising a recombinant DNA construct comprising a heterologous promoter operably linked to a nucleic acid encoding at least one small RNA molecule capable of reducing the expression of an endogenous mRNA that encodes a polypeptide selected from the group consisting of a cyclin, a cyclin-dependent kinase (CDK), a CDK inhibitor, a MYB, and a WRKY transcription factor.

Alkaloid compounds can be extracted, or isolated, from any tobacco plant or plant part provided herein. In an aspect, a tobacco product provided herein comprises an alkaloid extracted from a modified tobacco plant or part thereof. In another aspect, a tobacco product provided herein comprises nicotine extracted from a tobacco plant or tobacco plant part. In another aspect, a tobacco product provided herein comprises anatabine extracted from a tobacco plant or tobacco plant part. In another aspect, a tobacco product provided herein comprises anabasine extracted from a tobacco plant or tobacco plant part. In an aspect, a tobacco product provided herein comprises nornicotine extracted from a tobacco plant or plant part. In an aspect, a tobacco product provided herein comprises an alkaloid extracted from a modified tobacco plant, where the alkaloid is selected from the group consisting of nicotine, nornicotine, anatabine, and anabasine.

Alkaloid compounds extracted from tobacco plants or tobacco plant parts provided herein can be used to produce compositions suitable for use with non-combustible products. Exemplary non-combustible products include electronic cigarettes ("e-cigarettes"), electronic smoking articles, e-vapor products, aerosolized vapor products, and heated tobacco products. In an aspect, a non-combustible product provided herein comprises an alkaloid extracted from a tobacco plant or tobacco plant part provided herein. In an aspect, a non-combustible product provided herein comprises nicotine extracted from a tobacco plant or tobacco plant part provided herein. In an aspect, a non-combustible product provided herein comprises anabasine extracted from a tobacco plant or tobacco plant part provided herein. In an aspect, a non-combustible product provided herein comprises anatabine extracted from a tobacco plant or tobacco plant part provided herein. In an aspect, a non-combustible product provided herein comprises nornicotine extracted from a tobacco plant or tobacco plant part provided herein.

In one aspect, a non-combustible product provided herein is an e-cigarette. In another aspect, a non-combustible product provided herein is an electronic smoking article. In another aspect, a non-combustible product provided herein is an aerosolized vapor product. In another aspect, a non-combustible product provided herein is a heated tobacco product. In another aspect, a non-combustible product provided herein is an e-vapor product.

Tobacco products provided herein include, without limitation, cigarette products (e.g., cigarettes, bidi cigarettes, kreteks), cigar products (e.g., cigars, cigar wrapping tobacco, cigarillos), pipe tobacco products, products derived from tobacco, tobacco-derived nicotine products, smokeless tobacco products (e.g., moist snuff, dry snuff, chewing tobacco, moist smokeless tobacco, fine cut chewing tobacco, long cut chewing tobacco, pouched chewing tobacco, snus), films, chewables (e.g., gum), lozenges, dissolving strips, tabs, tablets, shaped parts, gels, consumable units, insoluble matrices, hollow shapes, reconstituted tobacco, expanded tobacco, and the like. See, for example, U.S. Patent Publication No. US 2006/0191548.

As used herein, "cigarette" refers a tobacco product having a "rod" and "filler". The cigarette "rod" includes the cigarette paper, filter, plug wrap (used to contain filtration materials), tipping paper that holds the cigarette paper (including the filler) to the filter, and all glues that hold these components together. The "filler" includes (1) all tobaccos, including but not limited to reconstituted and expanded tobacco, (2) non-tobacco substitutes (including but not limited to herbs, non-tobacco plant materials and other spices that may accompany tobaccos rolled within the cigarette paper), (3) casings, (4) flavorings, and (5) all other additives (that are mixed into tobaccos and substitutes and rolled into the cigarette).

In one aspect, this disclosure provides nicotine derived from and a method of producing nicotine from a modified tobacco plant provided herein for use in a product.

In one aspect, a method provided herein comprises preparing a tobacco product using a cured tobacco leaf from a modified tobacco plant provided herein.

As used herein, "reconstituted tobacco" refers to a part of tobacco filler made from tobacco dust and other tobacco scrap material, processed into sheet form and cut into strips to resemble tobacco. In addition to the cost savings, reconstituted tobacco is very important for its contribution to cigarette taste from processing flavor development using reactions between ammonia and sugars. In an aspect, a tobacco product provided herein comprises reconstituted tobacco derived from a modified tobacco plant.

As used herein, "expanded tobacco" refers to a part of tobacco filler which is processed through expansion of suitable gases so that the tobacco is "puffed" resulting in reduced density and greater filling capacity. It reduces the weight of tobacco used in cigarettes.

Tobacco products derived from plants of the present disclosure also include cigarettes and other smoking articles, particularly those smoking articles including filter elements, where the rod of smokable material includes cured tobacco within a tobacco blend. In an aspect, a tobacco product of the present disclosure is selected from the group consisting of a cigarette, a kretek, a bidi cigarette, a cigar, a cigarillo, a non-ventilated cigarette, a vented recess filter cigarette, pipe tobacco, snuff, snus, chewing tobacco, moist smokeless tobacco, fine cut chewing tobacco, long cut chewing tobacco, and pouched chewing tobacco product. In another aspect, a tobacco product of the present disclosure is selected from the group consisting of a gum, a tablet, a lozenge, and a dissolving strip.

In an aspect, a tobacco product provided herein comprises cured tobacco material from a modified tobacco plant. In another aspect, a tobacco product provided herein comprises cured tobacco leaf material from a modified tobacco plant. In another aspect, a tobacco product provided herein comprises cured tobacco stem material from a modified tobacco plant.

In another aspect, a tobacco product of the present disclosure is a smokeless tobacco product. Smokeless tobacco products are not combusted and include, but not limited to, chewing tobacco, moist smokeless tobacco, snus, and dry snuff. Chewing tobacco is coarsely divided tobacco leaf that is typically packaged in a large pouch-like package and used in a plug or twist. Moist smokeless tobacco is a moist, more finely divided tobacco that is provided in loose form or in pouch form and is typically packaged in round cans and used as a pinch or in a pouch placed between an adult tobacco consumer's cheek and gum. Snus is a heat treated smokeless tobacco. Dry snuff is finely ground tobacco that is placed in the mouth or used nasally. In a further aspect, a tobacco product of the present disclosure is selected from the group consisting of loose leaf chewing tobacco, plug chewing tobacco, moist snuff, and nasal snuff.

The present disclosure further provides a method manufacturing a tobacco product comprising tobacco material from modified tobacco plants provided herein. In one aspect, methods provided herein comprise conditioning aged tobacco material made from modified tobacco plants provided herein to increase its moisture content from between about 12.5% and about 13.5% to about 21%, blending the conditioned tobacco material to produce a desirable blend. In one aspect, the method of manufacturing a tobacco product provided herein further comprises casing or flavoring the blend. Generally, during the casing process, casing or sauce materials are added to blends to enhance their quality by balancing the chemical composition and to develop certain desired flavor characteristics. Further details for the casing process can be found in *Tobacco Production, Chemistry and Technology*, Edited by L. Davis and M. Nielsen, Blackwell Science, 1999.

This disclosure provides tobacco material from modified tobacco plants or parts thereof. Tobacco material obtained from tobacco plants, cells, lines, varieties, or hybrids of the present disclosure can be used to make tobacco products. In an aspect, tobacco material comprises leaf material. In an aspect, tobacco material comprises stem material. In an aspect, tobacco material comprises fresh tobacco material. In another aspect, tobacco material comprises dried tobacco material. In a further aspect, tobacco material comprises cured tobacco material. In still another aspect, tobacco material comprises fermented tobacco material. In an aspect, tobacco material provided herein can be used in any tobacco product provided herein. In an aspect, cured tobacco material provided herein comprises air-cured tobacco material. In another aspect, cured tobacco material provided herein comprises fire-cured tobacco material. In another aspect, cured tobacco material provided herein comprises sun-cured tobacco material. In another aspect, cured tobacco material provided herein comprises flue-cured tobacco material. In another aspect, cured tobacco material provided herein is selected from the group consisting of air-cured tobacco material, fire-cured tobacco material, sun-cured tobacco material, and flue-cured tobacco material.

Tobacco material provided herein can be also processed using methods including, but not limited to, heat treatment (e.g., cooking, toasting), flavoring, enzyme treatment, expansion and/or curing. Both fermented and non-fermented tobaccos can be processed using these techniques. Examples of suitable processed tobaccos include dark air-cured, dark fire cured, burley, flue cured, and cigar filler or wrapper, as well as the products from the whole leaf stemming operation. In one aspect, tobacco fibers include up to 70% dark tobacco on a fresh weight basis. For example, tobacco can be conditioned by heating, sweating and/or pasteurizing steps as described in U.S. Publication Nos. 2004/0118422 or 2005/0178398.

Tobacco material provided herein can be subject to fermentation. Fermenting typically is characterized by high initial moisture content, heat generation, and a 10 to 20% loss of dry weight. See, e.g., U.S. Pat. Nos. 4,528,993; 4,660,577; 4,848,373; and 5,372,149. In addition to modifying the aroma of the leaf, fermentation can change either or both the color and texture of a leaf. Also during the fermentation process, evolution gases can be produced, oxygen can be taken up, the pH can change, and the amount of water retained can change. See, for example, U.S. Publication No. 2005/0178398 and Tso (1999, Chapter 1 in Tobacco, Production, Chemistry and Technology, Davis & Nielsen, eds., Blackwell Publishing, Oxford). Cured, or cured and fermented tobacco can be further processed (e.g., cut, expanded, blended, milled or comminuted) prior to incorporation into the oral product. The tobacco, in some cases, is long cut fermented cured moist tobacco having an oven volatiles content of between 48 and 50 weight percent prior to mixing with a copolymer and, optionally, flavorants and other additives.

In one aspect, tobacco material provided herein can be processed to a desired size. In certain aspects, tobacco fibers can be processed to have an average fiber size of less than 200 micrometers. In one aspect, tobacco fibers are between 75 and 125 micrometers. In another aspect, tobacco fibers are processed to have a size of 75 micrometers or less. In one aspect, tobacco fibers include long cut tobacco, which can be cut or shredded into widths of about 10 cuts/inch up to about 110 cuts/inch and lengths of about 0.1 inches up to about 1 inch. Double cut tobacco fibers can have a range of particle sizes such that about 70% of the double cut tobacco fibers falls between the mesh sizes of −20 mesh and 80 mesh.

Tobacco material provided herein can be processed to have a total oven volatiles content of about 10% by weight or greater; about 20% by weight or greater; about 40% by weight or greater; about 15% by weight to about 25% by weight; about 20% by weight to about 30% by weight; about 30% by weight to about 50% by weight; about 45% by weight to about 65% by weight; or about 50% by weight to about 60% by weight. Those of skill in the art will appreciate that "moist" tobacco typically refers to tobacco that has an oven volatiles content of between about 40% by weight and about 60% by weight (e.g., about 45% by weight to about 55% by weight, or about 50% by weight). As used herein, "oven volatiles" are determined by calculating the percentage of weight loss for a sample after drying the sample in a pre-warmed forced draft oven at 110° C. for 3.25 hours. An oral product can have a different overall oven volatiles content than the oven volatiles content of the tobacco fibers used to make the oral product. The processing steps described herein can reduce or increase the oven volatiles content.

The following exemplary, non-limiting embodiments are envisioned:

1. A modified tobacco plant comprising a mutation in an endogenous gene encoding a polypeptide selected from the group consisting of a cyclin, a cyclin-dependent kinase (CDK), a CDK inhibitor, a MYB, and a WRKY transcription factor, wherein said mutation is not present in said endogenous gene in a control tobacco plant of the same variety, and wherein said modified tobacco plant comprises no suckers or reduced suckers after topping as compared to said control tobacco plant when grown under comparable growth conditions.

2. A modified tobacco plant comprising a mutation in an endogenous gene encoding a polypeptide selected from the group consisting of a cyclin, a cyclin-dependent kinase (CDK), a CDK inhibitor, a MYB, and a WRKY transcription factor, wherein said mutation is not present in said endogenous gene in a control tobacco plant of the same variety.

3. A modified tobacco plant comprising a polynucleotide sequence encoding a polypeptide selected from the group consisting of a cyclin, a cyclin-dependent kinase (CDK), a CDK inhibitor, a MYB, and a WRKY transcription factor operably linked to a heterologous promoter, wherein said modified tobacco plant comprises no suckers or reduced suckers after topping as compared to a control tobacco plant when grown under comparable growth conditions.

4. A modified tobacco plant comprising a polynucleotide sequence encoding a polypeptide selected from the group consisting of a cyclin, a cyclin-dependent kinase (CDK), a CDK inhibitor, a MYB, and a WRKY transcription factor operably linked to a heterologous promoter.

5. A modified tobacco plant comprising a recombinant DNA construct comprising a heterologous promoter operably linked to a nucleic acid encoding at least one small RNA molecule capable of reducing the expression of an endogenous mRNA that encodes a polypeptide selected from the group consisting of a cyclin, a cyclin-dependent kinase (CDK), a CDK inhibitor, a MYB, and a WRKY transcription factor, wherein said modified tobacco plant comprises no suckers or reduced suckers after topping as compared to a control tobacco plant when grown under comparable growth conditions.

6. A modified tobacco plant comprising a recombinant DNA construct comprising a heterologous promoter operably linked to a nucleic acid encoding at least one small RNA molecule capable of reducing the expression of an endogenous mRNA that encodes a polypeptide selected from the group consisting of a cyclin, a cyclin-dependent kinase (CDK), a CDK inhibitor, a MYB, and a WRKY transcription factor.

7. The modified tobacco plant of embodiment 1 or 2, wherein said mutation comprises a mutation selected from the group consisting of an insertion, a deletion, a substitution, and an inversion.

8. The modified tobacco plant of any one of embodiments 1, 2, or 7, wherein said mutation comprises a null mutation.

9. The modified tobacco plant of any one of embodiments 1, 2, 7, or 8, wherein said mutation results in a premature stop codon in an mRNA transcript of said endogenous gene.

10. The modified tobacco plant of any one of embodiments 1, 2, or 7-9, wherein said mutation results in a truncation of said polypeptide.

11. The modified tobacco plant of any one of embodiments 1, 2, or 7-10, wherein said mutation is positioned within an exon of said endogenous gene.

12. The modified tobacco plant of any one of embodiments 1, 2, or 7-10, wherein said mutation is positioned within an intron of said endogenous gene.

13. The modified tobacco plant of any one of embodiments 1, 2, or 7, wherein said mutation is positioned within a 5'-untranslated region (UTR) or a 3'-UTR of said endogenous gene.

14. The modified tobacco plant of any one of embodiments 1, 2, or 7, wherein said mutation is positioned within a promoter of said endogenous gene.

15. The modified tobacco plant of any one of embodiments 1, 2, or 7-14, wherein said endogenous gene comprises a polynucleotide sequence at least 80% identical to a polynucleotide sequence selected from the group consisting of SEQ ID NOs: 1-44 and 113.

16. The modified tobacco plant of any one of embodiments 1, 2, or 7-15, wherein said endogenous gene encodes a polypeptide comprising an amino acid sequence at least 80% identical or similar to an amino acid sequence selected from the group consisting of SEQ ID NOs: 45-88 and 114.

17. The modified tobacco plant of any one of embodiments 1, 2, or 7-16, wherein said mutation results in reduced level of expression of said endogenous gene as compared to said control tobacco plant.

18. The modified tobacco plant of any one of embodiments 1, 2, or 7-16, wherein said mutation results in increased level of expression of said endogenous gene as compared to said control tobacco plant.

19. The modified tobacco plant of any one of embodiments 1, 2, or 7-16, wherein said mutation results in reduced level of activity of said polypeptide as compared to said control tobacco plant.

20. The modified tobacco plant of any one of embodiments 1, 2, or 7-16, wherein said mutation results in increased level of activity of said polypeptide as compared to said control tobacco plant.

21. The modified tobacco plant of any one of embodiments 3-6, wherein said heterologous promoter comprises an axillary meristem-specific promoter.

22. The modified tobacco plant of any one of embodiments 3-6, wherein said heterologous promoter comprises an axillary meristem-preferred promoter.

23. The modified tobacco plant of any one of embodiments 3-6, wherein said heterologous promoter comprises a polynucleotide sequence at least 90% identical to a polynucleotide sequence selected from the group consisting of SEQ ID NOs: 89-109.

24. The modified tobacco plant of any one of embodiments 3-6, wherein said small RNA molecule is selected from the group consisting of a double-stranded RNA, a small interfering RNA (siRNA), a trans-acting siRNA, and a microRNA.

25. The modified tobacco plant of embodiments 5 or 6, wherein said small RNA molecule comprises between 18 nucleotides and 30 nucleotides.

26. The modified tobacco plant of embodiments 5 or 6, wherein said small RNA molecule comprises a polynucleotide sequence having at least 90% identity or complementarity with said endogenous mRNA.

27. The modified tobacco plant of embodiments 5 or 6, wherein said small RNA molecule comprises between 18 nucleotides and 30 nucleotides.

28. The modified tobacco plant of embodiments 5 or 6, wherein said small RNA molecule comprises a polynucleotide sequence having at least 90% identity or complementarity with a polynucleotide sequence selected from the group consisting of SEQ ID NOs: 1-44 and 113.

29. The modified tobacco plant of embodiments 5 or 6, wherein said small RNA molecule comprises a polynucleotide sequence identical to, or complementary to, at least 18 contiguous nucleotides of a polynucleotide sequence selected from the group consisting of SEQ ID NOs: 1-44 and 113.

30. The modified tobacco plant of any one of embodiments 1-29, wherein said polypeptide is a cyclin.

31. The modified tobacco plant of any one of embodiments 1-29, wherein said polypeptide is a CDK.

32. The modified tobacco plant of any one of embodiments 1-29, wherein said polypeptide is a CDK inhibitor.

33. The modified tobacco plant of any one of embodiments 1-29, wherein said polypeptide is a MYB.

34. The modified tobacco plant of any one of embodiments 1-29, wherein said polypeptide is a WRKY transcription factor.

35. The modified tobacco plant of embodiment 30, wherein said cyclin is encoded by a polynucleotide sequence at least 80% identical to SEQ ID NOs: 6-32.

36. The modified tobacco plant of embodiment 30, wherein said cyclin comprises an amino acid sequence at least 80% identical or similar to an amino acid sequence selected from the group consisting of SEQ ID NOs: 50-76.
37. The modified tobacco plant of embodiment 31, wherein said CDK is encoded by a polynucleotide sequence at least 80% identical to SEQ ID NOs: 1-4.
38. The modified tobacco plant of embodiment 31, wherein said CDK comprises an amino acid sequence at least 80% identical or similar to an amino acid sequence at least 80% identical or similar to an amino acid sequence selected from the group consisting of SEQ ID NOs: 45-48.
39. The modified tobacco plant of embodiment 32, wherein said CDK inhibitor is encoded by a polynucleotide sequence at least 80% identical to SEQ ID NO: 5.
40. The modified tobacco plant of embodiment 32, wherein said CDK inhibitor comprises an amino acid sequence at least 80% identical or similar to an amino acid sequence selected from the group consisting of SEQ ID NO: 49.
41. The modified tobacco plant of embodiment 33, wherein said MYB is encoded by a polynucleotide sequence at least 80% identical to SEQ ID NOs: 33-44.
42. The modified tobacco plant of embodiment 33, wherein said MYB comprises an amino acid sequence at least 80% identical or similar to an amino acid sequence at least 80% identical or similar to an amino acid sequence selected from the group consisting of SEQ ID NOs: 77-88.
43. The modified tobacco plant of embodiment 34, wherein said WRKY transcription factor is encoded by a polynucleotide sequence at least 80% identical to SEQ ID NO: 113.
44. The modified tobacco plant of embodiment 34, wherein said WRKY transcription factor comprises an amino acid sequence at least 80% identical or similar to an amino acid sequence at least 80% identical or similar to SEQ ID NO: 114.
45. The modified tobacco plant of any one of embodiments 1-44, wherein said modified tobacco plant is of a tobacco variety selected from the group consisting of a flue-cured variety, a bright variety, a Burley variety, a Virginia variety, a Maryland variety, a dark variety, a Galpao variety, an Oriental variety, and a Turkish variety.
46. The modified tobacco plant of any one of embodiments 1-45, wherein said modified tobacco plant is selected from the group consisting of a BU 64 plant, a CC 101 plant, a CC 200 plant, a CC 13 plant, a CC 27 plant, a CC 33 plant, a CC 35 plant, a CC 37 plant, a CC 65 plant, a CC 67 plant, a CC 301 plant, a CC 400 plant, a CC 500 plant, CC 600 plant, a CC 700 plant, a CC 800 plant, a CC 900 plant, a CC 1063 plant, a Coker 176 plant, a Coker 319 plant, a Coker 371 Gold plant, a Coker 48 plant, a CU 263 plant, a DF911 plant, a Galpao plant, a GL 26H plant, a GL 338 plant, a GL 350 plant, a GL 395 plant, a GL 600 plant, a GL 737 plant, a GL 939 plant, a GL 973 plant, a GF 157 plant, a GF 318 plant, an RJR 901 plant, an HB 04P plant, a K 149 plant, a K 326 plant, a K 346 plant, a K 358 plant, a K394 plant, a K 399 plant, a K 730 plant, an NC 196 plant, an NC 37NF plant, an NC 471 plant, an NC 55 plant, an NC 92 plant, an NC2326 plant, an NC 95 plant, an NC 925 plant, a PVH 1118 plant, a PVH 1452 plant, a PVH 2110 plant, a PVH 2254 plant, a PVH 2275 plant, a VA 116 plant, a VA 119 plant, a KDH 959 plant, a KT 200 plant, a KT204LC plant, a KY 10 plant, a KY 14 plant, a KY 160 plant, a KY 17 plant, a KY 171 plant, a KY 907 plant, a KY 907LC plant, a KTY14×L8 LC plant, a Little Crittenden plant, a McNair 373 plant, a McNair 944 plant, a male sterile KY 14×L8 plant, a Narrow Leaf Madole plant, a MS KY171 plant, a Narrow Leaf Madole (phph) plant, a MS Narrow Leaf Madole plant, a MS TND950 plant, a PD 7302LC plant, a PD 7305LC plant, a PD 7309LC plant, a PD 7312LC plant, a PD 7318LC plant, a PD 7319LC plant, a MSTKS 2002 plant, a TKF 2002 plant, a TKF 6400 plant, a TKF 4028 plant, a TKF 4024 plant, a KT206LC plant, a KT209LC plant, a KT210LC plant, a KT212LC plant, an NC 100 plant, an NC 102 plant, an NC 2000 plant, an NC 291 plant, an NC 297 plant, an NC 299 plant, an NC 3 plant, an NC 4 plant, an NC 5 plant, an NC 6 plant, an NC7 plant, an NC 606 plant, an NC 71 plant, an NC 72 plant, an NC 810 plant, an NC BH 129 plant, an NC 2002 plant, a Neal Smith Madole plant, an OXFORD 207 plant, a 'Perique' plant, a PVH03 plant, a PVH09 plant, a PVH19 plant, a PVH50 plant, a PVH51 plant, an R 610 plant, an R 630 plant, an R 7-11 plant, an R 7-12 plant, an RG 17 plant, an RG 81 plant, an RG H51 plant, an RGH 4 plant, an RGH 51 plant, an RS 1410 plant, a Speight 168 plant, a Speight 172 plant, a Speight 179 plant, a Speight 210 plant, a Speight 220 plant, a Speight 225 plant, a Speight 227 plant, a Speight 234 plant, a Speight G-28 plant, a Speight G-70 plant, a Speight H-6 plant, a Speight H20 plant, a Speight NF3 plant, a TI 1406 plant, a TI 1269 plant, a TN 86 plant, a TN86LC plant, a TN 90 plant, a TN90LC plant, a TN 97 plant, a TN97LC plant, a TN D94 plant, a TN D950 plant, a TR (Tom Rosson) Madole plant, a VA 309 plant, and a VA 359 plant.
47. The modified tobacco plant of any one of embodiments 1-46, wherein said modified tobacco plant is a hybrid.
48. The modified tobacco plant of any one of embodiments 1-47, wherein said modified tobacco plant is male sterile or cytoplasmically male sterile.
49. The modified tobacco plant of any one of embodiments 1-47, wherein said modified tobacco plant is female sterile.
50. The modified tobacco plant of any one of embodiments 1, 3 or [0008], wherein said reduced suckers comprises fewer total suckers, smaller average sucker size, or both, as compared to suckers of said control tobacco plant when grown under comparable growth conditions.
51. The modified tobacco plant of embodiment 50, wherein said smaller average sucker size comprises a measurement selected from the group consisting of reduced average mass, reduced average length, reduced average diameter, or any combination thereof, as compared to suckers of said control tobacco plant when grown under comparable growth conditions.
52. The modified tobacco plant of any one of embodiments 1-51, wherein said modified plant has increased leaf yield mass as compared to said control tobacco plant when grown under comparable growth conditions.
53. The modified tobacco plant of embodiment 52, wherein said increased leaf yield mass comprises an increase of at least 0.5%.
54. A tobacco leaf of the modified tobacco plant of any one of embodiments 1-53.
55. A tobacco seed of the modified tobacco plant of any one of c embodiments 1-53.
56. The tobacco leaf of embodiment 54, wherein said tobacco leaf is a cured tobacco leaf.
57. The tobacco leaf of embodiment 56, wherein said cured tobacco leaf is selected from the group consisting of is air-cured tobacco leaf, fire-cured tobacco leaf, sun-cured tobacco leaf, and flue-cured tobacco leaf.

58. A tobacco product comprising an alkaloid extracted from the modified tobacco plant, or a part thereof, of any one of embodiments 1-53.
59. The tobacco product of embodiment 58, wherein said alkaloid is selected from the group consisting of nicotine, nornicotine, anatabine, and anabasine.
60. The tobacco product of embodiment 58 or 59, wherein said tobacco product is selected from the group consisting of a cigarette, a kretek, a bidi cigarette, a cigar, a cigarillo, a non-ventilated cigarette, a vented recess filter cigarette, pipe tobacco, snuff, snus, chewing tobacco, moist smokeless tobacco, fine cut chewing tobacco, long cut chewing tobacco, and pouched chewing tobacco product.
61. The tobacco product of embodiment 58 or 59, wherein said tobacco product is selected from the group consisting of a gum, a tablet, a lozenge, and a dissolving strip.
62. The tobacco product of embodiment 58 or 59, wherein said tobacco product is a non-combustible product.
63. The tobacco product of embodiment 62, wherein said non-combustible product is selected from the group consisting of an electronic cigarette, an electronic smoking article, an aerosolized vapor product, and a heated tobacco product.
64. A tobacco product comprising cured tobacco material from a modified tobacco plant comprising a mutation in an endogenous gene encoding a polypeptide selected from the group consisting of a cyclin, a cyclin-dependent kinase (CDK), a CDK inhibitor, a MYB, and a WRKY transcription factor, wherein said mutation is not present in said endogenous gene in a control tobacco plant of the same variety, and wherein said modified tobacco plant comprises no suckers or reduced suckers after topping as compared to said control tobacco plant when grown under comparable growth conditions.
65. A tobacco product comprising cured tobacco material from a modified tobacco plant comprising a mutation in an endogenous gene encoding a polypeptide selected from the group consisting of a cyclin, a cyclin-dependent kinase (CDK), a CDK inhibitor, a MYB, and a WRKY transcription factor, wherein said mutation is not present in said endogenous gene in a control tobacco plant of the same variety.
66. A tobacco product comprising cured tobacco material from a modified tobacco plant comprising a polynucleotide sequence encoding a polypeptide selected from the group consisting of a cyclin, a cyclin-dependent kinase (CDK), a CDK inhibitor, a MYB, and a WRKY transcription factor operably linked to a heterologous promoter, and wherein said modified tobacco plant comprises no suckers or reduced suckers after topping as compared to a control tobacco plant when grown under comparable growth conditions.
67. A tobacco product comprising cured tobacco material from a modified tobacco plant comprising a polynucleotide sequence encoding a polypeptide selected from the group consisting of a cyclin, a cyclin-dependent kinase (CDK), a CDK inhibitor, a MYB, and a WRKY transcription factor operably linked to a heterologous promoter.
68. A tobacco product comprising cured tobacco material from a modified tobacco plant comprising a recombinant DNA construct comprising a heterologous promoter operably linked to a nucleic acid encoding at least one small RNA molecule capable of reducing the expression of an endogenous mRNA that encodes a polypeptide selected from the group consisting of a cyclin, a cyclin-dependent kinase (CDK), a CDK inhibitor, a MYB, and a WRKY transcription factor, wherein said modified tobacco plant comprises no suckers or reduced suckers after topping as compared to a control tobacco plant when grown under comparable growth conditions.
69. A tobacco product comprising cured tobacco material from a modified tobacco plant comprising a recombinant DNA construct comprising a heterologous promoter operably linked to a nucleic acid encoding at least one small RNA molecule capable of reducing the expression of an endogenous mRNA that encodes a polypeptide selected from the group consisting of a cyclin, a cyclin-dependent kinase (CDK), a CDK inhibitor, a MYB, and a WRKY transcription factor.
70. The tobacco product of any one of embodiments 64-69, wherein said tobacco product is selected from the group consisting of a cigarette, a kretek, a bidi cigarette, a cigar, a cigarillo, a non-ventilated cigarette, a vented recess filter cigarette, pipe tobacco, snuff, snus, chewing tobacco, moist smokeless tobacco, fine cut chewing tobacco, long cut chewing tobacco, and a pouched chewing tobacco product.
71. The tobacco product of any one of embodiments 64-69, wherein said cured tobacco material is from a tobacco variety selected from the group consisting of a flue-cured variety, a bright variety, a Burley variety, a Virginia variety, a Maryland variety, a dark variety, an Oriental variety, and a Turkish variety.
72. The tobacco product of any one of embodiments 64-69, wherein said cured tobacco material is selected from the group consisting of air-cured tobacco material, fire-cured tobacco material, sun-cured tobacco material, and flue-cured tobacco material.
73. The tobacco product of any one of embodiments 64-69, wherein said cured tobacco material comprises cured tobacco leaf material.
74. The tobacco product of any one of embodiments 64-69, wherein said cured tobacco material comprises cured tobacco stem material.
75. A method for producing a modified tobacco plant comprising:
   (a) inducing a mutation in at least one tobacco cell at a genomic locus encoding a polypeptide selected from the group consisting of a cyclin, a cyclin-dependent kinase (CDK), a CDK inhibitor, a MYB, and a WRKY transcription factor;
   (b) selecting at least one tobacco cell comprising said mutation from step (a); and (c) regenerating a modified tobacco plant from said at least one tobacco cell selected in step (b), wherein said modified tobacco plant comprises no suckers or reduced suckers after topping as compared to a control tobacco plant lacking said mutation when grown under comparable growth conditions.
76. A method for producing a modified tobacco plant comprising:
   (a) introducing a recombinant DNA construct to at least one tobacco cell, wherein said recombinant DNA construct comprises a heterologous promoter operably linked to a nucleic acid encoding a polypeptide selected from the group consisting of a cyclin, a cyclin-dependent kinase (CDK), a CDK inhibitor, a MYB, and a WRKY transcription factor;
   (b) selecting at least one tobacco cell comprising said recombinant DNA construct; and
   (c) regenerating a modified tobacco plant from said at least one tobacco cell selected in step (b), wherein said modified tobacco plant comprises no suckers or reduced suckers after topping as compared to a control tobacco plant lacking said recombinant DNA construct when grown under comparable growth conditions.

77. A method for producing a modified tobacco plant comprising:
(a) introducing a recombinant DNA construct to at least one tobacco cell, wherein said recombinant DNA construct comprises a heterologous promoter operably linked to a nucleic acid encoding at least one small RNA molecule capable of reducing the expression of an endogenous mRNA that encodes a polypeptide selected from the group consisting of a cyclin, a cyclin-dependent kinase (CDK), a CDK inhibitor, a MYB, and a WRKY transcription factor;
(b) selecting at least one tobacco cell comprising said recombinant DNA construct; and
(c) regenerating a modified tobacco plant from said at least one tobacco cell selected in step (b), wherein said modified tobacco plant comprises no suckers or reduced suckers after topping as compared to a control tobacco plant lacking said recombinant DNA construct when grown under comparable growth conditions.

78. The method of embodiment 75, wherein said inducing comprises the use of an agent selected from the group consisting of: a chemical mutagen, irradiation, a transposon, *Agrobacterium*, and a nuclease.

79. The method of embodiment 78, wherein said nuclease is selected from the group consisting of a meganuclease, a zinc-finger nuclease, a transcription activator-like effector nuclease, a CRISPR/Cas9 nuclease, a CRISPR/Cpf1 nuclease, a CRISPR/CasX nuclease, a CRISPR/CasY nuclease, a Csm1 nuclease, or any combination thereof.

80. The method of embodiment 78, wherein said chemical mutagen comprises ethyl methanesulfonate.

81. The method of embodiment 78, wherein said irradiation comprises gamma rays, X-rays, or ionizing radiation.

82. The method of embodiment 77, wherein said small RNA molecule is selected from the group consisting of a double-stranded RNA, a small interfering RNA (siRNA), a trans-acting siRNA, and a microRNA.

83. The method of embodiment 77 or 82, wherein said small RNA molecule comprises at least 18 nucleotides.

84. The method of any one of embodiments 77, 82, or 83, wherein said small RNA molecule comprises at least 90% identity or complementarity with said endogenous mRNA.

85. The method of any one of embodiments 77, 82, or 84, wherein said small RNA molecule comprises between 18 nucleotides and 30 nucleotides.

86. The method of any one of embodiments 77 or 82-85, wherein said small RNA molecule comprises at least 90% identity or complementarity with a polynucleotide sequence selected from the group consisting of SEQ ID NOs: 1-44 and 113.

87. The method of any one of embodiments 77 or 82-86, wherein said endogenous mRNA comprises a sequence identical to, or complementary to, at least 18 contiguous nucleotides of a polynucleotide sequence selected from the group consisting of SEQ ID NOs: 1-44 and 113.

88. The method of any one of embodiments 75-87, wherein said at least one tobacco cell is a tobacco protoplast cell.

89. The method of any one of embodiments 75-87, wherein said at least one tobacco cell is a tobacco callus cell.

90. The method of any one of embodiments 75-87, wherein said at least one tobacco cell is selected from the group consisting of a seed cell, a fruit cell, a leaf cell, a cotyledon cell, a hypocotyl cell, a meristem cell, an embryo cell, an endosperm cell, a root cell, a shoot cell, a stem cell, a flower cell, an inflorescence cell, a stalk cell, a pedicel cell, a style cell, a stigma cell, a receptacle cell, a petal cell, a sepal cell, a pollen cell, an anther cell, a filament cell, an ovary cell, an ovule cell, a pericarp cell, and a phloem cell.

91. The method of any one of embodiments 75-77, wherein said method further comprises:
(d) growing said modified tobacco plant regenerated in step (c).

92. The method of embodiment 91, wherein said method further comprises:
(e) crossing said modified tobacco plant grown in step (d) with a second tobacco plant; and
(f) obtaining at least one seed from said crossing in step (e).

93. The method of embodiments 76 or 77, wherein said heterologous promoter comprises an axillary meristem-specific promoter.

94. The modified tobacco plant of embodiment 93, wherein said heterologous promoter comprises a polynucleotide sequence at least 90% identical to a polynucleotide sequence selected from the group consisting of SEQ ID NOs: 89-109.

95. The method of embodiment 75, wherein said genomic locus comprises a polynucleotide sequence at least 80% identical to a polynucleotide sequence selected from the group consisting of SEQ ID NOs: 1-44 and 113.

96. The method of embodiment 75, wherein said genomic locus encodes a polypeptide comprising an amino acid sequence at least 80% identical or similar to an amino acid sequence selected from the group consisting of SEQ ID NOs: 45-88 and 114.

97. The method of embodiment 75, wherein said mutation results in reduced expression of said genomic locus as compared to said control tobacco plant.

98. The method of embodiment 75, wherein said mutation results in increased expression of said genomic locus as compared to said control tobacco plant.

99. The method of embodiment 75, wherein said mutation results in reduced activity of said polypeptide as compared to said control tobacco plant.

100. The method of embodiment 75, wherein said mutation results in increased activity of said polypeptide as compared to said control tobacco plant.

101. The method of any one of embodiments 75-100, wherein said polypeptide is a cyclin.

102. The method of any one of embodiments 75-100, wherein said polypeptide is a CDK.

103. The method of any one of embodiments 75-100, wherein said polypeptide is a CDK inhibitor.

104. The method of any one of embodiments 75-100, wherein said polypeptide is a MYB.

105. The method of any one of embodiments 75-100, wherein said polypeptide is a WRKY transcription factor.

106. The method of embodiment 101, wherein said cyclin is encoded by a polynucleotide sequence at least 80% identical to SEQ ID NOs: 6-32.

107. The method of embodiment 101, wherein said cyclin comprises an amino acid sequence at least 80% identical or similar to an amino acid sequence selected from the group consisting of SEQ ID NOs: 50-76.

108. The method of embodiment 102, wherein said CDK is encoded by a polynucleotide sequence at least 80% identical to SEQ ID NOs: 1-4.

109. The method of embodiment 102, wherein said CDK comprises an amino acid sequence at least 80% identical or similar to an amino acid sequence selected from the group consisting of SEQ ID NOs: 45-48.

110. The method of embodiment 103, wherein said CDK inhibitor is encoded by a polynucleotide sequence at least 80% identical to SEQ ID NO: 5.

111. The method of embodiment 103, wherein said CDK inhibitor comprises an amino acid sequence at least 80% identical or similar to an amino acid sequence selected from the group consisting of SEQ ID NO: 49.

112. The method of embodiment 104, wherein said MYB is encoded by a polynucleotide sequence at least 80% identical to SEQ ID NOs: 33-44.

113. The method of embodiment 104, wherein said MYB comprises an amino acid sequence at least 80% identical or similar to an amino acid sequence selected from the group consisting of SEQ ID NOs: 77-88.

114. The method of embodiment 105, wherein said WRKY transcription factor is encoded by a polynucleotide sequence at least 80% identical to SEQ ID NO: 113.

115. The method of embodiment 105, wherein said WRKY transcription factor comprises an amino acid sequence at least 80% identical or similar to SEQ ID NO: 114.

116. The method of any one of embodiments 75-114, wherein said modified tobacco plant is of a tobacco variety selected from the group consisting of a flue-cured variety, a bright variety, a Burley variety, a Virginia variety, a Maryland variety, a dark variety, an Oriental variety, and a Turkish variety.

117. The method of any one of embodiments 75-114, wherein said modified tobacco plant is selected from the group consisting of a BU 64 plant, a CC 101 plant, a CC 200 plant, a CC 13 plant, a CC 27 plant, a CC 33 plant, a CC 35 plant, a CC 37 plant, a CC 65 plant, a CC 67 plant, a CC 301 plant, a CC 400 plant, a CC 500 plant, CC 600 plant, a CC 700 plant, a CC 800 plant, a CC 900 plant, a CC 1063 plant, a Coker 176 plant, a Coker 319 plant, a Coker 371 Gold plant, a Coker 48 plant, a CU 263 plant, a DF911 plant, a Galpao plant, a GL 26H plant, a GL 338 plant, a GL 350 plant, a GL 395 plant, a GL 600 plant, a GL 737 plant, a GL 939 plant, a GL 973 plant, a GF 157 plant, a GF 318 plant, an RJR 901 plant, an HB 04P plant, a K 149 plant, a K 326 plant, a K 346 plant, a K 358 plant, a K394 plant, a K 399 plant, a K 730 plant, an NC 196 plant, an NC 37NF plant, an NC 471 plant, an NC 55 plant, an NC 92 plant, an NC2326 plant, an NC 95 plant, an NC 925 plant, a PVH 1118 plant, a PVH 1452 plant, a PVH 2110 plant, a PVH 2254 plant, a PVH 2275 plant, a VA 116 plant, a VA 119 plant, a KDH 959 plant, a KT 200 plant, a KT204LC plant, a KY 10 plant, a KY 14 plant, a KY 160 plant, a KY 17 plant, a KY 171 plant, a KY 907 plant, a KY 907LC plant, a KTY14×L8 LC plant, a Little Crittenden plant, a McNair 373 plant, a McNair 944 plant, a male sterile KY 14×L8 plant, a Narrow Leaf Madole plant, a MS KY171 plant, a Narrow Leaf Madole (phph) plant, a MS Narrow Leaf Madole plant, a MS TND950 plant, a PD 7302LC plant, a PD 7305LC plant, a PD 7309LC plant, a PD 7312LC plant, a PD 7318LC plant, a PD 7319LC plant, a MSTKS 2002 plant, a TKF 2002 plant, a TKF 6400 plant, a TKF 4028 plant, a TKF 4024 plant, a KT206LC plant, a KT209LC plant, a KT210LC plant, a KT212LC plant, an NC 100 plant, an NC 102 plant, an NC 2000 plant, an NC 291 plant, an NC 297 plant, an NC 299 plant, an NC 3 plant, an NC 4 plant, an NC 5 plant, an NC 6 plant, an NC7 plant, an NC 606 plant, an NC 71 plant, an NC 72 plant, an NC 810 plant, an NC BH 129 plant, an NC 2002 plant, a Neal Smith Madole plant, an OXFORD 207 plant, a 'Perique' plant, a PVH03 plant, a PVH09 plant, a PVH19 plant, a PVH50 plant, a PVH51 plant, an R 610 plant, an R 630 plant, an R 7-11 plant, an R 7-12 plant, an RG 17 plant, an RG 81 plant, an RG H51 plant, an RGH 4 plant, an RGH 51 plant, an RS 1410 plant, a Speight 168 plant, a Speight 172 plant, a Speight 179 plant, a Speight 210 plant, a Speight 220 plant, a Speight 225 plant, a Speight 227 plant, a Speight 234 plant, a Speight G-28 plant, a Speight G-70 plant, a Speight H-6 plant, a Speight H20 plant, a Speight NF3 plant, a TI 1406 plant, a TI 1269 plant, a TN 86 plant, a TN86LC plant, a TN 90 plant, a TN90LC plant, a TN 97 plant, a TN97LC plant, a TN D94 plant, a TN D950 plant, a TR (Tom Rosson) Madole plant, a VA 309 plant, and a VA 359 plant.

118. The method of any one of embodiments 75-117, wherein said modified tobacco plant is a hybrid.

119. The method of any one of embodiments 75-118, wherein said modified tobacco plant is male sterile or cytoplasmically male sterile.

120. The method of any one of embodiments 75-118, wherein said modified tobacco plant is female sterile.

121. The method of any one of embodiments 75-120, wherein said reduced suckers comprises fewer total suckers, smaller suckers, or both, as compared to suckers of said control tobacco plant when grown under comparable growth conditions.

122. The method of embodiment 121, wherein said smaller suckers comprise reduced average mass, reduced average length, reduced average diameter, or any combination thereof, as compared to suckers of said control tobacco plant when grown under comparable growth conditions.

123. The method of any one of embodiments 75-122, wherein said modified plant has increased leaf yield mass as compared to said control tobacco plant when grown under comparable growth conditions.

124. The method of embodiment 123, wherein said increased leaf yield mass comprises an increase of at least 0.5%.

125. A method comprising preparing a tobacco product using cured tobacco material from a modified tobacco plant comprising a mutation in an endogenous gene encoding a polypeptide selected from the group consisting of a cyclin, a cyclin-dependent kinase (CDK), a CDK inhibitor, a MYB, and a WRKY transcription factor, wherein said mutation is not present in said endogenous gene in a control tobacco plant of the same variety, and wherein said modified tobacco plant comprises no suckers or reduced suckers after topping as compared to a control tobacco plant when grown under comparable growth conditions.

126. A method comprising preparing a tobacco product using cured tobacco material from a modified tobacco plant comprising a polynucleotide sequence encoding a polypeptide selected from the group consisting of a cyclin, a cyclin-dependent kinase (CDK), a CDK inhibitor, a MYB, and a WRKY transcription factor operably linked to a heterologous promoter, and wherein said modified tobacco plant comprises no suckers or reduced suckers after topping as compared to a control tobacco plant when grown under comparable growth conditions.

127. A method comprising preparing a tobacco product using cured tobacco material from a modified tobacco plant comprising a polynucleotide sequence encoding a polypeptide selected from the group consisting of a cyclin, a cyclin-dependent kinase (CDK), a CDK inhibitor, a MYB, and a WRKY transcription factor operably linked to a heterologous promoter, wherein said modified tobacco plant comprises no suckers or reduced suckers after topping as compared to a control tobacco plant when grown under comparable growth conditions.

128. A method comprising preparing a tobacco product using cured tobacco material from a modified tobacco plant comprising a polynucleotide sequence encoding a polypeptide selected from the group consisting of a cyclin, a cyclin-dependent kinase (CDK), a CDK inhibitor, a MYB, and a WRKY transcription factor operably linked to a heterologous promoter.

129. A method comprising preparing a tobacco product using cured tobacco material from a modified tobacco plant comprising a recombinant DNA construct comprising a heterologous promoter operably linked to a nucleic acid encoding at least one small RNA molecule capable of reducing the expression of an endogenous mRNA that encodes a polypeptide selected from the group consisting of a cyclin, a cyclin-dependent kinase (CDK), a CDK inhibitor, a MYB, and a WRKY transcription factor, wherein said modified tobacco plant comprises no suckers or reduced suckers after topping as compared to a control tobacco plant when grown under comparable growth conditions.

130. A method comprising preparing a tobacco product using cured tobacco material from a modified tobacco plant comprising a recombinant DNA construct comprising a heterologous promoter operably linked to a nucleic acid encoding at least one small RNA molecule capable of reducing the expression of an endogenous mRNA that encodes a polypeptide selected from the group consisting of a cyclin, a cyclin-dependent kinase (CDK), a CDK inhibitor, a MYB, and a WRKY transcription factor.

131. The method of any one of embodiments 125-130, wherein said tobacco product is selected from the group consisting of a cigarette, a kretek, a bidi cigarette, a cigar, a cigarillo, a non-ventilated cigarette, a vented recess filter cigarette, pipe tobacco, snuff, snus, chewing tobacco, moist smokeless tobacco, fine cut chewing tobacco, long cut chewing tobacco, pouched chewing tobacco product, gum, a tablet, a lozenge, and a dissolving strip.

132. The method of any one of embodiments 125-131, wherein said cured tobacco material is from a tobacco variety selected from the group consisting of a flue-cured variety, a bright variety, a Burley variety, a Virginia variety, a Maryland variety, a dark variety, an Oriental variety, and a Turkish variety.

133. The method of any one of embodiments 125-132, wherein said cured tobacco material is selected from the group consisting of air-cured tobacco material, fire-cured tobacco material, sun-cured tobacco material, and flue-cured tobacco material.

134. The method of any one of embodiments 125-133, wherein said cured tobacco material comprises cured tobacco leaf material.

135. The method of any one of embodiments 125-133, wherein said cured tobacco material comprises cured tobacco stem material.

136. A method comprising transforming a tobacco cell with a recombinant DNA construct comprising a heterologous promoter operably linked to a nucleic acid encoding a polypeptide selected from the group consisting of a cyclin, a cyclin-dependent kinase (CDK), a CDK inhibitor, a MYB, and a WRKY transcription factor.

137. A method comprising transforming a tobacco cell with a recombinant DNA construct comprising a heterologous promoter operably linked to a nucleic acid encoding at least one small RNA molecule capable of reducing the expression of an endogenous mRNA that encodes a polypeptide selected from the group consisting of a cyclin, a cyclin-dependent kinase (CDK), a CDK inhibitor, a MYB, and a WRKY transcription factor.

138. The method of embodiments 136 or 137, wherein said method further comprises regenerating a modified tobacco plant from said tobacco cell, wherein said modified tobacco plant comprises said recombinant DNA construct.

139. The method of embodiment 138, wherein said modified tobacco plant comprises no or reduced suckers after topping as compared to a control tobacco plant lacking said recombinant DNA construct when grown under comparable conditions.

140. A method for producing a modified tobacco plant comprising:
   (a) crossing at least one tobacco plant of a first tobacco variety with at least one tobacco plant of a second tobacco variety, wherein said at least one tobacco plant of said first tobacco variety comprises a mutation in an endogenous gene encoding a polypeptide selected from the group consisting of a cyclin, a cyclin-dependent kinase (CDK), a CDK inhibitor, a MYB, and a WRKY transcription factor, wherein said mutation is not present in said endogenous gene in a control tobacco plant of the same variety, and wherein said at least one tobacco plant comprises no suckers or reduced suckers after topping as compared to said control tobacco plant when grown under comparable growth conditions; and
   (b) selecting for progeny tobacco plants that exhibit no suckers or reduced suckers after topping compared to a control tobacco plant of the same cross grown under comparable growth conditions.

141. A method for producing a modified tobacco plant comprising:
   (a) crossing at least one tobacco plant of a first tobacco variety with at least one tobacco plant of a second tobacco variety, wherein said at least one tobacco plant of said first tobacco variety comprises a recombinant DNA construct comprising a heterologous promoter operably linked to a nucleic acid encoding a polypeptide selected from the group consisting of a cyclin, a cyclin-dependent kinase (CDK), a CDK inhibitor, a MYB, and a WRKY transcription factor, wherein said at least one tobacco plant comprises no suckers or reduced suckers after topping as compared to a control tobacco plant when grown under comparable growth conditions; and
   (b) selecting for progeny tobacco plants that exhibit no suckers or reduced suckers after topping compared to a control tobacco plant of the same cross grown under comparable growth conditions.

142. A method for producing a modified tobacco plant comprising:
   (a) crossing at least one tobacco plant of a first tobacco variety with at least one tobacco plant of a second tobacco variety, wherein said at least one tobacco plant of said first tobacco variety comprises a recombinant DNA construct comprising a heterologous promoter operably linked to a nucleic acid encoding at least one small RNA molecule capable of reducing the expression of an endogenous genomic locus that encodes a polypeptide selected from the group consisting of a cyclin, a cyclin-dependent kinase (CDK), a CDK inhibitor, a MYB, and a WRKY transcription factor, wherein said at least one tobacco plant comprises no suckers or reduced suckers after topping as compared to a control tobacco plant when grown under comparable growth conditions; and (b) selecting for progeny tobacco plants that exhibit no suckers or reduced suckers after topping compared to a control tobacco plant of the same cross grown under comparable growth conditions.

Having now generally described the disclosure, the same will be more readily understood through reference to the following examples that are provided by way of illustration, and are not intended to be limiting of the present disclosure, unless specified.

EXAMPLES

Example 1. Identification of Differentially Expressed Genes

Two hundred ten TN90 tobacco plants are grown to lay by stage (eight to ten fully expanded leaves). At this stage, axillary buds are collected from 30 plants to form three replicates, each containing the pooled axillary buds from ten plants. The remaining 180 plants are topped. Ninety of the plants are sprayed with water, and ninety of the plants are sprayed with maleic hydrazide (MH) per the manufacturer's dosing instructions (Arysta LifeScience Royal MH-30® XTRA). Axillary buds from water-treated (control) and MH-treated plants are collected four hours after spraying, 24 hours after spraying, and 72 hours after spraying. See Table 2. RNA is extracted from each collection and sequenced using Hiseq (Illumina).

TABLE 2

Experimental groups

| Treatment | Description | Number of replicates |
|---|---|---|
| Control | Un-topped plants; no water or maleic hydrazide (MH) treatment | 3 |
| 4 hour-water | Plants topped and treated with water; axillary bud samples were collected 4 hours after treatment. | 3 |
| 4 hour-MH | Plants topped and treated with MH; axillary bud samples were collected 4 hours after treatment. | 3 |
| 24 hour-water | Plants topped and treated with water; axillary bud samples were collected 24 hours after treatment. | 3 |
| 24 hour-MH | Plants topped and treated with MH; axillary bud samples were collected 24 hours after treatment. | 3 |
| 72 hour-water | Plants topped and treated with water; axillary bud samples were collected 72 hours after treatment. | 3 |
| 72 hour-MH | Plants topped and treated with MH; axillary bud samples were collected 72 hours after treatment. | 3 |
| Total samples | | 21 |

The RNA sequences are mapped to a proprietary tobacco reference genome using CLC Genomics Workbench (version 11.0.1; QIAGEN) using default parameters. A read count matrix including all samples was generated by aggregating the raw counts of the mapped reads for a given gene in each sample against a total of 98,751 genes using the Expression Browser Tool in CLC Genomics Workbench. The read count matrix was subjected to differential gene expression analysis using the R package edgeR (version 3.0.8). See Robinson et al. "edgeR: a Bioconductor package for differential expression analysis of digital gene expression data," *Bioinformatics*, 26:139-140 (2010).

Genes with no expression or ubiquitously low expression were filtered out of the read count matrix in order to improve sensitivity of differential gene expression detection. Only genes having read counts per million reads of >1 in at least three RNA sequencing libraries were retained. These filters result in a filtered read count matrix containing 39,980 expressed genes.

The filtered read count matrix was normalized for compositional bias between libraries using the trimmed means of M (TMM) values method. See, for example, Robinson and Oshlack, "A scaling normalization method for differential expression analysis of RNA-seq data," *Genome Biology*, 11:R25 (2010). Differentially expressed genes were detected between three pairwise comparisons: control samples at 4 hours, 24 hours, and 72 hours post-topping vs. MH-treated samples at 4 hours, 24 hours, and 72 hours post-topping, respectively. Genes having a p-value of ≤0.05 and an absolute value of log 2 fold changes of ≥1 or ≤1 are considered to be differentially expressed. In total, over 6300 genes are differentially expressed between the control and MH-treated samples. Gene expression values (reads per kilobase of transcript per million mapped reads (RPKM)) from the differentially expressed genes are used to perform downstream analysis and identify candidate genes.

Seven hundred nine differentially expressed genes are identified only in the 4-hour post-topping pairwise comparison. Three hundred ninety-six differentially expressed genes are identified only in the 24-hour post-topping pairwise comparison. Three thousand five hundred thirty-eight differentially expressed genes are identified only in the 72-hour post-topping pairwise comparison. One hundred differentially expressed genes are identified in both the 4-hour and 24-hour post-topping pairwise comparisons. Four hundred thirty-one differentially expressed genes are identified in both the 4-hour and 72-hour pairwise comparisons. Six hundred forty-six differentially expressed genes are identified in both the 24-hour and 72-hour pairwise comparisons. Five hundred thirteen differentially expressed genes are identified in all three pairwise comparisons. FIG. 1 provides a Venn diagram depicting the overlap of differentially expressed genes between the different comparisons.

Differentially expressed genes that are predicted to play a role in cell proliferation (e.g., cyclins, cyclin-dependent kinases, MYBs, WRKY transcription factors) are identified as candidate genes.

Example 2. Transformation and Regeneration of Modified Tobacco Plants

An expression vector is used as a backbone to generate multiple transformation vectors comprising recombinant DNA constructs (See Examples 5-6). The expression vector contains an axillary meristem-preferred promoter (e.g., SEQ ID NOs: 89-109), a NOS terminator, and a cassette comprising a kanamycin selection marker (NPT II) operably linked to an Actin2 promoter and a NOS terminator. Nucleic acid vectors comprising transgenes of interest are introduced into tobacco leaf discs via *Agrobacterium* transformation. See, for example, Mayo et al., 2006, *Nat Protoc.* 1:1105-11 and Horsch et al., 1985, *Science* 227:1229-1231.

Narrow Leaf Madole (NLM) tobacco plants are grown in Magenta™ GA-7 boxes and leaf discs are cut and placed into Petri plates. *Agrobacterium tumefaciens* cells comprising a transformation vector are collected by centrifuging a 20 mL cell suspension in a 50 mL centrifuge tube at 3500

RPM for 10 minutes. The supernatant is removed and the *Agrobacterium tumefaciens* cell pellet is re-suspended in 40 mL liquid re-suspension medium. Tobacco leaves, avoiding the midrib, are cut into eight 0.6 cm discs with a #15 razor blade and placed upside down in a Petri plate. A thin layer of Murashige & Skoog with B5 vitamins liquid re-suspension medium is added to the Petri plate and the leaf discs are poked uniformly with a fine point needle. About 25 mL of the *Agrobacterium tumefaciens* suspension is added to the Petri plate and the leaf discs are incubated in the suspension for 10 minutes.

Leaf discs are transferred to co-cultivation Petri plates (½ MS medium) and discs are placed upside down in contact with filter paper overlaid on the co-cultivation TOM medium (MS medium with 20 g/L sucrose; 1 mg/L indole-3-acetic acid; and 2.5 mg/L 6-benzyl aminopurine (BAP)). The Petri plate is sealed with parafilm prior to incubation in dim light (60-80 mE/ms) with 18 hours on, 6 hours off photoperiods at 24 degrees Celsius for three days. After incubation, leaf discs are transferred to regeneration/selection TOM K medium Petri plates (TOM medium plus 300 mg/L kanamycin). Leaf discs are sub-cultured bi-weekly to fresh TOM K medium in dim light with 18 hours on, 6 hours off photoperiods at 24 degrees Celsius until shoots become excisable. Shoots from leaves are removed with forceps and inserted in MS basal medium with 100 mg/L kanamycin. Shoots on MS basal medium with 100 mg/L kanamycin are incubated at 24 degrees Celsius with 18 hours on, 6 hours off photoperiods with high intensity lighting (6080 mE/ms) to induce rooting.

Example 3. Phenotypic Screening

When plantlets regenerated in Example 2 containing both shoots and roots grow large enough (e.g., reach approximately half the height of a Magenta™ GA-7 box), they are transferred to soil. Established seedlings are transferred to a greenhouse for further analysis and to set seed. Evaluation of suckering phenotypes is conducted by growing modified plants (T0, T1, T2, or later generations) and control plants to layby stage. Control plants are either NLM plants that have not been transformed or NLM plants that have been transformed with an empty p45-2-7 vector. Plants that have reached layby stage are manually topped (the shoot apical meristem and surrounding tissue is removed), and axillary bud growth is evaluated at specific time points after topping. Observations are typically performed at the time of topping (i.e., 0 hours), 24 hours (i.e., 1 day) after topping, 7-8 days after topping (i.e., one week), and/or 14-15 days (i.e., two weeks) after topping. Observations comprise qualitatively examining the presence or absence of axillary bud growth and overall plant appearance. Observations also comprise quantitatively measuring the fresh weight of all axillary buds at a specific time point after topping and/or measuring the length of all axillary bud outgrowths at a specific time point after topping.

Example 4. Development of Modified Tobacco Plants Via Induced Mutation

Mutations are produced in CDK, CDK inhibitor, cyclin, MYB, and WRKY genes by specifically editing SEQ ID NOs: 1-44 and 113. Tobacco protoplasts are transfected using polyethylene glycol (PEG) with plasmids encoding a CRISPR protein or a CRISPR protein and specific guide RNA (gRNA) targeting individual genes at desired positions.

Transfected protoplasts are then immobilized in 1% agarose beads and subjected to tissue culture. When calli grow to approximately 1 millimeter in diameter, they are spread on TOM2 plates. Calli are screened for mutations (e.g., insertions or deletions (indels)) at the target positions using fragment analysis. Candidates, showing size shifts compared to wildtype control, are selected for further culture and the consequent shoots are tested by fragment analysis again to confirm the presence of mutations.

Modified tobacco plants (T0 generation) comprising the targeted mutations and control tobacco plants lacking the mutations are grown to the layby stage as described in Example 2. Then, plants are topped to remove the shoot apical meristem and modified and control tobacco plants are phenotypically evaluated as described in Example 3.

Example 5. Development of Modified Tobacco Plants Via Targeted Expression

Targeted over-expression of genes comprising SEQ ID NOs: 1-44 and 113 in axillary bud tissues can be used to reduce or eliminate sucker outgrowth in tobacco when operably linked to an axillary bud-preferred promoter (e.g. SEQ ID NOs: 83-109).

Six separate transformation vectors comprising SEQ ID NOs: 5, 33, or 36 driven by a promoter comprising SEQ ID NOs: 89 or 93 are constructed as described above in Example 2.

Modified tobacco plants (T0 generation) comprising one the transformation vectors and control tobacco plants are grown to the layby stage as described in Example 2. Then, plants are topped to remove the shoot apical meristem and modified and control tobacco plants are phenotypically evaluated as described in Example 3.

Figure 2:
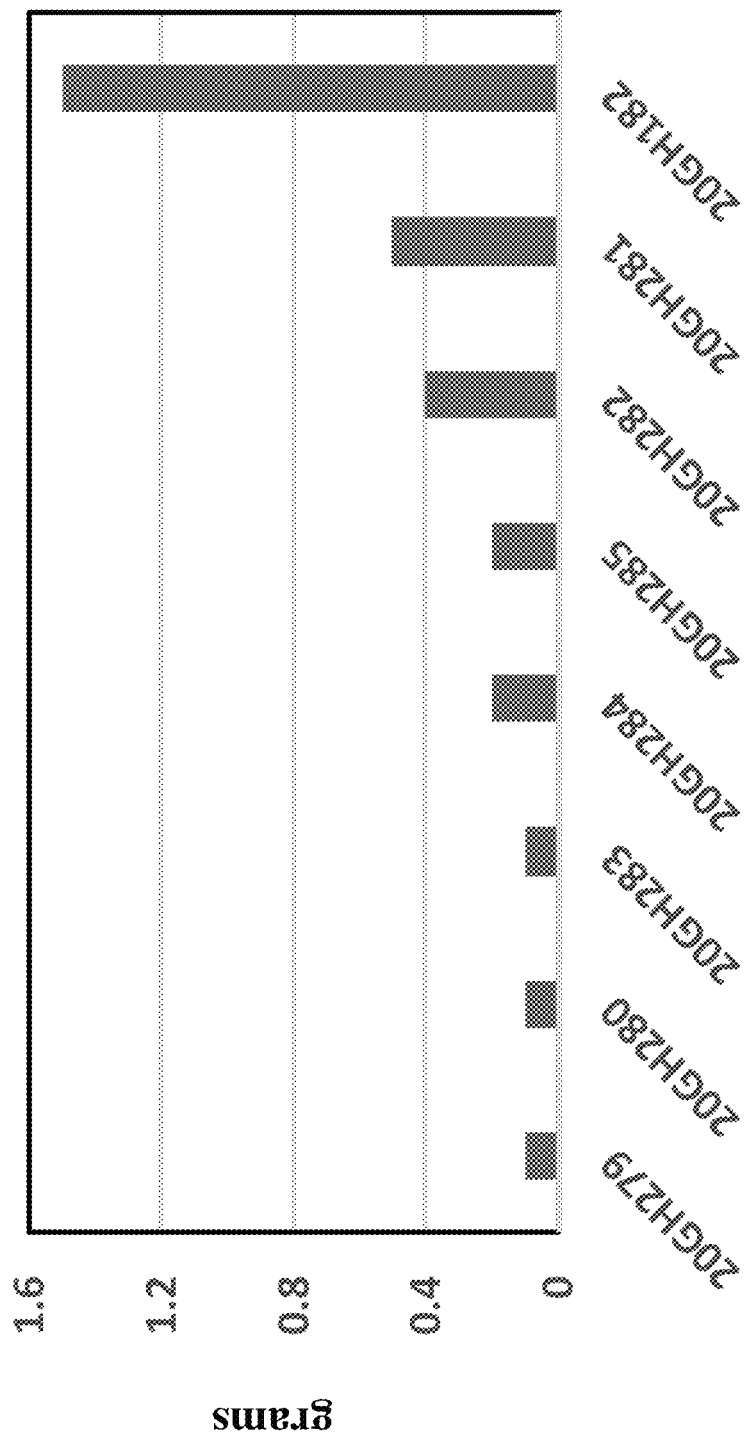
FIG. 2 depicts the collective mass of suckers from individual P1_2.4::MYB plants one week after topping.
Figure 3:
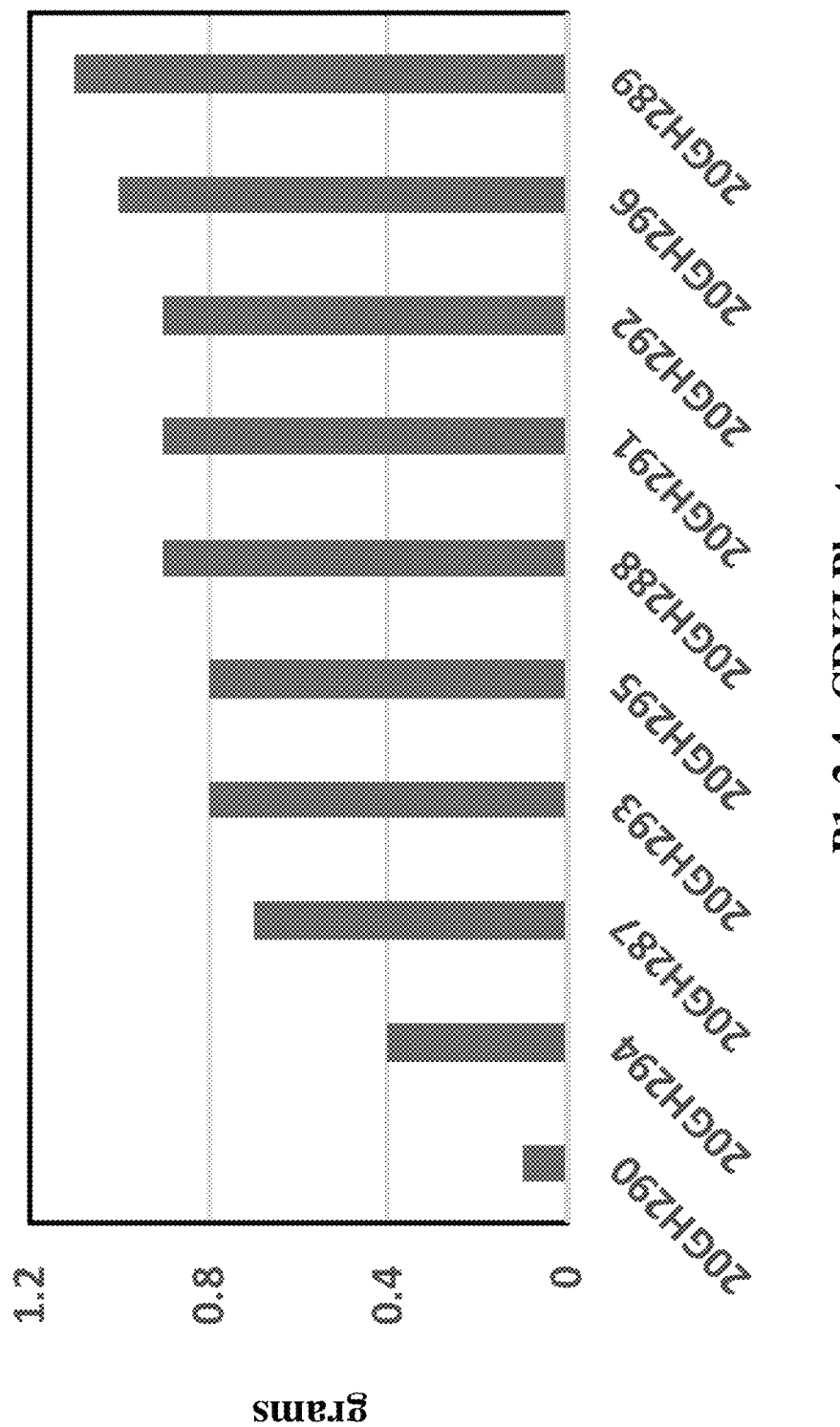
FIG. 3 depicts the collective mass of suckers from individual P1_2.4::CDKI plants one week after topping.

Additional transformation vectors comprising SEQ ID NO: 109 driving the expression of SEQ ID NO: 36 (P1_2.4:: MYB) and SEQ ID NO: 109 driving the expression of SEQ ID NO: 5 (P1_2.4::CDKI) are also constructed and transformed into tobacco as described above in Example 2. Resulting modified tobacco plants are grown and phenotypically screened as described above in Example 3. FIG. 2 depicts the collective mass of suckers from individual P1_2.4::MYB plants one week after topping. FIG. 3 depicts the collective mass of suckers from individual P1_2.4:: CDKI plants one week after topping.

Example 6. Development of Modified Tobacco Plants Via Small RNA Molecules

Targeted suppression of genes comprising SEQ ID NOs: 1-44 and 113 in axillary bud tissues can be used to reduce or eliminate sucker outgrowth in tobacco. Transformation vectors comprising an axillary bud-preferred promoter (e.g., SEQ ID NOs: 89-109) driving the expression of an artificial miRNA designed to reduce the transcription or translation of SEQ ID NOs: 1-44 or 113 are created by modifying the Nt-miR6147 pre-miRNA and inserting the modified pre-miRNA into the transformation vector described in Example 2.

Additional transformation vectors are constructed to generate artificial miRNAs capable of suppressing the expression of CDKs in axillary buds. Each artificial miRNA construct is capable of suppressing two CDK genes. See Table 3.

TABLE 3

Artificial miRNA vectors.

| Vector Name | Promoter SEQ ID NO. | First Targeted CDK SEQ ID NO | Second Targeted CDK SEQ ID NO | Artificial miRNA precursor SEQ ID NO | Artificial Mature miRNA SEQ ID NO | Artificial miRNA* SEQ ID NO |
|---|---|---|---|---|---|---|
| amiRNA-1 | 109 | 1 | 4 | 118 | 121 | 124 |
| amiRNA-2 | 109 | 2 | 3 | 119 | 122 | 125 |
| amiRNA-3 | 109 | 2 | 3 | 120 | 123 | 126 |

Figure 4:
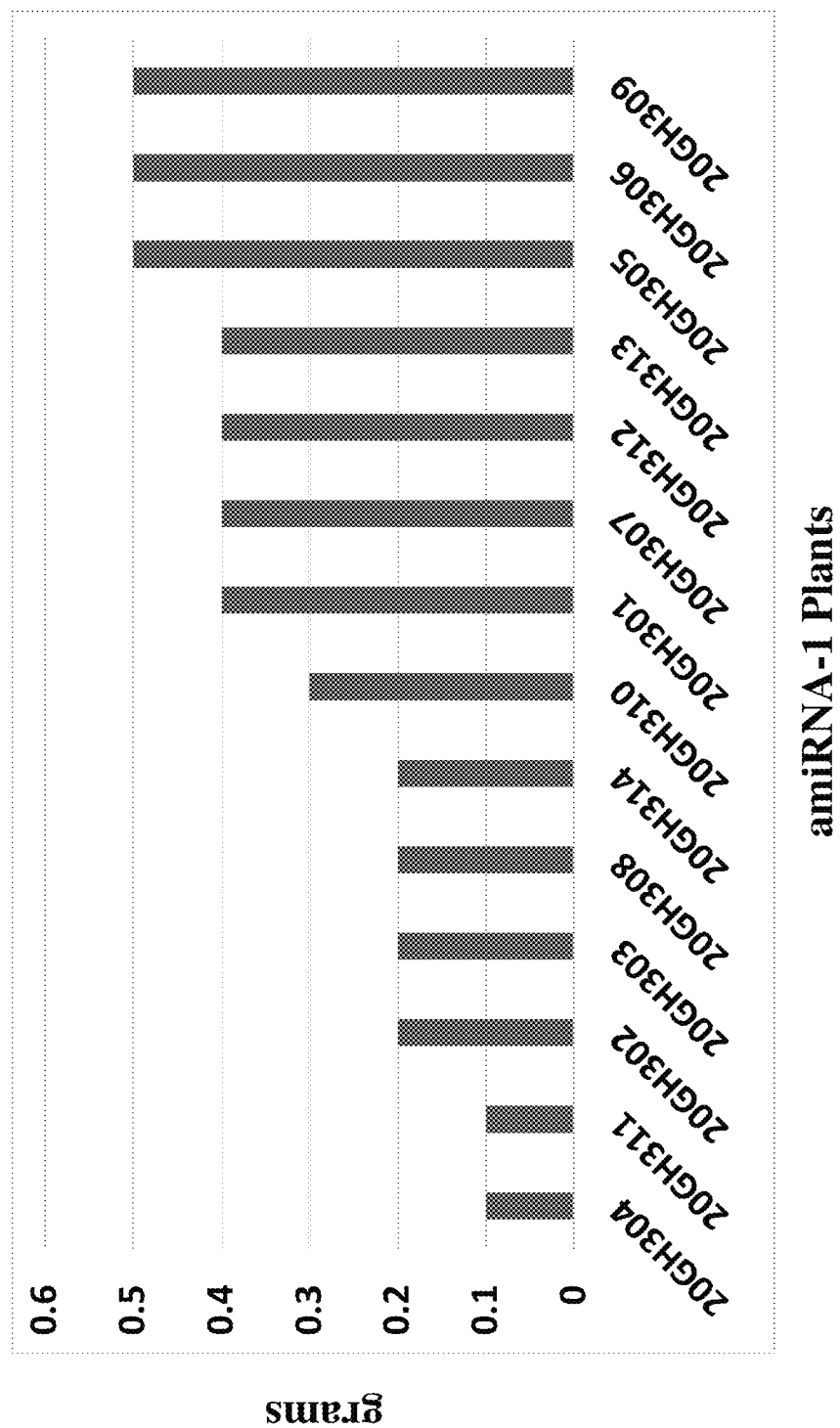
FIG. 4 depicts the collective mass of suckers from individual plants comprising the amiRNA-1 construct one week after topping.
Figure 5:
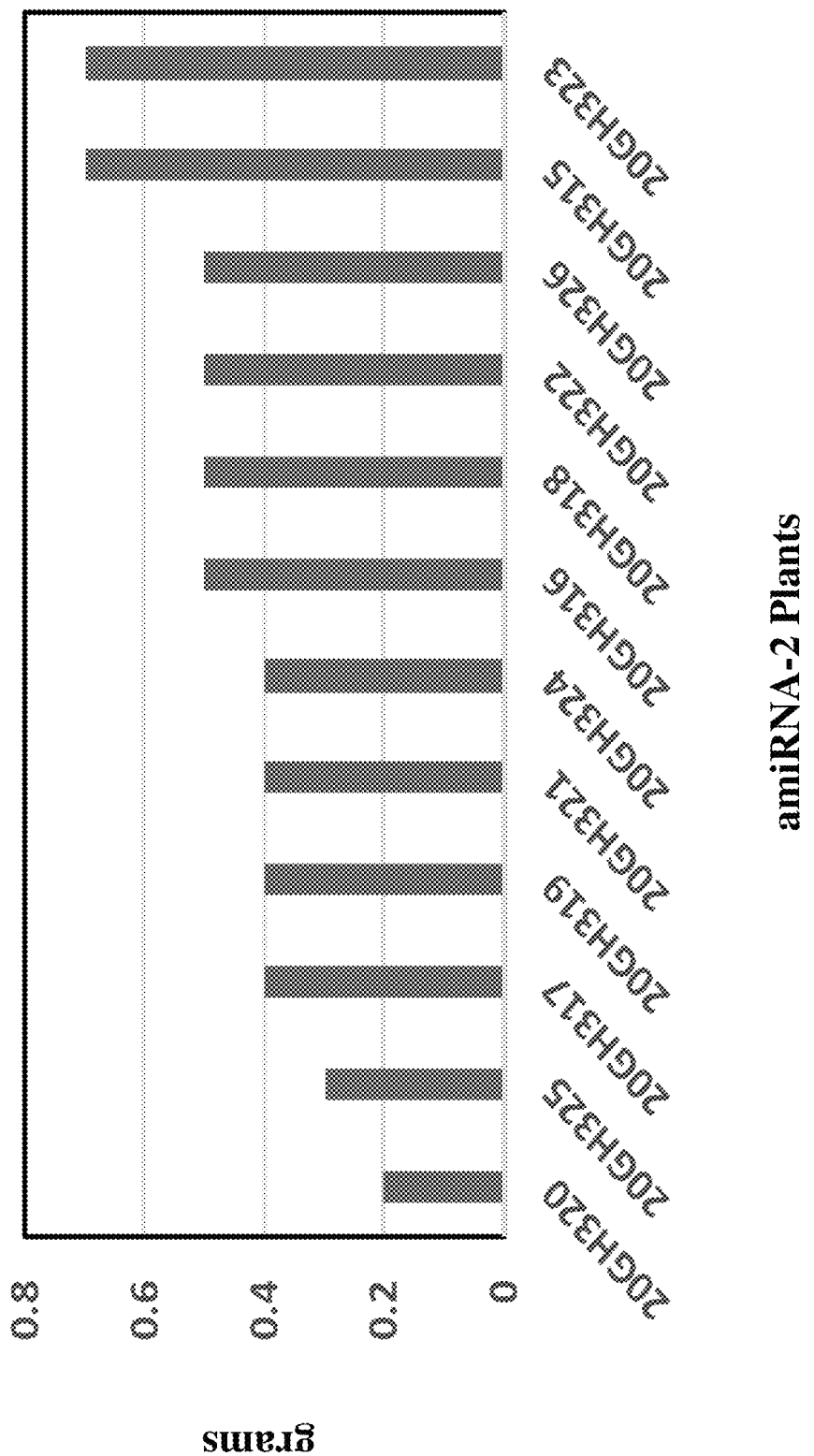
FIG. 5 depicts the collective mass of suckers from individual plants comprising the amiRNA-2 construct one week after topping.
Figure 6:
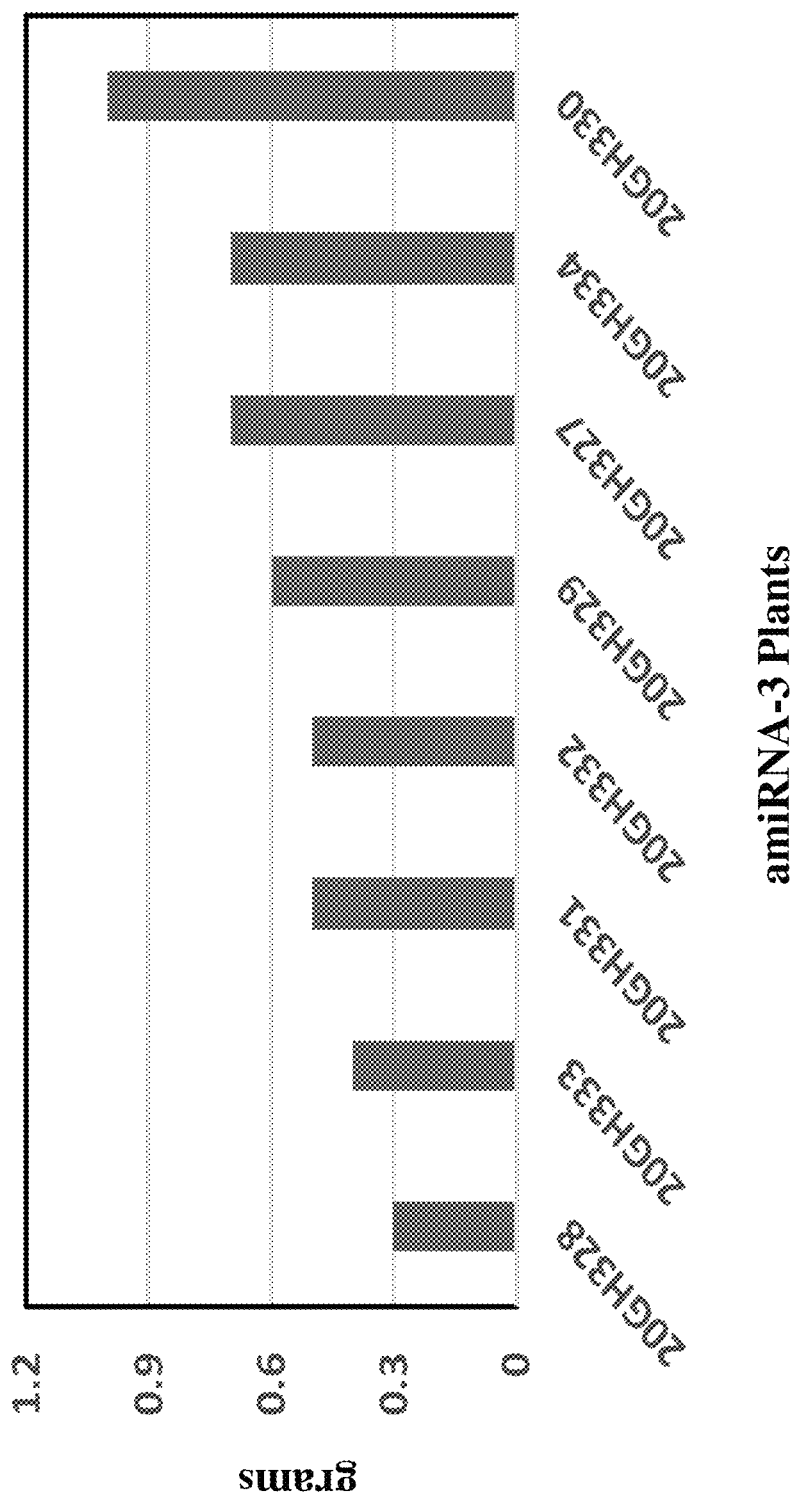
FIG. 6 depicts the collective mass of suckers from individual plants comprising the amiRNA-3 construct one week after topping.

Modified tobacco plants (T0 generation) comprising the transformation vectors and control tobacco plants are grown to the layby stage as described in Example 3. Then, plants are topped to remove the shoot apical meristem and modified and control tobacco plants are phenotypically evaluated as described in Example 4. FIGS. 4, 5, and 6 depict the collective mass of suckers from individual plants comprising amiRNA-1, amiRNA-2, and amiRNA-3, respectively, one week after topping.

The invention claimed is:

1. A modified tobacco plant, or part thereof, comprising a polynucleotide sequence encoding a cyclin-dependent kinase (CDK) inhibitor polypeptide operably linked to a heterologous promoter, wherein said modified tobacco plant comprises no suckers or reduced suckers after topping as compared to a control tobacco plant when grown under comparable growth conditions.

2. The modified tobacco plant, or part thereof, of claim 1, wherein said heterologous promoter comprises an axillary meristem-preferred promoter.

3. The modified tobacco plant, or part thereof, of claim 1, wherein said heterologous promoter comprises a polynucleotide sequence at least 99% identical to a polynucleotide sequence selected from the group consisting of SEQ ID NOs: 89-96, 98, 100, 102, 104, 106, 108, and 109.

4. The modified tobacco plant, or part thereof, of claim 1, wherein said modified tobacco plant is of a tobacco variety selected from the group consisting of a flue-cured variety, a bright variety, a Burley variety, a Virginia variety, a Maryland variety, a dark variety, a Galpão variety, an Oriental variety, and a Turkish variety.

5. The modified tobacco plant, or part thereof, of claim 1, wherein said modified tobacco plant is selected from the group consisting of a BU 64 plant, a CC 101 plant, a CC 200 plant, a CC 13 plant, a CC 27 plant, a CC 33 plant, a CC 35 plant, a CC 37 plant, a CC 65 plant, a CC 67 plant, a CC 301 plant, a CC 400 plant, a CC 500 plant, CC 600 plant, a CC 700 plant, a CC 800 plant, a CC 900 plant, a CC 1063 plant, a Coker 176 plant, a Coker 319 plant, a Coker 371 Gold plant, a Coker 48 plant, a CU 263 plant, a DF911 plant, a Galpao plant, a GL 26H plant, a GL 338 plant, a GL 350 plant, a GL 395 plant, a GL 600 plant, a GL 737 plant, a GL 939 plant, a GL 973 plant, a GF 157 plant, a GF 318 plant, an RJR 901 plant, an HB 04P plant, a K 149 plant, a K 326 plant, a K 346 plant, a K 358 plant, a K394 plant, a K 399 plant, a K 730 plant, an NC 196 plant, an NC 37NF plant, an NC 471 plant, an NC 55 plant, an NC 92 plant, an NC2326 plant, an NC 95 plant, an NC 925 plant, a PVH 1118 plant, a PVH 1452 plant, a PVH 2110 plant, a PVH 2254 plant, a PVH 2275 plant, a VA 116 plant, a VA 119 plant, a KDH 959 plant, a KT 200 plant, a KT204LC plant, a KY 10 plant, a KY 14 plant, a KY 160 plant, a KY 17 plant, a KY 171 plant, a KY 907 plant, a KY 907LC plant, a KTY14 ×L8 LC plant, a Little Crittenden plant, a McNair 373 plant, a McNair 944 plant, a male sterile KY 14 ×L8 plant, a Narrow Leaf Madole plant, a MS KY171 plant, a Narrow Leaf Madole (phph) plant, a MS Narrow Leaf Madole plant, a MS TND950 plant, a PD 7302LC plant, a PD 7305LC plant, a PD 7309LC plant, a PD 7312LC plant, a PD 7318LC plant, a PD 7319LC plant, a MSTKS 2002 plant, a TKF 2002 plant, a TKF 6400 plant, a TKF 4028 plant, a TKF 4024 plant, a KT206LC plant, a KT209LC plant, a KT210LC plant, a KT212LC plant, an NC 100 plant, an NC 102 plant, an NC 2000 plant, an NC 291 plant, an NC 297 plant, an NC 299 plant, an NC 3 plant, an NC 4 plant, an NC 5 plant, an NC 6 plant, an NC7 plant, an NC 606 plant, an NC 71 plant, an NC 72 plant, an NC 810 plant, an NC BH 129 plant, an NC 2002 plant, a Neal Smith Madole plant, an OXFORD 207 plant, a 'Perique' plant, a PVH03 plant, a PVH09 plant, a PVH19 plant, a PVH50 plant, a PVH51 plant, an R 610 plant, an R 630 plant, an R 7-11 plant, an R 7-12 plant, an RG 17 plant, an RG 81 plant, an RG H51 plant, an RGH 4 plant, an RGH 51 plant, an RS 1410 plant, a Speight 168 plant, a Speight 172 plant, a Speight 179 plant, a Speight 210 plant, a Speight 220 plant, a Speight 225 plant, a Speight 227 plant, a Speight 234 plant, a Speight G-28 plant, a Speight G-70 plant, a Speight H-6 plant, a Speight H2O plant, a Speight NF3 plant, a TI 1406 plant, a TI 1269 plant, a TN 86 plant, a TN86LC plant, a TN 90 plant, a TN9OLC plant, a TN 97 plant, a TN97LC plant, a TN D94 plant, a TN D950 plant, a TR (Tom Rosson) Madole plant, a VA 309 plant, and a VA 359 plant.

6. The modified tobacco plant, or part thereof, of claim 1, wherein said modified tobacco plant is male sterile or cytoplasmically male sterile.

7. The modified tobacco plant, or part thereof, of claim 1, wherein said reduced suckers comprises fewer total suckers, smaller average sucker size, or both, as compared to suckers of said control tobacco plant when grown under comparable growth conditions.

8. The modified tobacco plant, or part thereof, of claim 7, wherein said smaller average sucker size comprises a measurement selected from the group consisting of reduced average mass, reduced average length, reduced average diameter, or any combination thereof, as compared to suckers of said control tobacco plant when grown under comparable growth conditions.

9. The modified tobacco plant, or part thereof, of claim 1, wherein said modified plant has increased leaf yield mass as compared to said control tobacco plant when grown under comparable growth conditions.

10. A tobacco leaf of the modified tobacco plant of claim 1, wherein the tobacco leaf comprises the polynucleotide sequence.

11. A tobacco seed of the modified tobacco plant of claim 1, wherein the tobacco seed comprises the polynucleotide sequence.

12. The modified tobacco plant, or part thereof, of claim 1, wherein the cyclin-dependent kinase inhibitor comprises an amino acid sequence at least 90% identical or similar to SEQ ID NO: 49.

13. The modified tobacco plant, or part thereof, of claim 1, wherein the cyclin-dependent kinase inhibitor comprises an amino acid sequence at least 95% identical or similar to SEQ ID NO: 49.

14. The modified tobacco plant, or part thereof, of claim 1, wherein the cyclin-dependent kinase inhibitor comprises an amino acid sequence 100% identical or similar to SEQ ID NO: 49.

15. The modified tobacco plant, or part thereof, of claim 1, wherein the cyclin-dependent kinase inhibitor comprises a nucleic acid sequence at least 90% identical to SEQ ID NO: 5.

16. The modified tobacco plant, or part thereof, of claim 1, wherein the cyclin-dependent kinase inhibitor comprises a nucleic acid sequence at least 95% identical to SEQ ID NO: 5.

17. The modified tobacco plant, or part thereof, of claim 1, wherein the cyclin-dependent kinase inhibitor comprises a nucleic acid sequence 100% identical to SEQ ID NO: 5.

18. The modified tobacco plant, or part thereof, of claim 9, wherein said increased leaf yield mass comprises an increase of at least 0.5%.

19. The modified tobacco plant, or part thereof, of claim 1, wherein said modified tobacco plant is a hybrid.

20. The modified tobacco plant, or part thereof, of claim 1, wherein said modified tobacco plant is female sterile.

* * * * *

SEQUENCE LISTING

<160> NUMBER OF SEQ ID NOS: 126

<210> SEQ ID NO 1
<211> LENGTH: 912
<212> TYPE: DNA
<213> ORGANISM: Nicotiana tabacum

<400> SEQUENCE: 1

```
atggagaaat acgagaaatt ggagaaagta ggagaaggaa cgtacggcaa agtatataaa      60
gcaaaggaca aagcaacggg tcaattggtg gcgctgaaga aaactcggct agaaatggac     120
gaagaaggga ttccacccac tgctttaaga gaaatatcac ttcttcaaat gctttccaat     180
tctctctaca tcgttcgtct cctctgtgtc gagcaaattg acaaaaatgg gaagcctctt     240
ctttacctag tttttgagta tttggatact gatctgaaga aattcgtcga ttctcatcgt     300
aaaggtccta atcctagacc tctccctcct tctctcatcc agagtttctt atatcaattg     360
tgcaaagggg tcgctcactg ccatagccat ggagttctcc acagagattt gaagccacag     420
aacctattag tggacaaaga gaagggcata cttaagattg ctgatttggg tcttggaagg     480
gctttcactg tcccaataaa gagctacacc catgagattg ttactctatg gtacagagct     540
cctgaagtct tgttgggatc tactcattac tcaactgcgg ttgatatgtg gtctgtggga     600
tgtattttg ccgagatggt tcgaaggcag gccttatttc ctggtgactc tgagtttcag     660
caattgcttc acatattcag gttgttagga accccaactg agaagcagtg gcctggagtg     720
agttcactcc gcgactggca tgtttatcca aaatgggaac ctcagaactt ggcctctgct     780
gttccagcat tgggtcctga tggtgtggat ctcctcacga aaatgctcca atatgatccg     840
gcagatagga tttcagcaaa agctgcactt gatcatccat actttgatag cttggacaag     900
tcgcaattct ga                                                         912
```

<210> SEQ ID NO 2
<211> LENGTH: 858
<212> TYPE: DNA
<213> ORGANISM: Nicotiana tabacum

<400> SEQUENCE: 2

```
atggagactg taaaaaagag tgcatcggca atggaagcat tcgagaagct tgagaaggta      60
ggggaaggta cttacggaaa ggtgtacaga gcgagagata gggttactgg caaaatcgta     120
gcactgaaga agacgaggct tcacgaggac gaagaaggtg ttcctcccac tactctccgc     180
```

-continued

| | |
|---|---|
| gagatctctc ttctgcggat gctctctagg gatcctcaca ttgtcaaact gatggatgtt | 240 |
| aaacaaggcc agaacaaaga aggaaagacg gttctctact tggtctttga gtacatggat | 300 |
| actgatgtca agaaatttat tcgtagtttc cgcgcaaatg gagaaaacat tccccctaaa | 360 |
| actgtcaaga gcttgatgta ccaactatgc aaaggagttg ctttctgcca tggtcatggc | 420 |
| gtgttacaca gggatctgaa accacacaat cttctgatgg accgtaagac gaatgtgctc | 480 |
| aaattagcag attttggact tggcagagct tatactctgc ccatcaagaa gtacacgcat | 540 |
| gagatattaa ccctatggta tagagcccct gaggttcttc ttggagctac tcattactcc | 600 |
| acagcagttg acatgtggtc tgttggttgt atctttgctg aactggtcac aaaacaagcc | 660 |
| ctcttcccag agactctga gctgcaacaa ctgcttcaca ttttcagatt gctaggtact | 720 |
| cctaatgaag aactctggcc cggggtgagc aagctagtaa actggcatga ataccccaa | 780 |
| tggaaccccc agccactctc aactgctgtc cctggtctag atgaagatgg gctccacctt | 840 |
| ctaactgtaa gtgtttga | 858 |

<210> SEQ ID NO 3
<211> LENGTH: 939
<212> TYPE: DNA
<213> ORGANISM: Nicotiana tabacum

<400> SEQUENCE: 3

| | |
|---|---|
| atggagactg taaaaagag tgcatcggcc atggaggcat tcgagaagct tgagaaggta | 60 |
| ggggaaggta cttacggaaa ggtgtacaga gcgagagata gggttactgg caaaatcgta | 120 |
| gcactgaaga agacgaggct tcatgaggac gaagaaggtg tccctcctac tactctccgc | 180 |
| gagatctctc ttctgcggat gctttctagg gatcctcaca ttgtcaaact gatggatgtt | 240 |
| aaacaaggcc agaacaaaga aggaaagacg gtcctatact tggtgtttga gtacatggat | 300 |
| actgatgtca agaaatttat tcgtagtttc cgcgcaaatg gagaaaacat tccccctaaa | 360 |
| actgtcaaga gcttgatgta ccagctgtgc aaaggagttg ctttctgcca tggtcatggt | 420 |
| gtgttacaca gggatctgaa accacacaat cttctgatgg accgtaagac gaatgtgctc | 480 |
| aaattagcag attttggact tggcagagct tatactctgc ccatcaagaa gtatacgcat | 540 |
| gagatattaa ccctgtggta tagagcccct gaggttcttc ttggagctac tcattactcc | 600 |
| acagcagttg acatgtggtc tgttggttgt atatttgctg aactggtcac aaaacaagcc | 660 |
| ctcttcccag agactctga gctgcaacaa ctacttcaca ttttcagatt gctaggtact | 720 |
| cctaatgaag aactctggcc cggggtgagc aagctagtta actggcatga ataccccaa | 780 |
| tggaaccccc agccactctc aactgctgtc cctggtctag atgaagatgg gctccacctt | 840 |
| ctatctgaga tgttgcatta tgagccagct aagaggattt cagcaaagaa agctatggaa | 900 |
| catccctatt tcgatgatct ggacaaaact cctctctga | 939 |

<210> SEQ ID NO 4
<211> LENGTH: 912
<212> TYPE: DNA
<213> ORGANISM: Nicotiana tabacum

<400> SEQUENCE: 4

| | |
|---|---|
| atggagaaat acgagaaatt ggagaaagta ggagaaggaa cgtacggcaa agtatataaa | 60 |
| gcaaaggaca aggcgacggg acaattggtg gcgctgaaga aaactcggct agaaatggac | 120 |
| gaagaaggga tcccacccac tgccctaaga gaaatctcgc ttcttcaaat gctttcccat | 180 |
| tctctctaca tcgttcgtct cctctgtgtc gagcaaattg acaaaaatgg gaagcccctt | 240 |

```
ctttacctag tttttgagta tttggatact gatctgaaga aattcgtcga ttctcatcgt    300
aaaggtccca atcctagacc tctccctcct tctctcatcc agagtttctt atatcaattg    360
tgcaaagggg tagctcactg ccatagccat ggagttctcc acagagattt gaagccacag    420
aacctattag tggacaaaga aagggcata cttaagattg ctgatttggg ccttggaagg    480
gctttcactg tcccaataaa gagctacacc cacgagattg ttactctatg gtacagagct    540
cctgaggttt tgttgggatc tactcattac tcaactgcgg ttgatatgtg gtctgtggga    600
tgtatttttg ccgagatggt tcgaaggcaa gccttatttc ctggtgactc tgagtttcag    660
caactgcttc acatattcag gctgttagga accccaactg agaagcagtg gcctggagtc    720
agttcactcc gcgactggca tgtttatcca aaatgggaac tcagaacttt ggcctctgct    780
gttccagcat gggtcctga tggcgtggac ctcctcacga aaatgctcca atatgatccg    840
gcagatagga tttcagcaaa agctgcactt gatcatccat acttcgatag cttggacaag    900
tctcagtttt ga                                                       912

<210> SEQ ID NO 5
<211> LENGTH: 222
<212> TYPE: DNA
<213> ORGANISM: Nicotiana tabacum

<400> SEQUENCE: 5
atggaggggg tagatagtga ttgcgaggtg gtggaagaag gatgcatgac tccgaggcgt     60
gacacgtgta ggataatggt gaattctttg tgcccgccgc cgccgccgaa aagaaacga    120 gtttatgtca acaacagcg tcctccgcct aaggaaggtt attttcaacc acctgatctt    180
gagcttttct ttgccattgt aaggagagag gcttgtgctt aa                      222

<210> SEQ ID NO 6
<211> LENGTH: 1602
<212> TYPE: DNA
<213> ORGANISM: Nicotiana tabacum

<400> SEQUENCE: 6
atgcaaagct tgattttctc tggcgagaag aacatgattg ctgcttattt atttatacct     60
ctagaactgc atcggaatgt aatacaggtg tgtcatcgag ttcaacgcac tttctgctcg    120
atgaggcatg caaatataaa acatggatct tttcatcttg aagagcacaa tatgcgaatc    180
acacgagcac gagcaagagt gtcgggttca tcaggacgat taccacccct acacccatcc    240
acaaaacagg ataagaagca ggcattggga gcagagtcca aaagatcgaa aagatctgcc    300
tcagatgaga acagacctgg tacctctagt attgctactg tgttcagcc taagagaagg    360 gctgttctta aagacatgaa gaatgtactt catgagaact ctcacatgaa ttgcatcaac    420
ggaagcaaaa ttcaggttaa aaaggctcc gataaaagga acaataaggc gaaacctgct    480
gtttctctaa aattgtcaca gctccaagag aaaggaaaag aggatatagc tgataaagta    540
agaaaagtga aggttgaggg atcacaagaa atcagttcgg gggcaaactg caaggaggat    600
atgttaccac agctaagtag atatgtcact ccagcacaat gtggtttagt ccatctagtg    660
cctgtgaaca gaagttcctg caaggccttc ccacttcaga atgtaatgaa aaaagatgaa    720
agcaaagttt gccagaaaca agaaggcttt gctaatctag gaattgctga tattgattca    780
agacacaagg atccactgat gtgtagtctg tatgctcctg atatttataa caacttgcat    840
gccattgagt ttgaccgtag gccttctgtt gattacctgg aaaagctgca gctggacatt    900
```

| | |
|---|---|
| aacaagggta tgcgaggtat tctgattgat tggcttgtgg aggtttcaga agaatatagg | 960 |
| ctggttcctg acacacttta cctaactgtt aatcttattg accggttcct atctgaaaat | 1020 |
| tacattgaaa acaaaagct gcaactactt ggagttacct gcatgctaat agcttccaaa | 1080 |
| tttgaagaga tttgtgcacc tcgtgttgaa gaattttgct tcattacaga taacacttac | 1140 |
| tcgaaggaag aggtaataaa aatggaaagc agagtcttga acctttgag ctttcaactt | 1200 |
| gcttctccaa ccactaagaa attcctgagg agattcattc aagcagctca agcttcttac | 1260 |
| aaggttccct ctgtcgaact ggaattcatg gcaaattatt tagcagagtt aacacttgtt | 1320 |
| gactatgggt ttcttaagtt tcttccatct cttactgctg catcagctgt atttctagct | 1380 |
| agatggacgc ttgatcaatc taaccaccca tggaatccaa ctttggaaca ctataccaga | 1440 |
| tacaaggtat cagagcttag aactacagtt tttgcactgc aagagttaca gatgaacacc | 1500 |
| agtggctgca ccctcaatgc catacgtgaa aaatatagac aaccaaagtt caagtccgtg | 1560 |
| gctactttag cagcttcaaa accagtccaa tcactgttct aa | 1602 |

<210> SEQ ID NO 7
<211> LENGTH: 1245
<212> TYPE: DNA
<213> ORGANISM: Nicotiana tabacum
<400> SEQUENCE: 7

| | |
|---|---|
| atggatatat ctgatgagaa tcagttcact aggaaatcac tggttggtga ggcaggaatg | 60 |
| ggaaacagca agattggagt ggagacaaga cacaacagaa gagcactgag agtgattaat | 120 |
| cagaatttat taggacctaa tccatatcgt tgtgttgtta acaagagaag attatcacat | 180 |
| gcaaatggaa tcatctacga caagaatcct acgaggaaat tgactgcaca aattgctagc | 240 |
| tcacaccagc attccccga ggaaaccaag aaaccaaaac tagcagcgga agattttagg | 300 |
| atttgggaag aacatgtggc agctaaagac caacccatgt ctatgtcttt ggaacaagaa | 360 |
| gcaacatttt caaatgacaa gacagaaatg gaggttgaaa tggaggatat atttgaggag | 420 |
| gcactaatag atattgacag tgatgacact aacaatccgc ttgcagttgt tgactatgtg | 480 |
| gaagatctat atgccaacta cagaaaaatg gagggttata gctgtgtttc accaaaactat | 540 |
| atgacacaac agtttgacat caatgaaagg atgagagcta cattagtaga ctggctcatt | 600 |
| gaggtaaatc acaagtttga gctcagggaa gagacgttat tcttgactgt taattcgata | 660 |
| gacagatttt tggagaagca aatagttgca agaaagaagt tgcagcttgt tgggctggtt | 720 |
| gctatgctat agcatgcaa atatgaagag gtctctgtcc ctgtggtgga tgatttggtg | 780 |
| attatttcgg acaacgccta tacaaggaaa gaggttcttg aaatggaaac attaatgctc | 840 |
| gatacactgc agtttaatat gtcagttcca actgcatatg ttttatgag aagatttctc | 900 |
| aaggctgctc aagctgatag gaagcttgag gtcctgtctt tcttcttaat cgagctttgc | 960 |
| ctcgtggaat atgaaatgct taagtttcca ccatctttca tggctgctgc tgcaatttat | 1020 |
| acagctcagt gcacgctata tggtgtcatg caatggagta aaacatgtga atggcataca | 1080 |
| agttactcag aagatcaact tctgaaatgc tcgagatcta tcgtgatcta ccaccaaaag | 1140 |
| gcagcaacag ggaaactaac aggagtacat aggaagtata gcacatctaa atttggctat | 1200 |
| gcagcaaaat ttgagccagc acttttcctg gtgcagatca aataa | 1245 |

<210> SEQ ID NO 8
<211> LENGTH: 1311
<212> TYPE: DNA
<213> ORGANISM: Nicotiana tabacum

<400> SEQUENCE: 8

```
atggccatat ctgatgagaa caatcctaca atggttaaac ccacaaatgt gcaaggtggg      60
gctggaatgg gtaccagaaa gtttggtgga gtggaaacaa gaaacaacag aagagcattg     120
ggagtgatta atcagaattt agtgggtggt actcatccat ttccttgtgt tgttaacaag     180
agaggattat ctgaagcaaa tggaatctgt gacaagaatc ttcaaattcc agctcataga     240
cctatcacga ggaaatttgc agctcaaatt gctagctctc agcaaaatcg ctccgaggaa     300
aacaagaaag ctaaaatagc agcagaagaa ttcagtatat gggaggatat ccctctgaca     360
gatgtggagg aaaatgaggc agctaaagat caacctgttc ctatgtcttt ggaacaaaca     420
gaaacagtga ctaatgacaa gaatcaaatg gaggtagaaa tggaggatat atttgaggaa     480
actattatag atattgatgg cgacgatgca agaacccgc ttgcagttgt tgaatatgta     540
caagatttgt ttgcctccta tagaaaaatg gagggttgta gctgtgtttc tccggattat     600
atggcacaac agtttgacat caatgagaaa atgagatcca ttctaattga ctggctcatt     660
gaggtacatc acaagtttga gctcagagaa gagactttgt ttctgactgt taatttgata     720
gatagatttt tggagaagca aggtgttgtt aggaagaagt tgcagcttgt tgggttggtt     780
gccatgctat tagcatgcaa atatgaggaa gtttctgttc cattagtgga tgatttcgtg     840
tttatttcgg acaaagccta ttcaaggaag gaggttcttg aaatggaaag aatgatgctc     900
aacacactgc agtttaacat gtcagttcca actgcatatg ttttatgag aagatatctt     960
aaggctgctc aatctgatag gaagctcgag ctgctgtctt tcttcttggt tgagctttgt    1020
ctagtggaat atgaaatgct caagtttcca ccatcattca tagcagctgc agcaatctat    1080
acagctcaga ccacactcta cggtgtccag caatggagta agacatgcga gtggcatact    1140
agttactcgg aagatcaact tatggagtgt tcgagatcga ttgtgagcta tcaccagaag    1200
gcagcaacag gaaaactaac aggagtacat aggaagtaca gcacatctaa atttggttat    1260
gcagcaaagt gtgagcctgc ccattttctt gtgcagacac aacaacaata g             1311
```

<210> SEQ ID NO 9
<211> LENGTH: 432
<212> TYPE: DNA
<213> ORGANISM: Nicotiana tabacum

<400> SEQUENCE: 9

```
atggagaaaa ggattcttgg ccaattggag tggtacttaa cagttccaac accttacgtg      60
ttcctcgtcc gctacattaa agctgctgtt ccaatgcac agatggaaaa catggtttat     120
ttcctggctg aattggggtt aatgaattat gcaaccaata tatactgccc atcgatgatt     180
gctgcctcag cagtctatgt tgctcaacac acgctgaatt gcactccatt ttggaacgac     240
acactaaaat tgcatactgg tttctcagag tctcagctac tgggttgtgc aaagttgctc     300
gtaagctatc acatggaagc tccagaacac aagctgaaag tgatttacaa gaagtattcc     360
aaaccagaga gaggtgctgt tgcactgcaa cctccagcca aatccctctt ggctgcttct     420
tcatatgaat ag                                                          432
```

<210> SEQ ID NO 10
<211> LENGTH: 906
<212> TYPE: DNA
<213> ORGANISM: Nicotiana tabacum

<400> SEQUENCE: 10

```
atggcttcaa gaaacgttct tcaacagcag aatataggtg aggcagtccc cggggcgtta      60
aagcagaaaa atatggcagc agcagcacaa gggagaaatc gcaaggcgct tggtgacatt     120
gggaataata tggtaactgt tcgtggtgtc gagggaaagc cacttcctca acgcccata      180
acgaggggct tttgtgcaca attgctcgct aatgcacaag cagcagctga aaaccaaaag     240
aaatctatgg ttgttaatgg ggatgcaccg atcgttgcta aaggagttct accggttaaa     300
ggtgcagcaa agaaaccagt tcaaaagaaa gctgctgtta accaaagcc tgatgttatt      360
gaaattagtc ctgatactga agaacaagtg aaggaaaata gcaaaagaa gaaggctggt      420
gatgattctt cagtaaagaa agcaactctt acttcaactc tcactgctag gagcaaggct     480
gcctgtggac tgagtcataa accaaggtc cagattgtgg atattgatgc tgcagatgtg      540
aataatgagt tggctgtggt ggaatatgtt gaggatattt acaatttta taagatagct      600
gagaatgaga gcagaattca tgactacatg gattcacagc ctgagataac tgcaaggatg     660
agagctattc tgattgattg gttgattgaa gtgcatcaca aatttgagct tagtcaagag     720
actctttacc ttacaatcaa tatcgtcgat cgttacctcg ctgtgacaac tacatcaagg     780
agggaattgc agttagtagg catgagtgct atgctcattg cctctaaata tgaagaaatt     840
tgggctcctg aggtacattt caagtctaat tatgccaagt tactttccca ttttgaaagt     900
tgctaa                                                               906
```

<210> SEQ ID NO 11
<211> LENGTH: 1422
<212> TYPE: DNA
<213> ORGANISM: Nicotiana tabacum

<400> SEQUENCE: 11

```
atggcttcaa gaatcgttct tcaacagcag aatagaggtg aggcagtccc tggggcagta      60
aagcagaaaa agaatatggc accagaaggg agaaatagga agcacttgg cgatattggg     120
aatgtggcta caggtcgtgg gctcgaagga aaaaagccac ttcctcagaa acctgtggct     180
gttaaggtga aggagcaaa tgttgctaaa gtacctgcag caaggaaacc agctcagaag     240
aaagccacag ttaagccaaa ccccgaggat attattgaaa ttagtcctga cacccaagaa     300
aaactgaagg agaagatgca aggaagaag gctgataaag actcattaaa acagaaagca     360
actcttactt ctactctcac tgctcgaagc aaggctgcat gtggtctgag taaaaaacca     420
aaggagcagg tagtggacat tgatgctgca gatgtgaaca atgagttggc agttgtggaa     480
tatgttgaag acatttacag cttctacaaa cttgctgaga tgagacaag agttcatgac     540
tacatggact cacagcctga gataatgat aggatgaggg cagttctgat agattggttg     600
gttgaagtcc accaaaaatt tgaacttaat ccagagactc tttacctcac aatcaacatt     660
gtggatcgct accttgcggt gaagactaca tcaagaaggg aattgcagtt actgggcatt     720
agtgccatgc tcatagcctc caaatatgaa gaaatttggg ctcctgaggt caatgacttt     780
gtgtgcatct cagacaaaag ttacactcat gatcaggtgt tagctatgga gaagaaatt     840
cttgggcaat tggaatggta cttaacagtc ccaacaccct tacgtatttct cgcccgtttc     900
attaaagctt ctctacctga ttcagaaatt gagaacatgg tatattttct ggctgagctg     960
gggttgatga attatgcaac cattatctac tgccccctcga tgattgctgc ctcagcggtc    1020
tatgctgctc gacacaccct caataggaca ccattttgga atgagacact taagctgcac    1080
```

```
actggtttct cagagtctca gctaatagag tgtgcaaggt tgttagtgag ctatcaatct      1140
gcggctgcga ctcacaagct aaaggtgata tacaagaagt actccagtcc ggagagaggt      1200
gttgtttcat tactaactcc ggccaaatcc ttgttggctg catcatcatc aagtgtgttg      1260
tcggagcaag ctgatttacg caaaagcaca gaagcagcag caacatcatc atccaaaatg      1320
gtggtggtgg gttgtcaaag gtgccacatg tatgtcatgg taactgaagc tgatccaaga      1380
tgcccccaat gcaagagcac tactactagg aagatgactt aa                        1422
```

<210> SEQ ID NO 12
<211> LENGTH: 1608
<212> TYPE: DNA
<213> ORGANISM: Nicotiana tabacum

<400> SEQUENCE: 12

```
atgagtaggg cttgttccct ggttcaagag tactatgact gttgcttctt atttatacaa        60
agctctagaa ttgtggtgga acgcaatgca gttgtagccc agataatagg catatcacca       120
cctggatcaa tgaggaatgc aaatatgaca attggatctt ctaatcttaa agagcccact       180
atgcgaatca caagatcacg ggcaaaagcc ttgggttcat caggaggatt accacctcga       240
cacccgtctg tcagacagga taacaaacag ggactgggag cacagggaac taagtacaaa       300
agatctgcct cggatgagaa taatccagtt actaatgcta gtacagcctg tcaacagcct       360
aagcgaaggg ccgttctcag ggatgtcacc aatgtgcttt gtgaaaattc atacatgaat       420
tgcatcaata gaagcaaatt tcaggttaag aaattctctg atacgaggaa ttcaaaggtg       480
acacctgcta ttttggtaaa aagaccgcat aatgaagata gaaagaaaaa cacgattgaa       540
gaagcaaaaa aagtaaagat cgagaaatca caagaacact gttcacaagc acgcttcaag       600
gaccttacat taactcaccc aagtaaatat atcactccag cacagtgtgg ttttgttgat       660
cttatgcctg tgaataggag tttacctaca gccattgcag tcccgaatac aacagaaaaa       720
gatgaaacca aggtttgcca gaaacaagaa ggctccgatt ctcttggtat agcagatata       780
gattcaaagc acaaggatcc actaatgtgt agtctatatg ctcctgatat atatagcaat       840
ttgcatgcca tggagcttga ccggcggcct tcatttaatt acatggaaaa gctgcagcgg       900
gacgttaaca agggtatgcg aggtattcta attgattggc tggtggaggt ttctgaagaa       960
tataggctgg ttccggacac actttacctg actgtacatc tcattgatag gttcctctct      1020
gagaattaca ttgaaaaaca aaagctgcag ctgctcggag ttacctgcat gctaattgct      1080
tccaaatatg aagaaatttg tgcccctcgt gtggaagaat tttgctttat tacagacaac      1140
acttactcaa agaagaggt agtaagaatg gaaagtctag tattgaattt tttgggcttt      1200
caacttgctg ctccgaccac taaaaagttc ctgaggagat ttgttcaagc agcacaagct      1260
tcatatgagg ttccctctgt tgaactggaa ttcatggcaa actatttagc agagctaaca      1320
cttgttgact atagttttct taagtttctt ccgtctatca ctgctgcatc ggctgtatttt     1380 ctagccaaat ggacacttga tcaatctaac cacccatgga atccaacttt ggagcactac      1440
actagttata cagcgctaga gctgaaaacc acagttcttt tgctgcaaga tttacagctg      1500
aacaccagcg gaagcaccct gaatgccatt cgtgaaaagt atagacaacc aaagttcaag      1560
tccgtggcaa ctttatcatc tccggaacca gtccaatcac tgttctaa                   1608
```

<210> SEQ ID NO 13
<211> LENGTH: 2193
<212> TYPE: DNA
<213> ORGANISM: Nicotiana tabacum

<400> SEQUENCE: 13

```
atgggtaaat tgaactcgca gaaacatata tccaccataa agatggagt tacagaactc     60
aaggtttacg aagaggcaga taagataaaa atccaaagcc gtgattctct cagcaggcgc    120
tgcaagggaa tgtctggtgc gcctaacatg agtgatgtgc agaccagtcg gaagagctcg    180
gagagtgata tcaagcacat agagaggata aaagcaaaat gcagtacttc tgttaaggta    240
aatgtcaaaa gaaaagtatt gacagatatc agcaatatca ggggcaactc ttcgagaacc    300
aaatcatata atagctccaa actgctggtg tcaaatggta aatgcccaaa aaatgcaagc    360
aattcagcaa gaaaatttat catgggaaat gtgaggccaa acttgaacgg agctactggt    420
gacaagcaaa tcttgacacg gcaccattc aaagatacaa aagcctcatt tgatggccga    480
aagaccagaa ttcaaggccg taaatcagtt accactggaa tcaggccaac tggaaggaat    540
gatttaccgc catcaaggag gtctttacct atactacagc aggtgaacat cgagggtaca    600
gacaataaag agaagggaaa ggtgagggcg aacttgaata aagctactga tgacaagcaa    660
atcttgacac aggcaccacg caaagatatg aaagcctcct ttgatggccc aaagaccaga    720
attcaagtcc gtaaatcagt taccactgga atcaggagaa ctggaaggaa tgctttaccg    780
ccatcaaggc ggtctttacc aatactacag caggtgaacg tagaggacac gaacaataaa    840
gagaaggtaa attccaaaaa gctggagaaa ggcaaggaa taagtggtgt ttcagttttg    900
gcaaagccta aggccgcagg agatgtttta ccacagttaa gcaaccacag caacatacgg    960
agaaatcgag ttggtgatgc ctcggctaga atggctcccc ggggtcaagc taaggtggaa   1020
gttggagcat tgagaagaaa atcagtcagg acagttctga aaattactgc tagcagtctc   1080
aattcacaaa agtgttcaaa gtcgaactcc atgtcaggtg tgcacaaatg cacctctcga   1140
gtttccattc catgtaaaag gctggtggat gttaggacat cttccctatc aaaatatgca   1200
acatcagaga tttcagctga gcaacctcat caaaaggaag ttccttctag tagtagtggc   1260
agcttagcta caccggaatt gtcaattgcc aggaggaaat ctgatcgtag gaagtctttt   1320
acgtgtttac tgatggcaag atcaaagctt atgaaggagc tatgtggaaa tgtagagctg   1380
gacaaatttgt caaacattta tgatagttgc aatcatcttg aagttactga atatgttgat   1440
gacatctatc aatattattg ggttatagag gcacagaatc agcctatcaa aaactacatg   1500
gagactcaga aggaaataac accccaaatg cgtggcatat tgatcaactg gcttattgaa   1560
gtccatctga aatttgattt gatgcaagaa actctatttc tcatggttac actcctggac   1620
tactacttat cattagcaag ggtcaagaag aatgatttgc agttagttgg ccttacttca   1680
ctgttgttgg catcaaaata tgaggacctt ttccatccga gggtcatgga cttactaagc   1740
atctctgctg agtcatacac aagagatcag atgctggaaa tggagaaaga tatcttaagg   1800
aaattgaagt ttcgccttaa tgcagcaact ccttatgtct tcatgctaag gcttcttaag   1860
gctgctcaag cagacacaag gtttgaacat ctggcatttt acctcatcga gttgtgcttg   1920
gttgaatacg aagctttgaa ctacaagcca tccatgcttt gtgcatcagc tatttatgtg   1980
gcaagatgta cgatgcaaat gacgccagcc tggacaccac tgctggggat tcatggacgt   2040
tatcaagaat cccaattcag acattgtgcg gaaatgatct tgaggtttca caaagctgca   2100
agcacagcac ttttgaaagt cacgcatgag aaatatatgc agtccagtaa cagcaaagtt   2160
gctgctataa aacctttgca gagtctccct taa                                2193
```

<210> SEQ ID NO 14

<211> LENGTH: 1326
<212> TYPE: DNA
<213> ORGANISM: Nicotiana tabacum

<400> SEQUENCE: 14

| | | | | | |
|---|---|---|---|---|---|
| atggttggat | cagacgagaa | cttttcaggt | gtgatgaggg | cttcaaatct | tcaaggggggg | 60 |
| ttaaggcctg | tgttggagg | aggaaaattg | actgcaggag | tgggacaaaa | taggagggca | 120 |
| ttaagtacaa | tcaataggaa | tgtaattggc | gctcccccctt | taccctatgc | tgtcaacaag | 180 |
| agaaatggca | tttctgacaa | caaagccaat | gctgctaaca | aaatcccttc | tgttccgatt | 240 |
| catcgtccaa | tcacaaggaa | gttagctgca | caaatcgcaa | gcaaacagca | gcaacctgca | 300 |
| gtcgaggtaa | caaagccacc | agtcccagtg | gcaccaaata | gaaatggatc | agaagactgc | 360 |
| attattatcg | atgctgaaga | atacaaggcc | gctggtgatt | cttccgtgcc | aatgtttgtg | 420 |
| caacatactg | aagcaatgat | ggaggaaatt | gataggatgg | atgaggagat | agagatggaa | 480 |
| gatgtagaag | actggccaat | tgtggatata | gacagtgctg | ataaaaagaa | cacgcttgca | 540 |
| gttgtggagt | acatcgatga | catctatgct | tactacaaga | agactgaagt | tcttagctgt | 600 |
| gtccctccaa | actatatgga | acagcaaatt | gatgttaatg | aaaggatgag | agccatcctc | 660 |
| attgactggc | tgattgaggt | acactacaag | tttgaactga | tggaggagac | cttgtactta | 720 |
| accgtgaatc | tcatcgatag | attcctggcg | gttcagtcag | tgattaggaa | gaaacttcag | 780 |
| cttgtcggaa | taacagctat | gcttctcgcc | tgcaaatatg | aagaggtttc | tgtacctgta | 840 |
| gtggaggatc | taattttgat | atctgacaag | gcttacacca | gaaagaagt | gcttgacatg | 900 |
| gaaaagttga | tggttaatac | cttacagttc | aacgtaacag | tgcctacagc | atatgtgttt | 960 |
| attaggcgat | tcttaaagc | cgctctgtct | gataaaaagg | tggagctcat | gtctttcttc | 1020 |
| ttgatagagc | tatgtttggt | tgaatatgag | atgcttaaat | tcccaccatc | aatgctagca | 1080 |
| gctgcttcca | tctttactgc | tcaatgcact | cttggtgttt | ctaaggagtg | gaataaaacc | 1140 |
| tgtgagaagc | atagtagcta | tgctaaaaat | cagcttttgg | aatgctcgag | attgatggtt | 1200 |
| tctttccatc | agaaggcagc | aagtgggaag | cttactggcg | tgcaccgcaa | gtacagcact | 1260 |
| tgtaaatatg | gctatgctgc | tagatgtgaa | ccagcttctt | tcctgttaga | agcagcatgg | 1320 |
| ttctag | | | | | 1326 |

<210> SEQ ID NO 15
<211> LENGTH: 1452
<212> TYPE: DNA
<213> ORGANISM: Nicotiana tabacum

<400> SEQUENCE: 15

| | | | | | |
|---|---|---|---|---|---|
| atggcgacga | cccagaatag | acgttcgtca | gtttcgagtg | cgacggcaaa | gaggcaagcg | 60 |
| atgacggcta | attcgtcgtt | ggagaataat | aatcatggga | aattggtggc | caagaaacga | 120 |
| ccagccctca | ctaatatcag | taatcataca | actgcctccg | ctcgtaactc | gctctctcac | 180 |
| tcctccaaac | tcgcaccatg | tacatccaag | gctgtaagca | ttaagaagag | caatagtaat | 240 |
| gcagcttcct | cagttctgcc | aacatcctcc | tttgtcaaac | caatcagcaa | aactgtgtct | 300 |
| attccaagaa | gtgatgcagc | tatccctaag | atcactgcca | ttcctcttcc | tgctacttgc | 360 |
| agcatggaca | tttctccatc | tcactcggac | ggatcattgg | tctccatgga | tgaaactatg | 420 |
| tccacttctg | actcactgag | aagtccggat | gttgagtaca | ttgacgacaa | ccaaacagct | 480 |
| gcattcgatt | ccattgagaa | gaaggcgttt | agcaccctct | acatctcaga | agatgtcaaa | 540 |
| gcagcagata | tatgcaagag | agatgtactt | gtagacatcg | aatcagggga | taaaattgcc | 600 |

-continued

| | |
|---|---|
| aacattgata acaatttttgt tgatccacaa ttatgtgcta caatggcctg tgacatatac | 660 |
| aaacacttga gagccacaga ggtaaagaaa aggccttcca cagatttcat ggagaaagtt | 720 |
| cagaaggaca tcaacgctag catgcgtgct attttgattg actggcttgt tgaggttgcc | 780 |
| gaggaataca ggcttgtccc ggacacattg tatctgactg ttaactacat tgatcgatat | 840 |
| ctctccggca atttgatgga caggcaacga ctacagttgc ttggagtagc ttgcatgatg | 900 |
| atcgcatcca aatatgagga gatctgtgcg cctcaagtag aagagttctg ctacatcaca | 960 |
| gacaacactt acttcaagga ggaggtttta caaatggagt ctaccgtttt aaattacttg | 1020 |
| aagtttgaaa tgacagcccc aacagccaaa tgttttctga ggaggttcgt tcgtgctgct | 1080 |
| caaggactta atgaggttct gtcactgcag ttggaacact tggccagcta catagcagaa | 1140 |
| ctctctcttt tagagtacaa catgctttgt tatgctccat cagtcattgc tgcttctgca | 1200 |
| attttcttag ccaaatatat tcttctcccc tcaaagaaac cttggaactc taccttgagg | 1260 |
| cattatactc tgtatcaacc ctctgatcta cgagactgtg tcgtggcact acatagcctt | 1320 |
| tgttgcaaca acaacaattc tagtttacca gcaatcaggg aaaaatacag ccagcacaag | 1380 |
| tacaaatttg ttgcaaagaa gtattgccct ccaacaatac ctgtagagtt cttccagaac | 1440 |
| ataagctgct aa | 1452 |

<210> SEQ ID NO 16
<211> LENGTH: 1239
<212> TYPE: DNA
<213> ORGANISM: Nicotiana tabacum

<400> SEQUENCE: 16

| | |
|---|---|
| atgggtgtat ctaatgagaa caatcctacc atgattaaac ccacaaatgt gcaaggtgag | 60 |
| gcagaattgg gttgcagaaa gtttggaatg gaaacaagga caacagaag agcattaagt | 120 |
| gtgattaacc agaattttgt tggagctaag ccatacccct tgtgttgttaa taagagagta | 180 |
| ttatctgaag ctaatgggat ctgtaacaag aatcctcctg ttccagctca tagacctatt | 240 |
| acaaggaaat tgctgcaca aattgctaac tcaaagcagc attatcctga ggaaaacaag | 300 |
| aaaccaaaaa tagcagctga aggtttaagt gtgtatgagg atgtaccaat aatagatgtg | 360 |
| gaagaatatg aggcagcagc aaaagaccag ccagttccaa tgtctttgga acaaactcaa | 420 |
| atggaaattg agatggagga tatatttgag gagagtgtga tagatattga cagtaatgat | 480 |
| gcgaagaaca cgctcgcagt tgttgactat gtggaagatc tgtatgctta ctactcaaaa | 540 |
| atggagggct gcaatcgtat cccgccagac tatataggac aacagtttga catcaacgag | 600 |
| aggatgagat ctatactaat tgactggctc attgaggtac accacaagtt tgatctcagg | 660 |
| gaggagacat tattcctgac tgttaattttg atagatagat ttttggagaa acaatccgtt | 720 |
| gtgagaaaga agctgcagct tgttggtctc gtcgccatgt tactagcgtg caaatacgag | 780 |
| gaagtttctc tccctgtggt ggatgatttg gtggtcattt cggataaagc atacacaagg | 840 |
| aaggaggttc ttgaaatgga aaaattgatg ctcaacacac tacagtttaa tatgtcacatt | 900 |
| ccaactccat atgttttttat gagaagattt ctcaaagctg ctcaatcgga tagaaagctt | 960 |
| gagctacttt cgttcttctt gatcgagctt tgcctcgtgg aatatgaaat gcttaaattc | 1020 |
| ccaccatcgt ttatcgctgc tgctgcaatc tatacagctc agtgcacact ttatggtgtt | 1080 |
| aaacaatgga gtaagacgtg cgagcttcac acaaaatact cggcagatca actcctggag | 1140 |

| | | |
|---|---|---|
| tgttcaagat tgattgtgga attccaccaa aaggcagcga cagggaaact aacagggat | 1200 | |
| ctatattcta aacaaaatcc agaaaataaa gaagagtaa | 1239 | |

<210> SEQ ID NO 17
<211> LENGTH: 1320
<212> TYPE: DNA
<213> ORGANISM: Nicotiana tabacum

<400> SEQUENCE: 17

| | |
|---|---|
| atggtaggat cagacgagaa ttgccaaggt gttatcatgg cttcaaatgt tcaaggggct | 60 |
| ggaggaggaa aagtgacaat ggggcataat agaagggctc taagtacaat aaatgggaat | 120 |
| atagttgaag ctccagcata cccttgcaaa gtacacaaga gaaatggcat cactgacaag | 180 |
| agcgcgaatg tgttaagaa tcctcccatt ccaattcatc gaccggtaac gagtatgggg | 240 |
| gattcttgct gcttcaggaa atttgctgca caaatggcta ccaagctgca gcaaccaacg | 300 |
| gtaacaaagc agccagtcca acagcaact gatagaaatg aatcagaaga ccgcatcatt | 360 |
| attgatgtag aagattacaa ggccacaagt gactatgatc ctgtgccaat gtttgtgcaa | 420 |
| catacagaag caatgatgga ggaaattgat aggatgacg cagagacgga gatggaagat | 480 |
| gtagaggaga cactaattgt ggacatagac agtgctgata aaagaaccc acttgcagtt | 540 |
| gtggagtaca ttgatgacat gcatgcttac tacaagaaga ccgagagttc tagctgtgcc | 600 |
| cctccaaatt acatggaaca caatttgat attaatgaga ggatgagagc tattctcatt | 660 |
| gactggctga ttgaggtaca ttacaagttt gatctgatgg aagagacttt gtatttgacc | 720 |
| gtaaatctta tcgatagatt cttggcagtc caacaagtga ttaggaaaaa actccagctt | 780 |
| gttgggtaa cagctatgct tctagcctgc aagtatgaag aagtttcagt tcctgtcgtt | 840 |
| gaggatctta ttttgatctc tgataaggct tacaccagaa agaagtgct tgagatggag | 900 |
| aagttgatga tcaatacctt acagttcaac ctatcagtgc ctacagcata tgtgtttatg | 960 |
| atgcgatttc ttaaagctgc tcagtctgat aagaaggtgg agctcctgtc tttctttatg | 1020 |
| actgaactat gcctcgttga gtatgaaatg cttaggttcc caccttcaat gctagctgct | 1080 |
| gcggcaatat ttactgccca atgtgctcta agtgcgccta acgagttgag taaaacttgt | 1140 |
| gagaagtata gccactacac tcaagatcag cttttggagt gctcaagact gatggtttct | 1200 |
| ttccatcaga aggctgcaat tgggaagctt actggtgtat acagaaagta tagcatctct | 1260 |
| aaatatggat tgttgcaaa atgcccacct gcttcttttc ttttagaggc atgctttag | 1320 |

<210> SEQ ID NO 18
<211> LENGTH: 1104
<212> TYPE: DNA
<213> ORGANISM: Nicotiana tabacum

<400> SEQUENCE: 18

| | |
|---|---|
| atggcagacc aagaaaattg tgttagagtg actcgattag ccaagaaaag agcagcagaa | 60 |
| gcaatggttc agcacctgca acagcccaac aagaagagag tggtgttggg tgagattcgg | 120 |
| aatttgtcca atcagattca gatgtttgat tctgagcctc ttaagcccaa atgtaataag | 180 |
| cagactacta agaggaaggt gaaaaggtct gttagtgtga agagagaga atttagggag | 240 |
| gaggatgttg attctaaatt ggatgatgat ccccagatgt gcagtgctta tgtttctgat | 300 |
| atatatgagt atcttcatca aatggagatt gagaaaaaga gaagaccatt gtctgattac | 360 |
| cttgagaaag ttcagaagga tgtaactgca aacatgagag gggttttagt ggattggcta | 420 |

| | |
|---|---|
| gtggaagttg cagaggaata caagcttctt tcagacactt tatatctcgc tgtagcctac | 480 |
| atcgacagat acttatcgat aaaggtcatc cctagacaaa gacttcagct attgggtgtt | 540 |
| tcttcaatgc tcattgcctc gaagtatgag gagattaagc ctccacgtgt tgaggatttt | 600 |
| tgttacatta cagacaatac atatacaaag aaagatgtgg taaagatgga ggctgatgtg | 660 |
| ctacaatccc ttaaatttga atgggcaat cctacaacca aacattct cagaagattt | 720 |
| actaggggttg ctcaagaaga ttgtaaaaac tccaatttga agttagagtt cctggggtgt | 780 |
| tacctagcag agttaagttt attggattac aactgtgtga agttcttacc ttctttggta | 840 |
| gcagctgctg tgatattcct ttcaagattc acattgcagc caaagttaca tccttggagt | 900 |
| gtgggcctcg aacaaaactc gggatataga gcagcagatc taaaggaatg tgttcttatc | 960 |
| atacatgact tgcaattaag tagaagagga ggctctttgg tagctgcgag gaacaaaatac | 1020 |
| aagcaacata agttcaaata tgtgtcaaca ttgtcttctc ctctggaaat accagattca | 1080 |
| ttctttgaag atacaagaca atga | 1104 |

<210> SEQ ID NO 19
<211> LENGTH: 1449
<212> TYPE: DNA
<213> ORGANISM: Nicotiana tabacum

<400> SEQUENCE: 19

| | |
|---|---|
| atggcgacga ctcagaatag acgtaattca gtttcgagtg cggtggcaaa gcggcaagcg | 60 |
| atggcggaga ataatcacgg gaaattgccg gcgggtgggg ccaagaaaag accagccctc | 120 |
| actaatatca gtaatcatac aactgcttcc gctcgtaact cgctctctca ctcctccaaa | 180 |
| ctcgcaccat gtacatctaa ggttgtaagc attaagaaga caatagtaa tgcagcttcc | 240 |
| tcagttctgc caacatcctc ctcctttgtc aaaccaatca gcaaaactgt gtctcttcca | 300 |
| agaagtgatg cagctgtccc taagatcact gcaattcctc ctcttccttc cacttgcagc | 360 |
| atggacattt ctccgtctca ctcggacgga tcattggtct ccatggatga aactatgtcc | 420 |
| acttctaact cactgagaag tccggatgtt gagtacattg acgacaacca aacagctgca | 480 |
| tttgattcca ttgagaagaa ggcttttagc accctctaca tctcagaaga tgttaaagca | 540 |
| gcagatatat gcaagagaga tgtactcgtg gatatggaat caggggataa aattgccaac | 600 |
| attgataaca atcttgttga tccacaatta tgtgctacaa tggcctgtga catatacaaa | 660 |
| cacttgagag ccacagaggt aaagaaaagg ccttccacag atttcatgga gaaagttcag | 720 |
| aaagacataa atgctagcat gcgtgctatc ttgattgact ggcttgttga ggttgccgag | 780 |
| gaatacaggc ttgtcccaga cacattgtat ctgactgtta actacattga tcgatatctc | 840 |
| tctggcaatt tgatggacag gcaacgacta cagttgcttg gagtagcttg catgatgatc | 900 |
| gcatccaaat atgaggagat ctgtgcgcct caagtagaag aattctgcta cataacagac | 960 |
| aacacttact tcaaggagga ggtcttgcaa atggagtcta ccgttttaaa ttacttgaag | 1020 |
| tttgaaatga cagccccaac agccaaatgt tttctgagga ggttcgttcg cgctgctcaa | 1080 |
| ggacttaatg aggttctgtc actgcagttg aacacttggg ccagctacat agcagaactc | 1140 |
| tctcttttag agtacaacat gctttgttat gctccatcag tcattgctgc ttctgcaatt | 1200 |
| ttcttagcca aatatattct ctcccctca aagaaacctt ggaactctac cttgaggcat | 1260 |
| tatactctgt atcaaccctc tgatttacga gactgtgtca tggcactaca tagcctttgc | 1320 |
| tgcaacaaca acaattctag tttaccagca atcagggaaa aatacagcca gcacaagtac | 1380 |

```
aaatttgttg caaagaagta ttgtcctcca acaatacctg tagagttctt ccagaacata    1440
agctgctaa                                                            1449

<210> SEQ ID NO 20
<211> LENGTH: 1155
<212> TYPE: DNA
<213> ORGANISM: Nicotiana tabacum

<400> SEQUENCE: 20
atgaagaagc aagagaaaga ggcaataatg gcggatttag aaaattgtgg cagagttaca      60
cggctagcca agaaaagggc agcagaggct atggcctcac atcaacaaca acaccctagt     120
aagaaacggg tggttttggg cgagattcag aattttttcta atctgggtgt gagtcaaatt    180
aagggtttga acactgagcc taaaaaacaa cccaaatcga agcagcagca atctaagagg     240
aaactgaaaa gggctgtgac tagtaaaatt gataaggagg agttgaatgt ggataatgtt     300
gatgctaatt acgatgaccc tcagatgtgt agtgcttatg tttctgatat atatgattat     360
cttcgtaaaa tggagattga ggaaagagg agacctttgc ctgattactt agagaaagtt     420
cagaaggatt tgagcccaaa catgagaggg gtattagtcg attggctagt ggaagttgca     480
gaggaataca agctactttc agacactta tatcttgctg tttcctacat cgatagattc      540
ttatcaacaa atgtcatcac caggcaaaaa cttcagcttt gggtgtttc gtcaatgctc      600 atttctgcga agtatgagga gattagtcca ccacatgttg aagatttttg ttacataacg     660
gataacacat atactaagga agaggtggtg aaaatggaag ctgatgtgct taaaacactc     720
aactttgaga tgggaaatcc cacagtgaaa acatttctca gaagatttac tggggttgct     780
caagaagatt ataaaacccc caatttgcag ttggagtttt tgggctatta cctagcggag     840
ttaagcatat tggattatag ctgtgtgaaa tacgtaccctt cttgctggc tgctgctgtg     900 gtattcctt cgaggtttac actacaacct aatacacatc cttggagttt ggctcttcaa      960
caatactcgg gatataaagc agcggatttg aaggaatgta ttcttatctt acacgacttg    1020
caattaagta aagaggagg ctctttagcg gctgtgaggg acaaatataa gcagcataag     1080
tttaagtgtg tgtcatcgtt gacctctcca gtggaaatac cagcttcatt ctttgaagat    1140
atgagacaat tgtaa                                                    1155

<210> SEQ ID NO 21
<211> LENGTH: 1326
<212> TYPE: DNA
<213> ORGANISM: Nicotiana tabacum

<400> SEQUENCE: 21
atggttggat cagacgagaa cttttcaggt gtgatgaggg cttcaaatct tcaaggagga      60
ttaaggcctg ttgttggagg aggaaaattg actgcaggag ttggacaaaa tagaagggca     120
cttagtacaa tcaataggaa tgtaattgga gctcccccctt taccctatgc tgtcaacaag    180
agaaatggca tttctgacaa caaagccaat gctgctaaca aatccctcc tgttccgatt     240 catcgtccaa tcacaaggaa gttagctgca caaatcgcaa gcaaacagca gcaacctgca    300
gtcgaggtaa caaagccacc agtcccattg gcaccaaata gaaatgaatc agaagactgc     360
attattatcg atgctgaaga atacaaggct actggtgatt cttccgtgcc aatgtttgtg     420
caacatactg aagcaatgat ggaggaaatt gataggatgg acgaggagat agagatggaa     480
gatgtagaag actgtccaat tgtggatata gacagcactg ataaaaagaa cacgcttgca     540
```

```
gttgtggagt acattgacga catctatgct tactacaaga agactgaggt tcttagctgt    600
gtccctccaa actacatgga acagcaaatt gatgttaatg aaaggatgag agccatccta    660
attgactggc tgattgaggt cactacaag tttgaactga tggaggagac cctgtatttg    720
actgtgaatc ttatcgatag attcctagca gttcagtcag tgattaggaa aaaacttcaa    780
cttgtcggaa taactgcatt gcttcttgcc tgcaaatatg aagaggtttc tgtacctgta    840
gtggaggatc taattttaat ttctgacaag gcttacacca gaaatgaagt gcttgtgatg    900
gaaaagttga tggttaatac cttgcaattc aatgtaacag tgcctacagc atatgtgttt    960
atgaggcgat tcttaaagc cgctcagtct gataaaaagg tggagctcat gtctttcttc   1020
ttgatagagc tatgtttggt tgaatatgag atgcttaaat tcccaccatc aatgctagca   1080
gctgctgcta tctttactgc tcaatgcact cttggtgttt ctaaggagtg gaataaaacc   1140
tgtgagaagc atagcagcta tgctaaagat cagctttcgg aatgctcgag attgatggtt   1200
tctttccatc agaaggcagc aagtgggaag cttactggcg tgcaccgaaa gtacagcact   1260
tctaaatatg gctatgctgc tagatgtgaa ccagcttctt cctgttagag cagcatgg    1320
ttctag                                                              1326

<210> SEQ ID NO 22
<211> LENGTH: 1215
<212> TYPE: DNA
<213> ORGANISM: Nicotiana tabacum

<400> SEQUENCE: 22
atgaaaggtg gtgaggcaga atgggaaac aacaagtttg actttggagt ggagacaaga     60
cacaacagaa gagcactgag agtgattaat cagaatttgt taggacctaa tccatatcgt    120
tgtgttgtta acaagagagg attatcacat gcaaatggaa tcatctacga taagaatcct    180
acgaggaaat tgactgcacc aattgctagc tcacaccagc attccccga ggaaacaaag    240
aaaccaaaac tagcagctga agattttagg atttgggagg aacatgtggc agctaaagac    300
caactcatgc ctatgtcttt ggaacaagaa gcaacatttt caaatgacaa gacagaaatg    360
gagattcaaa tggaggatat atttgaggag gcactaatag atattgacag tgatgatgca    420
aagaacccac ttgcagttgt tgactatgtg aatgatctgt accccaacta cagaaaatg    480
gagggttata gctgtgtttc accaaaacta tgacacaac agtttgatat caatgaaagg    540
atgagagcta tattagtaga ctggctcatt gaggtacatc acaagtttga gctcagggaa    600
gagacgttat tcttgaccgt taattcgata gacagatttt tggagaagca acagttgca    660
agaaagaagt tgcagcttgt tgggctggtt gctatgctat tagcatgcaa atatgaagag    720
gtctctgtcc cagtagtgga tgatttggtg attatttcgg acaacgccta taggaggaaa    780
gaggttcttg aaatggaaac attaatgctc aatacactgc agtttaatat gtcagttcca    840
actgcgtatg ttttatgag aagatttctc aaggctgctc aagctgataa aaagcttgag    900
gtcctgtcct ttttcttaat cgagctttgc ctcgtggaat atgaaatgct taagtttcca    960
ccatctttca tggctgctgc ggtagtctat acagctcagt gcacgcttta tggtgtcaag   1020
caatggaata aaacctgtga atggcataca agttactcag aagatcaact tctggagtgc   1080
tcaagatcga tcgtgagcta ccaccgaaag gcagcaacag ggaaactaac aggagtacat   1140
aggaagtata gcacatctaa atatggctac gcagcaaaat atgagccagc actttttctg   1200
gtgcagatcc aataa                                                    1215
```

<210> SEQ ID NO 23
<211> LENGTH: 1314
<212> TYPE: DNA
<213> ORGANISM: Nicotiana tabacum

<400> SEQUENCE: 23

| | | | | | |
|---|---|---|---|---|---|
| atggccatat | ctgatgagaa | caatcctaca | atgattaaac | ctacaaatgt | gcaaggtggg | 60 |
| gctggaatgg | gtaccagaaa | gtttggtgga | gtggaaacaa | gaaacaacag | aagagcattg | 120 |
| ggagtgatta | atcagaattt | agtgggtggt | gctcatcctt | ttccttgtgt | tgttaacaaa | 180 |
| agaggattat | ctgaagcaaa | tggaagatgt | gacaagaatc | tgcctattcc | agctcataga | 240 |
| cctatcacga | ggaaatttgc | agcacaaatt | gctagctctc | atcaacatcg | ctccgaggaa | 300 |
| aacaagaaag | ctaaaatagc | atcagaagaa | ttcagtatat | gggaggatat | ccctctcaca | 360 |
| gatgtggagg | aaaatgaagc | agctaaagat | caacctgttc | ctatgtcttt | ggaactaaca | 420 |
| gaaacagtcc | caaatgacaa | caagaatcaa | atggaagtag | aaatggagga | tatattagag | 480 |
| gaaaatataa | tagatatcga | tggcgatgat | gcaaagaacc | cccttgcagt | tgttgaatat | 540 |
| gtacaagatt | tgtttgcctc | ctatagaaaa | atggagggtt | gtagctgtgt | ttctccggac | 600 |
| tatatggcac | aacagtttga | catcaacgag | agaatgagat | ccattctaat | cgactggctc | 660 |
| attgaggtac | atcacaagtt | cgagctcagg | gaagagacgt | tgttcctgac | tgttaatttg | 720 |
| atagatagat | ttttggagaa | gcaaggtgtt | gtcagaaaga | agctgcagct | tgtgggttg | 780 |
| gttgccatgc | tattagcatg | caaatatgag | gaagtttctg | ttccattggt | ggaagatttg | 840 |
| gtgtttattt | ctgacaaagc | ctattcaagg | aaggagattc | ttgaaatgga | agaatgatg | 900 |
| cttaacacac | tgcagtttaa | catgtcagtt | ccaactgcat | atgttttat | gagaagatat | 960 |
| cttaaggctg | ctcaatctga | taggaagctt | gagctgctgt | ctttcttctt | ggttgagctt | 1020 |
| tgtctagtgg | aatatgcaat | gctcaagttt | ccaccatcat | tcatagctgc | tgcagcaatc | 1080 |
| tatacagctc | agaccacact | ctacggtgtc | cagcagtgga | gtaagacatg | cgagtggcat | 1140 |
| actagttact | cggaagatca | acttatggag | tgctcgagat | cgattgtgag | ctatcaccag | 1200 |
| aaggcagcaa | caggaaaact | aacagggggtg | cataggaagt | acagtacatc | taaatttggt | 1260 |
| tatgcagcaa | aatgtgagcc | tgcccatttt | cttgtgcaga | cacaacaaca | atag | 1314 |

<210> SEQ ID NO 24
<211> LENGTH: 2181
<212> TYPE: DNA
<213> ORGANISM: Nicotiana tabacum

<400> SEQUENCE: 24

| | | | | | |
|---|---|---|---|---|---|
| atgggtaaat | tgaactcgca | gaaacatata | tccaccataa | aagatggagt | tacagaactc | 60 |
| aaggtttacg | aagaggtaga | taagataaaa | atccaaagcc | gtgattctct | cagcaggcgc | 120 |
| tgcaagggaa | agtctggtgc | gcctaacatg | agtgatgtgc | agaccagttg | aagagctcg | 180 |
| gagaggggta | tcaagcacat | agagaggata | aaagcaaaat | gcaggacttg | tgttaaggta | 240 |
| aatgtcaaaa | gaaaagtatt | gacggatatc | agcaatatca | ggggcaactc | ttcgagaacc | 300 |
| aaatcatata | atagctccaa | actgctggtg | tcagatggta | aatgcccaaa | aaatgcaagc | 360 |
| aattcagcaa | gaagatttat | catgggaaat | gtgaggacaa | acttgaacgg | agctactggt | 420 |
| gacaagcaaa | tcttgacacg | ggatatgaaa | gcctcctttg | atggcccaaa | gaccagaatt | 480 |
| caaggccgta | atcagttac | cactggaatc | aggccaactg | gaaggaatga | tctaccgcca | 540 |
| tcaaggaggt | ctttacctat | actacagcag | gtgaacatcg | agggtacaaa | caataaagag | 600 |

-continued

```
aagggaaagg tgagggcgaa cttgaataaa gctactgatg acaagcaaat cttgacacag      660
gcaccacgca aagatatgaa agcctccttt gatgggccaa agaccagaat tcaagtccgt      720
aaaccagtta ccactggaat caggagaact ggaaggaatg ctctaccgcc atcaaggagg      780
tctttaccaa tactacagca ggtgaacgtc gaggacacga acaataaaga gaaggaaaat      840
tccaaaaagt tggagaaagg caaggaata agtggtgttt cagttttggc aaagcctaag      900
gccgcaggag atgttttacc acagttaagc aaccacagca acatccggag aaatcgagtt      960
ggtgatgcct cggctagaat ggctccccgg ggtcaagcta aggtggaagt tggagcattg     1020
agaagaaaat cagtcaggac agttctgaaa attactgcta gtggtctcaa ttcacaaaag     1080
agttcaaagt cgaactccat gtcaggtgtg cacaaatgca cctctcgatt tgccagtcca     1140
tgtaaaaggc tggtggatgt taggacatct tccctatcaa aatctgcaac atcagagatt     1200
tcagctgagc aacctcatca aaaggaagtt ccttctagta gtagtggcag cttagctaca     1260
ccggaattgt caattgccag gaagaaatct gaccgtagga agtcttttac gtgtttactg     1320
atggcaagat caaagcttat gaaggagcta tgtggaactg tagagctgga caatttgtca     1380
aacatttatg atagttgcaa tcatcttgaa gttacagaat atgttgatga catctatcag     1440
tattattggg ttatagaggc acagaatcag cctatcaaaa actacatgga gactcagaag     1500
gaaataacac cccaaatgcg tggcatattg atcaactggc ttattgaagt ccatttgaaa     1560
tttgatttga tgcaagaaac tctatttctc atggttacac cctggactaa ctacttaaca     1620
ttagcaaggg tcaagaagaa tgatttgcag ttagttggcc ttacttcact gttgttggca     1680
tcaaaatatg aggacctttt ccatccgagg gtcatggact tactaagcat ctctgcagag     1740
tcatacacaa gagatcagat gctggaaatg gaaaaagata tcttaaggaa attgaagttt     1800
cgccttaatg cagcaactcc ttatgtcttc atgctaaggc ttcttaaggc tgctcaagca     1860
gacacaagga ttgaacatct ggcattttac ctcatcgagt tgtgcttggt tgaatatgaa     1920
gctttgaact acaagccatc catgctttgt gcatcagcta tttatgtggc aagatgtacg     1980
atgcaaatga cgccagcctg gacaccactg ctggggatgc atgcacgtta tcaagaatcc     2040
caactcagac attgcgcgga aatgatcttg aggtttcaca aagctgcaag cacagcactt     2100
ttgaaagtca cgcatgagaa atatatgcag tccagtaaca gcaaagttgc tgctataaaa     2160
cctttgcaga gtctccctta a                                                2181
```

<210> SEQ ID NO 25
<211> LENGTH: 1278
<212> TYPE: DNA
<213> ORGANISM: Nicotiana tabacum

<400> SEQUENCE: 25

```
atggataaca atagtgttgg tgttcctcac aatttaccca gaggagaaat gggaggaaaa       60
cagaaaaatg cacaagccga tggaagaaat aggcgtgctc tcggagacat tggcaacctt      120
gtgcctgctc ctgctgcaga aggaaagcct aaagcagctc agatttctcg ccctgtgact      180
aggagctttt gtgcacagtt gctagctaat gcacaagaag agaagaacaa gaaaccacta      240
gcagaagttg tcaataaaga tgtaccagcc aagaagaagg catcagataa ggaaatgaag      300
actgttgggg gaagtccatt gagcaaaaga aaagcaaaga agtctggaaa gactctcact      360
tctactctca ctgctagaag caaggctgct tgtggacttt ccaatagacc aaagtatgag      420
attgaggaca tcgatgtcgc tgatgctgat aatcatttgg ctgctgtaga gtatgttgag      480
gatatctaca acttctacaa gctcactgag ggtgaaagtc gagtggatga cgactacatg      540
```

```
aactttcaac cagacctgaa tcataagatg agagccattt tagtggactg gttaatagaa      600
gttcacagga aatttgagct tatgcctgag agcctttacc ttacaattac catactggac      660
cgtttcctct cgctgaagac ggttccaagg aaggaacttc agttagttgg cattagctca      720
atgctaattg cttgcaagta tgaagagatt tgggcaccag aggtgaatga tttcattcat      780
atatcagaca atgcatatgc cagagagcaa atacttcaga tggagaaagc aattcttggg      840
aagttggaat ggtatttgac agttccaaca ccatatgttt ttctggttag gtacattaaa      900
gctgcaacac catctgataa tcaggagatg agaacatga cattcttttt tgctgaactt      960
ggtcttatga actacaagat cacaatatca taccgcccat caatgctagc agcatcgtcc     1020
gtttatgctg ctcgtagcac tctcaacaaa actccactat ggactcaaac tctgcagcac     1080
catactggct actcagaaga tcagttgatg gaatgtgcaa agatattggt tagttatcac     1140
ttggatgctg cagaaagtaa gctgaaagca atttacagga agttttcgag tccagataga     1200
ggtgctgttg cattcttccc accagcaaga aatctcctac ctactactac tactgatgct     1260
gcttcctcct cttcttga                                                   1278
```

<210> SEQ ID NO 26
<211> LENGTH: 1311
<212> TYPE: DNA
<213> ORGANISM: Nicotiana tabacum

<400> SEQUENCE: 26

```
atggttggat caaacgagaa ttgccaaggt gttataatgg cttcaaatgt tcaagggga       60 ttagggggctg gaggaggaaa ggtgacaatg gggcctaata gaagggctct aagcacaata    120
aatgggaata tagttgaagc tccagcatac ccttgtaaag tacacaagag aaatggcatc    180
actgacaaga gcgcgaatgg tgttaagaat cctcccattc caattcatcg accaatcaca    240
aggaaatttg ctgcacaaat ggctaccaag cagcagcaac caacggttga ggtaacaaag    300
cagccagtcc aaacagcacc tgctaaaaat gaatcagaag actgcatcat tattgatgca    360
gaagattaca aggccacaag cgactatgat cctgtgccaa tgtttgtgca acatacagaa    420
gcaatgatgg aggaaattga tcggatggac gctgagatgg agatggaaga tgtagaagag    480
acactaattg tggacataga tagtgctgat aaaaagaacc cacttgcagt agcggagtac    540
attgatgaca tgcatgctta ctacaagaag accgagagtt ctagctgtgc ccctccaaat    600
tatatggaac aacaatttga tattaatgag aggatgagag ctattctcat tgactggctg    660
attgaggtac attacaagtt tgatctgatg gaagagactt tgtatttgac cgtaaatctt    720
atcgatagat tcttagcagt ccaacaagtg attaggaaaa aactccagct tgttggggta    780
acagctatgc ttctagcctg caagtatgaa gaagtttcag ttcctgtcgt tgaggatctt    840
attttgatct ctgataaggc ttacaccaga aaagaggtgc ttgagatgga agttgatg      900 atcaataccct tacagttcaa cctaccagtg cctacagcat atgtgtttat gatgcgattt    960
cttaaagctg ctcagtctga taagaaggtg gagctcctgt ctttttttcat gactgaacta   1020 tgcctcgttg agtatgaaat gcttaggttc ccaccttcaa tgctagctgc tgcagcaata   1080
tttacagccc aatgtactct aggtgtgctt aacgagtgga gtaaaacttg tgagaagtat   1140
agccactata ctcgagatca gcttttggag tgctcaagac tgatggtttc tttccatcag   1200
aatgctgcaa ctgggaagct tgctggtgtg catagaaagt atagcatctc taaatatggc   1260
tttgttgcaa aatgcccacc tgcttctttt cttttagagg caagcttta g             1311
```

<210> SEQ ID NO 27
<211> LENGTH: 1269
<212> TYPE: DNA
<213> ORGANISM: Nicotiana tabacum

<400> SEQUENCE: 27

| | | | | | |
|---|---|---|---|---|---|
| atgggtgtat | ctaatgagaa | caatcctagc | atgattaaac | ccagaaatgt | gcaaggtggg | 60 |
| gcagaattag | gttacagaaa | gtttggagtg | gagacaagga | ataacagaag | agcattaagt | 120 |
| gtgattaatc | agaattttgt | tggagctaag | ccatacccct | gtgttgttaa | taagagagga | 180 |
| ttatctgata | ctaacaagaa | tcctcctgtt | ccagctcata | gacctatcac | aaggaaattt | 240 |
| gctgcacaaa | ttgccaactc | aaagcagcat | tatcctgagg | aaaacaagaa | accaaagata | 300 |
| gcagctgaag | gtttaagtgt | atatgaggat | gtagctatag | tagatgtgga | agaatatgag | 360 |
| gcagcagcaa | aagaccagcc | agttccaatg | tctttggaac | aaactcaaat | ggagattgag | 420 |
| atggaggata | catttgagga | gagtgtgata | gatattgaca | gtaacgatgc | gaagaacccg | 480 |
| ctcgcagttg | ttgactatgt | ggaagatctc | tatgcctact | actcaaaaat | ggagggctgc | 540 |
| agtcgtatct | cgccagacta | tataggacaa | cagtttgaca | tcaacgagag | gatgagatct | 600 |
| atactaatcg | actggctcat | tgaggtacac | cacaagtttg | atctcaagga | agagacatta | 660 |
| ttcctaactg | ttaatttgat | agatagattt | ttggagaaac | aatctgttgt | gagaaagaaa | 720 |
| ctgcagcttg | ttggtctcgt | cgccatgtta | ctagcgtgca | aatatgagga | agtttctctc | 780 |
| cctgtggtgg | atgatttggt | ggtcatttcg | gataaagcat | acacaaggaa | ggaggttctt | 840 |
| gaaatggaaa | aattgatgct | caatacgctg | cagtttaata | tgtcggttcc | aactccatat | 900 |
| gtttttatga | agagatttct | caaagctgct | caatcggata | aaaagcttga | gctactttcg | 960 |
| ttcttcttga | tcgaactttg | cctcgtggaa | tatgaaatgc | ttaaatttcc | accatcattt | 1020 |
| atcgctgctg | ctgcaatcta | cacagctcag | tgcacatttt | atggtgttaa | acaatggagt | 1080 |
| aagacgtgcg | agctgcacac | taaatactcg | gaagatcaac | ttctggagtg | ttccagattg | 1140 |
| attacgggat | ccaccaaaaa | ggcagcaaca | gggaaattaa | ccggggtaca | tagaaagtac | 1200 |
| aatacatcta | aatttggtta | tgtggcaaaa | tgtgagcctg | ctcattttct | tcttgtgcag | 1260 |
| acccgataa | | | | | 1269 |

<210> SEQ ID NO 28
<211> LENGTH: 1479
<212> TYPE: DNA
<213> ORGANISM: Nicotiana tabacum

<400> SEQUENCE: 28

| | | | | | |
|---|---|---|---|---|---|
| atgaggaatg | caaatatgac | aattggatct | tctaatctta | aagagcccac | tatgcgaatc | 60 |
| acaagatcac | gggcaaaagc | cttgggttca | tcaggaggat | taccacctcg | acacccatct | 120 |
| gtcagacagg | ataacaaaca | gggactggga | gcaaagggaa | ctaagtacaa | aagatctgcc | 180 |
| tcggatgaga | ataatccagt | tactaatgct | agtacagcct | gtcaacagcc | taagcgaagg | 240 |
| gctgttctca | gggatgtcac | caatgtgctt | tgtgaaaatt | catatatgaa | ttgcatcaat | 300 |
| agaagcaaat | tcaggttaa | gaaattctct | gataagagga | attcaaaggt | gacacctgct | 360 |
| atttttggcaa | aaagaccgca | tcatgaagat | acaaaagaga | cacgattga | agaagcaaaa | 420 |
| aaagtaaaga | tcgagaaatc | acaagaacac | tgttcacaag | cacgcttcaa | ggaccataca | 480 |
| ttaactcagc | caagtaaata | tatcactcca | gcacagtgtg | gttttgttga | tcttatgcct | 540 |
| gtgaatagga | gtttacctac | agccattgca | gtcctgaata | caacagaaaa | agatgaaacc | 600 |

```
aaggtttgcc agaaacaaga aggctccgat tctcttggta tagcagatat agattcaaag      660
cacaaggatc cactaatgtg tagtctatat gctcctgata tatatagcaa tttgcatgcc      720
atggagcttg accggcggcc ttcatttaat tacatggaaa agctgcagcg ggacgttaac      780
aagggtatgc gaggtattct aattgattgg cttgtggagg tttctgaaga atataggctg      840
gttccggaca cactttacct gactgtacat ctcattgatc ggttcctctc tgagaattac      900
attgaaaaac aaaagctgca gctgctcgga gttacctgca tgctaattgc ttccaaatat      960
gaagaaattt gtgcccctcg tgtggaagaa ttttgcttta ttacagacaa cacttactca     1020
aaagaagagg tagtaagaat ggaaagtcta gtattgaatt ttttgggctt tcaacttgct     1080
gctccgacca ctaaaaagtt cctgaggaga tttgttcaag cagcacaagc ttcatatgag     1140
gttccctctg ttgaactgga attcatggca aactatttag cagagctaac acttgttgac     1200
tatagttttc ttaagtttct tccgtctatt actgctgcat cggctgtatt tctagccaaa     1260
tggacacttg atcaatctaa ccacccatgg aatccaactt tggagcacta cactaggtat     1320
acagcgctag agctgaaaac catagttctt ttgctgcaag atttacagct gaacaccagc     1380
ggaagcaccc tgaatgccat tcgtgaaaag tatagacaac caaagttcaa gtccgtggca     1440
actttatcgt ctccgcagcc agtccaatca ctgttctaa                           1479

<210> SEQ ID NO 29
<211> LENGTH: 1269
<212> TYPE: DNA
<213> ORGANISM: Nicotiana tabacum

<400> SEQUENCE: 29
atggataaca aaactgttgt tgttcctcac aatttaccca aaggagaaat gggaggaaaa       60
cagaaaaatg gacaagccga tggaagaaat aggcgtgctc tcggtgacat ggcaaccttt      120
gtgcctgctc ctgctgtaga aggaaagcct aaagcagctc agatttctcg ccctgtgact      180
cggagctttt gtgcacagtt gctagctaat gcacaagcag agaagaacaa gaaagcacta      240
gcagaaattg tcaataaaga tgcaccagcc aagaagaagg catcagataa ggaaataaag      300
actgttgagg gaagttcatt gagcaaaaga aaagcaaaga gagcggaaa gactctcact      360 tctactctca ctgctagaag caaggctgct tgtggacttt ccaatagacc aaagtatgag      420
attgatgaca tcgatgtcgt ggatgctgat aatcatttgg ctgctgtaga gtatgttgag      480
gatatctaca acttctacaa gctcactgag ggtgaaagtc gagtggatga ttacatgaac      540
tttcagccag acctgaatca agatgagag gccattttag tggactggtt gatagaagtt      600
cacaggaaat ttgagcttat gcctgagagc ctttaccttg caattaacat actggaccgg      660
ttcctctcgc tgaagacggt tccaaggaag gaacttcagt tagttggcat tagctcaatg      720
ctaattgctt gcaaatatga agagatttgg gcaccagagg tgaatgattt cattcatata      780
tcagacaatg catatgccag agagcaaata cttcagatgg agaaagctat tcttgggaaa      840
ttggaatggt atttgactgt tccaacacca tatgttttc tggttagata cattaaagct      900
gcaacaccat ctgataatca ggagatggag aacatgacat tcttttttgc tgaacttggt      960
cttatgaact acaagaccac aatatcatac tgcccatcaa tgctagcagc atcgtccgtt     1020
tatgctgctc gtagcactct caacaaaact ccattatgga ctcaaactct gcagcaccat     1080
actggctact cagaagatca gttgatgaa tgtgcaaagc aattggttag ttatcacttg     1140
ggtgctgcag aaagtaagct gaaagcaatt tacaggaagt tttcgagtcc ggatagaggt     1200
```

| | |
|---|---|
| gctgttgcct tcttcccgcc agcaagaaat ctcctaccta ctactactga tgctgcttcc | 1260 |
| tgttcttga | 1269 |

<210> SEQ ID NO 30
<211> LENGTH: 1488
<212> TYPE: DNA
<213> ORGANISM: Nicotiana tabacum

<400> SEQUENCE: 30

| | |
|---|---|
| atgaggcatg caaatataaa acatggatct tttcatcttg aagagcacaa tatgcgaatc | 60 |
| acacgagcac gagcaagagc aagtgtgttg ggttcatcag gacgattacc acccctacac | 120 |
| ccatccacaa aacaggataa gaagcatgta ttgggagcag agtccaaaag atcgaaaaga | 180 |
| tctgcctcag atgagaacag acctggtacc tctagtactg ctactggtgt tcagcctaag | 240 |
| agaagggctg ttcttaaaga catgacgaat gtacttcatg agaactctca catgaattgc | 300 |
| atcaacggaa gcaaaattca ggttaaaaaa ggctccgata gaggaacaa taaggcgaaa | 360 |
| cctgctgttt cggtaaaatt gtcacagctc aagagaaag gaaagagga tatagctgat | 420 |
| aaagtaaaga aagtgaaggt tgagggatca caagaaataa gttcggggc aaactgcaag | 480 |
| gaggatatgt tacctcagct aagtagatat gtcactccag cacaatgtgg tttagtccat | 540 |
| ctagtgcctg tgaacagaag ttcctgtaag gccatcccac ttcaggatat aatgaaaaaa | 600 |
| gatgaaagca aagtttgccg gaaacaagaa ggctttgcta atctaggagt tgctgatatt | 660 |
| gattcaagac acaaggatcc actgatgtgt agtctgtatg ctcctgatat ttataacaat | 720 |
| ttgcatgcca ttgagtttga ccgtaggcct tctgttgatt acctggaaaa gctgcagctg | 780 |
| gacattaaca agggtatgcg aggtattctg attgattggc ttgtggaggt ttcagaagaa | 840 |
| tataggctgg ttccagacac actttaccta actgttaatc ttattgaccg tttcctatct | 900 |
| gaaaattaca ttgaaaaaca aaagctgcaa ctacttggag ttacctgcat gctaatagct | 960 |
| tccaaatttg aagagatttg tgcacctcgt gttgaagaat tttgcttcat tacagataac | 1020 |
| acttactcga aggaagaggt aataaaaatg gaaagcagag tcttgaacct tttgagcttt | 1080 |
| caacttgctt ctccaaccac taagaaattc ctgaggagat tcattcaagc agctcaagct | 1140 |
| tcttacaagg ttccctctgt cgaactggaa ttcatggcaa attatttagc tgagttaaca | 1200 |
| cttgttgact atgggtttct taagtttctt ccatctctta ctgctgcatc agctgtatt | 1260 |
| ctagctagat ggacgcttga tcaatctaac cacccatgga tccaacttt ggagcactat | 1320 |
| accagataca aggtatcaga gcttagaact acagttttg cactgcaaga gttacagatg | 1380 |
| aacaccagtg gctgcaccct caatgccata cgtgaaaaat atagacaacc aaagttcaag | 1440 |
| tccgtggcta ctttagcagc ttcaaaacca gtccaatcac tgttctaa | 1488 |

<210> SEQ ID NO 31
<211> LENGTH: 1341
<212> TYPE: DNA
<213> ORGANISM: Nicotiana tabacum

<400> SEQUENCE: 31

| | |
|---|---|
| atggcttcaa gaaacgttct tcaacagcag aatataggtg aggcagtacc cggggcacta | 60 |
| aaacagaaga atatggcagc agcagcacaa ggtagaaacc gaaaggcgct tggtgatatt | 120 |
| gggaataatg tggtaactgt tcgtggcgtc gagggaaagc cacttcctca acgcccata | 180 |
| acaaggagct tttgtgcaca attgctcgct aatgcacaag cagcagctga aaaccaaaag | 240 |
| aaatctttgg tggttaatgg ggatgcaccg atcgttgcta aaggagctct agcggttaaa | 300 |

-continued

```
gctgcagcca aaaaaccagc tcataagaaa gttgctgtaa aaccaaagcc tgatgtgatt        360
gaaattagtc ctggtactga agaacaagtg aaggaaaata agcaaagaa gaaggctggt        420 gatgactctt cactaaagaa agcaactctt acttcaactc tcactgctag gagcaaggct        480
gcttgtggac tgagtcataa accaaaggtc cagattgtgg acattgatgc tgttgatgtg        540
aataatgagt tggctgtggt ggaatatgtt gaggatattt acaatttta taagatagct        600 gagaatgaga gcagaattca tgattacatg gattcacagc ttgagataac tgaaagaatg        660
agagctattc tgattgattg gttgattgaa gtgcatcaca aatttgagct tagtcaagag        720
actctttacc tcacaatcaa tatcgtcgat cgttatctcg cggtcacaac tacatcaagg        780
agggaattgc agttagtagg catgagtgct atgctcattg cctctaaata tgaagaaatc        840
tgggctcccg aggtgaatga ctttgtgtgc atctcagata aagcttacag tcatgagcag        900
gtgttgggaa tggagaaaag gattcttggc caattggagt ggtacttaac agttccaaca        960
ccttatgtgt tcctcgttcg ctttatcaaa gctgctgttt ctaatgcaca aatggaaaac       1020
atggtttatt tcctggctga attggggtta atgaattatg caacaaatat ctactgccca       1080
tcgatgattg ctgcctcagc agtctatgtt gctcaacaca cactgaattg cactccgttt       1140
tggaacgaca cactaaaatt gcatactggt ttctcagagt ctcagctact gggttgtgca       1200
aagttgctgg taagctatca catggaagct ccagaacaca agctgaaagt gatttacaag       1260
aagtattcga gacctgagag aggtgctgtt gcactgcaac ctccagccaa atccctgttg       1320
gctgcttctt tatatgaata a                                                 1341
```

<210> SEQ ID NO 32
<211> LENGTH: 1422
<212> TYPE: DNA
<213> ORGANISM: Nicotiana tabacum

<400> SEQUENCE: 32

```
atggcttcaa gaatcgtcct tcaacagcag aatagaggtg aggcagtccc tggggcatta         60
aagcagaaaa agaatgtggc agcagaagga agaaatagga aagcgcttgg tgatattggg        120
aatgtggcta caggtcgtgg ggtcgaagga aaaaagccac ttcctcagaa acctgttgct        180
gttattgtaa aaggagcaaa tgttgctaaa gtacctgcag taaggaaacc agctcagaag        240
aaagccacag ttaaaccaaa acctgaggag attattgaaa ttagtccgga cactcaagaa        300
aaactgaagg agaagatgca aaggaagaag gctgataaag actcattaaa acagaaagca        360
actcttactt caactctcac tgctcgaagc aaggctgcat gtggtctgag taaaaaacca        420
aaggagcaga tagtggatat tgatgctgca gatgtgaaca atgagttggc agttgtggaa        480
tatgttgaag acatttacag cttctacaaa cttgctgaga atgagacaag agtccatgac        540
tacatggatt cacagcctga ataaatgat aggatgagag cagttctgat tgattggttg        600
gttgaagtcc accaaaaatt tgaacttaat ccagagactc tttacctcac aatcaacatt        660
gtcgatcgct accttgctgt gaagagtaca tcaagaaggg acttgcagct agtgggtgtc        720
agtgccatgc tcatagcctc caaatatgaa gaaatttggg ctcctgaggt caatgacttt        780
gtgtgcatct cagacaaaag ttacactcat gatcaggtgt taactatgga gaagaaaatt        840
cttgggcaat tggaatggta cttaacagtt ccaacacctt atgtgttcct agcacgtttc        900
attaaagctt ctccacctga ttcagaaact gagaacatgg tatattttct ggctgagctg        960
gggttgatga attatccaac cattatctac tgcccttcaa tgattgctgc ctcagcggtc       1020
```

| | |
|---|---|
| tatgctgctc gacacaccct caataggaca ccattttgga atgagacact taagctgcac | 1080 |
| actggtttct cagaatctca gctaatagag tgtgcaaggt tgttagtgag ctatcaatct | 1140 |
| gcggctgcaa ctcacaagct aaaggtgata tacaagaagt actccagtcc ggaaagaggt | 1200 |
| gttgttgcat tgctaactcc agccaaatcc ctgttggctg catcatcatt acgtgtgtcg | 1260 |
| tcggagcaag ctgatttagg caaaagcaca gaagcagcag caacatcatc atcccctatg | 1320 |
| gtggtggtgg gttgtcaaag gtgccacatg tatgtcatgg taactgaagc tgatccaaga | 1380 |
| tgcccccaat gcaagaacac tactactagg aagatgactt aa | 1422 |

<210> SEQ ID NO 33
<211> LENGTH: 1767
<212> TYPE: DNA
<213> ORGANISM: Nicotiana tabacum

<400> SEQUENCE: 33

| | |
|---|---|
| atgatacaag ttaaggagga atctcagact ctggactttg gtggatttgc ttcttgttca | 60 |
| tctttctctg atagcagtta cgaggctagc actccaagat actcctccga acctggttct | 120 |
| agttatcgaa ggagctcagg tccaactaaa cgttcttccc aggcaggctg acagaagaa | 180 |
| gaggataatc tgttgactga cgtggtgaaa aggttcaaag ggagaaactg aaaaaaata | 240 |
| gctgagtgca tgaatggaag gactgatgtg cagtgcttgc atcgctggca gaaagttctg | 300 |
| aatcctgagc ttgtaaaggg tccttggtca aggaggagg atgacctgat tattgagtta | 360 |
| gttgagaaat atggctgtaa gaagtggtct tttattgcca agtctttgcc tggtcgcatt | 420 |
| ggtaagcaat gtagggaaag gtggcacaac catcttgacc caaccataaa agagatgct | 480 |
| tggactgaac aggaagaatc agtcctatgc cactatcacc aaatatatgg gaacaagtgg | 540 |
| gcagaaattg cgaggtttct gcctggaagg actgataatg caattaaaaa tcattggaat | 600 |
| tcctcagtta agaaaagatc gaacttgaat ttgccaagtg ggttagtgct ggataccgaa | 660 |
| agtgaggaat ctcctaattt ctctagtgac aagaaaaaac tagagatcca gaagcatcca | 720 |
| ttacaagctc aaaatgcaga acaaacaatc ttttaggcg agcagacagg attggataat | 780 |
| gctgctgttg ctttgtcaac tgatctgaga attggatatg cttattctgc tggaaatgct | 840 |
| ttgcataagg atacttcttt atttggagcc tgtatatcag cagaagaaaa tgtgagggat | 900 |
| ctgataaagc cacttggtgg aataccattt ggcaaggcag atgttcttcc aattggtgag | 960 |
| acagataaac catgtcaatc caatttaagt cgcactaaaa tatcatatcc actctcagcc | 1020 |
| tcttcttcag attttccttt ggatcagttg caccacacaa gatggagtac ttctcaagtt | 1080 |
| gaggctgttc atcctactac ttttgggagc atgtatgaat ctcccaagag gtctaggcac | 1140 |
| gacactgtta acgatcctga ccatgatttt ttgagtttgt cattggctag ctttactgag | 1200 |
| gttcgttccc aaagtaacaa gaagaataaa gcatatgaca cacaatcttc tttgggtctc | 1260 |
| aagcagcagg gctccttgta ttatgaacca ccacagttaa aggacatgct gattcctta | 1320 |
| acagatgaaa accttagtag agacaacctt atcacggaaa aaatggtca tccattttgc | 1380 |
| tctactcctc ctagtcttaa attaacagtc tctgctaatg gtagcagtcc agaatctgtc | 1440 |
| ttaaggaatt ctgcaatgag ttacacagga actccttcaa tcataagaaa gaagaattcc | 1500 |
| agatttcccg aagctgcgac gcattctagt tgcacaggca ccaccactcc cacacataat | 1560 |
| ttcccaagag cttctgacag ggaagacacc tcaaacctga aggacagatt ttctgggtgt | 1620 |
| aaatcatcag tttcgggaaa atctcttgga agacggttgg aatatgcctt tgatatggaa | 1680 |

-continued

| | |
|---|---|
| tgggatgcct ctagatgttg cacaccagtt tctgcagctt caccttgtgc acttagactt | 1740 |
| ggtgctaata cgatgctgac accataa | 1767 |

<210> SEQ ID NO 34
<211> LENGTH: 3132
<212> TYPE: DNA
<213> ORGANISM: Nicotiana tabacum

<400> SEQUENCE: 34

| | |
|---|---|
| atggaaagtg atagaataag cactccttca gatggcacta gcagtagtct ccaaagagtt | 60 |
| cggcctttgc atgggagaac tagtggtcct acgagacgtt cgacaaaggg gcagtggact | 120 |
| actgaagaag acgagatcct acgcaaagct gtccaacgtt taagggcaa aaactggaaa | 180 |
| aaaatagcgg aatgttttaa agaccggact gatgtacaat gcttgcaccg gtggcagaaa | 240 |
| gttcttaatc ctgaacttgt caaaggtcca tggtctaaag aggaggatga agtaatagtt | 300 |
| gaattagtta agaaatatgg ccccaaaaag tggtccacca tcgctcaaca tttgccggga | 360 |
| cgtattggaa acaatgtcg agaaaggtgg cacaatcatc tgaatcctgg aataaacaag | 420 |
| gaagcttgga cgcaggagga ggagttgact ctgattcgcg cccaccaaat ttacgggaat | 480 |
| aaatgggcag agttaacaaa gtatttgcct ggaaggacag ataatgcaat aaaaaatcac | 540 |
| tggaatagtt ctgtcaaaaa gaaattggac tcgtatttgg catccggttt acttgcacag | 600 |
| ttcccttctc tgcctaatgt caaccgtcag aaccaatcaa tcccttcttc gacgaagttg | 660 |
| caacagagta gtgaagatga cagtgttcgt aaagaaggaa tcgaaatgga ggaagcttca | 720 |
| gaatgcagtc aagggtcaaa tcttgcaggc tgttcccagt ctacaagtga catgggcaat | 780 |
| acatttgtac atacaagaga ggagggcaag ttgctggagg attcaaatta taggaaggac | 840 |
| ccaagctcca gttcagcacc atgctctgaa tactataccc cagcctttga agatattacc | 900 |
| ttttcaatgg cagaagtgcc tagtgaactt gacgaatcca agctcctgga gcataacttc | 960 |
| tcacatgact gggcagcatc catgggaaaa gaatggcagt ttaatccaga tgacatacct | 1020 |
| aatatttctc cgctggagtt gatgcaggat tcttcagggc tcttcatgca gtgtttaact | 1080 |
| ggtaatggga atcacgaaat ggttaccttt ccacagcaaa atgcagtgaa gtatgaaatg | 1140 |
| actaatgtcg gaagcatggt tgtgggttta gataagccca tgagatgtt tacctctgtg | 1200 |
| gagggttgcg ggatggtata ccctgaggca ggaattccac aatacattcc ctctgaaact | 1260 |
| ggtatgaacg tgctgatga aactgcagat tctttgattt gccaatcgtc gaactatcag | 1320 |
| atctctgaag gtgaaatat gtctatagag aattgctgca ccctctgtg ttcacatgtt | 1380 |
| atgggaactt catccggtca accattttct attccttcac agttttcttc agagcaaagc | 1440 |
| tcactcatgt ttggtactgc cgcaaatcac tttcataatc catcgcaggg aaacccagca | 1500 |
| caggagtccc acacaagtaa ctctgatggt tttctatatc cctttgaatc tggtactcct | 1560 |
| tgtgacaaca taatgacga tcctctcctg gaagagcaac tggatcaaac taagattct | 1620 |
| ctacagctag tttctgtcaa tgattttcgc tcaactcctt caaatactat tcaaacatgt | 1680 |
| ccattggtga acgaaaattc gagcgtacca gaagagcaga aggatggagg agccttatac | 1740 |
| tatgagcctc ctcgttttcc gagcttggac attccatttt tcagttgtga tcttatacaa | 1800 |
| tctggtgcag atgcacagca agagtatagc cctcttggca tccgccagtt gatgatgact | 1860 |
| tctgtgaact gtcttactcc atttaggctg tgggattcac catctagaga tggaagtcca | 1920 |
| gatgctgtcc tgagaagtgc tgccaaaact ttcaccagca caccttccat attaaagaag | 1980 |

```
cgacaccgtg atttggtgtc acctttgtca gaaaagagat gtgaaaagaa gcttggaagt    2040
gatctccgtc aagaatcatt ctctgatctg tctaaggatt tttctcgact agatgttatg    2100
tttgacgagg ctgcaaatga aaaagcaaca agtcttctc taactatgga tcagacgttg     2160
gaacttcaag cttcatctga agataaagaa aacataaatc caactgaaga tggaagtaag    2220
gaggaggaca aggtacgcaa tggactttcc agcgagagac agttagatgg aggtgaagtt    2280
cactataaag agaaagtaac aaggaagggc acaaagggtg gagccaatag tgcaattgga    2340
aagataaaac aaccttctgg agttctggtt gaactgaacg caagtgacct gttcttctct    2400
cctgatcgtt ttggagccaa gtctggtaga gctacaaatc tctgcagtaa agctctagga    2460
aatcagtatg ctagacgact cgaagctgca tcaaatcaag gttctgtttc atcttcattt    2520
gagacttcat gtttttctgt tatttgctct cctcgtatac gtggaaagaa agacggaagt    2580
agttttgtca tcactacatc aatgcaatct gctccagcac caacagcctt ggacaactca    2640
gctgaaactt caggaaatgg agttggcgct gagactgtaa gcatatctgg agaaacgcct    2700
tataaaagga gtattgaatc tccttcagct tggaaatctc catggttcat caactctttt    2760
ctgtcaagcc caagacttga taatgaactt aattttgagg atcttgcgct gtttatgagc    2820
ccaggtgaca aagctatga tgctattgga ttaatgaagc aattgagtga gcagactgca     2880
ggggcatttg cagatgccca ggaggtcttg ggaggtgaaa ctccagagtc gatcctacgg    2940
gggaggaact ccaaaaacca gaaagcagat gaaaatcatt ctcttttgtc agcaaatgtt    3000
atgagtgaga ggcgtactct tgatttcagt gaatgtggat ccctggaaa gggaaaggaa     3060 actgaaattt tttgcaccag caacaacagt tttgcaagtc cttcctccta cctattgaaa    3120
ggctgcaggt ag                                                        3132

<210> SEQ ID NO 35
<211> LENGTH: 474
<212> TYPE: DNA
<213> ORGANISM: Nicotiana tabacum

<400> SEQUENCE: 35
atgggcatga aaatgatgc cttactgaag tctaaggcaa gacgcaaaag ggtggagaaa       60
ccccagaaaa gtgttgggaa gataaatgca gaaaaagctc aagaaagacc cgtattattt     120
ctggctatta ataatctaac gataggaaaa tccagcaaca acagcttgac atcacctgat     180
gtttcttcat cctgcagcag cagcattatt acattcgggg aaaaccaaaa gatgaatatt     240
gaaatggaaa acacggttat cttggagagc aatcctgaaa tttatcagtc tgattgtttg     300
agtattgagt cattggatca gttcgatacg agttcattct ggtttatcta cttaatgatg    360
cccatcgtct tatttatga aagattaatt agaatctgcg acctccagag acagatccaa     420
aatttgatct ttatgggttc gagttcacga ctttactgca gcctattgtt ttag           474

<210> SEQ ID NO 36
<211> LENGTH: 879
<212> TYPE: DNA
<213> ORGANISM: Nicotiana tabacum

<400> SEQUENCE: 36
atggaaacag acatgtcttt cttgtctaaa agttcaagta gctctagtga tgaagaaatt     60
ggattgagga gaggtccatg gactgttgaa gaagacagtc tcctcgtaaa ttacatttcc    120
caacatggcg aaggccgatg gaacatgctt gcacaccgtg ctggattgaa gagaacaggc    180
aagagttgca gattgagatg gctgaattac ctgaaaccgg acgttaaaag agggaatctc    240
```

```
actcctcagg aacaactcct gattcttgaa cttcatttca agttgggtaa cagatggtca    300
aagattgcgc aatatctacc aggaagaaca gataatgaaa tcaagaatta ctggagaaca    360
agggtgcaga aacaagctaa gcatttgaag attgactcca atagtgcagc atttcaacac    420
atgattcgat gtatttggat acctcggctt ctacaaaaga tacaaggttc atctgctatt    480
ccatcaattc agacttcaca atcaacttca ttattggatt cacaatatgg tcctttaaat    540
atcacagaaa ttacacaaac cccacaagtt ttaagcttag agagaaacag catcagcagc    600
agcagatgct gcagttcgag atcaccttcg tcagaatcca tgagtatcta taaatctccc    660
aacattattt cggaatgtcc taaaattcca cctcgtgaga tgggtgattc tgttgtcaat    720
gttcattttc catttgacga acacagttat gatatggata ctttcagccc agcaactggc    780 aacttttttga caaattatga tcaaatggtg ggtggagaaa acaatatgat gaatggtgat    840
attttagctg acagcttctg gagcatggat caattttag                           879
```

<210> SEQ ID NO 37
<211> LENGTH: 738
<212> TYPE: DNA
<213> ORGANISM: Nicotiana tabacum

<400> SEQUENCE: 37

```
atggcaagga cacgttgcta tgacaaaagt ggattgaaga agggaacttg gacacctgat     60
gaagatagga aattagcagc ttatgttagt aaatatggtt gctggaattg cgtcaactt    120 cccaagtttg ctggattagc taggtgtggg aagagctgca gactgagatg gctgaattat    180
ctccaaccaa atatcaaaag aggaaactat actaagaag aagatgaaat tatcatgaag    240
ctccacgcag aaattggaaa caatggtcg taattgctg ctcacttacc tggaagatca     300
gacaatgaca taagaatca ttggcacacc tctctcaaaa agagatcaac tcgggaatat    360
tcaacttcaa ctgactcaat aaagagatca tctaacaaca gttatcaagc caacagtcaa    420
aaaaagagac gtgaaaatga aactcaacta aatgcaaatg agagttttca attgtcaccg    480
atgcaatcat gcagtactga ggtttcttct tgtgctacaa ttgatcaaaa tgtggaaaat    540
atacatggcg aacgcgaggt ttttcaagaa gaaatatttg aagtatctag cggaagttt    600 tggacagaac cattttttagt agatagtttt aacactgcta gtgattgttt tgtaccatca    660
ttcgatgatc atggagtatt tgtatctcca ttttcccctg ttatgagcta tggtgaatta    720
ctatgctcat attattaa                                                  738
```

<210> SEQ ID NO 38
<211> LENGTH: 708
<212> TYPE: DNA
<213> ORGANISM: Nicotiana tabacum

<400> SEQUENCE: 38

```
atggtgagaa ctccttctgt tgacaaaaat ggaataaaga gaggtgcatg gagtgaagaa     60
gaagacaaca aactaaaagc ttttgttgaa agattcggtc atccgaattg gaggcaattg    120
cctaaacatg ctggttttaat gagatgtgga aagagctgca gactgagatg gatgaattac    180
ttgaggcctg gtttgaagaa agggaattat agccttgaag aagaggaact cattattaaa    240
ctacacaagg aacatggaaa cagatggtca gtcattgctg caagattacc cggaagatcc    300
gacaacgatg tcaaaaacca gtggcatgct catctcaaga acgtgccaa acaaatact     360 aataacaatt caccaattat ggagcaattt tctgagtctt cgcagtctgg atctcaaagt    420
```

```
gagcaatatt ctcataaagt atcagaacag gaagctggct gtgatacggc tagtgtaaat      480
gccgttgata cttcagtaga ggtttcatca actgatttat attcgagttt ttcccttta      540 aatggaatgg attggattga agaagatcat atcaggtcaa tggaacaact tccagcagat      600
ttctttaact tttgttggac aaatcccatc gacaattttc agacagaacc ctttgacaat      660
tttcagacgg aaccttaga caatttctgg agacaaccat tcttttaa                    708

<210> SEQ ID NO 39
<211> LENGTH: 846
<212> TYPE: DNA
<213> ORGANISM: Nicotiana tabacum

<400> SEQUENCE: 39
atggtgagag ctccttgttg tgagaagatg gggttgaaaa aaggaccatg gactcctgaa       60
gaagatcaaa ttcttgtttc ttatattcaa acaaatggcc atggcaattg gagagccctc      120
cctaaactag ctggactttt gagatgtggg aagagttgca gattgcgttg gactaactat      180
ttgcgtccag atataaagag gggaaacttt actagagaag aagaagactc cattattcag      240
ttacatgaaa tgcttggcaa tagatggtct gcaatagcag cgagattacc gggacgaacg      300
gacaatgaaa ttaaaaatgt atggcacacc cacttgaaaa agaggcttaa aaattaccag      360
cctcctcaaa actccaaaag acactccaaa aacaaccttg attccaaagc tcctagtact      420
tctcaaacct tcaataattc agacaatttt agcaatatcc aagaagatat taatgggccc      480
gtgaccggcc cgaactcgcc acaacgatcg tctagtgaga tgtcgactgt cacggttgat      540
tcaacagcca tgacgaccat cacaatcgat gatcagaata tgtttaagca attagatgag      600
atggactcgt ctgaaaattt tattccagag attgatgaga gttttttggac ggatgattta      660 tccacaagcg ataactcgac ttttggtatg gagggtaccg gtggagaatt acaagtccaa      720
tttccatttt cttcggtgaa gcaagaaagt atggacatgg ttggagcaaa attagaggac      780
gacatggact tttggtacaa tgtttttcata agtccggggg acttactaga tttaccggaa      840
ttttga                                                                 846

<210> SEQ ID NO 40
<211> LENGTH: 1002
<212> TYPE: DNA
<213> ORGANISM: Nicotiana tabacum

<400> SEQUENCE: 40
atgggaaggc ctccttgttg tgataaagca aatgtgaaaa gaggcccttg gactgctgag       60
gaagatgcaa aaattcttgc ttatgtagcc agtcatggaa ttggcaactg gaccttggtc      120
cctcagaaag caggtctgaa taggtgtgga aaaagctgta ggctcagatg gaccaattat      180
ctacgtcctg atcttaagca tgacaacttc acacctcaag aagaagagtg catcattgag      240
cttcacaaaa ccattggtag caggtggtct ttaatagcaa agcaattacc tgggagaaca      300
gacaatgatg tcaaaaatta ttggaacaca aaactgaaga aaaagcttgt gaacatggga      360
attgaccctg taacacataa accatttgct caagtctttg ctgagtatgg aaaaatcagt      420
ggtctcccca ttcaaaatgc aagaaatcat atctgtttgc ccaacaatac tactgaaata      480
tcaaagcaac ttccattctc attacgagaa aactactcca ctcaaaaata cacatgggat      540
cctaaggctc agtatcaagt catccatgag gagactcttc aaacacacag ttttagtgaa      600 gtctcccct tgatttcatc agcaacttat tttaacccaa cagtattcag ctcatcgtct      660
tcttacgctt ccgtgcaatc tcaggttcat accacggcat cttcttcgtc aacatctact      720
```

```
tggaacgagt tgtatttgg agatctgtgt acatccacag atacagaaca aaaacaggaa        780
taccaactcc aagctgggat atatttgtca aggatctgt caaattcagt tcacaaggac         840
aatcctactt gtggggaagt gactgaagtt gaggaaaacc aatctgttga agaagccact        900
tgttcctctg ctgtggattc gttcgtggac accatcttgg ctcgcgacaa gcaaatgcta       960
atggattttc ctccactttt agatgtatac cttgattatt ga                         1002
```

<210> SEQ ID NO 41
<211> LENGTH: 2997
<212> TYPE: DNA
<213> ORGANISM: Nicotiana tabacum

<400> SEQUENCE: 41

```
atggaaagtg ataaaaccag cacgactcct tcagatgata tcagtagtct gcaaagagtt         60
cagcctttga acgggaggac gagtggtcct aagagacgtt ccagtcagtg gactcctgag        120
gaggatgaaa tcttgcgtca agctgtccaa ctgtttaagg ggaaaagctg aaaaggatt         180 gcggaatgtt ttaaggaccg gacagatgtg caatgcttgc acaggtggca gaaagttctt        240
gatcccgaac ttgtcaaagg ctcatggact aaggaggagg atgataaact aatcgaatta        300
gtgaacagat atggccccaa aaaatggtcc accattgcac aagagttagc aggacgtatt        360
ggaaagcaat gtcgggaaag gtggcacaat catctgaatc cttcaataaa caagaaccct       420
tggacacaag aggaggaatt gactctaatt cgtgcccatc aagtttatgg aaacaagtgg       480
gcagagttag caaagttttt gcatggaagg tctgacaatg caataaagaa tcattggcat       540
agttctgtta aaaagaaact ggactcgtat ttggcatcag gtttacttgc acagttccct       600
gctctaccta atgtcaacca tcagaaccaa tcagtcccct cttcttctat gacgttgcaa       660
caaaatagtg aagatgaaag cgttcacaaa caaggaacag aagcggagga tagttttgtt       720
aaaaagaaac tggactcata tttggcatca ggtctacttg gacagttccc tgctctgcct       780
aatgtcaacc atcagaacca atcagtccct tcttcttcta tgacgttgca acaaaatagt       840
gaagatgaaa gcgttcacaa agaaggaacg gaagcagagg aagtgcctga atgcagtcaa       900
ggctctactt tgctggctg ttctcagtct acaagtgact gggcaacac atttgtgcat         960 gtaagagaga tggtgggat gtcggaggaa tcaatttgta aaaaggatgc aacctccagc      1020
actgctccat gttgtaggaa ctataacccg gttttcaag atgtttcttg ttcaatgcta       1080
aaagttccta gtgaacttgt ggattccaag ttccttgagc ataatttatc acatgactgg      1140
ggcaattcca tggaagaaga ttggcagttt aataggatg acatacctaa tatttctcct       1200
cccgagctaa ttcaggaatc ttcagggatt tccgtgcact gtttaaatgg caatgaaaac      1260
catgacatga agcaactac taatgtagga acgtggttg agggtccata taatcccaac        1320
gaaatgtttg tttgtgtgga cggttgcatg atggtatacc tgaggaagg aattcctcaa       1380 tgctcctctg aaactggggt taatggctgt ggtcaacctg catattcttt attttaccga      1440
tcatcaaact atcagatccc tgaagtagga gatatggttc cacaaaactg caatgcttta      1500
agttttgatg attttgaagc ttcatcccat cagcctttt ctgttccttt acaatttct         1560 tcagaggata gatcgcctgt gtttgacctt gtttaaatc agttccataa tcctccgctt       1620
gaaagcccag atcatatgaa agattcctca aggatagttc ctgtgaatga tcttggctca      1680
actacatcaa acactgttca acatgtctg ctgaatgaaa aatcatttgt acaagaaaag       1740
cagaaagatg gaggaggttt atgctacgac cctcctcgtt ttccaagctc agatgttcct      1800
```

```
ttcttttgtt gtgatcttat gcaatctggt tcagatacac aggaagagta tagcccttt    1860 ggcatccggc agttgatgat gacttcagcc aactgcctta ctccattaag gttgtgggat    1920
tcaccatcaa gagatgatag tccagatgct atcttgaaaa gtgctgccaa aacttttaca    1980
gggacacctt ctatactaaa gaagcgacat cgtcatttac tgtcgccttt gtcagaaaag    2040
agatgtgaga aaaggcttga aagcgatctc aatcaggaat cattctctaa tatgacttca    2100
aacttttccc gactagacga tatgtttgat gagtcagcaa atgaaaaagc gtctatggaa    2160
gacggagaaa atctaccatc ctcagaagat ggaagaaaag aggagggtga aatttctgga    2220
gccaatgatg caatgggaaa ggtaaaaacag cctcctggag ttctggttga gcttagctca    2280
aatgacctgt tcttatctcc tgatagtttc ttgatcaagt gtgatagagc tacaagtcta    2340
agtaataaag ctctgggtaa gcagtatgct agacgacttg aagctgcatc aaatcaagtt    2400
actgtttcgt cctctttcga gacttcatgc ttttctgttg tttgctctcc tgacatacgt    2460
gggaagcgta gaagcagtgt tgtcctagct acatcagctg cattggggaa tacagctgaa    2520
gattctgaaa atagatttgg tactgagact ttaagcatat ctggagagac accttataaa    2580
aggagttttg aatctccttc agcatggaaa tctccatggt tcatgaattc ttttccgcca    2640
agcacaagat atgatataga acttgcattt gaggatcttg cgcgttttat gagccctggt    2700
gacagaagct atgatgctat tgggttaatg aagcaattaa gtgagcagac agcagcttca    2760
attgcagatc cccatcagat cttgggaagt gaaactccag aaacaaattt gtcgaaaagg    2820
aattccaaaa aacagaaagc agatgaaatt tgtaaggctt caaatgcaac gagtgagaga    2880
cgcacactcg atttcaatga atgtggaaca ccaggaaagg gaaaggaaac taccaaattt    2940
ggcagcaaca acagttttc aagtccttcc tcctacctgt tgaaatattg cagataa       2997

<210> SEQ ID NO 42
<211> LENGTH: 3048
<212> TYPE: DNA
<213> ORGANISM: Nicotiana tabacum

<400> SEQUENCE: 42
atgttggatt atccagattt gcctttgtct ttgaccatgg aaagtgataa aaccagcacg      60
acgccttcag atgatatcag tagtctgcaa agagttcagc cttcgcacgg gaggacgagt     120
ggtcctaaga gacgttccag tcagtggact cccgaggagg atgaaatctt gcgccaagct     180
gtccaacagt ttaaggggaa aagctggaaa aggattgcgg aatgttttaa ggaccggaca     240
gatgtgcaat gcttgcacag gtggcagaaa gttcttgatc ctgaacttgt caaaggctca     300
tggactaagg aggaggatga taaactaatc gaattagtga acagatatgg ccccaaaaaa     360
tggtccacca ttgcacaaga gttagcagga cgtattggaa agcaatgccg ggaaaggtgg     420
cacaatcatc tgaatcctgc aataaacaaa gaaccttgga cacaagagga ggaattgact     480
ctaattcgtg cccaccaagt ttatggaaac aagtgggcag agttagcaaa agttttgcat     540
ggaaggagtg acaatgcaat aaagaatcat tggcatagtt ctgttaaaaa gaaactggac     600
tcatatttgg catcaggttt acttgcacag ttccctgctc tacctaatgt caaccatcag     660
aaccaatcag tcccttcttc ttctatgacg ttgcaacaaa atagtgaaga tgaaagcgtt     720
cacaaagaag gaacagaagc ggaggatagt tctgttaaaa agaaactgga ctcatattcg     780
gcatcaggtc tacttggaca gttctctgct ctgcctaatg tcaaccatca gaaccaatca     840
gtcccttctt cttctatgac gttgcaacaa aatagtgaag atgaaagcgt tcacaaagaa     900
ggaatggaag cggaggaagt gcctgaatgc agtcaaggct cgaattttgc tggctgttct     960
```

-continued

```
cagtctacaa gtgacttggg caacacattt gtgcatataa gagagaacgg tgggatgtcg   1020
gaggaatcaa tttgtaaaaa ggatgcaacc tccagcactg ctccatgttg taggaactat   1080
agcccagttt ttcaagatgt ttcttgttca atgttaaaag ttcctagtga acttgcggat   1140
tccaagttcc ttgagcataa tttatcacat gactggggca attccatgga agaagattgg   1200
cagtttaata gggatgacat acctaatatt tctcctccgg agtttattca ggaatcttca   1260
gggatttccg tgcactgttt aactggcaac gacaaccatg acatggtagc aactgctaat   1320
gtaggaaacg tggttgagga tccatataag cccaacgaaa tgtttgtttc tgtggacggt   1380
tccatgatgg tataccccga ggaaggaatt cctcaatgct ctccgtctga aactgggggtt   1440 aatggctgtg gtcaaccttc atattcttta ttttaccaat catcaaacta tcagatccct   1500
gaagcaggag atatggttcc acaaaactgc aatgctttaa attttgatga ttttgaagct   1560
tcattccatc agccattttc tgttccttca caatttttctt cagaggatag atcgtctgtg   1620
tttgacattg ttttaaatca gttccataat cctccgcttg aaggcccaga tcatatgaaa   1680
gattcctcaa ggatagttcc cgtgaatgat attggctcaa ctacatcaaa cactgttcaa   1740
acatgtctgc tgaatgaaaa ttcatttgta caagaagagc agaaagatgg aggagcttta   1800
tgctatgacc ctcctcgttt tccaagctcg gatgttcctt tcttttgttg tgatcttata   1860
caatctggtt cagatacaca ggaagagtat agcccttttg gcatccggca gttgatgatg   1920
acttcggcga actgccttac tccattaagg ttgtgggatt caccatcaag agatgatagt   1980
ccagatgcta tcttgaaaag tgctgccaaa acttttacag ggacaccttc tatactaaag   2040
aagcgacatc gtcatttact gtcgcctttg tcagaaaaga gatgtgagaa aaagcttgaa   2100
agcaatctca atcaggaatc attctataat atgtctacaa acttttcccg accagacgat   2160
atgtttgatg agtcagcaaa tgaaaaagca tctatggaag acaaagaaaa tctacatcca   2220
tcctcagaag atggaagaaa agaggagggc gaaatttctg gagccaatga tgcaacggga   2280
atggtaaaac agcatcctgg agtgctggtt gagcttagct caaatgactt gttcttttct   2340
cctgatcgtt tcttaatcaa gtgtgataga gctacaagtc taagtaataa agctctgggt   2400
aggcagtatg ctagacgact tgaagctgca tcaaatcaag ttactgtttc gtcctctttt   2460
gaaacttcat gcttgtctgt tgtatgctct cctgacatat gtgggaagca tagaggcagt   2520
gttgtcatag ctacatcaac tgctttggag aatacagctg aagattctga aaatggattt   2580
ggtgctgaga ctttaagcat atttggagag acacctttta aaggagtttt tgaatctcct   2640
tcagcatgga aatctccatg gttcatgagt tcttttccgc caagcacaag atatgataca   2700
gaacttgaat ttgaggatct tgcccttttt atgagcccgg gtgacagaag ctatgatgct   2760
attgggttaa tgaagcaatt aagtgagcag acagcaccct tcaattgcag atgcccatcag   2820 atcttgggaa gtgaaactcc agaaacaaac ttgtcgaaaa ggaattccaa aaaaccgaaa   2880
gcagatgaaa attgtaccct tctggcttca aatgctacga gtgagagacg aacactcgat   2940
tttaatgaat gtgaattcc aggaaaggga aaggaaacta ccaaatttgg cagcaacaac   3000
aacagctttt caagtccttc ctcctacctg ttgaaatatt gcagataa               3048
```

<210> SEQ ID NO 43
<211> LENGTH: 3129
<212> TYPE: DNA
<213> ORGANISM: Nicotiana tabacum

<400> SEQUENCE: 43

```
atggaaagtg atagaataag cactccttca gatggcacta gcagtagtct ccaaagagtt    60
cggcctttgc atgggagaac tagtggtcct acgagacgtt caacaaaggg gcagtggact   120
actgaagaag acgagatcct acgcaaagct gtccaacgtt ttaagggcaa aaactggaaa   180
aaaatagcgg aatgttttaa agaccggact gatgtacaat gcttgcaccg gtggcagaaa   240
gttcttaatc ctgaacttgt caaaggtcca tggtctaaag aggaggatga agtaatagtt   300
gaattagtta agaaatatgg ccccaaaaag tggtccacca tcgctcaaca tttgccggga   360
cgtattggaa acaatgtcg agaaaggtgg cacaatcatc tgaatcctgg aataaacaag   420
gaagcttgga cgcaggagga ggagttgact ctgattcgtg cccatcaaat ttacgggaat   480
aaatgggcag agttaacgaa gtatttgcct ggaaggacag ataatgcaat aaaaaatcac   540
tggaatagtt ccgtcaaaaa gaaattggac tcgtatttgg catcaggttt acttgcacag   600
ttccctgctt tgcctaatgt caaccgtcag aaccaatcaa tcccttcttc ggcgaagttg   660
caacagagta gtgaagatga tagtgttcgt aaagaaggaa ccgaaatgga ggaagcttca   720
gaatgcagtc aagggtcaaa tcttgctggc tgttcccagt ctacaagtga catgggcaac   780
aaatttgtac atacaagaga ggagggcaag ttgctggagg attcaaatta taggaaggac   840
ccaagctcca gttcagcacc atgctctgaa tactataccc cagcctttga agatattacc   900
ttttcaatgg cagaagtgcc tagtgaactt gacgaatcca agctcctgga gcataccttc   960
tcacatgact gggcagcatc cattggaaaa gaatggcagt ttaatccaga tgacatacct  1020
aatatttctc cgctggagtt gatgcaggat tcttcagggc tcttcatgca gtgtttaact  1080
ggtaatggga atcacgatat ggttaccttt ccacagcaaa atgcagtgaa gtttgaaacg  1140
actaatgtcg ggagcatggt tgtgggtttt gataagccca atgagatgtt tacctctgtg  1200
gagggttgca ggatggtata ccctgaggca ggaattccac aatacattcc ctctgaagct  1260
ggtacgaacg gtgctgatga aactgcagat tctttgattt gccaatcatc gaactatcag  1320
atctctgaag gtggaaatat gtctatagag aattgcaacc ctctctgttc agatgttatg  1380
ggaacttcat ccggccaacc attttccatt ccttcacagt tttcttcaga gcaaagctca  1440
ctcatgtttg gtactgccgc aaatcagttt cataatccat tgcagggaaa cccagcacag  1500
gagtcccaca caagtaactc tgatggtttt ctatatccct ttgaatctgg tactccttgt  1560
gacaacataa tggacgatcc tctcctggaa gagcaactgg atcaaactaa agattctcta  1620
cagctagttt ctgtcaatga ttttcgcaca actccttcaa atactattca acatgtccaa  1680
ttggtgaacg aaaattcgag cataccagta gagcagaagg atggaggagc cttatactat  1740
gagcctcctc gttttccgag cttggacatt ccatttttca gttgtgatct tatacaatct  1800
ggtacagatg cacagcaaga gtacagccct cttggcatcc gccagttgat gatgacttct  1860
gtgaactgtc ttactccatt taggctgtgg gattcaccat ctagagatgg aagtacagat  1920
gccgtcctga aagtgctgc caaaactttc accagcacac cttctatatt aaagaagcga  1980
caccgtgatt tggtgtcacc tttgtcagaa aagagatgtg aaaagaagct tggaagtgat  2040
ttccgtcaag aatcattctc tgatctgtct aaggattttt ctcgactaga tgttatgttt  2100
gacgaggctg caaatgaaaa agcaacaaag tcttctctaa ctacggatca aacattggaa  2160
cttgaagctt catctgaaga taagaaaaac ataaatccaa ctgaagatgg aagtaaggag  2220
gaggacaagg tacgtaatgg actttccaac gagagacagt tagatggagg tgaagttcac  2280
```

| | |
|---|---|
| tataaagaga aaggaacaag ggagggcaca aagggtggag ccaatagtgc aattggaaag | 2340 |
| ataaaacaac cttctggagt tctggttgaa ctgaacgcaa gtgacctgtt cttctctcct | 2400 |
| gatcgttttg gagccaagtc tggtagagct acatatctca gcagtaaagc tctaggaaat | 2460 |
| cagtacgcta gacgactcga agctgcatca aatcaaggtt ctgtttcatc ttcatttgag | 2520 |
| acttcatgtt tttctgttat ttgctctcct cgtatacgtg aaagaaaga cggaagtagt | 2580 |
| tttatcatca ctacatcaat gcaatctgct ccagcaccaa cagccttgga caactcagct | 2640 |
| gaaacttcag gaaatggagt tggcgcggag actgtaagca tatctggaga aacgccttat | 2700 |
| aaaaggagta ttgaatctcc ttcagcttgg aaatctccat ggttcatcaa ctctcttctg | 2760 |
| tcaagcccaa gacttgataa tgaacttaat tttgaggatc ttgcactgtt tatgagtcca | 2820 |
| ggtgacagaa gctatgatgc tattggattg atgaagcaat tgagtgagca gactgcaggg | 2880 |
| gcatttgcag acgcacagga ggtcttggga ggtgaaactc cagagtcaat cctacggggg | 2940 |
| aggaactcca aaaccagaa agcagatgaa atcattcac ttttgtctgc aaatgttatg | 3000 |
| agtgagaggc gtactcttga tttcagtgaa tgtggtcac ctggaaaggg aaaggaaact | 3060 |
| gaaaattttt gcacgagcaa caacagcttt tcaagtcctt cctcctacct attgaaaggc | 3120 |
| tgcaggtag | 3129 |

<210> SEQ ID NO 44
<211> LENGTH: 954
<212> TYPE: DNA
<213> ORGANISM: Nicotiana tabacum

<400> SEQUENCE: 44

| | |
|---|---|
| atgggaagag ctccttgctg tgacaaaaac aacgttaaga gagggccatg gtcgcctgaa | 60 |
| gaagattcta agttgaagtc atatattgaa cagaatggga caggtggcaa ctggattgct | 120 |
| ttgcctccaa aaattggcct aaatagatgt ggaaagagct gtaggcttag atggttaaat | 180 |
| tatctgcgtc caaatattaa gcatggaggg ttctcagaag aagaagatag aatcatttgc | 240 |
| agcctctaca taagtattgg aagcaggtgg tcaataattg cagcacaact ccctggaaga | 300 |
| acagataatg atataaagaa ctactggaac actaggctga agaagaagct atttggaaag | 360 |
| cagcgccaaa agcaaggatc aagaaaagga aagaaaatca actccaatat ggtaatttcc | 420 |
| aataacaata caacaaccca attcccatgt tggcctgagc ttcccatctt gcagccaata | 480 |
| ccatactcta atgatgaacc aagatttaat gaccattctt ccataagaaa actgttgata | 540 |
| aaacttggag gtaaattttc agacgaagat caaccgataa atgaagcaac aaatcctcaa | 600 |
| tatcctatgg ataattcatt attgatgcag ccgatatatc agaatattcc tatcaatatg | 660 |
| atctcttctc ctccaataga taatgtcttg ggaaatgctc aatacaacat ggatagggca | 720 |
| gctagcagtt ttacagctga gcttgagcat atgattcaaa ataatcaaca aaaattggac | 780 |
| ggtcttgaat tttatatga ggattatatg cttattgata aatctgcgtc tacttctgga | 840 |
| ggaaacttgg actgggaatc gatgaatcct tttgtacttc ctcttcctcc tataaatgat | 900 |
| gaaggttttc aacaaggtgt tatatttcaa gagaataata ctatggcaca ataa | 954 |

<210> SEQ ID NO 45
<211> LENGTH: 303
<212> TYPE: PRT
<213> ORGANISM: Nicotiana tabacum

<400> SEQUENCE: 45

```
Met Glu Lys Tyr Glu Lys Leu Glu Lys Val Gly Glu Gly Thr Tyr Gly
1               5                   10                  15

Lys Val Tyr Lys Ala Lys Asp Lys Ala Thr Gly Gln Leu Val Ala Leu
            20                  25                  30

Lys Lys Thr Arg Leu Glu Met Asp Glu Gly Ile Pro Pro Thr Ala
        35                  40                  45

Leu Arg Glu Ile Ser Leu Leu Gln Met Leu Ser Asn Ser Leu Tyr Ile
50                  55                  60

Val Arg Leu Leu Cys Val Glu Gln Ile Asp Lys Asn Gly Lys Pro Leu
65                  70                  75                  80

Leu Tyr Leu Val Phe Glu Tyr Leu Asp Thr Asp Leu Lys Lys Phe Val
                85                  90                  95

Asp Ser His Arg Lys Gly Pro Asn Pro Arg Pro Leu Pro Pro Ser Leu
            100                 105                 110

Ile Gln Ser Phe Leu Tyr Gln Leu Cys Lys Gly Val Ala His Cys His
        115                 120                 125

Ser His Gly Val Leu His Arg Asp Leu Lys Pro Gln Asn Leu Leu Val
130                 135                 140

Asp Lys Glu Lys Gly Ile Leu Lys Ile Ala Asp Leu Gly Leu Gly Arg
145                 150                 155                 160

Ala Phe Thr Val Pro Ile Lys Ser Tyr Thr His Glu Ile Val Thr Leu
                165                 170                 175

Trp Tyr Arg Ala Pro Glu Val Leu Leu Gly Ser Thr His Tyr Ser Thr
            180                 185                 190

Ala Val Asp Met Trp Ser Val Gly Cys Ile Phe Ala Glu Met Val Arg
        195                 200                 205

Arg Gln Ala Leu Phe Pro Gly Asp Ser Glu Phe Gln Gln Leu Leu His
210                 215                 220

Ile Phe Arg Leu Leu Gly Thr Pro Thr Glu Lys Gln Trp Pro Gly Val
225                 230                 235                 240

Ser Ser Leu Arg Asp Trp His Val Tyr Pro Lys Trp Glu Pro Gln Asn
                245                 250                 255

Leu Ala Ser Ala Val Pro Ala Leu Gly Pro Asp Gly Val Asp Leu Leu
            260                 265                 270

Thr Lys Met Leu Gln Tyr Asp Pro Ala Asp Arg Ile Ser Ala Lys Ala
        275                 280                 285

Ala Leu Asp His Pro Tyr Phe Asp Ser Leu Asp Lys Ser Gln Phe
290                 295                 300
```

<210> SEQ ID NO 46
<211> LENGTH: 285
<212> TYPE: PRT
<213> ORGANISM: Nicotiana tabacum

<400> SEQUENCE: 46

```
Met Glu Thr Val Lys Lys Ser Ala Ser Ala Met Glu Ala Phe Glu Lys
1               5                   10                  15

Leu Glu Lys Val Gly Glu Gly Thr Tyr Gly Lys Val Tyr Arg Ala Arg
            20                  25                  30

Asp Arg Val Thr Gly Lys Ile Val Ala Leu Lys Lys Thr Arg Leu His
        35                  40                  45

Glu Asp Glu Glu Gly Val Pro Pro Thr Thr Leu Arg Glu Ile Ser Leu
50                  55                  60
```

Leu Arg Met Leu Ser Arg Asp Pro His Ile Val Lys Leu Met Asp Val
65                  70                  75                  80

Lys Gln Gly Gln Asn Lys Glu Gly Lys Thr Val Leu Tyr Leu Val Phe
                85                  90                  95

Glu Tyr Met Asp Thr Asp Val Lys Phe Ile Arg Ser Phe Arg Ala
            100                 105                 110

Asn Gly Glu Asn Ile Pro Pro Lys Thr Val Lys Ser Leu Met Tyr Gln
                115                 120                 125

Leu Cys Lys Gly Val Ala Phe Cys His Gly His Gly Val Leu His Arg
            130                 135                 140

Asp Leu Lys Pro His Asn Leu Leu Met Asp Arg Lys Thr Asn Val Leu
145                 150                 155                 160

Lys Leu Ala Asp Phe Gly Leu Gly Arg Ala Tyr Thr Leu Pro Ile Lys
                165                 170                 175

Lys Tyr Thr His Glu Ile Leu Thr Leu Trp Tyr Arg Ala Pro Glu Val
            180                 185                 190

Leu Leu Gly Ala Thr His Tyr Ser Thr Ala Val Asp Met Trp Ser Val
            195                 200                 205

Gly Cys Ile Phe Ala Glu Leu Val Thr Lys Gln Ala Leu Phe Pro Gly
210                 215                 220

Asp Ser Glu Leu Gln Gln Leu Leu His Ile Phe Arg Leu Leu Gly Thr
225                 230                 235                 240

Pro Asn Glu Glu Leu Trp Pro Gly Val Ser Lys Leu Val Asn Trp His
                245                 250                 255

Glu Tyr Pro Gln Trp Asn Pro Gln Pro Leu Ser Thr Ala Val Pro Gly
            260                 265                 270

Leu Asp Glu Asp Gly Leu His Leu Leu Thr Val Ser Val
            275                 280                 285

<210> SEQ ID NO 47
<211> LENGTH: 312
<212> TYPE: PRT
<213> ORGANISM: Nicotiana tabacum

<400> SEQUENCE: 47

Met Glu Thr Val Lys Lys Ser Ala Ser Ala Met Glu Ala Phe Glu Lys
1               5                   10                  15

Leu Glu Lys Val Gly Glu Gly Thr Tyr Gly Lys Val Tyr Arg Ala Arg
                20                  25                  30

Asp Arg Val Thr Gly Lys Ile Val Ala Leu Lys Lys Thr Arg Leu His
            35                  40                  45

Glu Asp Glu Glu Gly Val Pro Pro Thr Thr Leu Arg Glu Ile Ser Leu
        50                  55                  60

Leu Arg Met Leu Ser Arg Asp Pro His Ile Val Lys Leu Met Asp Val
65                  70                  75                  80

Lys Gln Gly Gln Asn Lys Glu Gly Lys Thr Val Leu Tyr Leu Val Phe
                85                  90                  95

Glu Tyr Met Asp Thr Asp Val Lys Phe Ile Arg Ser Phe Arg Ala
            100                 105                 110

Asn Gly Glu Asn Ile Pro Pro Lys Thr Val Lys Ser Leu Met Tyr Gln
            115                 120                 125

Leu Cys Lys Gly Val Ala Phe Cys His Gly His Gly Val Leu His Arg
130                 135                 140

```
Asp Leu Lys Pro His Asn Leu Leu Met Asp Arg Lys Thr Asn Val Leu
145                 150                 155                 160

Lys Leu Ala Asp Phe Gly Leu Gly Arg Ala Tyr Thr Leu Pro Ile Lys
                165                 170                 175

Lys Tyr Thr His Glu Ile Leu Thr Leu Trp Tyr Arg Ala Pro Glu Val
            180                 185                 190

Leu Leu Gly Ala Thr His Tyr Ser Thr Ala Val Asp Met Trp Ser Val
            195                 200                 205

Gly Cys Ile Phe Ala Glu Leu Val Thr Lys Gln Ala Leu Phe Pro Gly
        210                 215                 220

Asp Ser Glu Leu Gln Gln Leu Leu His Ile Phe Arg Leu Leu Gly Thr
225                 230                 235                 240

Pro Asn Glu Glu Leu Trp Pro Gly Val Ser Lys Leu Val Asn Trp His
                245                 250                 255

Glu Tyr Pro Gln Trp Asn Pro Gln Pro Leu Ser Thr Ala Val Pro Gly
            260                 265                 270

Leu Asp Glu Asp Gly Leu His Leu Leu Ser Glu Met Leu His Tyr Glu
            275                 280                 285

Pro Ala Lys Arg Ile Ser Ala Lys Lys Ala Met Glu His Pro Tyr Phe
        290                 295                 300

Asp Asp Leu Asp Lys Thr Pro Leu
305                 310

<210> SEQ ID NO 48
<211> LENGTH: 303
<212> TYPE: PRT
<213> ORGANISM: Nicotiana tabacum

<400> SEQUENCE: 48

Met Glu Lys Tyr Glu Lys Leu Glu Lys Val Gly Glu Gly Thr Tyr Gly
1               5                   10                  15

Lys Val Tyr Lys Ala Lys Asp Lys Ala Thr Gly Gln Leu Val Ala Leu
            20                  25                  30

Lys Lys Thr Arg Leu Glu Met Asp Glu Glu Gly Ile Pro Pro Thr Ala
        35                  40                  45

Leu Arg Glu Ile Ser Leu Leu Gln Met Leu Ser His Ser Leu Tyr Ile
    50                  55                  60

Val Arg Leu Leu Cys Val Glu Gln Ile Asp Lys Asn Gly Lys Pro Leu
65                  70                  75                  80

Leu Tyr Leu Val Phe Glu Tyr Leu Asp Thr Asp Leu Lys Lys Phe Val
                85                  90                  95

Asp Ser His Arg Lys Gly Pro Asn Pro Arg Pro Leu Pro Pro Ser Leu
            100                 105                 110

Ile Gln Ser Phe Leu Tyr Gln Leu Cys Lys Gly Val Ala His Cys His
        115                 120                 125

Ser His Gly Val Leu His Arg Asp Leu Lys Pro Gln Asn Leu Leu Val
130                 135                 140

Asp Lys Glu Lys Gly Ile Leu Lys Ile Ala Asp Leu Gly Leu Gly Arg
145                 150                 155                 160

Ala Phe Thr Val Pro Ile Lys Ser Tyr Thr His Glu Ile Val Thr Leu
                165                 170                 175

Trp Tyr Arg Ala Pro Glu Val Leu Leu Gly Ser Thr His Tyr Ser Thr
            180                 185                 190
```

```
Ala Val Asp Met Trp Ser Val Gly Cys Ile Phe Ala Glu Met Val Arg
            195                 200                 205

Arg Gln Ala Leu Phe Pro Gly Asp Ser Glu Phe Gln Gln Leu Leu His
        210                 215                 220

Ile Phe Arg Leu Leu Gly Thr Pro Thr Glu Lys Gln Trp Pro Gly Val
225                 230                 235                 240

Ser Ser Leu Arg Asp Trp His Val Tyr Pro Lys Trp Glu Pro Gln Asn
                245                 250                 255

Leu Ala Ser Ala Val Pro Ala Leu Gly Pro Asp Gly Val Asp Leu Leu
            260                 265                 270

Thr Lys Met Leu Gln Tyr Asp Pro Ala Asp Arg Ile Ser Ala Lys Ala
        275                 280                 285

Ala Leu Asp His Pro Tyr Phe Asp Ser Leu Asp Lys Ser Gln Phe
        290                 295                 300

<210> SEQ ID NO 49
<211> LENGTH: 73
<212> TYPE: PRT
<213> ORGANISM: Nicotiana tabacum

<400> SEQUENCE: 49

Met Glu Gly Val Asp Ser Asp Cys Glu Val Val Glu Glu Gly Cys Met
1               5                   10                  15

Thr Pro Arg Arg Asp Thr Cys Arg Ile Met Val Asn Ser Leu Cys Pro
            20                  25                  30

Pro Pro Pro Lys Lys Lys Arg Val Tyr Val Lys Gln Gln Arg Pro
        35                  40                  45

Pro Pro Lys Glu Gly Tyr Phe Gln Pro Pro Asp Leu Glu Leu Phe Phe
    50                  55                  60

Ala Ile Val Arg Arg Glu Ala Cys Ala
65                  70

<210> SEQ ID NO 50
<211> LENGTH: 533
<212> TYPE: PRT
<213> ORGANISM: Nicotiana tabacum

<400> SEQUENCE: 50

Met Gln Ser Leu Ile Phe Ser Gly Glu Lys Asn Met Ile Ala Ala Tyr
1               5                   10                  15

Leu Phe Ile Pro Leu Glu Leu His Arg Asn Val Ile Gln Val Cys His
            20                  25                  30

Arg Val Gln Arg Thr Phe Cys Ser Met Arg His Ala Asn Ile Lys His
        35                  40                  45

Gly Ser Phe His Leu Glu Glu His Asn Met Arg Ile Thr Arg Ala Arg
    50                  55                  60

Ala Arg Val Ser Gly Ser Ser Gly Arg Leu Pro Pro Leu His Pro Ser
65                  70                  75                  80

Thr Lys Gln Asp Lys Lys Gln Ala Leu Gly Ala Glu Ser Lys Arg Ser
                85                  90                  95

Lys Arg Ser Ala Ser Asp Glu Asn Arg Pro Gly Thr Ser Ser Ile Ala
            100                 105                 110

Thr Gly Val Gln Pro Lys Arg Arg Ala Val Leu Lys Asp Met Lys Asn
        115                 120                 125

Val Leu His Glu Asn Ser His Met Asn Cys Ile Asn Gly Ser Lys Ile
130                 135                 140
```

```
Gln Val Lys Lys Gly Ser Asp Lys Arg Asn Asn Lys Ala Lys Pro Ala
145                 150                 155                 160

Val Ser Leu Lys Leu Ser Gln Leu Gln Glu Lys Gly Lys Glu Asp Ile
            165                 170                 175

Ala Asp Lys Val Lys Lys Val Lys Val Glu Gly Ser Gln Glu Ile Ser
            180                 185                 190

Ser Gly Ala Asn Cys Lys Glu Asp Met Leu Pro Gln Leu Ser Arg Tyr
        195                 200                 205

Val Thr Pro Ala Gln Cys Gly Leu Val His Leu Val Pro Val Asn Arg
        210                 215                 220

Ser Ser Cys Lys Ala Phe Pro Leu Gln Asn Val Met Lys Lys Asp Glu
225                 230                 235                 240

Ser Lys Val Cys Gln Lys Gln Glu Gly Phe Ala Asn Leu Gly Ile Ala
            245                 250                 255

Asp Ile Asp Ser Arg His Lys Asp Pro Leu Met Cys Ser Leu Tyr Ala
            260                 265                 270

Pro Asp Ile Tyr Asn Asn Leu His Ala Ile Glu Phe Asp Arg Arg Pro
            275                 280                 285

Ser Val Asp Tyr Leu Glu Lys Leu Gln Leu Asp Ile Asn Lys Gly Met
290                 295                 300

Arg Gly Ile Leu Ile Asp Trp Leu Val Glu Val Ser Glu Glu Tyr Arg
305                 310                 315                 320

Leu Val Pro Asp Thr Leu Tyr Leu Thr Val Asn Leu Ile Asp Arg Phe
            325                 330                 335

Leu Ser Glu Asn Tyr Ile Glu Lys Gln Lys Leu Gln Leu Leu Gly Val
            340                 345                 350

Thr Cys Met Leu Ile Ala Ser Lys Phe Glu Glu Ile Cys Ala Pro Arg
            355                 360                 365

Val Glu Glu Phe Cys Phe Ile Thr Asp Asn Thr Tyr Ser Lys Glu Glu
            370                 375                 380

Val Ile Lys Met Glu Ser Arg Val Leu Asn Leu Leu Ser Phe Gln Leu
385                 390                 395                 400

Ala Ser Pro Thr Thr Lys Lys Phe Leu Arg Arg Phe Ile Gln Ala Ala
                405                 410                 415

Gln Ala Ser Tyr Lys Val Pro Ser Val Glu Leu Glu Phe Met Ala Asn
            420                 425                 430

Tyr Leu Ala Glu Leu Thr Leu Val Asp Tyr Gly Phe Leu Lys Phe Leu
            435                 440                 445

Pro Ser Leu Thr Ala Ala Ser Ala Val Phe Leu Ala Arg Trp Thr Leu
            450                 455                 460

Asp Gln Ser Asn His Pro Trp Asn Pro Thr Leu Glu His Tyr Thr Arg
465                 470                 475                 480

Tyr Lys Val Ser Glu Leu Arg Thr Thr Val Phe Ala Leu Gln Glu Leu
            485                 490                 495

Gln Met Asn Thr Ser Gly Cys Thr Leu Asn Ala Ile Arg Glu Lys Tyr
            500                 505                 510

Arg Gln Pro Lys Phe Lys Ser Val Ala Thr Leu Ala Ala Ser Lys Pro
            515                 520                 525

Val Gln Ser Leu Phe
            530

<210> SEQ ID NO 51
<211> LENGTH: 414
```

<212> TYPE: PRT
<213> ORGANISM: Nicotiana tabacum

<400> SEQUENCE: 51

```
Met Asp Ile Ser Asp Glu Asn Gln Phe Thr Arg Lys Ser Leu Val Gly
1               5                   10                  15

Glu Ala Gly Met Gly Asn Ser Lys Ile Gly Val Glu Thr Arg His Asn
            20                  25                  30

Arg Arg Ala Leu Arg Val Ile Asn Gln Asn Leu Leu Gly Pro Asn Pro
        35                  40                  45

Tyr Arg Cys Val Val Asn Lys Arg Arg Leu Ser His Ala Asn Gly Ile
    50                  55                  60

Ile Tyr Asp Lys Asn Pro Thr Arg Lys Leu Thr Ala Gln Ile Ala Ser
65                  70                  75                  80

Ser His Gln His Tyr Pro Glu Glu Thr Lys Pro Lys Leu Ala Ala
                85                  90                  95

Glu Asp Phe Arg Ile Trp Glu Glu His Val Ala Ala Lys Asp Gln Pro
            100                 105                 110

Met Ser Met Ser Leu Glu Gln Glu Ala Thr Phe Ser Asn Asp Lys Thr
        115                 120                 125

Glu Met Glu Val Glu Met Glu Asp Ile Phe Glu Glu Ala Leu Ile Asp
    130                 135                 140

Ile Asp Ser Asp Asp Thr Asn Asn Pro Leu Ala Val Val Asp Tyr Val
145                 150                 155                 160

Glu Asp Leu Tyr Ala Asn Tyr Arg Lys Met Glu Gly Tyr Ser Cys Val
            165                 170                 175

Ser Pro Asn Tyr Met Thr Gln Gln Phe Asp Ile Asn Glu Arg Met Arg
        180                 185                 190

Ala Thr Leu Val Asp Trp Leu Ile Glu Val Asn His Lys Phe Glu Leu
    195                 200                 205

Arg Glu Glu Thr Leu Phe Leu Thr Val Asn Ser Ile Asp Arg Phe Leu
210                 215                 220

Glu Lys Gln Ile Val Ala Arg Lys Lys Leu Gln Leu Val Gly Leu Val
225                 230                 235                 240

Ala Met Leu Leu Ala Cys Lys Tyr Glu Glu Val Ser Val Pro Val Val
            245                 250                 255

Asp Asp Leu Val Ile Ile Ser Asp Asn Ala Tyr Thr Arg Lys Glu Val
        260                 265                 270

Leu Glu Met Glu Thr Leu Met Leu Asp Thr Leu Gln Phe Asn Met Ser
    275                 280                 285

Val Pro Thr Ala Tyr Val Phe Met Arg Arg Phe Leu Lys Ala Ala Gln
290                 295                 300

Ala Asp Arg Lys Leu Glu Val Leu Ser Phe Phe Leu Ile Glu Leu Cys
305                 310                 315                 320

Leu Val Glu Tyr Glu Met Leu Lys Phe Pro Pro Ser Phe Met Ala Ala
            325                 330                 335

Ala Ala Ile Tyr Thr Ala Gln Cys Thr Leu Tyr Gly Val Met Gln Trp
        340                 345                 350

Ser Lys Thr Cys Glu Trp His Thr Ser Tyr Ser Glu Asp Gln Leu Leu
    355                 360                 365

Lys Cys Ser Arg Ser Ile Val Ile Tyr His Gln Lys Ala Ala Thr Gly
370                 375                 380

Lys Leu Thr Gly Val His Arg Lys Tyr Ser Thr Ser Lys Phe Gly Tyr
385                 390                 395                 400
```

```
Ala Ala Lys Phe Glu Pro Ala Leu Phe Leu Val Gln Ile Lys
            405                 410

<210> SEQ ID NO 52
<211> LENGTH: 436
<212> TYPE: PRT
<213> ORGANISM: Nicotiana tabacum

<400> SEQUENCE: 52

Met Ala Ile Ser Asp Glu Asn Asn Pro Thr Met Val Lys Pro Thr Asn
1               5                   10                  15

Val Gln Gly Gly Ala Gly Met Gly Thr Arg Lys Phe Gly Gly Val Glu
            20                  25                  30

Thr Arg Asn Asn Arg Arg Ala Leu Gly Val Ile Asn Gln Asn Leu Val
        35                  40                  45

Gly Gly Thr His Pro Phe Pro Cys Val Val Asn Lys Arg Gly Leu Ser
    50                  55                  60

Glu Ala Asn Gly Ile Cys Asp Lys Asn Leu Gln Ile Pro Ala His Arg
65                  70                  75                  80

Pro Ile Thr Arg Lys Phe Ala Ala Gln Ile Ala Ser Ser Gln Gln Asn
                85                  90                  95

Arg Ser Glu Glu Asn Lys Lys Ala Lys Ile Ala Ala Glu Glu Phe Ser
            100                 105                 110

Ile Trp Glu Asp Ile Pro Leu Thr Asp Val Glu Asn Glu Ala Ala
        115                 120                 125

Lys Asp Gln Pro Val Pro Met Ser Leu Glu Gln Thr Glu Thr Val Thr
130                 135                 140

Asn Asp Lys Asn Gln Met Glu Val Glu Met Glu Asp Ile Phe Glu Glu
145                 150                 155                 160

Thr Ile Ile Asp Ile Asp Gly Asp Asp Ala Lys Asn Pro Leu Ala Val
                165                 170                 175

Val Glu Tyr Val Gln Asp Leu Phe Ala Ser Tyr Arg Lys Met Glu Gly
            180                 185                 190

Cys Ser Cys Val Ser Pro Asp Tyr Met Ala Gln Gln Phe Asp Ile Asn
        195                 200                 205

Glu Lys Met Arg Ser Ile Leu Ile Asp Trp Leu Ile Glu Val His His
210                 215                 220

Lys Phe Glu Leu Arg Glu Glu Thr Leu Phe Leu Thr Val Asn Leu Ile
225                 230                 235                 240

Asp Arg Phe Leu Glu Lys Gln Gly Val Val Arg Lys Lys Leu Gln Leu
                245                 250                 255

Val Gly Leu Val Ala Met Leu Leu Ala Cys Lys Tyr Glu Glu Val Ser
            260                 265                 270

Val Pro Leu Val Asp Asp Phe Val Phe Ile Ser Asp Lys Ala Tyr Ser
        275                 280                 285

Arg Lys Glu Val Leu Glu Met Glu Arg Met Met Leu Asn Thr Leu Gln
290                 295                 300

Phe Asn Met Ser Val Pro Thr Ala Tyr Val Phe Met Arg Arg Tyr Leu
305                 310                 315                 320

Lys Ala Ala Gln Ser Asp Arg Lys Leu Glu Leu Leu Ser Phe Phe Leu
                325                 330                 335

Val Glu Leu Cys Leu Val Glu Tyr Glu Met Leu Lys Phe Pro Pro Ser
            340                 345                 350
```

-continued

Phe Ile Ala Ala Ala Ile Tyr Thr Ala Gln Thr Thr Leu Tyr Gly
         355                 360                 365

Val Gln Gln Trp Ser Lys Thr Cys Glu Trp His Thr Ser Tyr Ser Glu
370                 375                 380

Asp Gln Leu Met Glu Cys Ser Arg Ser Ile Val Ser Tyr His Gln Lys
385                 390                 395                 400

Ala Ala Thr Gly Lys Leu Thr Gly Val His Arg Lys Tyr Ser Thr Ser
                405                 410                 415

Lys Phe Gly Tyr Ala Ala Lys Cys Glu Pro Ala His Phe Leu Val Gln
                420                 425                 430

Thr Gln Gln Gln
        435

<210> SEQ ID NO 53
<211> LENGTH: 143
<212> TYPE: PRT
<213> ORGANISM: Nicotiana tabacum

<400> SEQUENCE: 53

Met Glu Lys Arg Ile Leu Gly Gln Leu Glu Trp Tyr Leu Thr Val Pro
1               5                   10                  15

Thr Pro Tyr Val Phe Leu Val Arg Tyr Ile Lys Ala Ala Val Ser Asn
                20                  25                  30

Ala Gln Met Glu Asn Met Val Tyr Phe Leu Ala Glu Leu Gly Leu Met
            35                  40                  45

Asn Tyr Ala Thr Asn Ile Tyr Cys Pro Ser Met Ile Ala Ala Ser Ala
50                  55                  60

Val Tyr Val Ala Gln His Thr Leu Asn Cys Thr Pro Phe Trp Asn Asp
65                  70                  75                  80

Thr Leu Lys Leu His Thr Gly Phe Ser Glu Ser Gln Leu Leu Gly Cys
                85                  90                  95

Ala Lys Leu Leu Val Ser Tyr His Met Glu Ala Pro Glu His Lys Leu
            100                 105                 110

Lys Val Ile Tyr Lys Lys Tyr Ser Lys Pro Glu Arg Gly Ala Val Ala
        115                 120                 125

Leu Gln Pro Pro Ala Lys Ser Leu Leu Ala Ala Ser Ser Tyr Glu
    130                 135                 140

<210> SEQ ID NO 54
<211> LENGTH: 301
<212> TYPE: PRT
<213> ORGANISM: Nicotiana tabacum

<400> SEQUENCE: 54

Met Ala Ser Arg Asn Val Leu Gln Gln Gln Asn Ile Gly Glu Ala Val
1               5                   10                  15

Pro Gly Ala Leu Lys Gln Lys Asn Met Ala Ala Ala Gln Gly Arg
                20                  25                  30

Asn Arg Lys Ala Leu Gly Asp Ile Gly Asn Asn Met Val Thr Val Arg
            35                  40                  45

Gly Val Glu Gly Lys Pro Leu Pro Gln Arg Pro Ile Thr Arg Gly Phe
        50                  55                  60

Cys Ala Gln Leu Leu Ala Asn Ala Gln Ala Ala Glu Asn Gln Lys
65                  70                  75                  80

Lys Ser Met Val Val Asn Gly Asp Ala Pro Ile Val Ala Lys Gly Val
                85                  90                  95

```
Leu Pro Val Lys Gly Ala Ala Lys Pro Val Gln Lys Lys Ala Ala
            100                 105                 110

Val Lys Pro Lys Pro Asp Val Ile Glu Ile Ser Pro Asp Thr Glu Glu
115                 120                 125

Gln Val Lys Glu Asn Lys Gln Lys Lys Ala Gly Asp Asp Ser Ser
    130                 135                 140

Val Lys Lys Ala Thr Leu Thr Ser Thr Leu Thr Ala Arg Ser Lys Ala
145                 150                 155                 160

Ala Cys Gly Leu Ser His Lys Pro Lys Val Gln Ile Val Asp Ile Asp
                165                 170                 175

Ala Ala Asp Val Asn Asn Glu Leu Ala Val Val Glu Tyr Val Glu Asp
            180                 185                 190

Ile Tyr Asn Phe Tyr Lys Ile Ala Glu Asn Glu Ser Arg Ile His Asp
    195                 200                 205

Tyr Met Asp Ser Gln Pro Glu Ile Thr Ala Arg Met Arg Ala Ile Leu
    210                 215                 220

Ile Asp Trp Leu Ile Glu Val His His Lys Phe Glu Leu Ser Gln Glu
225                 230                 235                 240

Thr Leu Tyr Leu Thr Ile Asn Ile Val Asp Arg Tyr Leu Ala Val Thr
                245                 250                 255

Thr Thr Ser Arg Arg Glu Leu Gln Leu Val Gly Met Ser Ala Met Leu
            260                 265                 270

Ile Ala Ser Lys Tyr Glu Glu Ile Trp Ala Pro Glu Val His Phe Lys
    275                 280                 285

Ser Asn Tyr Ala Lys Leu Leu Ser His Phe Glu Ser Cys
    290                 295                 300

<210> SEQ ID NO 55
<211> LENGTH: 473
<212> TYPE: PRT
<213> ORGANISM: Nicotiana tabacum

<400> SEQUENCE: 55

Met Ala Ser Arg Ile Val Leu Gln Gln Gln Asn Arg Gly Glu Ala Val
1               5                   10                  15

Pro Gly Ala Val Lys Gln Lys Asn Met Ala Pro Glu Gly Arg Asn
            20                  25                  30

Arg Lys Ala Leu Gly Asp Ile Gly Asn Val Ala Thr Gly Arg Gly Leu
        35                  40                  45

Glu Gly Lys Lys Pro Leu Pro Gln Lys Pro Val Ala Val Lys Val Lys
    50                  55                  60

Gly Ala Asn Val Ala Lys Val Pro Ala Ala Arg Lys Pro Ala Gln Lys
65                  70                  75                  80

Lys Ala Thr Val Lys Pro Asn Pro Glu Asp Ile Ile Glu Ile Ser Pro
                85                  90                  95

Asp Thr Gln Glu Lys Leu Lys Glu Lys Met Gln Arg Lys Lys Ala Asp
            100                 105                 110

Lys Asp Ser Leu Lys Gln Lys Ala Thr Leu Thr Ser Thr Leu Thr Ala
        115                 120                 125

Arg Ser Lys Ala Ala Cys Gly Leu Ser Lys Lys Pro Lys Glu Gln Val
    130                 135                 140

Val Asp Ile Asp Ala Ala Asp Val Asn Asn Glu Leu Ala Val Val Glu
145                 150                 155                 160
```

```
Tyr Val Glu Asp Ile Tyr Ser Phe Tyr Lys Leu Ala Glu Asn Glu Thr
                165                 170                 175

Arg Val His Asp Tyr Met Asp Ser Gln Pro Glu Ile Asn Asp Arg Met
            180                 185                 190

Arg Ala Val Leu Ile Asp Trp Leu Val Glu Val His Gln Lys Phe Glu
        195                 200                 205

Leu Asn Pro Glu Thr Leu Tyr Leu Thr Ile Asn Ile Val Asp Arg Tyr
    210                 215                 220

Leu Ala Val Lys Thr Thr Ser Arg Arg Glu Leu Gln Leu Leu Gly Ile
225                 230                 235                 240

Ser Ala Met Leu Ile Ala Ser Lys Tyr Glu Glu Ile Trp Ala Pro Glu
                245                 250                 255

Val Asn Asp Phe Val Cys Ile Ser Asp Lys Ser Tyr Thr His Asp Gln
            260                 265                 270

Val Leu Ala Met Glu Lys Glu Ile Leu Gly Gln Leu Glu Trp Tyr Leu
        275                 280                 285

Thr Val Pro Thr Pro Tyr Val Phe Leu Ala Arg Phe Ile Lys Ala Ser
    290                 295                 300

Leu Pro Asp Ser Glu Ile Glu Asn Met Val Tyr Phe Leu Ala Glu Leu
305                 310                 315                 320

Gly Leu Met Asn Tyr Ala Thr Ile Ile Tyr Cys Pro Ser Met Ile Ala
                325                 330                 335

Ala Ser Ala Val Tyr Ala Ala Arg His Thr Leu Asn Arg Thr Pro Phe
            340                 345                 350

Trp Asn Glu Thr Leu Lys Leu His Thr Gly Phe Ser Glu Ser Gln Leu
        355                 360                 365

Ile Glu Cys Ala Arg Leu Leu Val Ser Tyr Gln Ser Ala Ala Ala Thr
    370                 375                 380

His Lys Leu Lys Val Ile Tyr Lys Lys Tyr Ser Ser Pro Glu Arg Gly
385                 390                 395                 400

Val Val Ser Leu Leu Thr Pro Ala Lys Ser Leu Leu Ala Ala Ser Ser
                405                 410                 415

Ser Ser Val Leu Ser Glu Gln Ala Asp Leu Arg Lys Ser Thr Glu Ala
            420                 425                 430

Ala Ala Thr Ser Ser Ser Lys Met Val Val Gly Cys Gln Arg Cys
        435                 440                 445

His Met Tyr Val Met Val Thr Glu Ala Asp Pro Arg Cys Pro Gln Cys
    450                 455                 460

Lys Ser Thr Thr Thr Arg Lys Met Thr
465                 470

<210> SEQ ID NO 56
<211> LENGTH: 535
<212> TYPE: PRT
<213> ORGANISM: Nicotiana tabacum

<400> SEQUENCE: 56

Met Ser Arg Ala Cys Ser Leu Val Gln Glu Tyr Tyr Asp Cys Cys Phe
1               5                   10                  15

Leu Phe Ile Gln Ser Ser Arg Ile Val Val Glu Arg Asn Ala Val Val
            20                  25                  30

Ala Gln Ile Ile Gly Ile Ser Pro Pro Gly Ser Met Arg Asn Ala Asn
        35                  40                  45
```

-continued

Met Thr Ile Gly Ser Ser Asn Leu Lys Glu Pro Thr Met Arg Ile Thr
        50                  55                  60

Arg Ser Arg Ala Lys Ala Leu Gly Ser Ser Gly Leu Pro Pro Arg
65                  70                  75                  80

His Pro Ser Val Arg Gln Asp Asn Lys Gln Gly Leu Gly Ala Gln Gly
                85                  90                  95

Thr Lys Tyr Lys Arg Ser Ala Ser Asp Glu Asn Asn Pro Val Thr Asn
            100                 105                 110

Ala Ser Thr Ala Cys Gln Gln Pro Lys Arg Arg Ala Val Leu Arg Asp
        115                 120                 125

Val Thr Asn Val Leu Cys Glu Asn Ser Tyr Met Asn Cys Ile Asn Arg
    130                 135                 140

Ser Lys Phe Gln Val Lys Lys Phe Ser Asp Thr Arg Asn Ser Lys Val
145                 150                 155                 160

Thr Pro Ala Ile Leu Val Lys Arg Pro His Asn Glu Asp Arg Lys Glu
                165                 170                 175

Asn Thr Ile Glu Glu Ala Lys Lys Val Lys Ile Glu Lys Ser Gln Glu
            180                 185                 190

His Cys Ser Gln Ala Arg Phe Lys Asp Leu Thr Leu Thr His Pro Ser
        195                 200                 205

Lys Tyr Ile Thr Pro Ala Gln Cys Gly Phe Val Asp Leu Met Pro Val
    210                 215                 220

Asn Arg Ser Leu Pro Thr Ala Ile Ala Val Pro Asn Thr Thr Glu Lys
225                 230                 235                 240

Asp Glu Thr Lys Val Cys Gln Lys Gln Glu Gly Ser Asp Ser Leu Gly
                245                 250                 255

Ile Ala Asp Ile Asp Ser Lys His Lys Asp Pro Leu Met Cys Ser Leu
            260                 265                 270

Tyr Ala Pro Asp Ile Tyr Ser Asn Leu His Ala Met Glu Leu Asp Arg
        275                 280                 285

Arg Pro Ser Phe Asn Tyr Met Glu Lys Leu Gln Arg Asp Val Asn Lys
    290                 295                 300

Gly Met Arg Gly Ile Leu Ile Asp Trp Leu Val Glu Val Ser Glu Glu
305                 310                 315                 320

Tyr Arg Leu Val Pro Asp Thr Leu Tyr Leu Thr Val His Leu Ile Asp
                325                 330                 335

Arg Phe Leu Ser Glu Asn Tyr Ile Glu Lys Gln Lys Leu Gln Leu Leu
            340                 345                 350

Gly Val Thr Cys Met Leu Ile Ala Ser Lys Tyr Glu Glu Ile Cys Ala
        355                 360                 365

Pro Arg Val Glu Glu Phe Cys Phe Ile Thr Asp Asn Thr Tyr Ser Lys
    370                 375                 380

Glu Glu Val Val Arg Met Glu Ser Leu Val Leu Asn Phe Leu Gly Phe
385                 390                 395                 400

Gln Leu Ala Ala Pro Thr Thr Lys Lys Phe Leu Arg Arg Phe Val Gln
                405                 410                 415

Ala Ala Gln Ala Ser Tyr Glu Val Pro Ser Val Glu Leu Glu Phe Met
            420                 425                 430

Ala Asn Tyr Leu Ala Glu Leu Thr Leu Val Asp Tyr Ser Phe Leu Lys
        435                 440                 445

Phe Leu Pro Ser Ile Thr Ala Ala Ser Ala Val Phe Leu Ala Lys Trp
    450                 455                 460

```
Thr Leu Asp Gln Ser Asn His Pro Trp Asn Pro Thr Leu Glu His Tyr
465                 470                 475                 480

Thr Ser Tyr Thr Ala Leu Glu Leu Lys Thr Thr Val Leu Leu Leu Gln
            485                 490                 495

Asp Leu Gln Leu Asn Thr Ser Gly Ser Thr Leu Asn Ala Ile Arg Glu
            500                 505                 510

Lys Tyr Arg Gln Pro Lys Phe Lys Ser Val Ala Thr Leu Ser Ser Pro
            515                 520                 525

Glu Pro Val Gln Ser Leu Phe
            530             535
```

<210> SEQ ID NO 57
<211> LENGTH: 730
<212> TYPE: PRT
<213> ORGANISM: Nicotiana tabacum

<400> SEQUENCE: 57

```
Met Gly Lys Leu Asn Ser Gln Lys His Ile Ser Thr Ile Lys Asp Gly
1               5                   10                  15

Val Thr Glu Leu Lys Val Tyr Glu Ala Asp Lys Ile Lys Ile Gln
            20                  25                  30

Ser Arg Asp Ser Leu Ser Arg Cys Lys Gly Met Ser Gly Ala Pro
        35                  40                  45

Asn Met Ser Asp Val Gln Thr Ser Arg Lys Ser Glu Ser Asp Ile
    50                  55                  60

Lys His Ile Glu Arg Ile Lys Ala Lys Cys Ser Thr Ser Val Lys Val
65                  70                  75                  80

Asn Val Lys Arg Lys Val Leu Thr Asp Ile Ser Asn Ile Arg Gly Asn
                85                  90                  95

Ser Ser Arg Thr Lys Ser Tyr Asn Ser Ser Lys Leu Leu Val Ser Asn
            100                 105                 110

Gly Lys Cys Pro Lys Asn Ala Ser Asn Ser Ala Arg Lys Phe Ile Met
        115                 120                 125

Gly Asn Val Arg Pro Asn Leu Asn Gly Ala Thr Gly Asp Lys Gln Ile
    130                 135                 140

Leu Thr Arg Ala Pro Phe Lys Asp Thr Lys Ala Ser Phe Asp Gly Arg
145                 150                 155                 160

Lys Thr Arg Ile Gln Gly Arg Lys Ser Val Thr Thr Gly Ile Arg Pro
                165                 170                 175

Thr Gly Arg Asn Asp Leu Pro Pro Ser Arg Arg Ser Leu Pro Ile Leu
            180                 185                 190

Gln Gln Val Asn Ile Glu Gly Thr Asp Asn Lys Glu Lys Gly Lys Val
        195                 200                 205

Arg Ala Asn Leu Asn Lys Ala Thr Asp Asp Lys Gln Ile Leu Thr Gln
    210                 215                 220

Ala Pro Arg Lys Asp Met Lys Ala Ser Phe Asp Gly Pro Lys Thr Arg
225                 230                 235                 240

Ile Gln Val Arg Lys Ser Val Thr Thr Gly Ile Arg Arg Thr Gly Arg
                245                 250                 255

Asn Ala Leu Pro Pro Ser Arg Arg Ser Leu Pro Ile Leu Gln Gln Val
            260                 265                 270

Asn Val Glu Asp Thr Asn Asn Lys Glu Lys Val Asn Ser Lys Lys Leu
        275                 280                 285

Glu Lys Gly Lys Gly Ile Ser Gly Val Ser Val Leu Ala Lys Pro Lys
    290                 295                 300
```

```
Ala Ala Gly Asp Val Leu Pro Gln Leu Ser Asn His Ser Asn Ile Arg
305                 310                 315                 320

Arg Asn Arg Val Gly Asp Ala Ser Ala Arg Met Ala Pro Arg Gly Gln
            325                 330                 335

Ala Lys Val Glu Val Gly Ala Leu Arg Arg Lys Ser Val Arg Thr Val
            340                 345                 350

Leu Lys Ile Thr Ala Ser Ser Leu Asn Ser Gln Lys Cys Ser Lys Ser
            355                 360                 365

Asn Ser Met Ser Gly Val His Lys Cys Thr Ser Arg Val Ser Ile Pro
            370                 375                 380

Cys Lys Arg Leu Val Asp Val Arg Thr Ser Ser Leu Ser Lys Tyr Ala
385                 390                 395                 400

Thr Ser Glu Ile Ser Ala Glu Gln Pro His Gln Lys Glu Val Pro Ser
            405                 410                 415

Ser Ser Ser Gly Ser Leu Ala Thr Pro Glu Leu Ser Ile Ala Arg Arg
            420                 425                 430

Lys Ser Asp Arg Arg Lys Ser Phe Thr Cys Leu Leu Met Ala Arg Ser
            435                 440                 445

Lys Leu Met Lys Glu Leu Cys Gly Asn Val Gly Leu Asp Asn Leu Ser
            450                 455                 460

Asn Ile Tyr Asp Ser Cys Asn His Leu Glu Val Thr Glu Tyr Val Asp
465                 470                 475                 480

Asp Ile Tyr Gln Tyr Tyr Trp Val Ile Glu Ala Gln Asn Gln Pro Ile
            485                 490                 495

Lys Asn Tyr Met Glu Thr Gln Lys Glu Ile Thr Pro Gln Met Arg Gly
            500                 505                 510

Ile Leu Ile Asn Trp Leu Ile Glu Val His Leu Lys Phe Asp Leu Met
            515                 520                 525

Gln Glu Thr Leu Phe Leu Met Val Thr Leu Leu Asp Tyr Tyr Leu Ser
            530                 535                 540

Leu Ala Arg Val Lys Lys Asn Asp Leu Gln Leu Val Gly Leu Thr Ser
545                 550                 555                 560

Leu Leu Leu Ala Ser Lys Tyr Glu Asp Leu Phe His Pro Arg Val Met
            565                 570                 575

Asp Leu Leu Ser Ile Ser Ala Glu Ser Tyr Thr Arg Asp Gln Met Leu
            580                 585                 590

Glu Met Glu Lys Asp Ile Leu Arg Lys Leu Lys Phe Arg Leu Asn Ala
            595                 600                 605

Ala Thr Pro Tyr Val Phe Met Leu Arg Leu Leu Lys Ala Ala Gln Ala
            610                 615                 620

Asp Thr Arg Phe Glu His Leu Ala Phe Tyr Leu Ile Glu Leu Cys Leu
625                 630                 635                 640

Val Glu Tyr Glu Ala Leu Asn Tyr Lys Pro Ser Met Leu Cys Ala Ser
            645                 650                 655

Ala Ile Tyr Val Ala Arg Cys Thr Met Gln Met Thr Pro Ala Trp Thr
            660                 665                 670

Pro Leu Leu Gly Ile His Gly Arg Tyr Gln Glu Ser Gln Phe Arg His
            675                 680                 685

Cys Ala Glu Met Ile Leu Arg Phe His Lys Ala Ala Ser Thr Ala Leu
            690                 695                 700

Leu Lys Val Thr His Glu Lys Tyr Met Gln Ser Ser Asn Ser Lys Val
705                 710                 715                 720
```

-continued

Ala Ala Ile Lys Pro Leu Gln Ser Leu Pro
            725                 730

<210> SEQ ID NO 58
<211> LENGTH: 441
<212> TYPE: PRT
<213> ORGANISM: Nicotiana tabacum

<400> SEQUENCE: 58

Met Val Gly Ser Asp Glu Asn Phe Ser Gly Val Met Arg Ala Ser Asn
1               5                   10                  15

Leu Gln Gly Gly Leu Arg Pro Gly Val Gly Gly Lys Leu Thr Ala
            20                  25                  30

Gly Val Gly Gln Asn Arg Arg Ala Leu Ser Thr Ile Asn Arg Asn Val
            35                  40                  45

Ile Gly Ala Pro Pro Leu Pro Tyr Ala Val Asn Lys Arg Asn Gly Ile
50                  55                  60

Ser Asp Asn Lys Ala Asn Ala Ala Asn Lys Ile Pro Ser Val Pro Ile
65                  70                  75                  80

His Arg Pro Ile Thr Arg Lys Leu Ala Ala Gln Ile Ala Ser Lys Gln
            85                  90                  95

Gln Gln Pro Ala Val Glu Val Thr Lys Pro Val Pro Val Ala Pro
            100                 105                 110

Asn Arg Asn Gly Ser Glu Asp Cys Ile Ile Ile Asp Ala Glu Tyr
            115                 120                 125

Lys Ala Ala Gly Asp Ser Ser Val Pro Met Phe Val Gln His Thr Glu
            130                 135                 140

Ala Met Met Glu Glu Ile Asp Arg Met Asp Glu Ile Glu Met Glu
145                 150                 155                 160

Asp Val Glu Asp Trp Pro Ile Val Asp Ile Asp Ser Ala Asp Lys Lys
            165                 170                 175

Asn Thr Leu Ala Val Val Glu Tyr Ile Asp Asp Ile Tyr Ala Tyr Tyr
            180                 185                 190

Lys Lys Thr Glu Val Leu Ser Cys Val Pro Pro Asn Tyr Met Glu Gln
            195                 200                 205

Gln Ile Asp Val Asn Glu Arg Met Arg Ala Ile Leu Ile Asp Trp Leu
            210                 215                 220

Ile Glu Val His Tyr Lys Phe Glu Leu Met Glu Glu Thr Leu Tyr Leu
225                 230                 235                 240

Thr Val Asn Leu Ile Asp Arg Phe Leu Ala Val Gln Ser Val Ile Arg
            245                 250                 255

Lys Lys Leu Gln Leu Val Gly Ile Thr Ala Met Leu Leu Ala Cys Lys
            260                 265                 270

Tyr Glu Glu Val Ser Val Pro Val Glu Asp Leu Ile Leu Ile Ser
            275                 280                 285

Asp Lys Ala Tyr Thr Arg Lys Glu Val Leu Asp Met Glu Lys Leu Met
            290                 295                 300

Val Asn Thr Leu Gln Phe Asn Val Thr Val Pro Thr Ala Tyr Val Phe
305                 310                 315                 320

Ile Arg Arg Phe Leu Lys Ala Ala Leu Ser Asp Lys Lys Val Glu Leu
            325                 330                 335

Met Ser Phe Phe Leu Ile Glu Leu Cys Leu Val Glu Tyr Glu Met Leu
            340                 345                 350

Lys Phe Pro Pro Ser Met Leu Ala Ala Ser Ile Phe Thr Ala Gln
            355                 360                 365

```
Cys Thr Leu Gly Val Ser Lys Glu Trp Asn Lys Thr Cys Glu Lys His
            370                 375                 380

Ser Ser Tyr Ala Lys Asn Gln Leu Leu Glu Cys Ser Arg Leu Met Val
385                 390                 395                 400

Ser Phe His Gln Lys Ala Ala Ser Gly Lys Leu Thr Gly Val His Arg
            405                 410                 415

Lys Tyr Ser Thr Cys Lys Tyr Gly Tyr Ala Ala Arg Cys Glu Pro Ala
            420                 425                 430

Ser Phe Leu Leu Glu Ala Ala Trp Phe
            435                 440

<210> SEQ ID NO 59
<211> LENGTH: 483
<212> TYPE: PRT
<213> ORGANISM: Nicotiana tabacum

<400> SEQUENCE: 59

Met Ala Thr Thr Gln Asn Arg Arg Ser Ser Val Ser Ser Ala Thr Ala
1               5                   10                  15

Lys Arg Gln Ala Met Thr Ala Asn Ser Ser Leu Glu Asn Asn Asn His
            20                  25                  30

Gly Lys Leu Val Ala Lys Lys Arg Pro Ala Leu Thr Asn Ile Ser Asn
            35                  40                  45

His Thr Ala Ser Ala Arg Asn Ser Leu Ser His Ser Ser Lys Leu
            50                  55                  60

Ala Pro Cys Thr Ser Lys Ala Val Ser Ile Lys Lys Ser Asn Ser Asn
65                  70                  75                  80

Ala Ala Ser Ser Val Leu Pro Thr Ser Ser Phe Val Lys Pro Ile Ser
            85                  90                  95

Lys Thr Val Ser Ile Pro Arg Ser Asp Ala Ala Ile Pro Lys Ile Thr
            100                 105                 110

Ala Ile Pro Leu Pro Ala Thr Cys Ser Met Asp Ile Ser Pro Ser His
            115                 120                 125

Ser Asp Gly Ser Leu Val Ser Met Asp Glu Thr Met Ser Thr Ser Asp
            130                 135                 140

Ser Leu Arg Ser Pro Asp Val Glu Tyr Ile Asp Asn Gln Thr Ala
145                 150                 155                 160

Ala Phe Asp Ser Ile Glu Lys Lys Ala Phe Ser Thr Leu Tyr Ile Ser
            165                 170                 175

Glu Asp Val Lys Ala Ala Asp Ile Cys Lys Arg Asp Val Leu Val Asp
            180                 185                 190

Ile Glu Ser Gly Asp Lys Ile Ala Asn Ile Asp Asn Phe Val Asp
            195                 200                 205

Pro Gln Leu Cys Ala Thr Met Ala Cys Asp Ile Tyr Lys His Leu Arg
            210                 215                 220

Ala Thr Glu Val Lys Lys Arg Pro Ser Thr Asp Phe Met Glu Lys Val
225                 230                 235                 240

Gln Lys Asp Ile Asn Ala Ser Met Arg Ala Ile Leu Ile Asp Trp Leu
            245                 250                 255

Val Glu Val Ala Glu Glu Tyr Arg Leu Val Pro Asp Thr Leu Tyr Leu
            260                 265                 270

Thr Val Asn Tyr Ile Asp Arg Tyr Leu Ser Gly Asn Leu Met Asp Arg
            275                 280                 285
```

```
Gln Arg Leu Gln Leu Leu Gly Val Ala Cys Met Met Ile Ala Ser Lys
    290                 295                 300

Tyr Glu Glu Ile Cys Ala Pro Gln Val Glu Glu Phe Cys Tyr Ile Thr
305                 310                 315                 320

Asp Asn Thr Tyr Phe Lys Glu Glu Val Leu Gln Met Glu Ser Thr Val
                325                 330                 335

Leu Asn Tyr Leu Lys Phe Glu Met Thr Ala Pro Thr Ala Lys Cys Phe
                340                 345                 350

Leu Arg Arg Phe Val Arg Ala Ala Gln Gly Leu Asn Glu Val Leu Ser
            355                 360                 365

Leu Gln Leu Glu His Leu Ala Ser Tyr Ile Ala Glu Leu Ser Leu Leu
    370                 375                 380

Glu Tyr Asn Met Leu Cys Tyr Ala Pro Ser Val Ile Ala Ala Ser Ala
385                 390                 395                 400

Ile Phe Leu Ala Lys Tyr Ile Leu Leu Pro Ser Lys Lys Pro Trp Asn
                405                 410                 415

Ser Thr Leu Arg His Tyr Thr Leu Tyr Gln Pro Ser Asp Leu Arg Asp
                420                 425                 430

Cys Val Val Ala Leu His Ser Leu Cys Cys Asn Asn Asn Asn Ser Ser
            435                 440                 445

Leu Pro Ala Ile Arg Glu Lys Tyr Ser Gln His Lys Tyr Lys Phe Val
    450                 455                 460

Ala Lys Lys Tyr Cys Pro Pro Thr Ile Pro Val Glu Phe Phe Gln Asn
465                 470                 475                 480

Ile Ser Cys

<210> SEQ ID NO 60
<211> LENGTH: 412
<212> TYPE: PRT
<213> ORGANISM: Nicotiana tabacum

<400> SEQUENCE: 60

Met Gly Val Ser Asn Glu Asn Asn Pro Thr Met Ile Lys Pro Thr Asn
1               5                   10                  15

Val Gln Gly Glu Ala Glu Leu Gly Cys Arg Lys Phe Gly Met Glu Thr
                20                  25                  30

Arg Asn Asn Arg Arg Ala Leu Ser Val Ile Asn Gln Asn Phe Val Gly
            35                  40                  45

Ala Lys Pro Tyr Pro Cys Val Val Asn Lys Arg Val Leu Ser Glu Ala
        50                  55                  60

Asn Gly Ile Cys Asn Lys Asn Pro Pro Val Pro Ala His Arg Pro Ile
65                  70                  75                  80

Thr Arg Lys Phe Ala Ala Gln Ile Ala Asn Ser Lys Gln His Tyr Pro
                85                  90                  95

Glu Glu Asn Lys Lys Pro Lys Ile Ala Ala Glu Gly Leu Ser Val Tyr
                100                 105                 110

Glu Asp Val Pro Ile Ile Asp Val Glu Glu Tyr Glu Ala Ala Ala Lys
            115                 120                 125

Asp Gln Pro Val Pro Met Ser Leu Glu Gln Thr Gln Met Glu Ile Glu
    130                 135                 140

Met Glu Asp Ile Phe Glu Glu Ser Val Ile Asp Ile Asp Ser Asn Asp
145                 150                 155                 160

Ala Lys Asn Thr Leu Ala Val Val Asp Tyr Val Glu Asp Leu Tyr Ala
                165                 170                 175
```

Tyr Tyr Ser Lys Met Glu Gly Cys Asn Arg Ile Pro Pro Asp Tyr Ile
                180                 185                 190

Gly Gln Gln Phe Asp Ile Asn Glu Arg Met Arg Ser Ile Leu Ile Asp
            195                 200                 205

Trp Leu Ile Glu Val His His Lys Phe Asp Leu Arg Glu Glu Thr Leu
210                 215                 220

Phe Leu Thr Val Asn Leu Ile Asp Arg Phe Leu Glu Lys Gln Ser Val
225                 230                 235                 240

Val Arg Lys Lys Leu Gln Leu Val Gly Leu Val Ala Met Leu Leu Ala
                245                 250                 255

Cys Lys Tyr Glu Glu Val Ser Leu Pro Val Val Asp Asp Leu Val Val
            260                 265                 270

Ile Ser Asp Lys Ala Tyr Thr Arg Lys Glu Val Leu Glu Met Glu Lys
        275                 280                 285

Leu Met Leu Asn Thr Leu Gln Phe Asn Met Ser Leu Pro Thr Pro Tyr
    290                 295                 300

Val Phe Met Arg Arg Phe Leu Lys Ala Ala Gln Ser Asp Arg Lys Leu
305                 310                 315                 320

Glu Leu Leu Ser Phe Phe Leu Ile Glu Leu Cys Leu Val Glu Tyr Glu
                325                 330                 335

Met Leu Lys Phe Pro Pro Ser Phe Ile Ala Ala Ala Ile Tyr Thr
            340                 345                 350

Ala Gln Cys Thr Leu Tyr Gly Val Lys Gln Trp Ser Lys Thr Cys Glu
        355                 360                 365

Leu His Thr Lys Tyr Ser Ala Asp Gln Leu Leu Glu Cys Ser Arg Leu
    370                 375                 380

Ile Val Glu Phe His Gln Lys Ala Ala Thr Gly Lys Leu Thr Gly Asp
385                 390                 395                 400

Leu Tyr Ser Lys Gln Asn Pro Glu Asn Lys Glu Glu
                405                 410

<210> SEQ ID NO 61
<211> LENGTH: 439
<212> TYPE: PRT
<213> ORGANISM: Nicotiana tabacum

<400> SEQUENCE: 61

Met Val Gly Ser Asp Glu Asn Cys Gln Gly Val Ile Met Ala Ser Asn
1               5                   10                  15

Val Gln Gly Ala Gly Gly Gly Lys Val Thr Met Gly His Asn Arg Arg
                20                  25                  30

Ala Leu Ser Thr Ile Asn Gly Asn Ile Val Glu Ala Pro Ala Tyr Pro
            35                  40                  45

Cys Lys Val His Lys Arg Asn Gly Ile Thr Asp Lys Ser Ala Asn Gly
        50                  55                  60

Val Lys Asn Pro Pro Ile Pro Ile His Arg Pro Val Thr Ser Met Gly
65                  70                  75                  80

Asp Ser Cys Cys Phe Arg Lys Phe Ala Ala Gln Met Ala Thr Lys Leu
                85                  90                  95

Gln Gln Pro Thr Val Thr Lys Gln Pro Val Gln Thr Ala Thr Asp Arg
            100                 105                 110

Asn Glu Ser Glu Asp Arg Ile Ile Ile Asp Val Glu Asp Tyr Lys Ala
        115                 120                 125

```
Thr Ser Asp Tyr Asp Pro Val Pro Met Phe Val Gln His Thr Glu Ala
        130                 135                 140

Met Met Glu Glu Ile Asp Arg Met Asp Ala Glu Thr Glu Met Glu Asp
145                 150                 155                 160

Val Glu Glu Thr Leu Ile Val Asp Ile Asp Ser Ala Asp Lys Lys Asn
                165                 170                 175

Pro Leu Ala Val Val Glu Tyr Ile Asp Asp Met His Ala Tyr Tyr Lys
                180                 185                 190

Lys Thr Glu Ser Ser Ser Cys Ala Pro Pro Asn Tyr Met Glu Gln Gln
                195                 200                 205

Phe Asp Ile Asn Glu Arg Met Arg Ala Ile Leu Ile Asp Trp Leu Ile
        210                 215                 220

Glu Val His Tyr Lys Phe Asp Leu Met Glu Glu Thr Leu Tyr Leu Thr
225                 230                 235                 240

Val Asn Leu Ile Asp Arg Phe Leu Ala Val Gln Gln Val Ile Arg Lys
                245                 250                 255

Lys Leu Gln Leu Val Gly Val Thr Ala Met Leu Leu Ala Cys Lys Tyr
                260                 265                 270

Glu Glu Val Ser Val Pro Val Val Glu Asp Leu Ile Leu Ile Ser Asp
                275                 280                 285

Lys Ala Tyr Thr Arg Lys Glu Val Leu Glu Met Glu Lys Leu Met Ile
        290                 295                 300

Asn Thr Leu Gln Phe Asn Leu Ser Val Pro Thr Ala Tyr Val Phe Met
305                 310                 315                 320

Met Arg Phe Leu Lys Ala Ala Gln Ser Asp Lys Lys Val Glu Leu Leu
                325                 330                 335

Ser Phe Phe Met Thr Glu Leu Cys Leu Val Glu Tyr Glu Met Leu Arg
                340                 345                 350

Phe Pro Pro Ser Met Leu Ala Ala Ala Ile Phe Thr Ala Gln Cys
                355                 360                 365

Ala Leu Ser Ala Pro Asn Glu Leu Ser Lys Thr Cys Glu Lys Tyr Ser
        370                 375                 380

His Tyr Thr Gln Asp Gln Leu Leu Glu Cys Ser Arg Leu Met Val Ser
385                 390                 395                 400

Phe His Gln Lys Ala Ala Ile Gly Lys Leu Thr Gly Val Tyr Arg Lys
                405                 410                 415

Tyr Ser Ile Ser Lys Tyr Gly Phe Val Ala Lys Cys Pro Pro Ala Ser
                420                 425                 430

Phe Leu Leu Glu Ala Cys Phe
            435

<210> SEQ ID NO 62
<211> LENGTH: 367
<212> TYPE: PRT
<213> ORGANISM: Nicotiana tabacum

<400> SEQUENCE: 62

Met Ala Asp Gln Glu Asn Cys Val Arg Val Thr Arg Leu Ala Lys Lys
1               5                   10                  15

Arg Ala Ala Glu Ala Met Val Gln His Leu Gln Gln Pro Asn Lys Lys
                20                  25                  30

Arg Val Val Leu Gly Glu Ile Arg Asn Leu Ser Asn Gln Ile Gln Met
                35                  40                  45
```

```
Phe Asp Ser Glu Pro Leu Lys Pro Lys Cys Asn Lys Gln Thr Thr Lys
    50                  55                  60

Arg Lys Val Lys Arg Ser Val Ser Val Lys Glu Arg Glu Phe Arg Glu
65                  70                  75                  80

Glu Asp Val Asp Ser Lys Leu Asp Asp Pro Gln Met Cys Ser Ala
                85                  90                  95

Tyr Val Ser Asp Ile Tyr Glu Tyr Leu His Gln Met Glu Ile Glu Lys
                100                 105                 110

Lys Arg Arg Pro Leu Ser Asp Tyr Leu Glu Lys Val Gln Lys Asp Val
            115                 120                 125

Thr Ala Asn Met Arg Gly Val Leu Val Asp Trp Leu Val Glu Val Ala
130                 135                 140

Glu Glu Tyr Lys Leu Leu Ser Asp Thr Leu Tyr Leu Ala Val Ala Tyr
145                 150                 155                 160

Ile Asp Arg Tyr Leu Ser Ile Lys Val Ile Pro Arg Gln Arg Leu Gln
                165                 170                 175

Leu Leu Gly Val Ser Ser Met Leu Ile Ala Ser Lys Tyr Glu Glu Ile
            180                 185                 190

Lys Pro Pro Arg Val Glu Asp Phe Cys Tyr Ile Thr Asp Asn Thr Tyr
        195                 200                 205

Thr Lys Lys Asp Val Val Lys Met Glu Ala Asp Val Leu Gln Ser Leu
    210                 215                 220

Lys Phe Glu Met Gly Asn Pro Thr Thr Lys Thr Phe Leu Arg Arg Phe
225                 230                 235                 240

Thr Arg Val Ala Gln Glu Asp Cys Lys Asn Ser Asn Leu Lys Leu Glu
                245                 250                 255

Phe Leu Gly Cys Tyr Leu Ala Glu Leu Ser Leu Leu Asp Tyr Asn Cys
            260                 265                 270

Val Lys Phe Leu Pro Ser Leu Val Ala Ala Val Ile Phe Leu Ser
        275                 280                 285

Arg Phe Thr Leu Gln Pro Lys Leu His Pro Trp Ser Val Gly Leu Glu
    290                 295                 300

Gln Asn Ser Gly Tyr Arg Ala Ala Asp Leu Lys Glu Cys Val Leu Ile
305                 310                 315                 320

Ile His Asp Leu Gln Leu Ser Arg Arg Gly Gly Ser Leu Val Ala Ala
                325                 330                 335

Arg Asn Lys Tyr Lys Gln His Lys Phe Lys Tyr Val Ser Thr Leu Ser
            340                 345                 350

Ser Pro Leu Glu Ile Pro Asp Ser Phe Phe Glu Asp Thr Arg Gln
        355                 360                 365

<210> SEQ ID NO 63
<211> LENGTH: 482
<212> TYPE: PRT
<213> ORGANISM: Nicotiana tabacum

<400> SEQUENCE: 63

Met Ala Thr Thr Gln Asn Arg Arg Asn Ser Val Ser Ser Ala Val Ala
1               5                   10                  15

Lys Arg Gln Ala Met Ala Glu Asn Asn His Gly Lys Leu Pro Ala Gly
            20                  25                  30

Gly Ala Lys Lys Arg Pro Ala Leu Thr Asn Ile Ser Asn His Thr Thr
        35                  40                  45
```

```
Ala Ser Ala Arg Asn Ser Leu Ser His Ser Ser Lys Leu Ala Pro Cys
    50                  55                  60

Thr Ser Lys Val Val Ser Ile Lys Lys Asn Asn Ser Asn Ala Ala Ser
65                      70                  75                  80

Ser Val Leu Pro Thr Ser Ser Phe Val Lys Pro Ile Ser Lys Thr
                85                  90                  95

Val Ser Leu Pro Arg Ser Asp Ala Ala Val Pro Lys Ile Thr Ala Ile
                100                 105                 110

Pro Pro Leu Pro Ser Thr Cys Ser Met Asp Ile Ser Pro Ser His Ser
            115                 120                 125

Asp Gly Ser Leu Val Ser Met Asp Glu Thr Met Ser Thr Ser Asn Ser
    130                 135                 140

Leu Arg Ser Pro Asp Val Glu Tyr Ile Asp Asp Asn Gln Thr Ala Ala
145                 150                 155                 160

Phe Asp Ser Ile Glu Lys Lys Ala Phe Ser Thr Leu Tyr Ile Ser Glu
                165                 170                 175

Asp Val Lys Ala Ala Asp Ile Cys Lys Arg Asp Val Leu Val Asp Met
                180                 185                 190

Glu Ser Gly Asp Lys Ile Ala Asn Ile Asp Asn Asn Leu Val Asp Pro
            195                 200                 205

Gln Leu Cys Ala Thr Met Ala Cys Asp Ile Tyr Lys His Leu Arg Ala
        210                 215                 220

Thr Glu Val Lys Lys Arg Pro Ser Thr Asp Phe Met Glu Lys Val Gln
225                 230                 235                 240

Lys Asp Ile Asn Ala Ser Met Arg Ala Ile Leu Ile Asp Trp Leu Val
                245                 250                 255

Glu Val Ala Glu Glu Tyr Arg Leu Val Pro Asp Thr Leu Tyr Leu Thr
                260                 265                 270

Val Asn Tyr Ile Asp Arg Tyr Leu Ser Gly Asn Leu Met Asp Arg Gln
            275                 280                 285

Arg Leu Gln Leu Leu Gly Val Ala Cys Met Met Ile Ala Ser Lys Tyr
    290                 295                 300

Glu Glu Ile Cys Ala Pro Gln Val Glu Glu Phe Cys Tyr Ile Thr Asp
305                 310                 315                 320

Asn Thr Tyr Phe Lys Glu Glu Val Leu Gln Met Glu Ser Thr Val Leu
                325                 330                 335

Asn Tyr Leu Lys Phe Glu Met Thr Ala Pro Thr Ala Lys Cys Phe Leu
                340                 345                 350

Arg Arg Phe Val Arg Ala Ala Gln Gly Leu Asn Glu Val Leu Ser Leu
            355                 360                 365

Gln Leu Glu His Leu Ala Ser Tyr Ile Ala Glu Leu Ser Leu Leu Glu
    370                 375                 380

Tyr Asn Met Leu Cys Tyr Ala Pro Ser Val Ile Ala Ala Ser Ala Ile
385                 390                 395                 400

Phe Leu Ala Lys Tyr Ile Leu Leu Pro Ser Lys Pro Trp Asn Ser
                405                 410                 415

Thr Leu Arg His Tyr Thr Leu Tyr Gln Pro Ser Asp Leu Arg Asp Cys
            420                 425                 430

Val Met Ala Leu His Ser Leu Cys Cys Asn Asn Asn Ser Ser Leu
        435                 440                 445

Pro Ala Ile Arg Glu Lys Tyr Ser Gln His Lys Tyr Lys Phe Val Ala
    450                 455                 460
```

```
Lys Lys Tyr Cys Pro Pro Thr Ile Pro Val Glu Phe Phe Gln Asn Ile
465                 470                 475                 480

Ser Cys

<210> SEQ ID NO 64
<211> LENGTH: 384
<212> TYPE: PRT
<213> ORGANISM: Nicotiana tabacum

<400> SEQUENCE: 64

Met Lys Lys Gln Glu Lys Glu Ala Ile Met Ala Asp Leu Glu Asn Cys
1               5                   10                  15

Gly Arg Val Thr Arg Leu Ala Lys Lys Arg Ala Ala Glu Ala Met Ala
                20                  25                  30

Ser His Gln Gln Gln His Pro Ser Lys Lys Arg Val Val Leu Gly Glu
            35                  40                  45

Ile Gln Asn Phe Ser Asn Leu Gly Val Ser Gln Ile Lys Gly Leu Asn
        50                  55                  60

Thr Glu Pro Lys Lys Gln Pro Lys Ser Lys Gln Gln Ser Lys Arg
65                  70                  75                  80

Lys Leu Lys Arg Ala Val Thr Ser Lys Ile Asp Lys Glu Glu Leu Asn
                85                  90                  95

Val Asp Asn Val Asp Ala Asn Tyr Asp Asp Pro Gln Met Cys Ser Ala
            100                 105                 110

Tyr Val Ser Asp Ile Tyr Asp Tyr Leu Arg Lys Met Glu Ile Glu Glu
        115                 120                 125

Lys Arg Arg Pro Leu Pro Asp Tyr Leu Glu Lys Val Gln Lys Asp Leu
    130                 135                 140

Ser Pro Asn Met Arg Gly Val Leu Val Asp Trp Leu Val Glu Val Ala
145                 150                 155                 160

Glu Glu Tyr Lys Leu Leu Ser Asp Thr Leu Tyr Leu Ala Val Ser Tyr
                165                 170                 175

Ile Asp Arg Phe Leu Ser Thr Asn Val Ile Thr Arg Gln Lys Leu Gln
            180                 185                 190

Leu Leu Gly Val Ser Ser Met Leu Ile Ser Ala Lys Tyr Glu Glu Ile
        195                 200                 205

Ser Pro Pro His Val Glu Asp Phe Cys Tyr Ile Thr Asp Asn Thr Tyr
    210                 215                 220

Thr Lys Glu Glu Val Val Lys Met Glu Ala Asp Val Leu Lys Thr Leu
225                 230                 235                 240

Asn Phe Glu Met Gly Asn Pro Thr Val Lys Thr Phe Leu Arg Arg Phe
                245                 250                 255

Thr Gly Val Ala Gln Glu Asp Tyr Lys Thr Pro Asn Leu Gln Leu Glu
            260                 265                 270

Phe Leu Gly Tyr Tyr Leu Ala Glu Leu Ser Ile Leu Asp Tyr Ser Cys
        275                 280                 285

Val Lys Tyr Val Pro Ser Leu Leu Ala Ala Ala Val Val Phe Leu Ser
    290                 295                 300

Arg Phe Thr Leu Gln Pro Asn Thr His Pro Trp Ser Leu Ala Leu Gln
305                 310                 315                 320

Gln Tyr Ser Gly Tyr Lys Ala Ala Asp Leu Lys Glu Cys Ile Leu Ile
                325                 330                 335

Leu His Asp Leu Gln Leu Ser Arg Gly Gly Ser Leu Ala Ala Val
            340                 345                 350
```

```
Arg Asp Lys Tyr Lys Gln His Lys Phe Lys Cys Val Ser Ser Leu Thr
            355                 360                 365

Ser Pro Val Glu Ile Pro Ala Ser Phe Glu Asp Met Arg Gln Leu
    370                 375                 380

<210> SEQ ID NO 65
<211> LENGTH: 441
<212> TYPE: PRT
<213> ORGANISM: Nicotiana tabacum

<400> SEQUENCE: 65

Met Val Gly Ser Asp Glu Asn Phe Ser Gly Val Met Arg Ala Ser Asn
1               5                   10                  15

Leu Gln Gly Gly Leu Arg Pro Val Val Gly Gly Lys Leu Thr Ala
            20                  25                  30

Gly Val Gly Gln Asn Arg Arg Ala Leu Ser Thr Ile Asn Arg Asn Val
        35                  40                  45

Ile Gly Ala Pro Pro Leu Pro Tyr Ala Val Asn Lys Arg Asn Gly Ile
    50                  55                  60

Ser Asp Asn Lys Ala Asn Ala Ala Asn Lys Ile Pro Pro Val Pro Ile
65              70                  75                  80

His Arg Pro Ile Thr Arg Lys Leu Ala Ala Gln Ile Ala Ser Lys Gln
                85                  90                  95

Gln Gln Pro Ala Val Glu Val Thr Lys Pro Pro Val Pro Leu Ala Pro
            100                 105                 110

Asn Arg Asn Glu Ser Glu Asp Cys Ile Ile Ile Asp Ala Glu Glu Tyr
        115                 120                 125

Lys Ala Thr Gly Asp Ser Ser Val Pro Met Phe Val Gln His Thr Glu
    130                 135                 140

Ala Met Met Glu Glu Ile Asp Arg Met Asp Glu Ile Glu Met Glu
145                 150                 155                 160

Asp Val Glu Asp Cys Pro Ile Val Asp Ile Asp Ser Thr Asp Lys Lys
                165                 170                 175

Asn Thr Leu Ala Val Val Glu Tyr Ile Asp Asp Ile Tyr Ala Tyr Tyr
            180                 185                 190

Lys Lys Thr Glu Val Leu Ser Cys Val Pro Pro Asn Tyr Met Glu Gln
        195                 200                 205

Gln Ile Asp Val Asn Glu Arg Met Arg Ala Ile Leu Ile Asp Trp Leu
    210                 215                 220

Ile Glu Val His Tyr Lys Phe Glu Leu Met Glu Glu Thr Leu Tyr Leu
225                 230                 235                 240

Thr Val Asn Leu Ile Asp Arg Phe Leu Ala Val Gln Ser Val Ile Arg
                245                 250                 255

Lys Lys Leu Gln Leu Val Gly Ile Thr Ala Leu Leu Ala Cys Lys
        260                 265                 270

Tyr Glu Glu Val Ser Val Pro Val Val Glu Asp Leu Ile Leu Ile Ser
    275                 280                 285

Asp Lys Ala Tyr Thr Arg Asn Glu Val Leu Val Met Glu Lys Leu Met
    290                 295                 300

Val Asn Thr Leu Gln Phe Asn Val Thr Val Pro Thr Ala Tyr Val Phe
305                 310                 315                 320

Met Arg Arg Phe Leu Lys Ala Ala Gln Ser Asp Lys Lys Val Glu Leu
                325                 330                 335

Met Ser Phe Phe Leu Ile Glu Leu Cys Leu Val Glu Tyr Glu Met Leu
            340                 345                 350
```

-continued

```
Lys Phe Pro Ser Met Leu Ala Ala Ala Ile Phe Thr Ala Gln
        355                 360                 365

Cys Thr Leu Gly Val Ser Lys Glu Trp Asn Lys Thr Cys Glu Lys His
    370                 375                 380

Ser Ser Tyr Ala Lys Asp Gln Leu Ser Glu Cys Ser Arg Leu Met Val
385                 390                 395                 400

Ser Phe His Gln Lys Ala Ala Ser Gly Lys Leu Thr Gly Val His Arg
                405                 410                 415

Lys Tyr Ser Thr Ser Lys Tyr Gly Tyr Ala Ala Arg Cys Glu Pro Ala
            420                 425                 430

Ser Phe Leu Leu Glu Ala Ala Trp Phe
        435                 440

<210> SEQ ID NO 66
<211> LENGTH: 404
<212> TYPE: PRT
<213> ORGANISM: Nicotiana tabacum

<400> SEQUENCE: 66

Met Lys Gly Gly Glu Ala Glu Met Gly Asn Asn Lys Phe Asp Phe Gly
1               5                   10                  15

Val Glu Thr Arg His Asn Arg Arg Ala Leu Arg Val Ile Asn Gln Asn
            20                  25                  30

Leu Leu Gly Pro Asn Pro Tyr Arg Cys Val Val Asn Lys Arg Gly Leu
        35                  40                  45

Ser His Ala Asn Gly Ile Ile Tyr Asp Lys Asn Pro Thr Arg Lys Leu
    50                  55                  60

Thr Ala Pro Ile Ala Ser Ser His Gln His Tyr Pro Glu Glu Thr Lys
65                  70                  75                  80

Lys Pro Lys Leu Ala Ala Glu Asp Phe Arg Ile Trp Glu Glu His Val
                85                  90                  95

Ala Ala Lys Asp Gln Leu Met Pro Met Ser Leu Glu Gln Glu Ala Thr
            100                 105                 110

Phe Ser Asn Asp Lys Thr Glu Met Glu Ile Gln Met Glu Asp Ile Phe
        115                 120                 125

Glu Glu Ala Leu Ile Asp Ile Asp Ser Asp Asp Ala Lys Asn Pro Leu
    130                 135                 140

Ala Val Val Asp Tyr Val Asn Asp Leu Tyr Pro Asn Tyr Arg Lys Met
145                 150                 155                 160

Glu Gly Tyr Ser Cys Val Ser Pro Asn Tyr Met Thr Gln Gln Phe Asp
                165                 170                 175

Ile Asn Glu Arg Met Arg Ala Ile Leu Val Asp Trp Leu Ile Glu Val
            180                 185                 190

His His Lys Phe Glu Leu Arg Glu Glu Thr Leu Phe Leu Thr Val Asn
        195                 200                 205

Ser Ile Asp Arg Phe Leu Glu Lys Gln Thr Val Ala Arg Lys Lys Leu
    210                 215                 220

Gln Leu Val Gly Leu Val Ala Met Leu Leu Ala Cys Lys Tyr Glu Glu
225                 230                 235                 240

Val Ser Val Pro Val Val Asp Asp Leu Val Ile Ile Ser Asp Asn Ala
                245                 250                 255

Tyr Arg Arg Lys Glu Val Leu Glu Met Glu Thr Leu Met Leu Asn Thr
            260                 265                 270
```

```
Leu Gln Phe Asn Met Ser Val Pro Thr Ala Tyr Val Phe Met Arg Arg
        275                 280                 285

Phe Leu Lys Ala Ala Gln Ala Asp Lys Lys Leu Glu Val Leu Ser Phe
    290                 295                 300

Phe Leu Ile Glu Leu Cys Leu Val Glu Tyr Glu Met Leu Lys Phe Pro
305                 310                 315                 320

Pro Ser Phe Met Ala Ala Val Val Tyr Thr Ala Gln Cys Thr Leu
                325                 330                 335

Tyr Gly Val Lys Gln Trp Asn Lys Thr Cys Glu Trp His Thr Ser Tyr
                340                 345                 350

Ser Glu Asp Gln Leu Leu Glu Cys Ser Arg Ser Ile Val Ser Tyr His
                355                 360                 365

Arg Lys Ala Ala Thr Gly Lys Leu Thr Gly Val His Arg Lys Tyr Ser
    370                 375                 380

Thr Ser Lys Tyr Gly Tyr Ala Ala Lys Tyr Glu Pro Ala Leu Phe Leu
385                 390                 395                 400

Val Gln Ile Gln

<210> SEQ ID NO 67
<211> LENGTH: 437
<212> TYPE: PRT
<213> ORGANISM: Nicotiana tabacum

<400> SEQUENCE: 67

Met Ala Ile Ser Asp Glu Asn Asn Pro Thr Met Ile Lys Pro Thr Asn
1               5                   10                  15

Val Gln Gly Gly Ala Gly Met Gly Thr Arg Lys Phe Gly Gly Val Glu
                20                  25                  30

Thr Arg Asn Asn Arg Arg Ala Leu Gly Val Ile Asn Gln Asn Leu Val
            35                  40                  45

Gly Gly Ala His Pro Phe Pro Cys Val Val Asn Lys Arg Gly Leu Ser
        50                  55                  60

Glu Ala Asn Gly Arg Cys Asp Lys Asn Leu Pro Ile Pro Ala His Arg
65                  70                  75                  80

Pro Ile Thr Arg Lys Phe Ala Ala Gln Ile Ala Ser Ser His Gln His
                85                  90                  95

Arg Ser Glu Glu Asn Lys Lys Ala Lys Ile Ala Ser Glu Glu Phe Ser
                100                 105                 110

Ile Trp Glu Asp Ile Pro Leu Thr Asp Val Glu Glu Asn Glu Ala Ala
            115                 120                 125

Lys Asp Gln Pro Val Pro Met Ser Leu Glu Leu Thr Glu Thr Val Pro
        130                 135                 140

Asn Asp Asn Lys Asn Gln Met Glu Val Glu Met Glu Asp Ile Leu Glu
145                 150                 155                 160

Glu Asn Ile Ile Asp Ile Asp Gly Asp Ala Lys Asn Pro Leu Ala
                165                 170                 175

Val Val Glu Tyr Val Gln Asp Leu Phe Ala Ser Tyr Arg Lys Met Glu
                180                 185                 190

Gly Cys Ser Cys Val Ser Pro Asp Tyr Met Ala Gln Gln Phe Asp Ile
            195                 200                 205

Asn Glu Arg Met Arg Ser Ile Leu Ile Asp Trp Leu Ile Glu Val His
        210                 215                 220

His Lys Phe Glu Leu Arg Glu Glu Thr Leu Phe Leu Thr Val Asn Leu
225                 230                 235                 240
```

```
Ile Asp Arg Phe Leu Glu Lys Gln Gly Val Arg Lys Leu Gln
                245                 250                 255

Leu Val Gly Leu Val Ala Met Leu Ala Cys Lys Tyr Glu Val
            260                 265                 270

Ser Val Pro Leu Val Glu Asp Leu Val Phe Ile Ser Asp Lys Ala Tyr
            275                 280                 285

Ser Arg Lys Glu Ile Leu Glu Met Glu Arg Met Met Leu Asn Thr Leu
    290                 295                 300

Gln Phe Asn Met Ser Val Pro Thr Ala Tyr Val Phe Met Arg Arg Tyr
305                 310                 315                 320

Leu Lys Ala Ala Gln Ser Asp Arg Lys Leu Glu Leu Ser Phe Phe
                325                 330                 335

Leu Val Glu Leu Cys Leu Val Glu Tyr Ala Met Leu Lys Phe Pro Pro
                340                 345                 350

Ser Phe Ile Ala Ala Ala Ile Tyr Thr Ala Gln Thr Thr Leu Tyr
                355                 360                 365

Gly Val Gln Gln Trp Ser Lys Thr Cys Glu Trp His Thr Ser Tyr Ser
            370                 375                 380

Glu Asp Gln Leu Met Glu Cys Ser Arg Ser Ile Val Ser Tyr His Gln
385                 390                 395                 400

Lys Ala Ala Thr Gly Lys Leu Thr Gly Val His Arg Lys Tyr Ser Thr
                405                 410                 415

Ser Lys Phe Gly Tyr Ala Ala Lys Cys Glu Pro Ala His Phe Leu Val
                420                 425                 430

Gln Thr Gln Gln Gln
            435

<210> SEQ ID NO 68
<211> LENGTH: 726
<212> TYPE: PRT
<213> ORGANISM: Nicotiana tabacum

<400> SEQUENCE: 68

Met Gly Lys Leu Asn Ser Gln Lys His Ile Ser Thr Ile Lys Asp Gly
1               5                   10                  15

Val Thr Glu Leu Lys Val Tyr Glu Glu Val Asp Lys Ile Lys Ile Gln
            20                  25                  30

Ser Arg Asp Ser Leu Ser Arg Arg Cys Lys Gly Lys Ser Gly Ala Pro
        35                  40                  45

Asn Met Ser Asp Val Gln Thr Ser Trp Lys Ser Ser Glu Arg Gly Ile
    50                  55                  60

Lys His Ile Glu Arg Ile Lys Ala Lys Cys Arg Thr Cys Val Lys Val
65                  70                  75                  80

Asn Val Lys Arg Lys Val Leu Thr Asp Ile Ser Asn Ile Arg Gly Asn
                85                  90                  95

Ser Ser Arg Thr Lys Ser Tyr Asn Ser Ser Lys Leu Leu Val Ser Asp
            100                 105                 110

Gly Lys Cys Pro Lys Asn Ala Ser Asn Ser Ala Arg Arg Phe Ile Met
        115                 120                 125

Gly Asn Val Arg Thr Asn Leu Asn Gly Ala Thr Gly Asp Lys Gln Ile
    130                 135                 140

Leu Thr Arg Asp Met Lys Ala Ser Phe Asp Gly Pro Lys Thr Arg Ile
145                 150                 155                 160
```

```
Gln Gly Arg Lys Ser Val Thr Thr Gly Ile Arg Pro Thr Gly Arg Asn
            165                 170                 175

Asp Leu Pro Pro Ser Arg Arg Ser Leu Pro Ile Leu Gln Gln Val Asn
            180                 185                 190

Ile Glu Gly Thr Asn Asn Lys Glu Lys Gly Lys Val Arg Ala Asn Leu
            195                 200                 205

Asn Lys Ala Thr Asp Asp Lys Gln Ile Leu Thr Gln Ala Pro Arg Lys
            210                 215                 220

Asp Met Lys Ala Ser Phe Asp Gly Pro Lys Thr Arg Ile Gln Val Arg
225                 230                 235                 240

Lys Pro Val Thr Thr Gly Ile Arg Arg Thr Gly Arg Asn Ala Leu Pro
            245                 250                 255

Pro Ser Arg Arg Ser Leu Pro Ile Leu Gln Gln Val Asn Val Glu Asp
            260                 265                 270

Thr Asn Asn Lys Glu Lys Glu Asn Ser Lys Lys Leu Glu Lys Gly Lys
            275                 280                 285

Gly Ile Ser Gly Val Ser Val Leu Ala Lys Pro Lys Ala Ala Gly Asp
            290                 295                 300

Val Leu Pro Gln Leu Ser Asn His Ser Asn Ile Arg Arg Asn Arg Val
305                 310                 315                 320

Gly Asp Ala Ser Ala Arg Met Ala Pro Arg Gly Gln Ala Lys Val Glu
            325                 330                 335

Val Gly Ala Leu Arg Arg Lys Ser Val Arg Thr Val Leu Lys Ile Thr
            340                 345                 350

Ala Ser Gly Leu Asn Ser Gln Lys Ser Ser Lys Ser Asn Ser Met Ser
            355                 360                 365

Gly Val His Lys Cys Thr Ser Arg Phe Ala Ser Pro Cys Lys Arg Leu
            370                 375                 380

Val Asp Val Arg Thr Ser Ser Leu Ser Lys Ser Ala Thr Ser Glu Ile
385                 390                 395                 400

Ser Ala Glu Gln Pro His Gln Lys Glu Val Pro Ser Ser Ser Gly
            405                 410                 415

Ser Leu Ala Thr Pro Glu Leu Ser Ile Ala Arg Lys Lys Ser Asp Arg
            420                 425                 430

Arg Lys Ser Phe Thr Cys Leu Leu Met Ala Arg Ser Lys Leu Met Lys
            435                 440                 445

Glu Leu Cys Gly Thr Val Glu Leu Asp Asn Leu Ser Asn Ile Tyr Asp
450                 455                 460

Ser Cys Asn His Leu Glu Val Thr Glu Tyr Val Asp Asp Ile Tyr Gln
465                 470                 475                 480

Tyr Tyr Trp Val Ile Glu Ala Gln Asn Gln Pro Ile Lys Asn Tyr Met
            485                 490                 495

Glu Thr Gln Lys Glu Ile Thr Pro Gln Met Arg Gly Ile Leu Ile Asn
            500                 505                 510

Trp Leu Ile Glu Val His Leu Lys Phe Asp Leu Met Gln Glu Thr Leu
            515                 520                 525

Phe Leu Met Val Thr Leu Leu Asp Tyr Tyr Leu Thr Leu Ala Arg Val
            530                 535                 540

Lys Lys Asn Asp Leu Gln Leu Val Gly Leu Thr Ser Leu Leu Leu Ala
545                 550                 555                 560

Ser Lys Tyr Glu Asp Leu Phe His Pro Arg Val Met Asp Leu Leu Ser
            565                 570                 575
```

```
Ile Ser Ala Glu Ser Tyr Thr Arg Asp Gln Met Leu Glu Met Glu Lys
            580                 585                 590

Asp Ile Leu Arg Lys Leu Lys Phe Arg Leu Asn Ala Ala Thr Pro Tyr
            595                 600                 605

Val Phe Met Leu Arg Leu Leu Lys Ala Ala Gln Ala Asp Thr Arg Ile
            610                 615                 620

Glu His Leu Ala Phe Tyr Leu Ile Glu Leu Cys Leu Val Glu Tyr Glu
625                 630                 635                 640

Ala Leu Asn Tyr Lys Pro Ser Met Leu Cys Ala Ser Ala Ile Tyr Val
            645                 650                 655

Ala Arg Cys Thr Met Gln Met Thr Pro Ala Trp Thr Pro Leu Leu Gly
            660                 665                 670

Met His Ala Arg Tyr Gln Glu Ser Gln Leu Arg His Cys Ala Glu Met
            675                 680                 685

Ile Leu Arg Phe His Lys Ala Ser Thr Ala Leu Leu Lys Val Thr
            690                 695                 700

His Glu Lys Tyr Met Gln Ser Ser Asn Ser Lys Val Ala Ala Ile Lys
705                 710                 715                 720

Pro Leu Gln Ser Leu Pro
            725

<210> SEQ ID NO 69
<211> LENGTH: 425
<212> TYPE: PRT
<213> ORGANISM: Nicotiana tabacum

<400> SEQUENCE: 69

Met Asp Asn Asn Ser Val Gly Val Pro His Asn Leu Pro Arg Gly Glu
1               5                   10                  15

Met Gly Gly Lys Gln Lys Asn Ala Gln Ala Asp Gly Arg Asn Arg Arg
            20                  25                  30

Ala Leu Gly Asp Ile Gly Asn Leu Val Pro Ala Pro Ala Ala Glu Gly
            35                  40                  45

Lys Pro Lys Ala Ala Gln Ile Ser Arg Pro Val Thr Arg Ser Phe Cys
50                  55                  60

Ala Gln Leu Leu Ala Asn Ala Gln Glu Glu Lys Asn Lys Lys Pro Leu
65                  70                  75                  80

Ala Glu Val Val Asn Lys Asp Val Pro Ala Lys Lys Ala Ser Asp
            85                  90                  95

Lys Glu Met Lys Thr Val Gly Gly Ser Pro Leu Ser Lys Arg Lys Ala
            100                 105                 110

Lys Lys Ser Gly Lys Thr Leu Thr Ser Thr Leu Thr Ala Arg Ser Lys
            115                 120                 125

Ala Ala Cys Gly Leu Ser Asn Arg Pro Lys Tyr Glu Ile Glu Asp Ile
            130                 135                 140

Asp Val Ala Asp Ala Asp Asn His Leu Ala Ala Val Glu Tyr Val Glu
145                 150                 155                 160

Asp Ile Tyr Asn Phe Tyr Lys Leu Thr Glu Gly Glu Ser Arg Val Asp
            165                 170                 175

Asp Asp Tyr Met Asn Phe Gln Pro Asp Leu Asn His Lys Met Arg Ala
            180                 185                 190

Ile Leu Val Asp Trp Leu Ile Glu Val His Arg Lys Phe Glu Leu Met
            195                 200                 205

Pro Glu Ser Leu Tyr Leu Thr Ile Thr Ile Leu Asp Arg Phe Leu Ser
            210                 215                 220
```

Leu Lys Thr Val Pro Arg Lys Glu Leu Gln Leu Val Gly Ile Ser Ser
225                 230                 235                 240

Met Leu Ile Ala Cys Lys Tyr Glu Glu Ile Trp Ala Pro Glu Val Asn
                245                 250                 255

Asp Phe Ile His Ile Ser Asp Asn Ala Tyr Ala Arg Glu Gln Ile Leu
            260                 265                 270

Gln Met Glu Lys Ala Ile Leu Gly Lys Leu Glu Trp Tyr Leu Thr Val
        275                 280                 285

Pro Thr Pro Tyr Val Phe Leu Val Arg Tyr Ile Lys Ala Ala Thr Pro
    290                 295                 300

Ser Asp Asn Gln Glu Met Glu Asn Met Thr Phe Phe Ala Glu Leu
305                 310                 315                 320

Gly Leu Met Asn Tyr Lys Ile Thr Ile Ser Tyr Arg Pro Ser Met Leu
                325                 330                 335

Ala Ala Ser Ser Val Tyr Ala Ala Arg Ser Thr Leu Asn Lys Thr Pro
            340                 345                 350

Leu Trp Thr Gln Thr Leu Gln His His Thr Gly Tyr Ser Glu Asp Gln
        355                 360                 365

Leu Met Glu Cys Ala Lys Ile Leu Val Ser Tyr His Leu Asp Ala Ala
    370                 375                 380

Glu Ser Lys Leu Lys Ala Ile Tyr Arg Lys Phe Ser Ser Pro Asp Arg
385                 390                 395                 400

Gly Ala Val Ala Phe Phe Pro Pro Ala Arg Asn Leu Leu Pro Thr Thr
                405                 410                 415

Thr Thr Asp Ala Ala Ser Ser Ser Ser
            420                 425

<210> SEQ ID NO 70
<211> LENGTH: 436
<212> TYPE: PRT
<213> ORGANISM: Nicotiana tabacum

<400> SEQUENCE: 70

Met Val Gly Ser Asn Glu Asn Cys Gln Gly Val Ile Met Ala Ser Asn
1               5                   10                  15

Val Gln Gly Gly Leu Gly Ala Gly Gly Lys Val Thr Met Gly Pro
            20                  25                  30

Asn Arg Arg Ala Leu Ser Thr Ile Asn Gly Asn Ile Val Glu Ala Pro
            35                  40                  45

Ala Tyr Pro Cys Lys Val His Lys Arg Asn Gly Ile Thr Asp Lys Ser
    50                  55                  60

Ala Asn Gly Val Lys Asn Pro Pro Ile Pro Ile His Arg Pro Ile Thr
65                  70                  75                  80

Arg Lys Phe Ala Ala Gln Met Ala Thr Lys Gln Gln Pro Thr Val
                85                  90                  95

Glu Val Thr Lys Gln Pro Val Gln Thr Ala Pro Ala Lys Asn Glu Ser
            100                 105                 110

Glu Asp Cys Ile Ile Ile Asp Ala Glu Asp Tyr Lys Ala Thr Ser Asp
        115                 120                 125

Tyr Asp Pro Val Pro Met Phe Val Gln His Thr Glu Ala Met Met Glu
    130                 135                 140

Glu Ile Asp Arg Met Asp Ala Glu Met Glu Met Glu Asp Val Glu Glu
145                 150                 155                 160

Thr Leu Ile Val Asp Ile Asp Ser Ala Asp Lys Lys Asn Pro Leu Ala
            165                 170                 175

Val Ala Glu Tyr Ile Asp Asp Met His Ala Tyr Tyr Lys Lys Thr Glu
        180                 185                 190

Ser Ser Ser Cys Ala Pro Pro Asn Tyr Met Glu Gln Gln Phe Asp Ile
    195                 200                 205

Asn Glu Arg Met Arg Ala Ile Leu Ile Asp Trp Leu Ile Glu Val His
210                 215                 220

Tyr Lys Phe Asp Leu Met Glu Glu Thr Leu Tyr Leu Thr Val Asn Leu
225                 230                 235                 240

Ile Asp Arg Phe Leu Ala Val Gln Gln Val Ile Arg Lys Lys Leu Gln
            245                 250                 255

Leu Val Gly Val Thr Ala Met Leu Leu Ala Cys Lys Tyr Glu Glu Val
            260                 265                 270

Ser Val Pro Val Val Glu Asp Leu Ile Leu Ile Ser Asp Lys Ala Tyr
    275                 280                 285

Thr Arg Lys Glu Val Leu Glu Met Glu Lys Leu Met Ile Asn Thr Leu
    290                 295                 300

Gln Phe Asn Leu Pro Val Pro Thr Ala Tyr Val Phe Met Met Arg Phe
305                 310                 315                 320

Leu Lys Ala Ala Gln Ser Asp Lys Lys Val Glu Leu Leu Ser Phe Phe
            325                 330                 335

Met Thr Glu Leu Cys Leu Val Glu Tyr Glu Met Leu Arg Phe Pro Pro
            340                 345                 350

Ser Met Leu Ala Ala Ala Ala Ile Phe Thr Ala Gln Cys Thr Leu Gly
            355                 360                 365

Val Leu Asn Glu Trp Ser Lys Thr Cys Glu Lys Tyr Ser His Tyr Thr
    370                 375                 380

Arg Asp Gln Leu Leu Glu Cys Ser Arg Leu Met Val Ser Phe His Gln
385                 390                 395                 400

Asn Ala Ala Thr Gly Lys Leu Ala Gly Val His Arg Lys Tyr Ser Ile
            405                 410                 415

Ser Lys Tyr Gly Phe Val Ala Lys Cys Pro Pro Ala Ser Phe Leu Leu
            420                 425                 430

Glu Ala Ser Phe
            435

<210> SEQ ID NO 71
<211> LENGTH: 422
<212> TYPE: PRT
<213> ORGANISM: Nicotiana tabacum

<400> SEQUENCE: 71

Met Gly Val Ser Asn Glu Asn Asn Pro Ser Met Ile Lys Pro Arg Asn
1               5                   10                  15

Val Gln Gly Gly Ala Glu Leu Gly Tyr Arg Lys Phe Gly Val Glu Thr
            20                  25                  30

Arg Asn Asn Arg Arg Ala Leu Ser Val Ile Asn Gln Asn Phe Val Gly
        35                  40                  45

Ala Lys Pro Tyr Pro Cys Val Val Asn Lys Arg Gly Leu Ser Asp Thr
    50                  55                  60

Asn Lys Asn Pro Pro Val Pro Ala His Arg Pro Ile Thr Arg Lys Phe
65                  70                  75                  80

Ala Ala Gln Ile Ala Asn Ser Lys Gln His Tyr Pro Glu Glu Asn Lys
            85                  90                  95

Lys Pro Lys Ile Ala Ala Glu Gly Leu Ser Val Tyr Glu Asp Val Ala
        100                 105                 110

Ile Val Asp Val Glu Glu Tyr Glu Ala Ala Lys Asp Gln Pro Val
    115                 120                 125

Pro Met Ser Leu Glu Gln Thr Gln Met Glu Ile Glu Met Glu Asp Thr
130                 135                 140

Phe Glu Glu Ser Val Ile Asp Ile Asp Ser Asn Asp Ala Lys Asn Pro
145                 150                 155                 160

Leu Ala Val Val Asp Tyr Val Glu Asp Leu Tyr Ala Tyr Tyr Ser Lys
                165                 170                 175

Met Glu Gly Cys Ser Arg Ile Ser Pro Asp Tyr Ile Gly Gln Gln Phe
            180                 185                 190

Asp Ile Asn Glu Arg Met Arg Ser Ile Leu Ile Asp Trp Leu Ile Glu
        195                 200                 205

Val His His Lys Phe Asp Leu Lys Glu Glu Thr Leu Phe Leu Thr Val
    210                 215                 220

Asn Leu Ile Asp Arg Phe Leu Glu Lys Gln Ser Val Val Arg Lys Lys
225                 230                 235                 240

Leu Gln Leu Val Gly Leu Val Ala Met Leu Leu Ala Cys Lys Tyr Glu
                245                 250                 255

Glu Val Ser Leu Pro Val Val Asp Asp Leu Val Val Ile Ser Asp Lys
            260                 265                 270

Ala Tyr Thr Arg Lys Glu Val Leu Glu Met Glu Lys Leu Met Leu Asn
        275                 280                 285

Thr Leu Gln Phe Asn Met Ser Val Pro Thr Pro Tyr Val Phe Met Arg
    290                 295                 300

Arg Phe Leu Lys Ala Ala Gln Ser Asp Lys Lys Leu Glu Leu Leu Ser
305                 310                 315                 320

Phe Phe Leu Ile Glu Leu Cys Leu Val Glu Tyr Glu Met Leu Lys Phe
                325                 330                 335

Pro Pro Ser Phe Ile Ala Ala Ala Ile Tyr Thr Ala Gln Cys Thr
            340                 345                 350

Phe Tyr Gly Val Lys Gln Trp Ser Lys Thr Cys Glu Leu His Thr Lys
    355                 360                 365

Tyr Ser Glu Asp Gln Leu Leu Glu Cys Ser Arg Leu Ile Thr Gly Phe
    370                 375                 380

His Gln Lys Ala Ala Thr Gly Lys Leu Thr Gly Val His Arg Lys Tyr
385                 390                 395                 400

Asn Thr Ser Lys Phe Gly Tyr Val Ala Lys Cys Glu Pro Ala His Phe
                405                 410                 415

Leu Leu Val Gln Thr Arg
            420

<210> SEQ ID NO 72
<211> LENGTH: 492
<212> TYPE: PRT
<213> ORGANISM: Nicotiana tabacum

<400> SEQUENCE: 72

Met Arg Asn Ala Asn Met Thr Ile Gly Ser Ser Asn Leu Lys Glu Pro
1               5                   10                  15

```
Thr Met Arg Ile Thr Arg Ser Arg Ala Lys Ala Leu Gly Ser Ser Gly
            20                  25                  30

Gly Leu Pro Pro Arg His Pro Ser Val Arg Gln Asp Asn Lys Gln Gly
            35                  40                  45

Leu Gly Ala Lys Gly Thr Lys Tyr Lys Arg Ser Ala Ser Asp Glu Asn
 50                  55                  60

Asn Pro Val Thr Asn Ala Ser Thr Ala Cys Gln Gln Pro Lys Arg Arg
 65                  70                  75                  80

Ala Val Leu Arg Asp Val Thr Asn Val Leu Cys Glu Asn Ser Tyr Met
            85                  90                  95

Asn Cys Ile Asn Arg Ser Lys Phe Gln Val Lys Phe Ser Asp Lys
            100                 105                 110

Arg Asn Ser Lys Val Thr Pro Ala Ile Leu Ala Lys Arg Pro His His
            115                 120                 125

Glu Asp Thr Lys Glu Asn Thr Ile Glu Glu Ala Lys Lys Val Lys Ile
    130                 135                 140

Glu Lys Ser Gln Glu His Cys Ser Gln Ala Arg Phe Lys Asp His Thr
145                 150                 155                 160

Leu Thr Gln Pro Ser Lys Tyr Ile Thr Pro Ala Gln Cys Gly Phe Val
                165                 170                 175

Asp Leu Met Pro Val Asn Arg Ser Leu Pro Thr Ala Ile Ala Val Leu
            180                 185                 190

Asn Thr Thr Glu Lys Asp Glu Thr Lys Val Cys Gln Lys Gln Glu Gly
            195                 200                 205

Ser Asp Ser Leu Gly Ile Ala Asp Ile Asp Ser Lys His Lys Asp Pro
210                 215                 220

Leu Met Cys Ser Leu Tyr Ala Pro Asp Ile Tyr Ser Asn Leu His Ala
225                 230                 235                 240

Met Glu Leu Asp Arg Arg Pro Ser Phe Asn Tyr Met Glu Lys Leu Gln
            245                 250                 255

Arg Asp Val Asn Lys Gly Met Arg Gly Ile Leu Ile Asp Trp Leu Val
            260                 265                 270

Glu Val Ser Glu Glu Tyr Arg Leu Val Pro Asp Thr Leu Tyr Leu Thr
            275                 280                 285

Val His Leu Ile Asp Arg Phe Leu Ser Glu Asn Tyr Ile Glu Lys Gln
            290                 295                 300

Lys Leu Gln Leu Leu Gly Val Thr Cys Met Leu Ile Ala Ser Lys Tyr
305                 310                 315                 320

Glu Glu Ile Cys Ala Pro Arg Val Glu Glu Phe Cys Phe Ile Thr Asp
                325                 330                 335

Asn Thr Tyr Ser Lys Glu Glu Val Val Arg Met Glu Ser Leu Val Leu
            340                 345                 350

Asn Phe Leu Gly Phe Gln Leu Ala Ala Pro Thr Thr Lys Lys Phe Leu
            355                 360                 365

Arg Arg Phe Val Gln Ala Ala Gln Ala Ser Tyr Glu Val Pro Ser Val
            370                 375                 380

Glu Leu Glu Phe Met Ala Asn Tyr Leu Ala Glu Leu Thr Leu Val Asp
385                 390                 395                 400

Tyr Ser Phe Leu Lys Phe Leu Pro Ser Ile Thr Ala Ala Ser Ala Val
                405                 410                 415

Phe Leu Ala Lys Trp Thr Leu Asp Gln Ser Asn His Pro Trp Asn Pro
            420                 425                 430
```

```
Thr Leu Glu His Tyr Thr Arg Tyr Thr Ala Leu Glu Leu Lys Thr Ile
            435                 440                 445

Val Leu Leu Leu Gln Asp Leu Gln Leu Asn Thr Ser Gly Ser Thr Leu
450                 455                 460

Asn Ala Ile Arg Glu Lys Tyr Arg Gln Pro Lys Phe Lys Ser Val Ala
465                 470                 475                 480

Thr Leu Ser Ser Pro Gln Pro Val Gln Ser Leu Phe
            485                 490

<210> SEQ ID NO 73
<211> LENGTH: 422
<212> TYPE: PRT
<213> ORGANISM: Nicotiana tabacum

<400> SEQUENCE: 73

Met Asp Asn Lys Thr Val Val Pro His Asn Leu Pro Lys Gly Glu
1               5                   10                  15

Met Gly Gly Lys Gln Lys Asn Gly Gln Ala Asp Gly Arg Asn Arg Arg
            20                  25                  30

Ala Leu Gly Asp Ile Gly Asn Leu Val Pro Ala Pro Ala Val Glu Gly
            35                  40                  45

Lys Pro Lys Ala Ala Gln Ile Ser Arg Pro Val Thr Arg Ser Phe Cys
50                  55                  60

Ala Gln Leu Leu Ala Asn Ala Gln Ala Glu Lys Asn Lys Lys Ala Leu
65                  70                  75                  80

Ala Glu Ile Val Asn Lys Asp Ala Pro Ala Lys Lys Ala Ser Asp
            85                  90                  95

Lys Glu Ile Lys Thr Val Gly Ser Ser Leu Ser Lys Arg Lys Ala
            100                 105                 110

Lys Lys Ser Gly Lys Thr Leu Thr Ser Thr Leu Thr Ala Arg Ser Lys
            115                 120                 125

Ala Ala Cys Gly Leu Ser Asn Arg Pro Lys Tyr Glu Ile Asp Asp Ile
            130                 135                 140

Asp Val Val Asp Ala Asp Asn His Leu Ala Ala Val Glu Tyr Val Glu
145                 150                 155                 160

Asp Ile Tyr Asn Phe Tyr Lys Leu Thr Glu Gly Ser Arg Val Asp
            165                 170                 175

Asp Tyr Met Asn Phe Gln Pro Asp Leu Asn His Lys Met Arg Ala Ile
            180                 185                 190

Leu Val Asp Trp Leu Ile Glu Val His Arg Lys Phe Glu Leu Met Pro
            195                 200                 205

Glu Ser Leu Tyr Leu Ala Ile Asn Ile Leu Asp Arg Phe Leu Ser Leu
210                 215                 220

Lys Thr Val Pro Arg Lys Glu Leu Gln Leu Val Gly Ile Ser Ser Met
225                 230                 235                 240

Leu Ile Ala Cys Lys Tyr Glu Glu Ile Trp Ala Pro Glu Val Asn Asp
            245                 250                 255

Phe Ile His Ile Ser Asp Asn Ala Tyr Ala Arg Glu Gln Ile Leu Gln
            260                 265                 270

Met Glu Lys Ala Ile Leu Gly Lys Leu Glu Trp Tyr Leu Thr Val Pro
            275                 280                 285

Thr Pro Tyr Val Phe Leu Val Arg Tyr Ile Lys Ala Ala Thr Pro Ser
            290                 295                 300

Asp Asn Gln Glu Met Glu Asn Met Thr Phe Phe Phe Ala Glu Leu Gly
305                 310                 315                 320
```

```
Leu Met Asn Tyr Lys Thr Thr Ile Ser Tyr Cys Pro Ser Met Leu Ala
                325                 330                 335

Ala Ser Ser Val Tyr Ala Ala Arg Ser Thr Leu Asn Lys Thr Pro Leu
            340                 345                 350

Trp Thr Gln Thr Leu Gln His His Thr Gly Tyr Ser Glu Asp Gln Leu
            355                 360                 365

Met Glu Cys Ala Lys Gln Leu Val Ser Tyr His Leu Gly Ala Ala Glu
    370                 375                 380

Ser Lys Leu Lys Ala Ile Tyr Arg Lys Phe Ser Ser Pro Asp Arg Gly
385                 390                 395                 400

Ala Val Ala Phe Phe Pro Pro Ala Arg Asn Leu Leu Pro Thr Thr Thr
                405                 410                 415

Asp Ala Ala Ser Cys Ser
            420

<210> SEQ ID NO 74
<211> LENGTH: 495
<212> TYPE: PRT
<213> ORGANISM: Nicotiana tabacum

<400> SEQUENCE: 74

Met Arg His Ala Asn Ile Lys His Gly Ser Phe His Leu Glu Glu His
1               5                   10                  15

Asn Met Arg Ile Thr Arg Ala Arg Ala Arg Ala Ser Val Leu Gly Ser
            20                  25                  30

Ser Gly Arg Leu Pro Pro Leu His Pro Ser Thr Lys Gln Asp Lys Lys
        35                  40                  45

His Val Leu Gly Ala Glu Ser Lys Arg Ser Lys Arg Ser Ala Ser Asp
    50                  55                  60

Glu Asn Arg Pro Gly Thr Ser Ser Thr Ala Thr Gly Val Gln Pro Lys
65                  70                  75                  80

Arg Arg Ala Val Leu Lys Asp Met Thr Asn Val Leu His Glu Asn Ser
                85                  90                  95

His Met Asn Cys Ile Asn Gly Ser Lys Ile Gln Val Lys Lys Gly Ser
            100                 105                 110

Asp Lys Arg Asn Asn Lys Ala Lys Pro Ala Val Ser Val Lys Leu Ser
        115                 120                 125

Gln Leu Gln Glu Lys Gly Lys Glu Asp Ile Ala Asp Lys Val Lys Lys
    130                 135                 140

Val Lys Val Glu Gly Ser Gln Glu Ile Ser Ser Gly Ala Asn Cys Lys
145                 150                 155                 160

Glu Asp Met Leu Pro Gln Leu Ser Arg Tyr Val Thr Pro Ala Gln Cys
                165                 170                 175

Gly Leu Val His Leu Val Pro Val Asn Arg Ser Ser Cys Lys Ala Ile
            180                 185                 190

Pro Leu Gln Asp Ile Met Lys Lys Asp Glu Ser Lys Val Cys Arg Lys
        195                 200                 205

Gln Glu Gly Phe Ala Asn Leu Gly Val Ala Asp Ile Asp Ser Arg His
    210                 215                 220

Lys Asp Pro Leu Met Cys Ser Leu Tyr Ala Pro Asp Ile Tyr Asn Asn
225                 230                 235                 240

Leu His Ala Ile Glu Phe Asp Arg Arg Pro Ser Val Asp Tyr Leu Glu
                245                 250                 255
```

```
Lys Leu Gln Leu Asp Ile Asn Lys Gly Met Arg Gly Ile Leu Ile Asp
                260                 265                 270

Trp Leu Val Glu Val Ser Glu Glu Tyr Arg Leu Val Pro Asp Thr Leu
                275                 280                 285

Tyr Leu Thr Val Asn Leu Ile Asp Arg Phe Leu Ser Glu Asn Tyr Ile
                290                 295                 300

Glu Lys Gln Lys Leu Gln Leu Leu Gly Val Thr Cys Met Leu Ile Ala
305                 310                 315                 320

Ser Lys Phe Glu Glu Ile Cys Ala Pro Arg Val Glu Phe Cys Phe
                325                 330                 335

Ile Thr Asp Asn Thr Tyr Ser Lys Glu Val Ile Lys Met Glu Ser
                340                 345                 350

Arg Val Leu Asn Leu Leu Ser Phe Gln Leu Ala Ser Pro Thr Thr Lys
                355                 360                 365

Lys Phe Leu Arg Arg Phe Ile Gln Ala Ala Gln Ala Ser Tyr Lys Val
                370                 375                 380

Pro Ser Val Glu Leu Glu Phe Met Ala Asn Tyr Leu Ala Glu Leu Thr
385                 390                 395                 400

Leu Val Asp Tyr Gly Phe Leu Lys Phe Leu Pro Ser Leu Thr Ala Ala
                405                 410                 415

Ser Ala Val Phe Leu Ala Arg Trp Thr Leu Asp Gln Ser Asn His Pro
                420                 425                 430

Trp Asn Pro Thr Leu Glu His Tyr Thr Arg Tyr Lys Val Ser Glu Leu
                435                 440                 445

Arg Thr Thr Val Phe Ala Leu Gln Glu Leu Gln Met Asn Thr Ser Gly
                450                 455                 460

Cys Thr Leu Asn Ala Ile Arg Glu Lys Tyr Arg Gln Pro Lys Phe Lys
465                 470                 475                 480

Ser Val Ala Thr Leu Ala Ala Ser Lys Pro Val Gln Ser Leu Phe
                485                 490                 495

<210> SEQ ID NO 75
<211> LENGTH: 446
<212> TYPE: PRT
<213> ORGANISM: Nicotiana tabacum

<400> SEQUENCE: 75

Met Ala Ser Arg Asn Val Leu Gln Gln Gln Asn Ile Gly Glu Ala Val
1               5                   10                  15

Pro Gly Ala Leu Lys Gln Lys Asn Met Ala Ala Ala Gln Gly Arg
                20                  25                  30

Asn Arg Lys Ala Leu Gly Asp Ile Gly Asn Asn Val Val Thr Val Arg
                35                  40                  45

Gly Val Glu Gly Lys Pro Leu Pro Gln Arg Pro Ile Thr Arg Ser Phe
                50                  55                  60

Cys Ala Gln Leu Leu Ala Asn Ala Gln Ala Ala Ala Glu Asn Gln Lys
65                  70                  75                  80

Lys Ser Leu Val Val Asn Gly Asp Ala Pro Ile Val Ala Lys Gly Ala
                85                  90                  95

Leu Ala Val Lys Ala Ala Ala Lys Lys Pro Ala His Lys Lys Val Ala
                100                 105                 110

Val Lys Pro Lys Pro Asp Val Ile Glu Ile Ser Pro Gly Thr Glu Glu
                115                 120                 125
```

Gln Val Lys Glu Asn Lys Gln Lys Lys Ala Gly Asp Asp Ser Ser
    130                 135                 140

Leu Lys Lys Ala Thr Leu Thr Ser Thr Leu Thr Ala Arg Ser Lys Ala
145                 150                 155                 160

Ala Cys Gly Leu Ser His Lys Pro Lys Val Gln Ile Val Asp Ile Asp
                165                 170                 175

Ala Val Asp Val Asn Asn Glu Leu Ala Val Val Glu Tyr Val Glu Asp
                180                 185                 190

Ile Tyr Asn Phe Tyr Lys Ile Ala Glu Asn Glu Ser Arg Ile His Asp
                195                 200                 205

Tyr Met Asp Ser Gln Leu Glu Ile Thr Glu Arg Met Arg Ala Ile Leu
    210                 215                 220

Ile Asp Trp Leu Ile Glu Val His His Lys Phe Glu Leu Ser Gln Glu
225                 230                 235                 240

Thr Leu Tyr Leu Thr Ile Asn Ile Val Asp Arg Tyr Leu Ala Val Thr
                245                 250                 255

Thr Thr Ser Arg Arg Glu Leu Gln Leu Val Gly Met Ser Ala Met Leu
                260                 265                 270

Ile Ala Ser Lys Tyr Glu Glu Ile Trp Ala Pro Glu Val Asn Asp Phe
                275                 280                 285

Val Cys Ile Ser Asp Lys Ala Tyr Ser His Glu Gln Val Leu Gly Met
    290                 295                 300

Glu Lys Arg Ile Leu Gly Gln Leu Glu Trp Tyr Leu Thr Val Pro Thr
305                 310                 315                 320

Pro Tyr Val Phe Leu Val Arg Phe Ile Lys Ala Ala Val Ser Asn Ala
                325                 330                 335

Gln Met Glu Asn Met Val Tyr Phe Leu Ala Glu Leu Gly Leu Met Asn
                340                 345                 350

Tyr Ala Thr Asn Ile Tyr Cys Pro Ser Met Ile Ala Ala Ser Ala Val
                355                 360                 365

Tyr Val Ala Gln His Thr Leu Asn Cys Thr Pro Phe Trp Asn Asp Thr
    370                 375                 380

Leu Lys Leu His Thr Gly Phe Ser Glu Ser Gln Leu Leu Gly Cys Ala
385                 390                 395                 400

Lys Leu Leu Val Ser Tyr His Met Glu Ala Pro Glu His Lys Leu Lys
                405                 410                 415

Val Ile Tyr Lys Lys Tyr Ser Arg Pro Glu Arg Gly Ala Val Ala Leu
                420                 425                 430

Gln Pro Pro Ala Lys Ser Leu Leu Ala Ala Ser Leu Tyr Glu
                435                 440                 445

<210> SEQ ID NO 76
<211> LENGTH: 473
<212> TYPE: PRT
<213> ORGANISM: Nicotiana tabacum

<400> SEQUENCE: 76

Met Ala Ser Arg Ile Val Leu Gln Gln Gln Asn Arg Gly Glu Ala Val
1               5                   10                  15

Pro Gly Ala Leu Lys Gln Lys Asn Val Ala Ala Glu Gly Arg Asn
            20                  25                  30

Arg Lys Ala Leu Gly Asp Ile Gly Asn Val Ala Thr Gly Arg Gly Val
            35                  40                  45

-continued

```
Glu Gly Lys Lys Pro Leu Pro Gln Lys Pro Val Ala Ile Val Lys
 50              55                  60
Gly Ala Asn Val Ala Lys Val Pro Ala Val Arg Lys Pro Ala Gln Lys
 65                  70                  75                  80
Lys Ala Thr Val Lys Pro Lys Pro Glu Glu Ile Ile Glu Ile Ser Pro
                     85                  90                  95
Asp Thr Gln Glu Lys Leu Lys Glu Lys Met Gln Arg Lys Lys Ala Asp
                100             105                 110
Lys Asp Ser Leu Lys Gln Lys Ala Thr Leu Thr Ser Thr Leu Thr Ala
            115             120                 125
Arg Ser Lys Ala Ala Cys Gly Leu Ser Lys Lys Pro Lys Glu Gln Ile
        130             135                 140
Val Asp Ile Asp Ala Ala Asp Val Asn Asn Glu Leu Ala Val Val Glu
145             150                 155                 160
Tyr Val Glu Asp Ile Tyr Ser Phe Tyr Lys Leu Ala Glu Asn Glu Thr
                165                 170                 175
Arg Val His Asp Tyr Met Asp Ser Gln Pro Glu Ile Asn Asp Arg Met
            180                 185                 190
Arg Ala Val Leu Ile Asp Trp Leu Val Glu Val His Gln Lys Phe Glu
        195                 200                 205
Leu Asn Pro Glu Thr Leu Tyr Leu Thr Ile Asn Ile Val Asp Arg Tyr
    210                 215                 220
Leu Ala Val Lys Ser Thr Ser Arg Arg Asp Leu Gln Leu Val Gly Val
225                 230                 235                 240
Ser Ala Met Leu Ile Ala Ser Lys Tyr Glu Glu Ile Trp Ala Pro Glu
                245                 250                 255
Val Asn Asp Phe Val Cys Ile Ser Asp Lys Ser Tyr Thr His Asp Gln
            260                 265                 270
Val Leu Thr Met Glu Lys Glu Ile Leu Gly Gln Leu Glu Trp Tyr Leu
        275                 280                 285
Thr Val Pro Thr Pro Tyr Val Phe Leu Ala Arg Phe Ile Lys Ala Ser
    290                 295                 300
Pro Pro Asp Ser Glu Thr Glu Asn Met Val Tyr Phe Leu Ala Glu Leu
305                 310                 315                 320
Gly Leu Met Asn Tyr Pro Thr Ile Ile Tyr Cys Pro Ser Met Ile Ala
                325                 330                 335
Ala Ser Ala Val Tyr Ala Ala Arg His Thr Leu Asn Arg Thr Pro Phe
            340                 345                 350
Trp Asn Glu Thr Leu Lys Leu His Thr Gly Phe Ser Glu Ser Gln Leu
        355                 360                 365
Ile Glu Cys Ala Arg Leu Leu Val Ser Tyr Gln Ser Ala Ala Ala Thr
    370                 375                 380
His Lys Leu Lys Val Ile Tyr Lys Lys Tyr Ser Ser Pro Glu Arg Gly
385                 390                 395                 400
Val Val Ala Leu Leu Thr Pro Ala Lys Ser Leu Leu Ala Ala Ser Ser
                405                 410                 415
Leu Arg Val Ser Ser Glu Gln Ala Asp Leu Gly Lys Ser Thr Glu Ala
            420                 425                 430
Ala Ala Thr Ser Ser Ser Pro Met Val Val Gly Cys Gln Arg Cys
        435                 440                 445
His Met Tyr Val Met Val Thr Glu Ala Asp Pro Arg Cys Pro Gln Cys
    450                 455                 460
```

```
Lys Asn Thr Thr Thr Arg Lys Met Thr
465                 470
```

<210> SEQ ID NO 77
<211> LENGTH: 588
<212> TYPE: PRT
<213> ORGANISM: Nicotiana tabacum

<400> SEQUENCE: 77

```
Met Ile Gln Val Lys Glu Glu Ser Gln Thr Leu Asp Phe Gly Gly Phe
1               5                   10                  15

Ala Ser Cys Ser Ser Phe Ser Asp Ser Ser Tyr Glu Ala Ser Thr Pro
            20                  25                  30

Arg Tyr Ser Ser Glu Pro Gly Ser Ser Tyr Arg Arg Ser Ser Gly Pro
        35                  40                  45

Thr Lys Arg Ser Ser Gln Ala Gly Trp Thr Glu Glu Asp Asn Leu
50                  55                  60

Leu Thr Asp Val Val Lys Arg Phe Lys Gly Arg Asn Trp Lys Lys Ile
65                  70                  75                  80

Ala Glu Cys Met Asn Gly Arg Thr Asp Val Gln Cys Leu His Arg Trp
                85                  90                  95

Gln Lys Val Leu Asn Pro Glu Leu Val Lys Gly Pro Trp Ser Lys Glu
            100                 105                 110

Glu Asp Asp Leu Ile Ile Glu Leu Val Glu Lys Tyr Gly Cys Lys Lys
        115                 120                 125

Trp Ser Phe Ile Ala Lys Ser Leu Pro Gly Arg Ile Gly Lys Gln Cys
130                 135                 140

Arg Glu Arg Trp His Asn His Leu Asp Pro Thr Ile Lys Arg Asp Ala
145                 150                 155                 160

Trp Thr Glu Gln Glu Glu Ser Val Leu Cys His Tyr His Gln Ile Tyr
                165                 170                 175

Gly Asn Lys Trp Ala Glu Ile Ala Arg Phe Leu Pro Gly Arg Thr Asp
            180                 185                 190

Asn Ala Ile Lys Asn His Trp Asn Ser Ser Val Lys Lys Arg Ser Asn
        195                 200                 205

Leu Asn Leu Pro Ser Gly Leu Val Leu Asp Thr Glu Ser Glu Glu Ser
210                 215                 220

Pro Asn Phe Ser Ser Asp Lys Lys Leu Glu Ile Gln Lys His Pro
225                 230                 235                 240

Leu Gln Ala Gln Asn Ala Glu Gln Thr Ile Phe Leu Gly Glu Gln Thr
                245                 250                 255

Gly Leu Asp Asn Ala Ala Val Ala Leu Ser Thr Asp Leu Arg Ile Gly
            260                 265                 270

Tyr Ala Tyr Ser Ala Gly Asn Ala Leu His Lys Asp Thr Ser Leu Phe
        275                 280                 285

Gly Ala Cys Ile Ser Ala Glu Glu Asn Val Arg Asp Leu Ile Lys Pro
290                 295                 300

Leu Gly Gly Ile Pro Phe Gly Lys Ala Asp Val Leu Pro Ile Gly Glu
305                 310                 315                 320

Thr Asp Lys Pro Cys Gln Ser Asn Leu Ser Arg Thr Lys Ile Ser Tyr
                325                 330                 335

Pro Leu Ser Ala Ser Ser Asp Phe Pro Leu Asp Gln Leu His His
        340                 345                 350

Thr Arg Trp Ser Thr Ser Gln Val Glu Ala Val His Pro Thr Thr Phe
355                 360                 365
```

```
Gly Ser Met Tyr Glu Ser Pro Lys Arg Ser Arg His Asp Thr Val Asn
            370                 375                 380

Asp Pro Asp His Asp Phe Leu Ser Leu Ser Leu Ala Ser Phe Thr Glu
385                 390                 395                 400

Val Arg Ser Gln Ser Asn Lys Lys Asn Lys Ala Tyr Asp Thr Gln Ser
            405                 410                 415

Ser Leu Gly Leu Lys Gln Gln Gly Ser Leu Tyr Tyr Glu Pro Pro Gln
            420                 425                 430

Leu Lys Asp Met Leu Ile Pro Leu Thr Asp Glu Asn Leu Ser Arg Asp
            435                 440                 445

Asn Leu Ile Thr Glu Lys Asn Gly His Pro Phe Cys Ser Thr Pro Pro
            450                 455                 460

Ser Leu Lys Leu Thr Val Ser Ala Asn Gly Ser Ser Pro Glu Ser Val
465                 470                 475                 480

Leu Arg Asn Ser Ala Met Ser Tyr Thr Gly Thr Pro Ser Ile Ile Arg
            485                 490                 495

Lys Lys Asn Ser Arg Phe Pro Glu Ala Ala Thr His Ser Ser Cys Thr
            500                 505                 510

Gly Thr Thr Pro Thr His Asn Phe Pro Arg Ala Ser Asp Arg Glu
            515                 520                 525

Asp Thr Ser Asn Leu Lys Asp Arg Phe Ser Gly Cys Lys Ser Ser Val
530                 535                 540

Ser Gly Lys Ser Leu Gly Arg Arg Leu Glu Tyr Ala Phe Asp Met Glu
545                 550                 555                 560

Trp Asp Ala Ser Arg Cys Cys Thr Pro Val Ser Ala Ala Ser Pro Cys
            565                 570                 575

Ala Leu Arg Leu Gly Ala Asn Thr Met Leu Thr Pro
            580                 585

<210> SEQ ID NO 78
<211> LENGTH: 1043
<212> TYPE: PRT
<213> ORGANISM: Nicotiana tabacum

<400> SEQUENCE: 78

Met Glu Ser Asp Arg Ile Ser Thr Pro Ser Asp Gly Thr Ser Ser Ser
1               5                   10                  15

Leu Gln Arg Val Arg Pro Leu His Gly Arg Thr Ser Gly Pro Thr Arg
            20                  25                  30

Arg Ser Thr Lys Gly Gln Trp Thr Thr Glu Glu Asp Glu Ile Leu Arg
            35                  40                  45

Lys Ala Val Gln Arg Phe Lys Gly Lys Asn Trp Lys Lys Ile Ala Glu
            50                  55                  60

Cys Phe Lys Asp Arg Thr Asp Val Gln Cys Leu His Arg Trp Gln Lys
65                  70                  75                  80

Val Leu Asn Pro Glu Leu Val Lys Gly Pro Trp Ser Lys Glu Glu Asp
            85                  90                  95

Glu Val Ile Val Glu Leu Val Lys Tyr Gly Pro Lys Lys Trp Ser
            100                 105                 110

Thr Ile Ala Gln His Leu Pro Gly Arg Ile Gly Lys Gln Cys Arg Glu
            115                 120                 125

Arg Trp His Asn His Leu Asn Pro Gly Ile Asn Lys Glu Ala Trp Thr
            130                 135                 140
```

```
Gln Glu Glu Glu Leu Thr Leu Ile Arg Ala His Gln Ile Tyr Gly Asn
145                 150                 155                 160

Lys Trp Ala Glu Leu Thr Lys Tyr Leu Pro Gly Arg Thr Asp Asn Ala
            165                 170                 175

Ile Lys Asn His Trp Asn Ser Ser Val Lys Lys Leu Asp Ser Tyr
            180                 185                 190

Leu Ala Ser Gly Leu Leu Ala Gln Phe Pro Ser Leu Pro Asn Val Asn
        195                 200                 205

Arg Gln Asn Gln Ser Ile Pro Ser Ser Thr Lys Leu Gln Gln Ser Ser
        210                 215                 220

Glu Asp Asp Ser Val Arg Lys Glu Gly Ile Glu Met Glu Glu Ala Ser
225                 230                 235                 240

Glu Cys Ser Gln Gly Ser Asn Leu Ala Gly Cys Ser Gln Ser Thr Ser
            245                 250                 255

Asp Met Gly Asn Thr Phe Val His Thr Arg Glu Glu Gly Lys Leu Leu
            260                 265                 270

Glu Asp Ser Asn Tyr Arg Lys Asp Pro Ser Ser Ser Ala Pro Cys
        275                 280                 285

Ser Glu Tyr Tyr Thr Pro Ala Phe Glu Asp Ile Thr Phe Ser Met Ala
        290                 295                 300

Glu Val Pro Ser Glu Leu Asp Glu Ser Lys Leu Leu Glu His Asn Phe
305                 310                 315                 320

Ser His Asp Trp Ala Ala Ser Met Gly Lys Glu Trp Gln Phe Asn Pro
            325                 330                 335

Asp Asp Ile Pro Asn Ile Ser Pro Leu Glu Leu Met Gln Asp Ser Ser
            340                 345                 350

Gly Leu Phe Met Gln Cys Leu Thr Gly Asn Gly Asn His Glu Met Val
        355                 360                 365

Thr Phe Pro Gln Gln Asn Ala Val Lys Tyr Glu Met Thr Asn Val Gly
        370                 375                 380

Ser Met Val Val Gly Leu Asp Lys Pro Asn Glu Met Phe Thr Ser Val
385                 390                 395                 400

Glu Gly Cys Gly Met Val Tyr Pro Glu Ala Gly Ile Pro Gln Tyr Ile
            405                 410                 415

Pro Ser Glu Thr Gly Met Asn Gly Ala Asp Glu Thr Ala Asp Ser Leu
            420                 425                 430

Ile Cys Gln Ser Ser Asn Tyr Gln Ile Ser Glu Gly Gly Asn Met Ser
        435                 440                 445

Ile Glu Asn Cys Cys Asn Pro Leu Cys Ser His Val Met Gly Thr Ser
450                 455                 460

Ser Gly Gln Pro Phe Ser Ile Pro Ser Gln Phe Ser Ser Glu Gln Ser
465                 470                 475                 480

Ser Leu Met Phe Gly Thr Ala Ala Asn His Phe His Asn Pro Ser Gln
            485                 490                 495

Gly Asn Pro Ala Gln Glu Ser His Thr Ser Asn Ser Asp Gly Phe Leu
            500                 505                 510

Tyr Pro Phe Glu Ser Gly Thr Pro Cys Asp Asn Ile Met Asp Asp Pro
        515                 520                 525

Leu Leu Glu Glu Gln Leu Asp Gln Thr Lys Asp Ser Leu Gln Leu Val
        530                 535                 540

Ser Val Asn Asp Phe Arg Ser Thr Pro Ser Asn Thr Ile Gln Thr Cys
545                 550                 555                 560
```

```
Pro Leu Val Asn Glu Asn Ser Ser Val Pro Glu Glu Gln Lys Asp Gly
                565                 570                 575

Gly Ala Leu Tyr Tyr Glu Pro Pro Arg Phe Pro Ser Leu Asp Ile Pro
            580                 585                 590

Phe Phe Ser Cys Asp Leu Ile Gln Ser Gly Ala Asp Ala Gln Gln Glu
        595                 600                 605

Tyr Ser Pro Leu Gly Ile Arg Gln Leu Met Met Thr Ser Val Asn Cys
    610                 615                 620

Leu Thr Pro Phe Arg Leu Trp Asp Ser Pro Arg Asp Gly Ser Pro
625                 630                 635                 640

Asp Ala Val Leu Arg Ser Ala Ala Lys Thr Phe Thr Ser Thr Pro Ser
                645                 650                 655

Ile Leu Lys Lys Arg His Arg Asp Leu Val Ser Pro Leu Ser Glu Lys
            660                 665                 670

Arg Cys Glu Lys Lys Leu Gly Ser Asp Leu Arg Gln Glu Ser Phe Ser
        675                 680                 685

Asp Leu Ser Lys Asp Phe Ser Arg Leu Asp Val Met Phe Asp Glu Ala
    690                 695                 700

Ala Asn Glu Lys Ala Thr Lys Ser Ser Leu Thr Met Asp Gln Thr Leu
705                 710                 715                 720

Glu Leu Gln Ala Ser Ser Glu Asp Lys Glu Asn Ile Asn Pro Thr Glu
                725                 730                 735

Asp Gly Ser Lys Glu Glu Asp Lys Val Arg Asn Gly Leu Ser Ser Glu
            740                 745                 750

Arg Gln Leu Asp Gly Gly Glu Val His Tyr Lys Glu Lys Val Thr Arg
        755                 760                 765

Lys Gly Thr Lys Gly Gly Ala Asn Ser Ala Ile Gly Lys Ile Lys Gln
    770                 775                 780

Pro Ser Gly Val Leu Val Glu Leu Asn Ala Ser Asp Leu Phe Phe Ser
785                 790                 795                 800

Pro Asp Arg Phe Gly Ala Lys Ser Gly Arg Ala Thr Asn Leu Cys Ser
                805                 810                 815

Lys Ala Leu Gly Asn Gln Tyr Ala Arg Arg Leu Glu Ala Ala Ser Asn
            820                 825                 830

Gln Gly Ser Val Ser Ser Phe Glu Thr Ser Cys Phe Ser Val Ile
        835                 840                 845

Cys Ser Pro Arg Ile Arg Gly Lys Lys Asp Gly Ser Ser Phe Val Ile
    850                 855                 860

Thr Thr Ser Met Gln Ser Ala Pro Ala Pro Thr Ala Leu Asp Asn Ser
865                 870                 875                 880

Ala Glu Thr Ser Gly Asn Gly Val Gly Ala Glu Thr Val Ser Ile Ser
                885                 890                 895

Gly Glu Thr Pro Tyr Lys Arg Ser Ile Glu Ser Pro Ser Ala Trp Lys
            900                 905                 910

Ser Pro Trp Phe Ile Asn Ser Phe Leu Ser Ser Pro Arg Leu Asp Asn
        915                 920                 925

Glu Leu Asn Phe Glu Asp Leu Ala Leu Phe Met Ser Pro Gly Asp Arg
    930                 935                 940

Ser Tyr Asp Ala Ile Gly Leu Met Lys Gln Leu Ser Glu Gln Thr Ala
945                 950                 955                 960

Gly Ala Phe Ala Asp Ala Gln Glu Val Leu Gly Gly Glu Thr Pro Glu
                965                 970                 975
```

-continued

Ser Ile Leu Arg Gly Arg Asn Ser Lys Asn Gln Lys Ala Asp Glu Asn
            980                 985                 990

His Ser Leu Leu Ser Ala Asn Val Met Ser Glu Arg Arg Thr Leu Asp
        995                 1000                1005

Phe Ser Glu Cys Gly Ser Pro Gly Lys Gly Lys Glu Thr Glu Ile
    1010                1015                1020

Phe Cys Thr Ser Asn Asn Ser Phe Ala Ser Pro Ser Ser Tyr Leu
    1025                1030                1035

Leu Lys Gly Cys Arg
    1040

<210> SEQ ID NO 79
<211> LENGTH: 157
<212> TYPE: PRT
<213> ORGANISM: Nicotiana tabacum

<400> SEQUENCE: 79

Met Gly Met Lys Asn Asp Ala Leu Leu Lys Ser Lys Ala Arg Arg Lys
1               5                   10                  15

Arg Val Glu Lys Pro Gln Lys Ser Val Gly Lys Ile Asn Ala Glu Lys
            20                  25                  30

Ala Gln Glu Arg Pro Val Leu Phe Leu Ala Ile Asn Asn Leu Thr Ile
        35                  40                  45

Gly Lys Ser Ser Asn Asn Ser Leu Thr Ser Pro Asp Val Ser Ser Ser
    50                  55                  60

Cys Ser Ser Ser Ile Ile Thr Phe Gly Glu Asn Gln Lys Met Asn Ile
65                  70                  75                  80

Glu Met Glu Asn Thr Val Ile Leu Glu Ser Asn Pro Glu Ile Tyr Gln
                85                  90                  95

Ser Asp Cys Leu Ser Ile Glu Ser Leu Asp Gln Phe Asp Thr Ser Ser
            100                 105                 110

Phe Trp Phe Ile Tyr Leu Met Met Pro Ile Val Leu Phe Tyr Glu Arg
        115                 120                 125

Leu Ile Arg Ile Cys Asp Leu Gln Arg Gln Ile Gln Asn Leu Ile Phe
    130                 135                 140

Met Gly Ser Ser Ser Arg Leu Tyr Cys Ser Leu Leu Phe
145                 150                 155

<210> SEQ ID NO 80
<211> LENGTH: 292
<212> TYPE: PRT
<213> ORGANISM: Nicotiana tabacum

<400> SEQUENCE: 80

Met Glu Thr Asp Met Ser Phe Leu Ser Lys Ser Ser Ser Ser Ser Ser
1               5                   10                  15

Asp Glu Glu Ile Gly Leu Arg Arg Gly Pro Trp Thr Val Glu Glu Asp
            20                  25                  30

Ser Leu Leu Val Asn Tyr Ile Ser Gln His Gly Glu Gly Arg Trp Asn
        35                  40                  45

Met Leu Ala His Arg Ala Gly Leu Lys Arg Thr Gly Lys Ser Cys Arg
    50                  55                  60

Leu Arg Trp Leu Asn Tyr Leu Lys Pro Asp Val Lys Arg Gly Asn Leu
65                  70                  75                  80

Thr Pro Gln Glu Gln Leu Leu Ile Leu Glu Leu His Phe Lys Leu Gly
                85                  90                  95

```
Asn Arg Trp Ser Lys Ile Ala Gln Tyr Leu Pro Gly Arg Thr Asp Asn
            100                 105                 110

Glu Ile Lys Asn Tyr Trp Arg Thr Arg Val Gln Lys Gln Ala Lys His
        115                 120                 125

Leu Lys Ile Asp Ser Asn Ser Ala Ala Phe Gln His Met Ile Arg Cys
    130                 135                 140

Ile Trp Ile Pro Arg Leu Leu Gln Lys Ile Gln Gly Ser Ser Ala Ile
145                 150                 155                 160

Pro Ser Ile Gln Thr Ser Gln Ser Thr Ser Leu Leu Asp Ser Gln Tyr
                165                 170                 175

Gly Pro Leu Asn Ile Thr Glu Ile Thr Gln Thr Pro Gln Val Leu Ser
            180                 185                 190

Leu Glu Arg Asn Ser Ile Ser Ser Arg Cys Cys Ser Ser Arg Ser
        195                 200                 205

Pro Ser Ser Glu Ser Met Ser Ile Tyr Lys Ser Pro Asn Ile Ile Ser
    210                 215                 220

Glu Cys Pro Lys Ile Pro Pro Arg Glu Met Gly Asp Ser Val Val Asn
225                 230                 235                 240

Val His Phe Pro Phe Asp Asp Asn Ser Tyr Asp Met Asp Thr Phe Ser
                245                 250                 255

Pro Ala Thr Gly Asn Phe Leu Thr Asn Tyr Asp Gln Met Val Gly Gly
            260                 265                 270

Glu Asn Asn Met Met Asn Gly Asp Ile Leu Ala Asp Ser Phe Trp Ser
        275                 280                 285

Met Asp Gln Phe
    290

<210> SEQ ID NO 81
<211> LENGTH: 245
<212> TYPE: PRT
<213> ORGANISM: Nicotiana tabacum

<400> SEQUENCE: 81

Met Ala Arg Thr Arg Cys Tyr Asp Lys Ser Gly Leu Lys Lys Gly Thr
1               5                   10                  15

Trp Thr Pro Asp Glu Asp Arg Lys Leu Ala Ala Tyr Val Ser Lys Tyr
            20                  25                  30

Gly Cys Trp Asn Trp Arg Gln Leu Pro Lys Phe Ala Gly Leu Ala Arg
        35                  40                  45

Cys Gly Lys Ser Cys Arg Leu Arg Trp Leu Asn Tyr Leu Gln Pro Asn
    50                  55                  60

Ile Lys Arg Gly Asn Tyr Thr Lys Glu Glu Asp Glu Ile Ile Met Lys
65                  70                  75                  80

Leu His Ala Glu Ile Gly Asn Lys Trp Ser Val Ile Ala Ala His Leu
                85                  90                  95

Pro Gly Arg Ser Asp Asn Asp Ile Lys Asn His Trp His Thr Ser Leu
            100                 105                 110

Lys Lys Arg Ser Thr Arg Glu Tyr Ser Thr Ser Thr Asp Ser Ile Lys
        115                 120                 125

Arg Ser Ser Asn Asn Ser Tyr Gln Ala Asn Ser Gln Lys Lys Arg Arg
    130                 135                 140

Glu Asn Glu Thr Gln Leu Asn Ala Asn Glu Ser Phe Gln Leu Ser Pro
145                 150                 155                 160
```

```
Met Gln Ser Cys Ser Thr Glu Val Ser Cys Ala Thr Ile Asp Gln
            165                 170                 175

Asn Val Glu Asn Ile His Gly Glu Arg Glu Val Phe Gln Glu Ile
            180                 185                 190

Phe Glu Val Ser Ser Gly Ser Phe Trp Thr Glu Pro Phe Leu Val Asp
            195                 200                 205

Ser Phe Asn Thr Ala Ser Asp Cys Phe Val Pro Ser Phe Asp Asp His
            210                 215                 220

Gly Val Phe Val Ser Pro Phe Ser Pro Val Met Ser Tyr Gly Glu Leu
225                 230                 235                 240

Leu Cys Ser Tyr Tyr
            245

<210> SEQ ID NO 82
<211> LENGTH: 235
<212> TYPE: PRT
<213> ORGANISM: Nicotiana tabacum

<400> SEQUENCE: 82

Met Val Arg Thr Pro Ser Val Asp Lys Asn Gly Ile Lys Arg Gly Ala
1               5                   10                  15

Trp Ser Glu Glu Glu Asp Asn Lys Leu Lys Ala Phe Val Glu Arg Phe
            20                  25                  30

Gly His Pro Asn Trp Arg Gln Leu Pro Lys His Ala Gly Leu Met Arg
            35                  40                  45

Cys Gly Lys Ser Cys Arg Leu Arg Trp Met Asn Tyr Leu Arg Pro Gly
    50                  55                  60

Leu Lys Lys Gly Asn Tyr Ser Leu Glu Glu Glu Leu Ile Ile Lys
65                  70                  75                  80

Leu His Lys Glu His Gly Asn Arg Trp Ser Val Ile Ala Ala Arg Leu
                85                  90                  95

Pro Gly Arg Ser Asp Asn Asp Val Lys Asn Gln Trp His Ala His Leu
            100                 105                 110

Lys Lys Arg Ala Lys Thr Asn Thr Asn Asn Ser Pro Ile Met Glu
            115                 120                 125

Gln Phe Ser Glu Ser Ser Gln Ser Gly Ser Gln Ser Glu Gln Tyr Ser
    130                 135                 140

His Lys Val Ser Glu Gln Glu Ala Gly Cys Asp Thr Ala Ser Val Asn
145                 150                 155                 160

Ala Val Asp Thr Ser Val Glu Val Ser Ser Thr Asp Leu Tyr Ser Ser
                165                 170                 175

Phe Ser Leu Leu Asn Gly Met Asp Trp Ile Glu Glu Asp His Ile Arg
            180                 185                 190

Ser Met Glu Gln Leu Pro Ala Asp Phe Phe Asn Phe Cys Trp Thr Asn
            195                 200                 205

Pro Ile Asp Asn Phe Gln Thr Glu Pro Phe Asn Phe Gln Thr Glu
    210                 215                 220

Pro Leu Asp Asn Phe Trp Arg Gln Pro Phe Phe
225                 230                 235

<210> SEQ ID NO 83
<211> LENGTH: 281
<212> TYPE: PRT
<213> ORGANISM: Nicotiana tabacum
```

<400> SEQUENCE: 83

Met Val Arg Ala Pro Cys Cys Glu Lys Met Gly Leu Lys Lys Gly Pro
1               5                   10                  15

Trp Thr Pro Glu Glu Asp Gln Ile Leu Val Ser Tyr Ile Gln Thr Asn
            20                  25                  30

Gly His Gly Asn Trp Arg Ala Leu Pro Lys Leu Ala Gly Leu Leu Arg
        35                  40                  45

Cys Gly Lys Ser Cys Arg Leu Arg Trp Thr Asn Tyr Leu Arg Pro Asp
    50                  55                  60

Ile Lys Arg Gly Asn Phe Thr Arg Glu Glu Asp Ser Ile Ile Gln
65                  70                  75              80

Leu His Glu Met Leu Gly Asn Arg Trp Ser Ala Ile Ala Ala Arg Leu
                85                  90                  95

Pro Gly Arg Thr Asp Asn Glu Ile Lys Asn Val Trp His Thr His Leu
            100                 105                 110

Lys Lys Arg Leu Lys Asn Tyr Gln Pro Gln Asn Ser Lys Arg His
        115                 120                 125

Ser Lys Asn Asn Leu Asp Ser Lys Ala Pro Ser Thr Ser Gln Thr Phe
130                 135                 140

Asn Asn Ser Asp Asn Phe Ser Asn Ile Gln Glu Asp Ile Asn Gly Pro
145                 150                 155                 160

Val Thr Gly Pro Asn Ser Pro Gln Arg Ser Ser Ser Glu Met Ser Thr
                165                 170                 175

Val Thr Val Asp Ser Thr Ala Met Thr Thr Ile Thr Ile Asp Asp Gln
            180                 185                 190

Asn Met Phe Lys Gln Leu Asp Glu Met Asp Ser Ser Glu Asn Phe Ile
        195                 200                 205

Pro Glu Ile Asp Glu Ser Phe Trp Thr Asp Asp Leu Ser Thr Ser Asp
    210                 215                 220

Asn Ser Thr Phe Gly Met Glu Gly Thr Gly Glu Leu Gln Val Gln
225                 230                 235                 240

Phe Pro Phe Ser Ser Val Lys Gln Glu Ser Met Asp Met Val Gly Ala
                245                 250                 255

Lys Leu Glu Asp Asp Met Asp Phe Trp Tyr Asn Val Phe Ile Lys Ser
            260                 265                 270

Gly Asp Leu Leu Asp Leu Pro Glu Phe
        275                 280

<210> SEQ ID NO 84
<211> LENGTH: 333
<212> TYPE: PRT
<213> ORGANISM: Nicotiana tabacum

<400> SEQUENCE: 84

Met Gly Arg Pro Pro Cys Cys Asp Lys Ala Asn Val Lys Arg Gly Pro
1               5                   10                  15

Trp Thr Ala Glu Glu Asp Ala Lys Ile Leu Ala Tyr Val Ala Ser His
            20                  25                  30

Gly Ile Gly Asn Trp Thr Leu Val Pro Gln Lys Ala Gly Leu Asn Arg
        35                  40                  45

Cys Gly Lys Ser Cys Arg Leu Arg Trp Thr Asn Tyr Leu Arg Pro Asp
    50                  55                  60

Leu Lys His Asp Asn Phe Thr Pro Gln Glu Glu Glu Cys Ile Ile Glu
65                  70                  75                  80

```
Leu His Lys Thr Ile Gly Ser Arg Trp Ser Leu Ile Ala Lys Gln Leu
                85                  90                  95

Pro Gly Arg Thr Asp Asn Asp Val Lys Asn Tyr Trp Asn Thr Lys Leu
            100                 105                 110

Lys Lys Lys Leu Val Asn Met Gly Ile Asp Pro Val Thr His Lys Pro
            115                 120                 125

Phe Ala Gln Val Phe Ala Glu Tyr Gly Lys Ile Ser Gly Leu Pro Ile
        130                 135                 140

Gln Asn Ala Arg Asn His Ile Cys Leu Pro Asn Asn Thr Thr Glu Ile
145                 150                 155                 160

Ser Lys Gln Leu Pro Phe Ser Leu Arg Glu Asn Tyr Ser Thr Gln Lys
                165                 170                 175

Tyr Thr Trp Asp Pro Lys Ala Gln Tyr Gln Val Ile His Glu Glu Thr
            180                 185                 190

Leu Gln Thr His Ser Phe Ser Glu Val Ser Pro Leu Ile Ser Ser Ala
        195                 200                 205

Thr Tyr Phe Asn Pro Thr Val Phe Ser Ser Ser Ser Tyr Ala Ser
        210                 215                 220

Val Gln Ser Gln Val His Thr Ala Ser Ser Ser Thr Ser Thr
225                 230                 235                 240

Trp Asn Glu Phe Val Phe Gly Asp Leu Cys Thr Ser Thr Asp Thr Glu
                245                 250                 255

Gln Lys Gln Glu Tyr Gln Leu Gln Ala Gly Ile Tyr Leu Ser Lys Asp
            260                 265                 270

Leu Ser Asn Ser Val His Lys Asp Asn Pro Thr Cys Gly Glu Val Thr
        275                 280                 285

Glu Val Glu Glu Asn Gln Ser Val Glu Glu Ala Thr Cys Ser Ser Ala
    290                 295                 300

Val Asp Ser Phe Asp Thr Ile Leu Ala Arg Asp Lys Gln Met Leu
305                 310                 315                 320

Met Asp Phe Pro Pro Leu Leu Asp Val Tyr Leu Asp Tyr
                325                 330
```

<210> SEQ ID NO 85
<211> LENGTH: 998
<212> TYPE: PRT
<213> ORGANISM: Nicotiana tabacum

<400> SEQUENCE: 85

```
Met Glu Ser Asp Lys Thr Ser Thr Thr Pro Ser Asp Asp Ile Ser Ser
1               5                   10                  15

Leu Gln Arg Val Gln Pro Leu Asn Gly Arg Thr Ser Gly Pro Lys Arg
            20                  25                  30

Arg Ser Ser Gln Trp Thr Pro Glu Glu Asp Glu Ile Leu Arg Gln Ala
        35                  40                  45

Val Gln Leu Phe Lys Gly Lys Ser Trp Lys Arg Ile Ala Glu Cys Phe
    50                  55                  60

Lys Asp Arg Thr Asp Val Gln Cys Leu His Arg Trp Gln Lys Val Leu
65                  70                  75                  80

Asp Pro Glu Leu Val Lys Gly Ser Trp Thr Lys Glu Glu Asp Asp Lys
                85                  90                  95

Leu Ile Glu Leu Val Asn Arg Tyr Gly Pro Lys Lys Trp Ser Thr Ile
            100                 105                 110
```

-continued

```
Ala Gln Glu Leu Ala Gly Arg Ile Gly Lys Gln Cys Arg Glu Arg Trp
            115                 120                 125
His Asn His Leu Asn Pro Ser Ile Asn Lys Glu Pro Trp Thr Gln Glu
        130                 135                 140
Glu Glu Leu Thr Leu Ile Arg Ala His Gln Val Tyr Gly Asn Lys Trp
145                 150                 155                 160
Ala Glu Leu Ala Lys Val Leu His Gly Arg Ser Asp Asn Ala Ile Lys
                165                 170                 175
Asn His Trp His Ser Ser Val Lys Lys Lys Leu Asp Ser Tyr Leu Ala
            180                 185                 190
Ser Gly Leu Leu Ala Gln Phe Pro Ala Leu Pro Asn Val Asn His Gln
        195                 200                 205
Asn Gln Ser Val Pro Ser Ser Ser Met Thr Leu Gln Gln Asn Ser Glu
    210                 215                 220
Asp Glu Ser Val His Lys Gln Gly Thr Glu Ala Glu Asp Ser Phe Val
225                 230                 235                 240
Lys Lys Lys Leu Asp Ser Tyr Leu Ala Ser Gly Leu Leu Gly Gln Phe
                245                 250                 255
Pro Ala Leu Pro Asn Val Asn His Gln Asn Gln Ser Val Pro Ser Ser
            260                 265                 270
Ser Met Thr Leu Gln Gln Asn Ser Glu Asp Glu Ser Val His Lys Glu
        275                 280                 285
Gly Thr Glu Ala Glu Glu Val Pro Glu Cys Ser Gln Gly Ser Thr Phe
    290                 295                 300
Ala Gly Cys Ser Gln Ser Thr Ser Asp Leu Gly Asn Thr Phe Val His
305                 310                 315                 320
Val Arg Glu Asn Gly Gly Met Ser Glu Glu Ser Ile Cys Lys Lys Asp
                325                 330                 335
Ala Thr Ser Ser Thr Ala Pro Cys Cys Arg Asn Tyr Asn Pro Val Phe
            340                 345                 350
Gln Asp Val Ser Cys Ser Met Leu Lys Val Pro Ser Glu Leu Val Asp
        355                 360                 365
Ser Lys Phe Leu Glu His Asn Leu Ser His Asp Trp Gly Asn Ser Met
    370                 375                 380
Glu Glu Asp Trp Gln Phe Asn Arg Asp Asp Ile Pro Asn Ile Ser Pro
385                 390                 395                 400
Pro Glu Leu Ile Gln Glu Ser Ser Gly Ile Ser Val His Cys Leu Asn
                405                 410                 415
Gly Asn Glu Asn His Asp Met Glu Ala Thr Thr Asn Val Gly Asn Val
            420                 425                 430
Val Glu Gly Pro Tyr Asn Pro Asn Glu Met Phe Val Cys Val Asp Gly
        435                 440                 445
Cys Met Met Val Tyr Pro Glu Glu Gly Ile Pro Gln Cys Ser Ser Glu
    450                 455                 460
Thr Gly Val Asn Gly Cys Gly Gln Pro Ala Tyr Ser Leu Phe Tyr Arg
465                 470                 475                 480
Ser Ser Asn Tyr Gln Ile Pro Glu Val Gly Asp Met Val Pro Gln Asn
                485                 490                 495
Cys Asn Ala Leu Ser Phe Asp Asp Phe Glu Ala Ser Ser His Gln Pro
            500                 505                 510
Phe Ser Val Pro Leu Gln Phe Ser Ser Glu Asp Arg Ser Pro Val Phe
        515                 520                 525
```

```
Asp Leu Val Leu Asn Gln Phe His Asn Pro Pro Leu Glu Ser Pro Asp
    530                 535                 540

His Met Lys Asp Ser Ser Arg Ile Val Pro Val Asn Asp Leu Gly Ser
545                 550                 555                 560

Thr Thr Ser Asn Thr Val Gln Thr Cys Leu Leu Asn Glu Lys Ser Phe
                565                 570                 575

Val Gln Glu Lys Gln Lys Asp Gly Gly Leu Cys Tyr Asp Pro Pro
            580                 585                 590

Arg Phe Pro Ser Ser Asp Val Pro Phe Cys Cys Asp Leu Met Gln
        595                 600                 605

Ser Gly Ser Asp Thr Gln Glu Glu Tyr Ser Pro Phe Gly Ile Arg Gln
    610                 615                 620

Leu Met Met Thr Ser Ala Asn Cys Leu Thr Pro Leu Arg Leu Trp Asp
625                 630                 635                 640

Ser Pro Ser Arg Asp Asp Ser Pro Asp Ala Ile Leu Lys Ser Ala Ala
                645                 650                 655

Lys Thr Phe Thr Gly Thr Pro Ser Ile Leu Lys Lys Arg His Arg His
                660                 665                 670

Leu Leu Ser Pro Leu Ser Glu Lys Arg Cys Glu Lys Arg Leu Glu Ser
            675                 680                 685

Asp Leu Asn Gln Glu Ser Phe Ser Asn Met Thr Ser Asn Phe Ser Arg
    690                 695                 700

Leu Asp Asp Met Phe Asp Glu Ser Ala Asn Glu Lys Ala Ser Met Glu
705                 710                 715                 720

Asp Gly Glu Asn Leu Pro Ser Ser Glu Asp Gly Arg Lys Glu Glu Gly
                725                 730                 735

Glu Ile Ser Gly Ala Asn Asp Ala Met Gly Lys Val Lys Gln Pro Pro
                740                 745                 750

Gly Val Leu Val Glu Leu Ser Ser Asn Asp Leu Phe Leu Ser Pro Asp
            755                 760                 765

Ser Phe Leu Ile Lys Cys Asp Arg Ala Thr Ser Leu Ser Asn Lys Ala
    770                 775                 780

Leu Gly Lys Gln Tyr Ala Arg Arg Leu Glu Ala Ala Ser Asn Gln Val
785                 790                 795                 800

Thr Val Ser Ser Ser Phe Glu Thr Ser Cys Phe Ser Val Val Cys Ser
                805                 810                 815

Pro Asp Ile Arg Gly Lys Arg Arg Ser Ser Val Val Leu Ala Thr Ser
            820                 825                 830

Ala Ala Leu Gly Asn Thr Ala Glu Asp Ser Glu Asn Arg Phe Gly Thr
    835                 840                 845

Glu Thr Leu Ser Ile Ser Gly Glu Thr Pro Tyr Lys Arg Ser Phe Glu
850                 855                 860

Ser Pro Ser Ala Trp Lys Ser Pro Trp Phe Met Asn Ser Phe Pro Pro
865                 870                 875                 880

Ser Thr Arg Tyr Asp Ile Glu Leu Ala Phe Glu Asp Leu Ala Arg Phe
                885                 890                 895

Met Ser Pro Gly Asp Arg Ser Tyr Asp Ala Ile Gly Leu Met Lys Gln
            900                 905                 910

Leu Ser Glu Gln Thr Ala Ala Ser Ile Ala Asp Ala His Gln Ile Leu
    915                 920                 925

Gly Ser Glu Thr Pro Glu Thr Asn Leu Ser Lys Arg Asn Ser Lys Lys
930                 935                 940
```

```
Gln Lys Ala Asp Glu Ile Cys Lys Ala Ser Asn Ala Thr Ser Glu Arg
945                 950                 955                 960

Arg Thr Leu Asp Phe Asn Glu Cys Gly Thr Pro Gly Lys Gly Lys Glu
            965                 970                 975

Thr Thr Lys Phe Gly Ser Asn Asn Ser Phe Ser Ser Pro Ser Ser Tyr
            980                 985                 990

Leu Leu Lys Tyr Cys Arg
        995

<210> SEQ ID NO 86
<211> LENGTH: 1015
<212> TYPE: PRT
<213> ORGANISM: Nicotiana tabacum

<400> SEQUENCE: 86

Met Leu Asp Tyr Pro Asp Leu Pro Leu Ser Leu Thr Met Glu Ser Asp
1               5                   10                  15

Lys Thr Ser Thr Thr Pro Ser Asp Asp Ile Ser Ser Leu Gln Arg Val
            20                  25                  30

Gln Pro Ser His Gly Arg Thr Ser Gly Pro Lys Arg Arg Ser Ser Gln
        35                  40                  45

Trp Thr Pro Glu Glu Asp Glu Ile Leu Arg Gln Ala Val Gln Gln Phe
50                  55                  60

Lys Gly Lys Ser Trp Lys Arg Ile Ala Glu Cys Phe Lys Asp Arg Thr
65                  70                  75                  80

Asp Val Gln Cys Leu His Arg Trp Gln Lys Val Leu Asp Pro Glu Leu
                85                  90                  95

Val Lys Gly Ser Trp Thr Lys Glu Glu Asp Asp Lys Leu Ile Glu Leu
            100                 105                 110

Val Asn Arg Tyr Gly Pro Lys Lys Trp Ser Thr Ile Ala Gln Glu Leu
        115                 120                 125

Ala Gly Arg Ile Gly Lys Gln Cys Arg Glu Arg Trp His Asn His Leu
130                 135                 140

Asn Pro Ala Ile Asn Lys Glu Pro Trp Thr Gln Glu Glu Glu Leu Thr
145                 150                 155                 160

Leu Ile Arg Ala His Gln Val Tyr Gly Asn Lys Trp Ala Glu Leu Ala
                165                 170                 175

Lys Val Leu His Gly Arg Ser Asp Asn Ala Ile Lys Asn His Trp His
            180                 185                 190

Ser Ser Val Lys Lys Lys Leu Asp Ser Tyr Leu Ala Ser Gly Leu Leu
        195                 200                 205

Ala Gln Phe Pro Ala Leu Pro Asn Val Asn His Gln Asn Gln Ser Val
210                 215                 220

Pro Ser Ser Ser Met Thr Leu Gln Gln Asn Ser Glu Asp Glu Ser Val
225                 230                 235                 240

His Lys Glu Gly Thr Glu Ala Glu Asp Ser Ser Val Lys Lys Lys Leu
                245                 250                 255

Asp Ser Tyr Ser Ala Ser Gly Leu Leu Gly Gln Phe Ser Ala Leu Pro
            260                 265                 270

Asn Val Asn His Gln Asn Gln Ser Val Pro Ser Ser Ser Met Thr Leu
        275                 280                 285

Gln Gln Asn Ser Glu Asp Glu Ser Val His Lys Glu Gly Met Glu Ala
290                 295                 300
```

-continued

Glu Glu Val Pro Glu Cys Ser Gln Gly Ser Asn Phe Ala Gly Cys Ser
305                 310                 315                 320

Gln Ser Thr Ser Asp Leu Gly Asn Thr Phe Val His Ile Arg Glu Asn
            325                 330                 335

Gly Gly Met Ser Glu Glu Ser Ile Cys Lys Lys Asp Ala Thr Ser Ser
        340                 345                 350

Thr Ala Pro Cys Cys Arg Asn Tyr Ser Pro Val Phe Gln Asp Val Ser
    355                 360                 365

Cys Ser Met Leu Lys Val Pro Ser Glu Leu Ala Asp Ser Lys Phe Leu
370                 375                 380

Glu His Asn Leu Ser His Asp Trp Gly Asn Ser Met Glu Glu Asp Trp
385                 390                 395                 400

Gln Phe Asn Arg Asp Asp Ile Pro Asn Ile Ser Pro Pro Glu Phe Ile
                405                 410                 415

Gln Glu Ser Ser Gly Ile Ser Val His Cys Leu Thr Gly Asn Asp Asn
            420                 425                 430

His Asp Met Val Ala Thr Ala Asn Val Gly Asn Val Val Glu Asp Pro
        435                 440                 445

Tyr Lys Pro Asn Glu Met Phe Val Ser Val Asp Gly Ser Met Met Val
450                 455                 460

Tyr Pro Glu Glu Gly Ile Pro Gln Cys Ser Pro Ser Glu Thr Gly Val
465                 470                 475                 480

Asn Gly Cys Gly Gln Pro Ser Tyr Ser Leu Phe Tyr Gln Ser Ser Asn
            485                 490                 495

Tyr Gln Ile Pro Glu Ala Gly Asp Met Val Pro Gln Asn Cys Asn Ala
        500                 505                 510

Leu Asn Phe Asp Asp Phe Glu Ala Ser Phe His Gln Pro Phe Ser Val
    515                 520                 525

Pro Ser Gln Phe Ser Ser Glu Asp Arg Ser Ser Val Phe Asp Ile Val
530                 535                 540

Leu Asn Gln Phe His Asn Pro Pro Leu Glu Gly Pro Asp His Met Lys
545                 550                 555                 560

Asp Ser Ser Arg Ile Val Pro Val Asn Asp Ile Gly Ser Thr Thr Ser
                565                 570                 575

Asn Thr Val Gln Thr Cys Leu Leu Asn Glu Asn Ser Phe Val Gln Glu
            580                 585                 590

Glu Gln Lys Asp Gly Gly Ala Leu Cys Tyr Asp Pro Pro Arg Phe Pro
        595                 600                 605

Ser Ser Asp Val Pro Phe Phe Cys Cys Asp Leu Ile Gln Ser Gly Ser
    610                 615                 620

Asp Thr Gln Glu Glu Tyr Ser Pro Phe Gly Ile Arg Gln Leu Met Met
625                 630                 635                 640

Thr Ser Ala Asn Cys Leu Thr Pro Leu Arg Leu Trp Asp Ser Pro Ser
                645                 650                 655

Arg Asp Asp Ser Pro Asp Ala Ile Leu Lys Ser Ala Ala Lys Thr Phe
            660                 665                 670

Thr Gly Thr Pro Ser Ile Leu Lys Lys Arg His Arg His Leu Leu Ser
        675                 680                 685

Pro Leu Ser Glu Lys Arg Cys Glu Lys Lys Leu Glu Ser Asn Leu Asn
    690                 695                 700

Gln Glu Ser Phe Tyr Asn Met Ser Thr Asn Phe Ser Arg Pro Asp Asp
705                 710                 715                 720

```
Met Phe Asp Glu Ser Ala Asn Glu Lys Ala Ser Met Glu Asp Lys Glu
                725                 730                 735

Asn Leu His Pro Ser Ser Glu Asp Gly Arg Lys Glu Glu Gly Glu Ile
        740                 745                 750

Ser Gly Ala Asn Asp Ala Thr Gly Met Val Lys Gln His Pro Gly Val
            755                 760                 765

Leu Val Glu Leu Ser Ser Asn Asp Leu Phe Phe Ser Pro Asp Arg Phe
        770                 775                 780

Leu Ile Lys Cys Asp Arg Ala Thr Ser Leu Ser Asn Lys Ala Leu Gly
785                 790                 795                 800

Arg Gln Tyr Ala Arg Arg Leu Glu Ala Ala Ser Asn Gln Val Thr Val
            805                 810                 815

Ser Ser Ser Phe Glu Thr Ser Cys Leu Ser Val Val Cys Ser Pro Asp
            820                 825                 830

Ile Cys Gly Lys His Arg Gly Ser Val Val Ile Ala Thr Ser Thr Ala
            835                 840                 845

Leu Glu Asn Thr Ala Glu Asp Ser Glu Asn Gly Phe Gly Ala Glu Thr
        850                 855                 860

Leu Ser Ile Phe Gly Glu Thr Pro Phe Lys Arg Ser Phe Glu Ser Pro
865                 870                 875                 880

Ser Ala Trp Lys Ser Pro Trp Phe Met Ser Ser Phe Pro Pro Ser Thr
            885                 890                 895

Arg Tyr Asp Thr Glu Leu Glu Phe Glu Asp Leu Ala Leu Phe Met Ser
            900                 905                 910

Pro Gly Asp Arg Ser Tyr Asp Ala Ile Gly Leu Met Lys Gln Leu Ser
            915                 920                 925

Glu Gln Thr Ala Pro Ser Ile Ala Asp Ala His Gln Ile Leu Gly Ser
        930                 935                 940

Glu Thr Pro Glu Thr Asn Leu Ser Lys Arg Asn Ser Lys Pro Lys
945                 950                 955                 960

Ala Asp Glu Asn Cys Thr Leu Leu Ala Ser Asn Ala Thr Ser Glu Arg
                965                 970                 975

Arg Thr Leu Asp Phe Asn Glu Cys Gly Ile Pro Gly Lys Gly Lys Glu
            980                 985                 990

Thr Thr Lys Phe Gly Ser Asn Asn  Asn Ser Phe Ser Ser  Pro Ser Ser
            995                 1000                1005

Tyr  Leu  Leu Lys Tyr Cys Arg
    1010                1015

<210> SEQ ID NO 87
<211> LENGTH: 1042
<212> TYPE: PRT
<213> ORGANISM: Nicotiana tabacum

<400> SEQUENCE: 87

Met Glu Ser Asp Arg Ile Ser Thr Pro Ser Asp Gly Thr Ser Ser Ser
1               5                   10                  15

Leu Gln Arg Val Arg Pro Leu His Gly Arg Thr Ser Gly Pro Thr Arg
            20                  25                  30

Arg Ser Thr Lys Gly Gln Trp Thr Thr Glu Glu Asp Glu Ile Leu Arg
        35                  40                  45

Lys Ala Val Gln Arg Phe Lys Gly Lys Asn Trp Lys Lys Ile Ala Glu
    50                  55                  60

Cys Phe Lys Asp Arg Thr Asp Val Gln Cys Leu His Arg Trp Gln Lys
65                  70                  75                  80
```

```
Val Leu Asn Pro Glu Leu Val Lys Gly Pro Trp Ser Lys Glu Glu Asp
                85                  90                  95

Glu Val Ile Val Glu Leu Val Lys Lys Tyr Gly Pro Lys Lys Trp Ser
            100                 105                 110

Thr Ile Ala Gln His Leu Pro Gly Arg Ile Gly Lys Gln Cys Arg Glu
        115                 120                 125

Arg Trp His Asn His Leu Asn Pro Gly Ile Asn Lys Glu Ala Trp Thr
    130                 135                 140

Gln Glu Glu Glu Leu Thr Leu Ile Arg Ala His Gln Ile Tyr Gly Asn
145                 150                 155                 160

Lys Trp Ala Glu Leu Thr Lys Tyr Leu Pro Gly Arg Thr Asp Asn Ala
                165                 170                 175

Ile Lys Asn His Trp Asn Ser Ser Val Lys Lys Lys Leu Asp Ser Tyr
            180                 185                 190

Leu Ala Ser Gly Leu Leu Ala Gln Phe Pro Ala Leu Pro Asn Val Asn
        195                 200                 205

Arg Gln Asn Gln Ser Ile Pro Ser Ser Ala Lys Leu Gln Gln Ser Ser
    210                 215                 220

Glu Asp Asp Ser Val Arg Lys Glu Gly Thr Glu Met Glu Glu Ala Ser
225                 230                 235                 240

Glu Cys Ser Gln Gly Ser Asn Leu Ala Gly Cys Ser Gln Ser Thr Ser
                245                 250                 255

Asp Met Gly Asn Lys Phe Val His Thr Arg Glu Glu Gly Lys Leu Leu
            260                 265                 270

Glu Asp Ser Asn Tyr Arg Lys Asp Pro Ser Ser Ser Ala Pro Cys
        275                 280                 285

Ser Glu Tyr Tyr Thr Pro Ala Phe Glu Asp Ile Thr Phe Ser Met Ala
    290                 295                 300

Glu Val Pro Ser Glu Leu Asp Glu Ser Lys Leu Leu Glu His Thr Phe
305                 310                 315                 320

Ser His Asp Trp Ala Ala Ser Ile Gly Lys Glu Trp Gln Phe Asn Pro
                325                 330                 335

Asp Asp Ile Pro Asn Ile Ser Pro Leu Glu Leu Met Gln Asp Ser Ser
            340                 345                 350

Gly Leu Phe Met Gln Cys Leu Thr Gly Asn Gly Asn His Asp Met Val
        355                 360                 365

Thr Phe Pro Gln Gln Asn Ala Val Lys Phe Glu Thr Thr Asn Val Gly
    370                 375                 380

Ser Met Val Val Gly Phe Asp Lys Pro Asn Glu Met Phe Thr Ser Val
385                 390                 395                 400

Glu Gly Cys Arg Met Val Tyr Pro Glu Ala Gly Ile Pro Gln Tyr Ile
                405                 410                 415

Pro Ser Glu Ala Gly Thr Asn Gly Ala Asp Glu Thr Ala Asp Ser Leu
            420                 425                 430

Ile Cys Gln Ser Ser Asn Tyr Gln Ile Ser Glu Gly Asn Met Ser
        435                 440                 445

Ile Glu Asn Cys Asn Pro Leu Cys Ser Asp Val Met Gly Thr Ser Ser
    450                 455                 460

Gly Gln Pro Phe Ser Ile Pro Ser Gln Phe Ser Glu Gln Ser Ser
465                 470                 475                 480

Leu Met Phe Gly Thr Ala Ala Asn Gln Phe His Asn Pro Leu Gln Gly
                485                 490                 495
```

```
Asn Pro Ala Gln Glu Ser His Thr Ser Asn Ser Asp Gly Phe Leu Tyr
            500                 505                 510

Pro Phe Glu Ser Gly Thr Pro Cys Asp Asn Ile Met Asp Asp Pro Leu
        515                 520                 525

Leu Glu Glu Gln Leu Asp Gln Thr Lys Asp Ser Leu Gln Leu Val Ser
    530                 535                 540

Val Asn Asp Phe Arg Thr Thr Pro Ser Asn Thr Ile Gln Thr Cys Pro
545                 550                 555                 560

Leu Val Asn Glu Asn Ser Ser Ile Pro Val Glu Gln Lys Asp Gly Gly
                565                 570                 575

Ala Leu Tyr Tyr Glu Pro Pro Arg Phe Pro Ser Leu Asp Ile Pro Phe
            580                 585                 590

Phe Ser Cys Asp Leu Ile Gln Ser Gly Thr Asp Ala Gln Gln Glu Tyr
        595                 600                 605

Ser Pro Leu Gly Ile Arg Gln Leu Met Met Thr Ser Val Asn Cys Leu
    610                 615                 620

Thr Pro Phe Arg Leu Trp Asp Ser Pro Ser Arg Asp Gly Ser Thr Asp
625                 630                 635                 640

Ala Val Leu Arg Ser Ala Ala Lys Thr Phe Thr Ser Thr Pro Ser Ile
                645                 650                 655

Leu Lys Lys Arg His Arg Asp Leu Val Ser Pro Leu Ser Glu Lys Arg
            660                 665                 670

Cys Glu Lys Lys Leu Gly Ser Asp Phe Arg Gln Glu Ser Phe Ser Asp
        675                 680                 685

Leu Ser Lys Asp Phe Ser Arg Leu Asp Val Met Phe Asp Glu Ala Ala
    690                 695                 700

Asn Glu Lys Ala Thr Lys Ser Ser Leu Thr Thr Asp Gln Thr Leu Glu
705                 710                 715                 720

Leu Glu Ala Ser Ser Glu Asp Lys Glu Asn Ile Asn Pro Thr Glu Asp
                725                 730                 735

Gly Ser Lys Glu Glu Asp Lys Val Arg Asn Gly Leu Ser Asn Glu Arg
            740                 745                 750

Gln Leu Asp Gly Gly Glu Val His Tyr Lys Lys Gly Thr Arg Glu
        755                 760                 765

Gly Thr Lys Gly Gly Ala Asn Ser Ala Ile Gly Lys Ile Lys Gln Pro
    770                 775                 780

Ser Gly Val Leu Val Glu Leu Asn Ala Ser Asp Leu Phe Phe Ser Pro
785                 790                 795                 800

Asp Arg Phe Gly Ala Lys Ser Gly Arg Ala Thr Tyr Leu Ser Ser Lys
                805                 810                 815

Ala Leu Gly Asn Gln Tyr Ala Arg Arg Leu Glu Ala Ala Ser Asn Gln
            820                 825                 830

Gly Ser Val Ser Ser Ser Phe Glu Thr Ser Cys Phe Ser Val Ile Cys
        835                 840                 845

Ser Pro Arg Ile Arg Gly Lys Lys Asp Gly Ser Ser Phe Ile Ile Thr
    850                 855                 860

Thr Ser Met Gln Ser Ala Pro Ala Pro Thr Ala Leu Asp Asn Ser Ala
865                 870                 875                 880

Glu Thr Ser Gly Asn Gly Val Gly Ala Glu Thr Val Ser Ile Ser Gly
                885                 890                 895

Glu Thr Pro Tyr Lys Arg Ser Ile Glu Ser Pro Ser Ala Trp Lys Ser
            900                 905                 910
```

```
Pro Trp Phe Ile Asn Ser Leu Leu Ser Ser Pro Arg Leu Asp Asn Glu
        915                 920                 925

Leu Asn Phe Glu Asp Leu Ala Leu Phe Met Ser Pro Gly Asp Arg Ser
    930                 935                 940

Tyr Asp Ala Ile Gly Leu Met Lys Gln Leu Ser Glu Gln Thr Ala Gly
945                 950                 955                 960

Ala Phe Ala Asp Ala Gln Glu Val Leu Gly Gly Glu Thr Pro Glu Ser
            965                 970                 975

Ile Leu Arg Gly Arg Asn Ser Lys Asn Gln Lys Ala Asp Glu Asn His
            980                 985                 990

Ser Leu Leu Ser Ala Asn Val Met  Ser Glu Arg Arg Thr  Leu Asp Phe
        995                 1000                1005

Ser Glu  Cys Gly Ser Pro Gly  Lys Gly Lys Glu Thr  Glu Asn Phe
    1010                1015                1020

Cys Thr  Ser Asn Asn Ser Phe  Ser Ser Pro Ser Ser  Tyr Leu Leu
    1025                1030                1035

Lys Gly  Cys Arg
    1040

<210> SEQ ID NO 88
<211> LENGTH: 317
<212> TYPE: PRT
<213> ORGANISM: Nicotiana tabacum

<400> SEQUENCE: 88

Met Gly Arg Ala Pro Cys Cys Asp Lys Asn Asn Val Lys Arg Gly Pro
1               5                   10                  15

Trp Ser Pro Glu Glu Asp Ser Lys Leu Lys Ser Tyr Ile Glu Gln Asn
            20                  25                  30

Gly Thr Gly Gly Asn Trp Ile Ala Leu Pro Pro Lys Ile Gly Leu Asn
        35                  40                  45

Arg Cys Gly Lys Ser Cys Arg Leu Arg Trp Leu Asn Tyr Leu Arg Pro
    50                  55                  60

Asn Ile Lys His Gly Gly Phe Ser Glu Glu Asp Arg Ile Ile Cys
65                  70                  75                  80

Ser Leu Tyr Ile Ser Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Arg
            100                 105                 110

Leu Lys Lys Lys Leu Phe Gly Lys Gln Arg Gln Lys Gln Gly Ser Arg
        115                 120                 125

Lys Gly Lys Glu Ile Asn Ser Asn Met Val Ile Ser Asn Asn Asn Asn
    130                 135                 140

Asn Asn Gln Phe Pro Cys Trp Pro Glu Leu Pro Ile Leu Gln Pro Ile
145                 150                 155                 160

Pro Tyr Ser Asn Asp Glu Pro Arg Phe Asn Asp His Ser Ser Ile Arg
                165                 170                 175

Lys Leu Leu Ile Lys Leu Gly Gly Lys Phe Ser Asp Gly Asp Gln Pro
            180                 185                 190

Ile Asn Glu Ala Thr Asn Pro Gln Tyr Pro Met Asp Asn Ser Leu Leu
        195                 200                 205

Met Gln Pro Ile Tyr Gln Asn Ile Pro Ile Asn Met Ile Ser Ser Ala
    210                 215                 220
```

| | | | | | | | | | | | |
|---|---|---|---|---|---|---|---|---|---|---|---|
| Pro | Ile | Asp | Asn | Val | Leu | Gly | Asn | Ala | Gln | Tyr | Asn | Met | Asp | Arg | Ala |
| 225 | | | | 230 | | | | | 235 | | | | | 240 | |

Pro Ile Asp Asn Val Leu Gly Asn Ala Gln Tyr Asn Met Asp Arg Ala
225                 230                     235                 240

Ala Ser Ser Phe Thr Ala Glu Leu Glu His Met Ile Gln Asn Asn Gln
                245                 250                 255

Gln Lys Leu Asp Gly Leu Glu Phe Leu Tyr Glu Asp Tyr Met Leu Ile
            260                 265                 270

Asp Lys Ser Ala Ser Thr Ser Gly Gly Asn Leu Asp Trp Glu Ser Met
        275                 280                 285

Asn Pro Phe Val Leu Pro Leu Pro Ile Asn Asp Glu Gly Phe Gln
    290                 295                 300

Gln Gly Val Ile Phe Gln Glu Asn Asn Thr Met Ala Gln
305                 310                 315

```
<210> SEQ ID NO 89
<211> LENGTH: 2499
<212> TYPE: DNA
<213> ORGANISM: Nicotiana tabacum

<400> SEQUENCE: 89
```

| | | |
|---|---|---|
| tctaggagca aaaaaaaaaa aaaaaaaaaa aacaagtagt agtagtagta gtaaatggaa | 60 |
| aaatagagag gcaatttttt ttagtatctt actttatcca ttagcactta aaaaacatag | 120 |
| gtttacatgc tctcattgtc acgccaggcc gctaattaaa tggtacattt catcatcccc | 180 |
| atttttggc ctcatagtta attatcacaa tttctgaaag caacatcaga acaaccccac | 240 |
| atttcttgtg gtcctataat tactgctaga tagtccaaac ccatctgcct atttagggct | 300 |
| tgtgaatgag gattgaaaat ggtagagaat atttgcaaag gcatcatgca tatatggaaa | 360 |
| agactaaaga gagagttagt gccttgcaaa gcggattctc acagttgtag aaaaggactc | 420 |
| accattttca agaatactcc cggcatgaag atggacaatt aatataaaa aacaaagaaa | 480 |
| atagtaatta agtgcgttga gatgaatgaa atttatccgc tcttaattga atatggggaa | 540 |
| ttgaaagaaa tttctgataa taaattaatg agtcttacat gacgtggatc cgacttaatc | 600 |
| tagtctattt aaactaagaa tagataagaa tagagaatat agacaaaaga gaggctcatt | 660 |
| ggctagggtt tcaagggagt tccttgaaca taagtggcaa gtacaagcac aaagccaatt | 720 |
| tccatggact aaagatgaat aagatgtgtc gtgtggtatg gtgggaaggt gaggaggtat | 780 |
| ggggtaattg gagatgctaa acctctctaa aagctctttt gctccaaata tctaaatcca | 840 |
| tctctatcac ttttggcgac tgccccaaaa tttgcaactt atgaattaaa gttttaatat | 900 |
| ttttaagtta ataaattctg aattaataat ttaacatatt caataaactt tttaaaacaa | 960 |
| attacgtata taccatcaaa ctggctgcac catgatcact ttctaaactc acaatgacat | 1020 |
| atggatttaa tcaggcacaa agtcatgttg atagaaagag atagtacgga gaatgaagaa | 1080 |
| aaaaggtagg ggagagagat ggggtgagtg gggaaaagat agggttctct ttttagtgaa | 1140 |
| agcgacaggg tctgagaacc ctaggtcaaa agttgcataa acctctatac aggcttcttc | 1200 |
| actcccttac tactaatata ctctcattaa ggcttgaggt ttaattcatt aaaattgtgg | 1260 |
| tttaattatt gtatccccctc aaacgaaata attgtccttg tcgaggttag acaatgttgc | 1320 |
| gtactatttt caaacgcagt cagccattat tctcctatcc tttacagtcg agattcaaag | 1380 |
| acagaaagta gcatgcaagc tgttattaat ttactttgat taggactttg ccaagaaaat | 1440 |
| gaagaacctt ttcttttttc ttttaattta gttatcttac aacatgtaat ttttcctagc | 1500 |
| aagcaaatac ggtaacttt ttttttattc tcatttaatt tgttggagct attgctactt | 1560 |

| | |
|---|---|
| tgatgacttc aaccaaatcc tggttggtag gcggagggtg ctgacgatgg aaactacccc | 1620 |
| tcttgtccaa atacgataac ctaaaaaata gaataatagc ttattgtact gtgctgcaaa | 1680 |
| aattgcattg tcagtataca taattaaaat ctattttgaa tgtgtggagg gcaaagaggg | 1740 |
| gtgactggtc tagggttgta gaaatcaggt gggagagaga atggtatttg tctctgtgtc | 1800 |
| agctgatatc acgtgaagag gcacaataag aagtccttcg tatccattca cttcccaaaa | 1860 |
| ataccggcat tactacaaat atagtactag cacttgcttt ctctatcccc atctttgcta | 1920 |
| tttcctttcc ctttccaact ttttggcttt agaattgcaa agatggaggg aattgtggtt | 1980 |
| ctttgtatct gtaaaatttt tcctccaagc tccagttgta gctagcttaa tgcgtggacg | 2040 |
| cgcgcgcaca cactagaaat ctgcaatcta tatatatatt cacaaggcac tcacatatca | 2100 |
| aaaaccacat agacattgta tagagagagc tgtcgttctc aagcagaaaa aatgatatga | 2160 |
| tttcatcagc atgtggtcaa ccaaatagtt caattctagt ctttgcttcc tctttctaat | 2220 |
| tactgtataa atagagccac aaggacatag aattgagaaa ataaaagaca ataaaaacaa | 2280 |
| atctagctac ttaagcgaat gatgatgact ctctctcagt agtcttaact cttaataccc | 2340 |
| ttgttttcct tcttgtgctg cagtttgatt ggttaattaa cctaatcaaa agatgtttta | 2400 |
| actgtgtttt atccgtcttt ctcaagatct atcttagtcc caccacatag ctccctcaag | 2460 |
| ctacagctgc aaaatatata ctatatatat ataacaa | 2499 |

<210> SEQ ID NO 90
<211> LENGTH: 2500
<212> TYPE: DNA
<213> ORGANISM: Nicotiana tabacum

<400> SEQUENCE: 90

| | |
|---|---|
| tgacattgct ttggtggttt aagttctcag ccagtatatg cattgtccta ataggtctca | 60 |
| catggaagca gcactgagag ttgtaagata cataaaagaa gctcctggct taggtctctt | 120 |
| cttgcctgta aaatcttcag atcaactaag tgcttttgt gactcagatt ggggagcatg | 180 |
| tatacaaatt agaaggttag ttacagggta cttggtaaag tttgaaagtg ctcttatatc | 240 |
| ctggaagtct aagaagcaga gtactgtgtc taggagctct aatgaagctg agtttataag | 300 |
| tatggcttca tgtgcagcag aagttacctg gccggtagga ctgttcagtg aacttggtgt | 360 |
| caaggttaaa cttcctataa acttggtatg tgatagtaaa gctgcaatcc aaattgcagc | 420 |
| aaatccaatc ttccatgaaa gaacaaaaca tattgatata gactgtcact tgtaaaggaa | 480 |
| aaagctaagt ctaaggatgc taaaaactga gtatgtcaac atgaggatca actggcagat | 540 |
| atacttacaa aaggattgtg aagagctcaa catgtacatt tgctgaacaa gctagggttg | 600 |
| aagaatctgt atcaaccatc agcttgagag ggagtgttaa tcaacatggt taccactagt | 660 |
| ttatttataa agtgtaaatg ctaaaccata gctagtgagt tagttaatag ttagttgagt | 720 |
| ttgttataaa tattagtcag ctgtacagtt taacatagct tctctttcag aaatgaaaat | 780 |
| tgctcttctc tcatttcctc tcttctagat tcttcttctc cctccttctc ttagctcaga | 840 |
| tctctcttat gacagctaac aataaatacg aatatttctt gtaacggttg ctcattgaat | 900 |
| gttgtctttc tcaaccgata tctttctttc aagttttccc cccgattcga gtattttga | 960 |
| aactcactca gcaccggtca catattcgta atcggtgcca gctatttgct tactcatatc | 1020 |
| ttatttgact tcattgtcac gtgtcagaca gaagtatgtg cgcatatacc atcaagtctc | 1080 |
| aatttgaaat aaaatcaact taagcagtta aaagtcaaat ctcttttagt tcggtcttta | 1140 |
| aaataataat ttaaataatg aacctataaa acacgcaact cacactgaat atagggggcag | 1200 |

```
acataaaagc cgaaagactg aattccgaac cggaccgaat tatttcggta tttcgatatc    1260
ggtttattca gtatttcggt actatttcgg tataggattt ttagttattc ggtatttcgg    1320
tacgatcctc ggtattgaaa tttcgatatt tcggtatacc gaaataccga ataatttaag    1380
tacaccttcc ttcactgccc agcccgttat caattttcag cccaagtttc taacttgtta    1440
tttctttccc ttagccagta gcctactaag attaagccca acgccccaac ctaacattag    1500
aaattattat aattagaaaa gtataaagaa agtactcaca ttctactgct atgctcatgt    1560
agtgatttct attagaaatt attagaagtg aaggtactgc ccacattttc ttgttgctat    1620
actcattatc acgcaattag aaattttcta atgaattaga attcagtagt tcagcacaga    1680
ggcggatgta gcgtattacc tacgggttca actgaaccta taactttcga cacagagtaa    1740
aaatttatat gtaaaaattc tttaaaattg taaaaatcgt agatatgaac ccataacttt    1800
aaaaatataa tgggtaacat taaaattgaa cccatagaat ttaaatcctg gattcgcctc    1860
tggttcagca ttgtttagtt cacaaaaata tggtacgatg ccgaaccgta tcgaaaccat    1920
accgaaccaa acaagaagat atcgaacaat accgaactac tttggtacag tatttggtat    1980
gcacacttga tatatcgaat accgaaatac cgaaccgtaa ttttcgaata ccgtaccgaa    2040
ataccgaaca ctcacccata actaaacatt aaaaagctag aactcaggtg tttaatgact    2100
aaacggaagt aagatctaga taatccgtca ctctgttgat ttgtaaggct atcgacatgc    2160
aaaagtggaa gcaaaatgga gccgaaattt taacaaaaat gctgaaccaa taccatgaaa    2220
ttgatgaatg gtgggaccct atttcactct tttagaattt gcgtaagacc agaaaataac    2280
ttcaatcgaa atcaaaataa ataccaaccc ttttaggccc caaatcacta cgtgtgattt    2340
gcaaacgtca ttagccttat gtaaacagtg acctcatgcc aacatattat cgcagccctat   2400 aaatcttagt ttacatttca ttttctttca aacacacaca cctcacaata gaactaagtt    2460
gtaagagttt cattttcttt gttctttctc acaaaccaaa                          2500
```

<210> SEQ ID NO 91
<211> LENGTH: 2499
<212> TYPE: DNA
<213> ORGANISM: Nicotiana tabacum

<400> SEQUENCE: 91

```
tgccagacag tctaaaattc aaaaatagga cagcccacat cccctccacc ccactagatc      60
tcactacttc ttaattagga cttgtggggg ggagtagagg gatttgcaaa ggcggccgcg     120
gcatgcatat acgaaaaga gaagttagtg gtttgcaaag atgattgtgg aaaagggctt     180
acctaacaat gaagaagagg aagagggtag atggataata ataactcaaa aatagaaaga     240
agagggacaa gtgggggctc aatggctaag gttttaaggg aggtcttgga aacatcatta     300
gcaagtacat gcagtattac caccctacat cagactgtgg ggtctgatgg aatattcttc     360
tactatactc ttttaaatag agggaattaa tgagccttta taatgttgaa atttataaga     420
aaatagtata actttttaaa tctcttaatt atgtatcaaa tcaaatctca tatttaccct     480
ttagtggatc tattcactga agtctgaata aatcgtacca gtaattcata ccgaatgtgt     540
aaataatttg aaagaaagat agacaaggcc tcaatgctag ggatttgtta gcatcaatag     600
caagtataag cagaaatata taccaccaag gagtgaggtg gaagaattaa gatttactct     660
aatgaaatat atatatcaag attgagtcat gtgaatgaag aatttcttag taccttaaat     720
taagcgaata tcacataaca gaggtgtaaa aaaacgaaag atggacaagc taagtggctc     780
```

| | |
|---|---|
| tcaatggctg gggttttaag ggatcggagg tcttgttaac atcagacgga agtacaatta | 840 |
| gagtatatat gctactctaa taatacttgg ctacaaacat aaaaaaatat ctctatcact | 900 |
| atctctcaac tcgccatata gacttaattg gcacaaagtc atgctgatgg aaagagatat | 960 |
| aaggagaatg ggaagacaaa aaaaaaagtg gggatagaaa gagtgtccaa gtagctagaa | 1020 |
| gggggtgggg gtgggggtg ggggagttgt tgttttagtt gtggaagaga taggtttctc | 1080 |
| tttttagtga aagtgacata tatagctaga ctgagaaccc tggtcaaaag ttgctttgcc | 1140 |
| ttaacgtttc taaatgcctg acctctgaga ggctatcttc tcctctcatt ctctcgaccc | 1200 |
| ttactgttca tacccccca aatttgaggt ctaatttatc cacactatgg tttcttactg | 1260 |
| ttgtcttctt ctctgaaaca atattgcttg tcgatcttgg acttggccac gtcaacgtgt | 1320 |
| aacttcagca actagggtga ctccaagtca tagacagatc taggtcgact tctgtgaatt | 1380 |
| taactaaaca aattatttaa tttcgactca aaatagatat gtactatata tatatatagt | 1440 |
| aaacttattg tgaacttact aacttaaaat tttcaagttt gcagtatttt ttggaataag | 1500 |
| aaaggggaaa aagaggcaga aaaccccata tttcttcctc tttggagttg acgctaaagg | 1560 |
| gataaagcta acatgcaagc tcttaacaaa taacatactc agtataatct cacaaatggg | 1620 |
| gtatagagag gataaaacgt acacaaatct taacaatata cacagtgtaa ttccataagt | 1680 |
| gagttctgtg gacggtagta gcttacccct tgccttttaac atgcaagctc ttaagctttg | 1740 |
| tatttttatt ttgttctttc tttttggaga ggaagaagtg gtggttgaag actagagata | 1800 |
| aggaagaaaa gagaaggatt tttgtcagtt gctatcacgt gaactgaagg ggcacaatta | 1860 |
| gagagaagtc tatatgcttc acttcccata aaatcagttg taactacaac aagtactaag | 1920 |
| agtgtcccct ccattttctt tctttccctc aattcccttt catacttttta aagcttaatt | 1980 |
| ccacagctag aaaaagaagc ctttcttttt ctctagaggt atttagcaaa gatggaagga | 2040 |
| caatattaca gctctctttg tctctacagg taacaaacca ttgcctgtct ttctcaatct | 2100 |
| ccagtatttc cagctatctt ataatgcttt gagtactccc acaaaacaca tgcattatag | 2160 |
| ccactagcta catatatata tatatttgta aaaccacaca ttaatttagc tgtcattctc | 2220 |
| aaccaaaaag ctatgttatc atcaacatat tgacaaatta cctataattc cttcccctct | 2280 |
| agctatatga tctatctcac tttattatgc acttaaaaag ttatgttgtc cctctcaaaa | 2340 |
| gtcttaatta attaaccttg ttttgcatct tgctgcagct agctagctta ttaaaattgac | 2400 |
| aaactcagaa gatgttgtgg ttctttcaac ttcaataaaa agctaagagt agtacttgtg | 2460 |
| cttgtatatc cgtccttctc aagctcaagt cccacttca | 2499 |

<210> SEQ ID NO 92
<211> LENGTH: 3425
<212> TYPE: DNA
<213> ORGANISM: Nicotiana tabacum

<400> SEQUENCE: 92

| | |
|---|---|
| gttggagcta aaaataagag aaatggacaa gtgtcaaatt ctagcgtcca tggtagcgcg | 60 |
| acgcactatt gtggcgctag aaatagaaga ccaaaatttc caatgttggc gtcgaccttg | 120 |
| cgttgcggta ttttttctat ttcgctaggg acaagattat ttcaacaaaa ggggttctaa | 180 |
| acctaatttg gaggatatct aacatacttt gaaggcgaat tcacgtaagg gaatacaaac | 240 |
| cacgcttgga aggggctttc aactagtttt tcttctcttc ttttctcttc ctttcatctc | 300 |
| attatgtatt agttctaggg ttgttggtac ttacattaac gttatagttt gaagcttgga | 360 |
| ttatcttatt attttatcat attggtttat ttattcaatc ttgcgcttga aatttaatt | 420 |

```
ttaattgatt gatcaccaat taaatactat ctacgaattt aggattgaaa tcgggagaga      480
aaattttaga ttgcatatag gattgagtag agtaagatct tgaacctgaa ttacgaggga      540
acgaatttgc gattaggata taaggatata cctaatcgtc ttgcttggtt actatacggg      600
aattattaat acgttcttat taatcctaat ccactggaat ataggcgttg agttagcttg      660
aacaggcgag tagtacttcg ggagaatact acgagtaata ttaaattgtc aatcaataaa      720
ctagataaat ttataagata gtttaagtaa aaaactcaat gagattgtta gttgacccat      780
aactctgaaa tattttctcc cattagattg tctttaagct tgccggcata gttttctag       840 ttttctagtt tacaactcta gattagttat agttaacaat cacactttag aaaatcgctt      900
gagtagatta attgttaatt tagttgatag ttaatcataa gtcatcgagg aacgatact       960 ctacttatca ctttattact tatcgaccac gtatacttga gtgcgtttgg gagcaacaaa     1020 ttttgacgc cgttgccggg acgttagttg atgttttcaa ctagtgaaca aaatgcaaat      1080
atgttatgca attcggtgcc atttacacgt ctatgaggag ttatattaaa gaactttatg     1140
taggatgttg gttggatcct acaagctaaa attatggcta agaaaattgt gaattactaa     1200
taaacttgta ataagataaa aaataatttc ctagaacgta atagaattga agtgagatta     1260
gaccgacacc tcttcgtcgg aaaactatgt tatatatgta ggttatttta tatatatata     1320
tatatatata tataattttc ttggcgttta atttttttata ttttgattct tcctactaat    1380
aattctaact ctatcactga attaaacgta caggattcat ttcttataca aagaggttg      1440 atcattatta ggtctgggca ctgtcagagg ctgaccgata tgagtagttc ttcacatgct     1500
tggcagcaat ttgaactgtg attgcttgag gggcgaaaaa gagagtagaa tctaagttcg     1560
gtaattttta tctgaattct gtatttgtct taaaaattta ttgagtatgc ataaaattat     1620
tattttaaac tcagtaattt aaaaaattta gaattcgaac tcataaattt caaattggga    1680
ctccacctct gattgtttgt aagtggagtt taggggcaga actagctcaa aaagttcggg    1740
ttcgattgaa ctcagtaaat ttgattcaaa gtctatatat ttattgaaaa atcaactaaa    1800
tatgtatata tacaataaat ttcaaattca taaaaattta aatcctgaat taacctaata   1860
gtaaaaccgc agactctaac tagtggtcta gtttagagag tcaaattatg gttttttaaca    1920 accttaaaca agcacaaata cttttccact attggttcaa ttttggttgt taacaacctt    1980
gattggtaat tacgtacttg catgggcatt tgaaaattaa gttacgtacg tgtaaaacgt     2040
tttagagtag tccgtactaa ttaagaacac aaacactgct tgagattttg tggcggaagt    2100
ttgttttgac ttagcatggg taggcccacg aattccccat tttgaataaa agacaacctg    2160
tgctagtcga ttagctatta tttaattact agaatattac ttactccctc ctttttaatt    2220
tagacgattt agtttgactt ggcacaaagt ttaaagaaaa aaaaaagact ttgaaatat     2280 gtggtgttaa aatcttaatg ggcaaaagct aagtggagtc atgatatttg tgtgactata    2340
aaaacttctc attaagaata aagtgagtaa aataaaaaat taaagtcaaa ttatttctaa    2400
atatagaaat atatcattct tttttgaacg gactaatacg gaaagtgtgt catttaaatt    2460
aaaataaata aagtaatatt tatcatatga ttttaacatg taaatatcat acaagtaatc    2520
taatcgtcaa gcgcggatct aataaataag ggacgggtat tttgtttagg ctgtgtatat    2580 ataattttt aaaatctact aaaaagaac aaataataga tttgtaaatt agagggatat     2640
ggtagaatct aactataaac ccttaaagtt caaatcttgt atctgcttgt ggtaatagtg    2700
tatatatatt ttttacacgt ttttgttgta tagaactcaa actaaaaagg gcattccagt    2760
```

| | |
|---|---|
| gcacaaagca tctcctattc acacacaatt cggtgaaggg ccgcactgta tgcaagdggt | 2820 |
| gtgatatcgg cagtctatcc tgatgcaagc atcaatggtt gattccacgg ctcgaatccg | 2880 |
| ttacctatag gtcatacgga gataaacttta ccgttactcc aagtccccct tctacataaa | 2940 |
| acttgcatca atagctgatt tcacgactcg aacccataac ctagttgata cgaagataac | 3000 |
| tttaccgttg cttcaaggtc cgtctacaca aaactgatca aattattttc ataaataaag | 3060 |
| aagctatcat ttctctataa atagaactag agtccttgca tattccaaca taagtatcag | 3120 |
| ttccaggaaa atcaagacat aatctgttag cttttctctt tgccattctc atggattcct | 3180 |
| taccagtctc ctccattgaa tctctagtca ttgagatcaa gaaagagatg ttctcaaacc | 3240 |
| aagaatttaa cacttttgtc accccaatat ctgcctatga cactgcttgg ttggccatga | 3300 |
| tttcttataa taatcaagaa gaagccatta atggtcattc ttttctggc cctatgttta | 3360 |
| agagttgttt aaattggatt ctcaacaacc aaaatgagca aggattttgg ggagaatcca | 3420 |
| atggt | 3425 |

<210> SEQ ID NO 93
<211> LENGTH: 2512
<212> TYPE: DNA
<213> ORGANISM: Nicotiana tabacum

<400> SEQUENCE: 93

| | |
|---|---|
| aagctggtac ccttatgttt agtccaagaa aaataaccat acccaaatat aagggtttgt | 60 |
| tgaagacgga aatatataaa caaataaaca aatatcatca tatctccgat agtttaaaat | 120 |
| tttagattgg atatttcaca caattttatca aaattttcaa aaaaaaattc tacttttttct | 180 |
| tgcttggaac ttggaagggg aaggggtggt ggtggagata gggcggggca tcttctatct | 240 |
| agtctatgtg attaatataa caaaacaaaa agggcgaggc aaaaacatgg atgaatggtg | 300 |
| gtccttttct atatttatat ggattgttac gatacgtcga tttcactttg caaaatacca | 360 |
| attagattca tttagttatc ttttttgatca ctctgctttt actatcatat atatatagga | 420 |
| gtccttccac gtttcgcatg tgtcattgtt tatattttcc atggtcttcc ttccaaatgg | 480 |
| ctaaaaaaat ttgacacagt ggtcccaaaa gtttatagaa atagaattca acagtgaggc | 540 |
| atatacctat gaattctatt ttacatcttc atcgtataaa atagaatgtg ttataaactt | 600 |
| tacctcgtga tgcttacaag gggtgaaaat ataaaagcac tttatagatt tacaagagtc | 660 |
| acaccttgat ttatcctaag attttatttt tttacatgcc aaacaatgaa gtatgggaga | 720 |
| tccaattgga ataacatcaa atttaataaa attcgaaata gtcagagagc tgtcactga | 780 |
| ggtatattga aacttatttt tttttaatag aaaatatcaa atacttagca atatattaaa | 840 |
| atgtttcata aattacattg tttaaaccaa gcgttgaaac atatgctgat acgaggtagg | 900 |
| cttattgatg aatttataag ggcctcattg gaaaagacga tccaaagcaa tgggctaaaa | 960 |
| aattggccca ttttctgcca cccagtgtat ggttattact agtttcaccc acacagattt | 1020 |
| gcacttcatt agaggacaat gttgctgaat ttgaaacata agtccattta tctccactgt | 1080 |
| acagtccttc ctggagtcca atcctgacca tatcttcatg attttatgta atgtggtgaa | 1140 |
| taagcaaagt ttcatgttat gctttgtctc attttatagc aaattcattt cctcataaaa | 1200 |
| tttacttcaa aaaagtttcg tttgattttc agaaatcaaa atatgctttt cggtaaccaa | 1260 |
| atggttttca atttttgttta cgaagaactt aaaactttcc aacaccctac atctatgatt | 1320 |
| gcaagttaaa attgcagaaa tatgacactt tttggagtgg tctttatcgt ttaacttcac | 1380 |
| ttgcacttta agggcaaaag ttaaaagtgt ttccatgaag caagcgaggg ataacactta | 1440 |

```
ttaaacttga aattctactc atagaccaaa acaaggacaa aaattcaaga ctatctatgt    1500
gggtaaacgt acgaaaattg ggcttctcca gattagagcc ggaccttgtg gaaagacaga    1560
gaaattcgag gcccacttcc agtttctaag gagattaagc ctatcaaacg atggtccaga    1620
acgaaatatg tctttcttta ttctctacta tatagctgac tcagaatcgt tagaatttgc    1680
aatttcctca taataaaatg tgaggcagta tagattcgaa aacctttgtt gaagattatt    1740
gactcagcta cgcgaaacaa actgtagtat ccaatgtacc gattaacaag cgactggtta    1800
actatgaatt tgttagctcg acaaaatcac cggttaataa tgagtttgtg agttcgataa    1860
aatctaattt tctgatagaa attttatata ttatgcagaa atttaataaa agtagactta    1920
acttatatat tttagcattg actcttttga agtaaaatcc attccatcta aattatgact    1980
tccctacatc gagtaagtaa gttgcgtctg tatcctcatt ttacccactt ttcgctatgc    2040
aattattcaa ggatctttac acaaatagca agccaatatt aattatttat ttttttagt    2100 catatatata aattatacat atattatata cccattaatt attttaatt taagtgatag    2160 attggacgac tatttggatt aattcttcgt tattcaagat aatagatgtc gtctctaata    2220
catgagctag aagataataa ggattactag gccgaaaggc tgatggaaat gaacaagaag    2280
ataagctcct aaatggaaac agtacggaaa aagtcaaaga gcagtgcatg ggaggaatca    2340
tcagtcagaa aaggaagcca cgtgtcaagt agaaacaagc acgtgtccat gcaaaagcca    2400
cgtaactccc ttccatcaca tcttccttct tcaaaacctc gtgttttact ctctcttttc    2460
tcactgccag tgatcgtcag gactgtgcat gtttgtttaa aaactaaagg ca           2512

<210> SEQ ID NO 94
<211> LENGTH: 941
<212> TYPE: DNA
<213> ORGANISM: Nicotiana tabacum

<400> SEQUENCE: 94
tttaaaacgc caaaaaataa gggacggcca tggcgtagca atgactattg ttccgtaggt      60
catttgtgaa ggaccgacaa aattttaggc gatccgggtc cgattttcg gttctgctca    120 agaaaactcg atctgcacga atagcttata atcaaaccct ttttttttt tcaagaatgt    180 ctaattgatc ctaaaaagac aaccttatat gttccaccat ggcaggatcg gccttattac    240
taagggtttg ccaatagaca cgttttttaac attcaagtaa aaaaaacatt tattcttaat    300
aacccaccta ctatagtacg ttatttggca gtagactacg ttgtacattt gggaccattt    360
ggaacactcg tctttcacga gtcactaatt tttgtgttga atgcataaaa tttgtttttt    420 tcttttcga aattgaacaa tttatcttc gatcacacct atagtatatt attaccttat    480
tgttagaaaa tattttatt tattattgac tcctaataaa aagtggggta aatttgggtc    540 tttttttaa agaatgtgaa ctactcattt cactttggtt agaacaaata tgagaagatt    600
tgctaatgac agcaaaatga atagaccaaa agcgtaacga atattaaaaa taaacaattc    660
cgaataactg gttactgaaa attgtggaac tctacatagc cgttgtgagt atggtattgt    720
ttgttcttgt gggcagaata actagttacg gaaaatttat gaatttgctt cacattattt    780
tttttcattt ctttttttgct tcaaaagata agtacaagtt tttatactct tatttcattg    840 cctataaaata cctctattga gttactgctc attcacaact ctaaatagca atctttctta    900
ttattaaaat tcctatcctt ttttactcat tcagagaaac g                         941

<210> SEQ ID NO 95
```

```
<211> LENGTH: 5000
<212> TYPE: DNA
<213> ORGANISM: Nicotiana tabacum

<400> SEQUENCE: 95
```

| | | | | | |
|---|---|---|---|---|---|
| aaaaatatga | gaatcgtgcg | gaatttcagt | tttatggaac | taaaacgcca | aaaatggagg     60 |
| aacggtcatg | gagaggcgat | aactaatgtt | ccttaggttt | ttttagatgg | gccgaaaaaa    120 |
| ttttaggcga | tacgggtaag | gcgtccgaaa | cacacgaaaa | tttgaaaatc | gggcgaattc    180 |
| ttgttttatg | acactacaac | accaaaaagt | atggaagatt | atggcgatgc | gatgcgatga    240 |
| ataatgttcc | ttaggttatt | tttgatgggt | gacaacattt | taggttatac | gagaccgggt    300 |
| tcccgggccc | acaccagtgg | cgtgggctat | attgcacacg | aaaatatggg | aatcgagcga    360 |
| atttctacat | ttatggcact | aaaatgcaaa | acaaaaagga | acagtcatgg | cgaggcaatg    420 |
| actaatgttc | ctagggttat | ttagatgggc | cggaaaagtt | ttaggtgatc | ctggtcgtgg    480 |
| cgctcgagcc | cacgatggta | gtgtgggcac | acgaaaatct | gggaaccgtg | ctgaattcta    540 |
| gttttatggc | cttaaaacac | caaaaccaac | aaagaggaat | tctcatggag | gggcgatgaa    600 |
| taatgttcct | taggttgttt | tagatattcc | agaaagattt | taggtgatcc | gggttgcggt    660 |
| gcctgggccc | acacccagtg | gggtgggcta | tagcgcatgc | aaatgtggga | atcgagcgga    720 |
| attctaattt | tatagcccta | aaacaccaaa | taatgttgaa | cggtcatgac | acgatgatga    780 |
| ctaatgttcc | ttaggttatt | tttgatgggc | tagcaaaatg | ttagaagatt | cgggtccggc    840 |
| tgcccgggcc | catgccagca | caagaaaatc | tgggaatcag | gcaaattcca | tattatggcg    900 |
| attatggcga | ggcgatgaat | aatattactt | agattgtttt | ttacaggctg | gcagaatttt    960 |
| aggttatcca | ggtgcgggcg | tctgggcctc | tgccggtggc | gtgggctgta | gtacacaaaa   1020 |
| attagggaat | caggtagaat | tttagtttta | tggccctaaa | ataccaaaaa | aggaggaaaa   1080 |
| gtcatggcga | ggtgatgact | aatgtgcctt | aggtaatatt | ttatgttccg | aaaaaaattt   1140 |
| atgtgattca | ggtccgggag | ctcgtgccca | tgcagatggc | gtgggctata | gcacccgaaa   1200 |
| atctcaaaat | catgtggaat | tccattttta | tggccataaa | atgctaaaca | taaggaacgg   1260 |
| tcatggagag | gcgatggcta | atgttcattg | ggtcgtattt | gataggacgg | caaaattata   1320 |
| ggcgattcag | gtccggcgcc | gggcccatgc | agatggcgtg | ggctaataat | agcacacgaa   1380 |
| aatctgagaa | tcgggtggaa | ttcatgtttt | atggccctaa | aacgcaaaaa | acaaatgaga   1440 |
| aacggtcatg | gcgaggcgat | gacaaatgtt | ccatgagtca | ttttttgatgg | gccagcaaaa   1500 |
| gtttaggcga | ttcggtttcg | ggggcccggg | cccatgcaga | tggcctgggc | tattgcacac   1560 |
| gaacaactag | gaatctggtg | gaattccact | tttacagcaa | taaaatacca | aacaatgaga   1620 |
| aacggttatg | gcgaggcgac | gactagtgtt | ccttaggtcg | gtttagatgt | ccggaaaaat   1680 |
| aataggcgat | cgggtccagg | cgtccgggcc | tgcgccaatt | gcgtgggcca | tagcatatga   1740 |
| aaatatggga | atcgggtgaa | attcgagttt | tatggcccta | aaatactaaa | aaggaggacg   1800 |
| gtcatggcga | ggcgatgatt | aatgttcctt | aggtcacttt | ttatgggcag | acataatttt   1860 |
| tggcgatctg | tgtctgggag | accgaggcca | tgtaggtagc | gtaagctata | gcacacgaca   1920 |
| taattccagg | tttatggacc | taaaacatca | aaaatggagg | aacggtcatg | gtgagccgat   1980 |
| tactaatatt | ccttaggtcg | ttttggatgg | gccgaaaaaa | tttagggcga | ttcgggtgcg   2040 |
| gacgcccgag | cacatacaaa | tggtgtgggc | tataccacac | gaaaatctga | ttacctgaca   2100 |
| gaattccagt | tttatggccc | taaaatgcca | aaatcgaaga | acggtcatgg | tgaggcgatg   2160 |
| actaatgttc | ctaaggtcgt | tcttgatggg | ccgacaaaat | tttaggcgat | tcgggtgcgg   2220 |

```
acgcccaagc acatgtagat ggcgtgggct ataccacacg taaagcaggg aatcgggcgg    2280
aattcaagtt ttatggccct aaaacgccat aaacgaagaa cggttatggc gaggcgatga    2340
ctaatgttcc ttaaatcatt tttgatgggc cgtcaaaatt ttaagcgatt cgggtcaggg    2400
cgccctggtc catgcagatg gcgtagcaca cgaaaatcta agaattgagc agaattctag    2460
ttttatggcc ttaaaacgcc aaggaacgag gaacggtcat gtgaaggcta tgattaatgt    2520
tccttaggtc gttttttaagg gcaggcaaaa ctttaggcta ttcagttctg gacgcccaga    2580
cccatgtaga tggcgtggct atagaacacg aaaatctagg aatcaggcgg aattccagtt    2640
ttatggtcat aaaatgctaa aaatgaggaa ctgtcatgga gaggcgacaa ctaatattcg    2700
ttgggtcatt tttgatggtc cagcaatatt ttagatgatt cgggtttggg cgcccgggcc    2760
catgcagatg gcatgtgcta ttgcatacac aaatctgtga accgggtgga attcaagttt    2820
tatggcccta aaatacaaaa aaatagagaa acggtcatgg cgatgcgatg gatatgttcc    2880
ataaggcatt tttgatggga tagcaaactt ttaggtgatt ctggtccggg agctagggtc    2940
tatgcagatg gcgtgggcta ttgcacacga aaatttaggt atcggtggaa tttcagtttt    3000
atggccataa aatgcataaa atgagaaacg gttatagcga ggctatgacc agtgtgtcct    3060
taggtcgttt tagatgggct ggcaaaatgt taggcgattt gagtccgggt gcccgggcct    3120
gcgccaattg cgtgggtcat agcatacgaa aatataggaa tcggacgaaa ttctagtttt    3180
atggccctaa aatactaaaa aggaggaact gtcatgacga ggcgatgact aatgtttctt    3240
aggtcgtgtt tgttaggccg gcataatttt aggcgatctg ggtctggacg cccagggtca    3300
tgcaggtagc ataggctgta gcacacgaaa attttgaaat cgggcgaaat tctagtttta    3360
tggccttaaa acgcgaaaaa caaaatgaat ggtcatggag atgcgatgac taatgttcct    3420
taggtcgttc ttgatgggac ggcaaaatgt taggcgattc gggtgtgggc gcctgggcac    3480
atgcatatgg cgtgggccat catagcatat gaaaatatgg gaatcgggca gaatttcagt    3540
tttatggccc taaaacgcca aaaacgaaaa acggccatgg cgaggtgatg actaatattc    3600
cttaggtcat ttctgatagg ccggcaaaat tttagacgat tcgggtaagg acgccctggc    3660
ccatgcagat ggcgtagcac acgaaaatct gggaatcgag aagaattcca gttttatggc    3720
cctaaaatgc gaaataacat ggaacggtca tgtcaaggcg atgattaatt tttcttaggt    3780 ttttttttgat gggcaggaaa aatattaggt tatgcccatg cagatggcgt ggctatagca    3840
cacgaaaatc tgggaatcgg gcggaattct agttttatgg ccctaaaacg ccaaaatgtg    3900
aggaacggtc atgtcaaagc aatgattatt attccttagt tcattttttga ttgtcggaca    3960 aaatgttagg caattcgggt ccgttcaccc ggatggatgc atatggtgtg gctagtaca    4020 cgaaaatctt ggaatcggac ggaattccag ttttatggct ttaaaacgcc aaaaaataag    4080
ggacggccat ggcgtagcaa tgactattgt tccgtaggtc atttgtgaag gaccgacaaa    4140 atttaggcg atccgggtcc gattttttcgg ttctgctcaa gaaaactcga tctgcacgaa    4200
tagcttataa tcaaaccctt tttttttttt caagaatgtc taattgatcc taaaaagaca    4260
accttatatg ttccaccatg gcaggatcgg ccttattact aagggtttgc caatagacac    4320 gttttttaaca ttcaagtaaa aaaaacattt attcttaata acccacctac tatagtacgt    4380
tatttggcag tagactacgt tgtacatttg ggaccatttg gaacactcgt ctttcacgag    4440
tcactaattt ttgtgttgaa tgcataaaat ttgttttttt cttttttcgaa attgaacaat    4500 tttatcttcg atcacaccta tagtatatta ttaccttatt gttagaaaat attttatttt    4560
```

```
attattgact cctaataaaa agtggggtaa atttgggtct ttttttttaaa gaatgtgaac    4620 tactcatttc actttggtta gaacaaatat gagaagattt gctaatgaca gcaaatgaa     4680 tagaccaaaa gcgtaacgaa tattaaaaat aaacaattcc gaataactgg ttactgaaaa    4740
ttgtggaact ctacatagcc gttgtgagta tggtattgtt tgttcttgtg ggcagaataa    4800
ctagttacgg aaaatttatg aatttgcttc acattatttt tttcattttc tttttgctt    4860 caaaagataa gtacaagttt ttatactctt atttcattgc ctataaatac ctctattgag    4920
ttactgctca ttcacaactc taaatagcaa tctttcttat tattaaaatt cctatccttt    4980
tttactcatt cagagaaacg                                                5000
```

<210> SEQ ID NO 96
<211> LENGTH: 5000
<212> TYPE: DNA
<213> ORGANISM: Nicotiana tabacum

<400> SEQUENCE: 96

```
gctgatctac aaagggctta gaaagaagta agaaaagaaa tggataaagg aaagggaaag     60
attgcagaat cctcagagct gttgaggaag aggagatgga actggtccat caagaaaggg    120
gtacatcagt ggaggttcct accccaagcc aaaaagccca agacttcctc caagaagtct    180
tcctctgtgt ctgaggctgt tgaacctaca ctagccaaga ggacaagatc tgcagtgaaa    240
acaacaatca aaaatttctg aagatgatga ctggagtgga gaagaagaag aaaatgattc    300
tgagaaggaa caggatagct tgccagtttg gcaaagaaaa gattttaaag ggtagactgc    360
tgaaagacct ggtggaacca ggaatgatga gatgtgatg ctttagctgc tcaggatgga    420
aggacatggt ccttcagatg gatggtaggc tagccagaaa tgagctaatt gaatttatgg    480
caatgtctgg ttaaggatgg catgttagta gcctggtgaa aggagttcaa gtgcagtttg    540
atgcaaagaa actgggagag atcctggaca taccctctga agggtttgat gactatacaa    600
ggcaaaggtg gccctgcctg gactccctcc ctactgctct tgtaattacc aggaggtttt    660
gtgattctga agatgtgaat gaagccaggg ctgtgcagaa aagtgaaatg aggcctgagc    720
acaaggactt gtttgaattt gtcaacaagt gtttattgcc cagacaggag agaagtcaca    780
ttgccaatta catggatcta gttcttatag agtgcctgga gagaggaaag caaatcaatt    840
gtctgccttc attatcaagc tgctcgacag ggttataaat ggctccaagg ctcatgctac    900
tctttatggc tttattctaa ccacagttct ggatagtctc aatgtgcctc taaagaaatg    960
ggaaatgatc tcgagaaagg atcactttgg catcaatact cttcttgctt gtgactatgc   1020
agtcaatgac atcccaaatg aacctggtac atcctagaag acacccatca acagcaaagt   1080
caggactctg gttcaggaat atgtagccaa ggatgctgaa atagctaggc ttttggctcg   1140
tgtgattgaa gtgaaatttg agagggatgg tctcagaact gagcttgaca agaaaaagga   1200
gaaaaatgat ggaattcttc ataacatgct gaaccttctc caagcccaaa cccaaccata   1260
tagttcttcc aagccttagg actcctagct tttgtctcct gaacttgttt agtacctcag   1320
tgacccagat tagggatttt tctatctttt attttttgctc atgatttgga tgttttctt    1380 tctttttgtg gattgttggt ggcaacatat ctctgtcaat gataactact attttgctct   1440
tgtttaatgt taatttgtcc ttgatatttt aaatatattt tcttgattac tgatgattac   1500
tccatgatta catttgcagt tgccgcagtg gccatgggta cttattaaaa tctgggaatc   1560
acactttgta tgtaacattt cgatgatgcc aaaaggggaga agagagttgt gctttacaca   1620
cattctgaaa taagtaatat ttataaccta attaacctgg tccttgatgt aagtgaatt    1680
```

-continued

```
ttctaagttt agtattgatg gttaagctga gttcttacag gtcccaaata agtaaaaagc    1740
acagagtttg tcatcatcaa aaagggaat ttgttggccc aagaacaggt gaagttttga     1800
agatgacaaa agaactcaga catggaccag gtccatcttg tgaagcacag tcatgatcaa    1860
cctatacatg tgagatgcac gtgaaagaga taagtcttac tgattaagca acaatatctc   1920
ttgatctgat cgaaaggat gaagatagtg ttagagtttg agatcatcat gaactcttcc    1980
acgatagaag agcagcaatt gagtcacaat caaactctga ttactaaccct attaaatgtc   2040 agtttgttct cttttacagg aaatacacat acgcaaaagt taaactaaat tgagagcaaa   2100
agagcaaggc gattttgcaa gcaatttatg tggatttgag tgtgcactcc tgaagctact   2160
tgaacgagat agaagaacca gttccatcgt gtctatcttt ttctagttca attgtagtag   2220
gtggtttaaa ttatacccttt cagctttcat agaagcaatt gtattagata cctgagagtgt  2280 tcaagttata gctaacttga agttgtcgca acagttgagg ttgtgtgcca caacgggatt   2340
agagttaatc cttaggttta taagagtttt ttgtaaaagc tattttggct cagtgatttt   2400
agtggaagtt tgggaaaatc ctactgagtt gtaggtcatg gtttttttcac cttttgagcc   2460 aggtgttttc cacgtaaaaa tctccgtgtt ctttatttct gtatttatta ttccgcaatt   2520
agtagtagtt ggaacaccta gaaaaccaag ttcttctata gagtagttaa gcgaaaattg   2580
ggtgccacac aaacacccct ctagtgtggt attgacgctt aaacatcaat tagttaatttt   2640 ctggagcaac tagctactag ttgttattaa aatagttagt ttctttgtta gctaatatgt   2700
tgttttggtt gtaaattagt tccggtgtgt agtttggact ttggaagaag acttgtacca   2760
attgtgtttg ttattttctt tggtcttatg aatgctcaca ctaaacatca agttggtatt   2820
tgattttgca tttgaattag aagtagtatt gagacgtgtt gttgctatgc ataagtagta   2880
aaagattggt ttgagcttag ttggtttcgt gataagattg gaaataaaag aaatgtgtca   2940
aagttatgta aaaatcagta aaataggctg ctaccttta atattaccac aagtccacat     3000
ttattttagt tttaaacaat ataaatttgt taaggtaatc ttcttacaat agtctcaact   3060
tttaatttag taacagataa ttgcaaagtc aatccaacta atcatacact acccatatgt   3120 aaaaaaaaa aaaaaaaaa aaaaaaaaa aagtgaacaa tcaatgcaca aaaagaaaaa     3180
aaaatatttt tcttctttaa ttaattccat aacatagtcc ttaaaattag ttaattcttg   3240
ttttagaaaa attgtaacag tctagttaat tctccaaaat gaagcaaaag attttttttc   3300
ttaagtatta cgtcactttt tttattaatc caccaaataa attaaattag atttagttca   3360
ctaaataaac tcataagat cagatgtttt atttatttta aaaataactc aattacttaa    3420
tcacaaatga tcatgactaa ctcaaaagta atttgtttta acaaaaataa ttaatttcgt   3480
cttaaccgat gtcgggacga ctcattttgg aataaataca taaataaaat ggccaggtcg   3540
cgaggacacg tcatattcca attctttcaa ataagcttgt tatttattaa cttgagtagg   3600 ctccaattt aggtgcggcg cacgaactaa ggtcggagat attcatcttg ttagcgtaa    3660 gctagggttg gggatattcg tcctagtttg agattaatta agtcatcaac agtaaaagtg   3720
gacataggca aaacatgaaa accgaataaa gcacaattta tccataatta attcatgcca   3780
aatttaagtt aataaagcaa ctgtgctaga accacggact cggagaatgc tttacacttc   3840
tccccgatca acaaaaatct ttattcggac tttattttttg cagaccgata ataatagagt   3900
caaatcttcc tttgactagg gattcaaata aaaagtgact tggaacatgc aaaaatcaat   3960
tccaagcggg cgaatctgta aacaaaaaat ccttattcaa atttgtcact ttaattgaaa   4020
```

```
aactctttaa cccactattc ataacatata tattttgggg gtagaaaagg ggttgacagt    4080
tatgacctac tttatgcatc agtgttcgaa tttattttga tcaacaccct tttggaagag    4140
cgtttgatag aaatggttgg cttaataaac aatcatatta tcatcacctg cggaatcata    4200
tcattaactt tgaaaatta aaatggtttt caaagacgtt ttgataaaag aattcctatt    4260
gtcgcagttg aatctacaa gaccaagatg ttgatctagt gctatatttg gagaaagtgc    4320
cttaattaaa aaaaattgtt cattagttgt cttaagattt tttattattt aaaaaaaaat    4380
taagacacaa agaaacacat ttacgagtat atgtcggccg actaatgtga agttcccacg    4440
gacaacccac acatattgtg gtcaagatgg attctatcat aatcaaaagt catcatcaat    4500
tcaattctca tatttggcat ctcaagtaca tgcacaaaag caacttagga tgtaagttta    4560
tatgcacatt cttgaaatag aacctattta tacgtagtac ttaattagtt acagtagtat    4620
tatttattct ctgctacaga gctatggttt atcaaatata tcagattatc atttgttgtg    4680
taggccattt ccttatttgt acttggtatt aattctggca aaagcacaaa actgggaaat    4740
gaggttcttc ttccttaata tgagtcacag attagtacca ctactatagc caagaaaatg    4800
tgaaatcata tagtactaaa tattaatttc agatgccaaa accataaatt tcccctcctc    4860
catcattgaa aaccctctg tcctttcccc tagagagacc ccttttttcct ctctctctcc    4920
ttctctttt attagacgca tatattctct cttctttctc tttctagggt tttcacctga    4980
aatagtttta tttcggtgat                                                5000

<210> SEQ ID NO 97
<211> LENGTH: 5000
<212> TYPE: DNA
<213> ORGANISM: Nicotiana tabacum

<400> SEQUENCE: 97
atttaaaacc ctaaaaaaca agatttttat ctatctgcat ggtgaaggac aaagaggtct      60
tcaatctcag gttctttttt ttttttttt ttatatatat atcttgtttg ggtttaaggt     120
tattgggctg atgaatgttt taattttaac ataggtctac ttacgtagta gttataggtt     180
gataatgaga tataattaac taagtctttg tataatgcag atcctgaact taatctttat     240
ttgtattatt ttttttttgtt actgaaagat tctgttacca aattttatca gtctatttaa     300
ttagaggcca acgattgtta ggtatgtggc acttcgagtg ggaaatgata tattcccatt     360
aaaggtgtta attaaccacc aaattgttct ttaggtctgt ttgtcatttt gtattaaggt     420
ggatggttta ttatatat cttctctta atgctaatca tgcttaactt tttcatttag     480
taccagcaag catatttgtt tactttattg gttattcctt atcaaagtct tcatcttgtt     540
gcttttttt attgtacttt acaaaagatt tctagtatta atggaaagtg ctcatatttg     600
gaaaagaca tggccaacaa gaaatgtcta tatacccat ttcttcttct tcttcttttt     660
ttccgaaaat tcttattttt tgttttatt tctgtttctt gttgagtgct tcatggtag     720
aagaagaagt aggagattct tggacatggc tgcatgagaa ttgttaaata accccgtata     780
catacacaag tagtgttggc tgtctttgat atcaaaccat ttattgccct aatttctgcc     840
ttttgtcccc tcaacaaaac catcaaagtt ctcaagagg gttattctt gtttcccact     900
ttgcccccca cctattaggg ccaccccacc aaagggatct ctctcgtgtc tagtgttttt     960
tcccaaggac caccactcct ttttttttct ctaccataac ttcgtccaca ccatcttatt    1020
gtgatatttt cgtttaatga atttgcagcc atgccttcat tcatcatcag aactcagtca    1080
taagcacaga ttctgagaga gtaattaatg aatgaatcag tggtgatttg acgtaaagta    1140
```

```
tacatgatta tggtttttag ctgaataagc agagggagaa aatatataca tatataaaca   1200
agtagagtaa aagaatgacg caagattagt accaaaagag tgaaggaaga gatttaatat   1260
tatagggaaa agggaagtag taggtgatac ttgacaggtt gataagatgg ttattactac   1320
aagttgatgt attgacgcta actcacgcaa gagagaccta ctcactgtac aatatttta    1380 caagaataag cgattctttc tctctttact tgcaagaatt gtgtgttgtg tgagttgtat   1440
ggcgcatttt ctaggagcct gtggtagtga tggatgtatt catataatac aatacaatac   1500
atatggaata gatagataga taagatggtg cacgcatgag aggcaattat gcaacttacg   1560
tcaactactt ccatccatcc atctttctt ccttctgttt ctgtctgata tagtgagtat    1620
atgcttgtgc tggtgttgtg tgcttttctg gcctgggatt ttcctaacac tttagataat   1680
ttaggttccc atcaataata atgtcttttt agaggagcat catcgataga tattcaaata   1740
ttaaacctgg cctagctact atctagggcg tctgctaggt ttttccatta ccctttgtat   1800
atctcttatg tgggaccttt tgtttatgga agaatatgga gtacttttat tcatctcgta   1860
gggtcttgaa tacaagattt tatatatatc actctttaaa aatgaccatc ctaaaattct   1920
tcctcttcca tttgcattta ccagaattga tattagtacc taaactagta ctcttcactg   1980
aggccttttg tatttagtcc tattatattt gaatttggca ctatttaaat taaaaaaata   2040
atctacaata aaaattctt ccctaaacat tacccatcaa atactcacca cctaaggtaa    2100
ctctaccatg tattaatttt ttggatcaaa tctagtgagg attaattctc cacttatgtt   2160
ctttcggaac tggctaagta atcttcaaaa gctagggcat ctccgcagtc atatcgtgcc   2220
ctcccaagta tagcgaccgc ttctatattt tccctgaatt tcatctgtgc tagggcttgt   2280
tttcacgttg atttcaaaca aaggctaaca atttcattga gtaactttt ctcatttcag    2340 gactcgaacc ttaaacctct gttcaaataa cttctaagaa gtatatatgt atacaatgtt   2400
tgtattcatt gtgacaaagt attatgagtt gtacaacttt cttgtgaaga tagagcataa   2460
tgttaaacaa ggatctatat agagcataat gtcaacaaaa caacaacatc aacccagtaa   2520
tcatcctact aataggattt ggggagggta gagtgtacgt aaaccttacc catcaggggg   2580 aggggggtaaa gaggttatt tcgggagacc ctcggctcag agacaaaaaa atctataata   2640
acaacagaaa ccagacaaat aatatcagca tcataagaga caacaaataa gtggaatgac   2700
aataattatg ccaataataa cattgaaaaa aataaaatta aaaattaaaa ataaaaatag   2760
tgtgatgaac aaaaatcgct agcagtctta gacaaaacac tatcagacta gctggaacaa   2820
cgaggaaaaa cgctgaagta cccctaacc tacaacccta atgctcgaca tccacacctc    2880
cctatccagg gtcatgtcct cggaaatctc aaatcgcgtc atgtcctgcc tgatcacctc   2940
gccccattac ttcttaggtc gccctctacc tcttctcata cctgtcaaag ccaaccgtca   3000
cacctcctaa ctggggcatc taggcttctc ggggccggcc agcccgtaga tctaaaagga   3060
tccatccata gcgcccgaac catccacgcc tcgctttccg catcttgtcg tccatgggag   3120
ccacgcccac cttatccagc cttatccagc ctagtgtgcc cccacatcat ctcaacatcc   3180
tcatttcgac tactttcatc ttctggatac aagaattctt gactggccaa cattcagctc   3240
catacaacat ggtcgatcta accaccactc tataaaactt gcctttaaat ttcagtggca   3300
tgttagtatg tttactttag atacaatgtt ttttagagtc ttatagtctt gttagaatac   3360
tatatattat aaaatatgga gacttctggg cacttttgtt ttattttata taagatagga   3420
ttggaatgaa ttcaattgga gggacatgca tgataaatga atattcatgt agccgatata   3480
```

```
tgtttgggac tgaaacgaca ttattattgt gaaatatttt acaattgcat ttcacactca    3540
ctgaagtgaa actttgattc cacgtcggtc aatacttagg tgttacggtt tggctgcgag    3600
gggaatcgaa gagagcaaat taattaaagt atttaatgag gaatcatgag ttagttggtg    3660 gaattatatat agtcaaatga atgagttatt cgcctgataa tatagttgat agtagtatat    3720
actatatatg ttgatactag ttattggtgg tgacctaatt aagtaaagag aagagaagag    3780
tggttatgta aaggaatcta ggtatagtgg gggatggggg gaggcaaggt taaaagaaag    3840
gtggaaaatc caagaatcct gcttcctcta gtaacatagc atatcctgca attcgtgctt    3900
ttgtttcctc tcacaagata actacttttt tgattaatta ttacatttga cacatacata    3960
caaacctata aaattagaca tccttatgga atcttacgac tccgaacttg tcatatatcc    4020
tttaattatg cttagctttt tgctaaaaac aaaaaggata tccttattcc aaaatgcaac    4080
taggagcatc ttcccacatt tcttttttat gcctctgcat catcaaatcc cataatgccg    4140
cacaacaatt tctttttact taagtatatt ctagcttagc tatttcatac gaataatggg    4200
tatacaaatt tgcttatttt aggttttaaa taccgattta aatatattgg atgggttcaa    4260
cttttaaaat tcttcacactg atatacatgc atagaatatg tggaaaactt taatattaat    4320
tacaactgct aaacatttga atggattctt catgccgtgt gctcctttgt tgaagaacac    4380
gtactccctc cgttcgcatt tatttggcac gttttgactt tcacgccccc ttaagaaata    4440
ataaataaaa tgcataattt atcatgataa acatatcaat ttatgcatat tttattagat    4500
ttgagaaaat aatttgaaat gagtaataaa tactgtgagt ataacaggaa attttttttt    4560
gtcttctctt gatatgcata aaatagcaag taaaaataaa aatctatttt taatataaat    4620
gtcaagtaaa agtgaatgga ggaagtattt ggaagggcga tatcgaataa aaaagttata    4680
ctaataacaa acagcaacaa ttacaagaaa ctgtagagtt ggccagtacc aggtatatat    4740
gtagaatttt ttttatgagg aatttagtga aacgctagct atttcaacac ttcagacata    4800
tcaataccaa ttttatggtt tctcttaggt gttgatagat tctctttgt cagcaaacat    4860 tatttatgaa atttataata aaatgctgct cttttcgagt ttacattctc cgtcccaata    4920
caatatatac ttgatttgac gaaagaaatg taacaataga atcttaagtc ggaaaaagtc    4980
aaatcaaatt tgaaaaaaat                                                5000
```

<210> SEQ ID NO 98
<211> LENGTH: 5000
<212> TYPE: DNA
<213> ORGANISM: Nicotiana tabacum

<400> SEQUENCE: 98

```
gaaaactaaa aaagaactaa aggcatttac actaggtctt caccggggct cgtcccatca      60
ccagaacccg ttggcctcag gtctcttggc ttctttaatc ttggccgaca ggtcaaaacc     120
tcgggaatgg atatcctcga gggtctctct ctggtatagc cgctttacgt actcggtctt     180
catctttaag cgggcctcag ctatctccac atcagcctta tactgggcca gcatttcctc     240
gacgtcggag gaatcaatag aagttgcctc caacttggat ctcagcgcgt tatattcttg     300
gtcgagggca tcccattccg tgacggctga gttcagctgt gctcggagtt catcatttag     360
ccgagatcac ttgtcggcct tgtcctttgc cacccggagt tggtccttta tcgatgtcaa     420
ctcctctttt gcagcctctt tttccgaagc cagtaggtcc atcctgccct tctacgcctc     480
ggtcgtggcc ttgacctcat ccatctcagc ccgaagccgg tcgatcaggt ctaccttctc     540
ttggacctgg gaagttgcgt tgttagtcac cacgagtagc ttctcatttt tagcctcaaa     600
```

```
gatccttacc ttctcgacca agtcagcgtg ctcccacttc atggacaagg cctccttctg    660
agccttttcc agctcggctc agagaattgg gaggtacttg agggcctcgt cttattgttc    720
gctgagagac ctgtaaatgt ccttctcccg gatcagttct ttaagctcga actcaagctg    780
actgatttgc aagagagacc gaaggaagct ttcatgatga agcattcaaa tctgaaatat    840
aataaggtca ttagaatatg cggagcaaat attcgcaaag gatacaaagg atagacgtct    900
tacccggttc aatgcctatt gcacctcgtt gaagaggctc tacgtgccta cttcattcat    960
ctttgcctaa tccttatcgg tcaccaggca acgaaggtag ctggctatgc cgaccggagc   1020
ggacagggct cgggcgtcca tcgggatagt aagaatgacc attctcttac ggtcggggtc   1080
aacacccggg gggagggaac ttcttcacta gtttcgggct caagctcgag ctcggcttgc   1140
tcgctcccga tgacacatcc tttttgggga cctccaggtg accaagcctg agaagtcct    1200 ccaatgcgac catgtccatg ccatcaaaga acgtgttgag ggcattatct ggacccgacg   1260
ctatctcatt taatttctct ttattagctt gaacctcttc gagcatggac tcagtatagg   1320
acggcgtctc tgcgatgtca atgatactag ctacatcctt cgggacagga gcggcttctc   1380
gataggccat ggactccgtc tctccctctg gttctcgagc tagaggggga tcgacctctt   1440
ggtcaccttt cctggttgcc accttctccc tctcgttgag ggtcgactca tgagcaatga   1500
actcaaggtc gtcatcctca ggataatccc taagccggta gagggaatca gatttcggta   1560
ccctcgactt ggtgctcttt tgttttttct ggacctggac gaccaccctc ttcttcttca   1620
cctcgacatc cggggagcct gtggatttcc ttttattctt cttttttctct tcccttacgg   1680 cggcctcggg ctgtcccgaa gcggagggtt cagcgagcga ggacggatcc tcgtcctcat   1740
ccaatggctt gagctcggtg gtcatgggtg aacctgtgag aagaaagaag acttagcgat   1800
atattcatca agtatatgaa tgtaatcatt cgggagagag actcactatg ggaacgagcc   1860
tcccatttgc ccttcgagag cttgcgccat acgctcgaag taggacatct atttgcacat   1920
cccctcgatt cactccttga agcaggggaa tgtattagga acctgggcaa ctgctacata   1980
atggcaaata caggcaatta gaaaaaagaa taaaggaaaa tgccagatac tcgagaggga   2040
aaagacttac gggatgcgtt tcacttttg aggaatggta gaaattcgga gaggatgagg   2100
tcttcggttt tcacccgaac gaacctcccc taccaacctc gatctcggtc ctcgtcgatg   2160
ctcgagaacg gagccttgct tgctcggcga acgatcttaa tcaaccctc tcggaagatt    2220 cgaggactgt atagatgaag tagatgttcg agggtgaact gaggtgcttc agttttgttt   2280
acaaagtgtt ggaggaggat tacgatcctc caaaaggaca ggtgaaggca gaccttgcac   2340
cttttataga tgtcgaggac tatggggtcc accgggacga gcgtgaagga gtaagtgtaa   2400
acacttaggt accccctccac gtgagtggtg atgtctttgt tgggcccggg gacgaccacc   2460
tcctttccct cccagttaca ctctacccga actatgggta gtgtctcctc agtaacagag   2520
catatgtacc tccatgctcc ctcgtctcgg tcctgttgac tggaggcttt ctcgacgttg   2580
aagtcattct cgatagagca gcccccgagt acgaagctct tcaagggagg ctcatgggct   2640
acctcaggaa tggccacctc ggcatttatg ccagattgg aaaataaagg agcggtttgt    2700
tgaggaacga atttgaaagt ttttgctatc gggttctgaa aaatatgaag gtttgaagaa   2760
aaaatatgaa gatttgaaga tagaatggaa atatgaaggt ctgggttgaa gattgaaaga   2820
gaatgtatga agattgagga tgaaggtatg aaaatctaag gagcaatcta tgaagatttg   2880
aaggagttaa aggtatgtaa agaattcaag ggtaaatcaa ggagctctag aatcgaaaag   2940
```

```
tggagaagtg aaaaagggqt cggagctttt atagaggaag gacaatcaat gcatgacgtt    3000
tcacattcga ggacagtcaa tcaacggccg atacgtgtcc gatgttagaa cgatgcgact    3060
aatgggacgt ttcattgatc cgtcatctcg gttgtaacgt acgaagaaag gaatcggggt    3120
tcatttatcg cttcccgtcg tttcgataaa tctatcctcc gaaaaacaag gggactatct    3180
gtatacgggt aaaatcaggc aatgtctacc ctgattctcc tataagagaa taaaggggga    3240
gcgcggatcc gcgagattgt aatcgaggac agagacccat cgtatcaaga tccaagaaga    3300
gtgaacgata tatctaacat cagacacggc aaagcgatgt accccggacc gaatataact    3360
cctagacctc gggagaagcg ggggacggtt atgcatgaca gataggagac tgtatactcg    3420
ccctcaatcg gatattacga cgcgaatctc gtcagtaaca attatggatc aataattact    3480
ggaaaaagaa gatttttacc tttttagac ttatactagg actgaaattc tcgtactata    3540
taaaggtaaa gttttctttt gatctgacac attgtaacac gcaattcaaa gaaataaaaa    3600
tttgttttg ccttctaact aatgttaaaa attttgctca cttgttctgt tcttcattca    3660
cgactggact cgaaccgagg gtccaatcga gtacgaggtc actgttcaat ctaagatcat    3720
gcttggtcat aacattgcga ttggtttgat catttatttc gtctttaatt catttatctg    3780
ttatttttaa ttattcgtgt tgaattaaat cacgtatcat ttaaaccgcg tacaaattta    3840
attgttaccc atttttaagg taaacaacta tagacgaaaa aaaaaatata aatattaaat    3900
attatgtttc gaaagataca caatagacaa gaaaagaaaa gaaaaatccc ttataaaatt    3960
tggatttagc ccaccagttt tattgagacg tctttgtgtg ttagttaccc ggcaaaggtt    4020
atgaacctac tttatgcgtc aatgtccgaa tttattttta tcaacatcct tttggaagag    4080
cttttgatag aaatggttgg cttaattagc aatcatatta tcatcacctg cgctttggtg    4140
ttatatcatt cggaatcata tcattacctt ttgaaattta aaatggtttt caaagacgtt    4200
tcgataaaaa aattcctatt gtcgcagttg gaatctacaa gacgaagatg ttgatctagt    4260
gctatatttg gagaaagtgc cttaattaaa aataaaaaat tgttgatcag ttgtcttaag    4320
atttttatt attaaaaaaa aaaattaag atacaaagaa acacatttac gagtatatgt    4380
cggccgacta attaatgtga agttccacac ggtcaaccca cacatattgt ggtcaagata    4440
gattctatca taatcaaaag tcattatcga ctcaattttc atatttggca tcttaagtac    4500
atgcacaaaa gctacttagg atgtaagttt ataatcattc attcttgaaa tagaacctat    4560
ttaatagtac ttaattagtt acagtagtat aatttattct ctgctaaaga gctattgttc    4620
atcaaatata tcagattatc ctttgtggtg tagaccattt ccttatttgt acttagtatt    4680
aattctggca aaagcacaaa actgggaaat gaggttcttc ttcattaatg ttgagtcaag    4740
attagtacta ctactatagc caagaaaatg tgaaatcata tagtactaac tttcccttct    4800
ccctagctac tgataactct aattaatttc agatgccaaa accataaatt tcccctcctc    4860
catcattgaa aaccccttg tccttccccc ccagaccccc ttttcctctc tctctctctc    4920
cttctctttt ttattagacg catattctct cttctttctc tttctagggt tttcacctga    4980
aatagtttta tttcgttgat                                                5000
```

<210> SEQ ID NO 99
<211> LENGTH: 5000
<212> TYPE: DNA
<213> ORGANISM: Nicotiana tabacum

<400> SEQUENCE: 99

```
attataaggg aaattaaaac cctaaaaaca agattttatc tatctgcatg gtgaaggaca      60
aagaggtctt caatctcagg ttcttttgt ttttttaact tgtttggata tgaggttatt     120
gagctgatga atgttttaat tttaacatag gcctacttac gtagtagtta taggttgata     180
atgatatata tttaactaag tctttgtata atgcagatcc tgaacttaat ttttattttt     240
attattttgt tgttaatgaa agattctgtt accaaatttt atcagtctat ttaattagag     300
gccaaagatt gttaggtatg tggcacttgg agtgggaaat gatatattcc cattaaaggt     360
gttaattaac caccaaattg ttctttaggt ctgtttgtca ttttgtatta aggtggatgg     420
ttcattatct tctctttaat gctaatcatg cttcacctt tcatttagta ctagcaagca     480
tatttgttta ctttattggt tattccttat caaagtcttt atcttgttgc ttttttttt     540
attgtacttt acaaaagatt tctggtatta atggaaagtg ctcatatttg gaaaagaca      600
tggccaacaa gaaggtgta taccccattt cttttctt ttctccaaat ttttttttt        660
ttttttctg tttcttgttg agttcttca tggaagaaga agaagagtag gagattcttg       720
gacatggctg catgagaatt gttattgttt tgtgcactta ataacccgc tatacataca     780
caagtagtgt tggctgtctt tgatattgca ccatttattg ccctaatttc tgccttttgt     840
cccctcaaca aaaccatcaa agttctcaaa tagggtttat tcttgtttcc cactttgccc     900
cccacccatt agggccaccc caccaaaggg atctctctcg tgtctagtgt ttttccccaa    960
ggaccaccac tactttttt tttttctcta ccataacttc cacaccatct tgtgatcttt    1020
cgtttaataa tgattttgca gccatgcctt cgttcatcag aactcggtca taagcacaga   1080
ttctgagaga gtaattaatg aatgaatcag tggtgatttg acttatacat gattatggtt   1140
tttagctcaa taagcagagg gagaaaatat atataaacaa gtaaatctag tagaagaagt   1200
agaagtttta tagctagagt agtgggaaag aatgacgcaa gattagtacc aaaagagtga   1260
aggaagagct ttaatatagg gaaaagggaa gtagtaggtg atacttgaca ggttgataag   1320
atggttacta ctacaagttg atgtattgac gctaactcac gcaagagacc tactcactgt   1380
gcaatattta caagaagcga ttcttctct ctttacttgc aagagttgtg tgttccgagt    1440
tgtatggcgc atatgaacct tttttcatac aatacaatac atatggaata gatgataag   1500
acggtgcacg catgaggcaa ttatgcaact taacatcaac tacttccatc atctttctt    1560
ccctctgttt ctgttctgt ttctgtttct gtctgatata ctatatgctt ctctggcctg    1620
gattttccta actctttga taatttaggt tcccatcaat aatgtctttt tagaggagca   1680
tcatatcgat agatattcaa atattaaacc tggcctaggg ctaggcgtc tgctaggttt    1740
ttgcattact ctttgtatat ctcatctgtg ggacctttg tttatggaag aatatacttt    1800
tattcatctt gttgggtctt aaattcaaga tttaatatta ctctttaaaa attaatgact   1860
atcctaaaat tcttcctctt ttatttgcat ttacaagaat tgatattagt acctaaaact   1920
cttctctggg gccttttgta tttagtcctt ttatgtttga aattgacact atttaaataa   1980
aacataatct acaataagat gttcttcacc cttcggttg cccggttggt ttggatggga   2040
tcgattcccc cgatatcttc tgggttgagc atatcgcaca gggcttgtct agtgcggttt   2100
gcattcccta tgtggtttgc attccctatg tggtttgcat gctattatac atgggtttac   2160
ccagtggaca caaagtattc aatacagagt gttcacccga agaacagagg ctgtggcaaa   2220
gattgtaacg gccgcgggtt tcccctctta caaaaaaaaa aatgttcttc cttaaacatt   2280
```

```
acccatcaaa gactcaccaa agatagctct accaagtatt attttttggat caaatggcat      2340 ttccacggtc atatctcctc cccccccct caccccccc cccaaagcta gtgatcactt         2400 ccatatttt tcctgatttc atcggtgctc aaatacttgt tcattcatct tcattccaaa        2460
caaaggcgaa aaacttcact attgagtgct ttttcctat tccaagtgtc aaaccctaaa        2520
cttctagtca aataatatct aagatgtata ctcttatact atgtttgtat tcattatgac       2580
aaagtatgat gagttgtaca attttcttgc ggacttagtg aaaatagagc ataatgttaa       2640
aaaaatattt acatgatatt aattagccgg attaagttta taacgttagt atatatgtct       2700
actttaggta caatacaagt cttatactct tgtcagaatt tatatgtcac aaaatataga      2760
aacttctagc tactttttt taatttata taatataata ttggaatgaa tttaagtgga         2820
gcaaaagtga atattcatgt agtcgatata ttctaatctg tttggggctg agatgacatg       2880
attgtagtga aatattgtac cattgcattt cacactcact gaactgaaac tttggttcca      2940
cgtcggtgat catttgcatg tttcattagt caatactgtg gctgttatga tttggctgcg     3000
agggggatcg aagagagcac attaaagtat ttaatcagga tttatgagtt gaatgctgtt      3060
agttggcgga attaatagtc aaataatgaa tgagttactc gctgatatag ttaatagtac      3120
tccgtatata tgttgattct agttattggt ggtgacctaa gtaaagagaa tagatgagag      3180
gagtggtggt atgtaaagga atctaggtaa aggggtgggg gtgggggag gcaaagttga       3240 aaagaaaggt ggaaaatcca agaatcctgc ttcctctagt aacatagcat atcctgctat     3300 tcgtgcttt gtttcctctc acaagataac tactttttga ttaattatta catttgacgc       3360
atacaaacct ataaaattaa actaatcaac gacatcctta tggaatctta cgagtccgaa      3420
cttgtcatat ataactttt aaagtacttt gtcacttctt aatatgctcc tttaattgtg       3480
cttagctttt tgctaaaaaa caaaaaggat atccttattc caaaatgcaa ctgggagcat      3540
cttctcactt ttctttttta tgcctctgca tcatcaaatc ccacaatgcc gcacaacaaa      3600
ctcttgttac ttaagtatat attctacttc ataagaataa tgggtataaa aatttgctta     3660
ttttatgttt taaataccac cgaaaattca taagcaaatt caggatttaa atatattaaa     3720
tgaattcaac ttttaaaatt gttgcactta tatatatata tatatatata tatgcatatc     3780
caagttgagg gatacgggtt cacatgaact catattactt tctctaaacc atgtataaca     3840
atgttatatt ttttcaaaat tatttaaata tatgtgtgtg aacccattct caaaatctct      3900
tatggtgcaa ttattattgg gtgcacatct acaagtgaaa tttgcagctc aaaacctcat     3960
ctgggcggtc ttgttttccg catggagtat aactatatat gtgaaaatta ctagaatttc      4020
aaaatgaata taatttgaa atgttgtggg ttcctggtaa gagactaaag ttaaactcgt       4080
caaatataaa ttctagatcc acctcttcac aatagtgcac ccattctttt gaaattctgg     4140
atctgcctct gttaataata tatatatata tatatatata tatatatata tatatatata     4200
tatatatata taaacacaaa aaaatatgtg gaaaacttta ctattaatta ccactgctaa     4260
acatttgaat ggattcttca tgccgtgtgc tcctttgttg aagaacacgt acttgggagg     4320
gcgagatttc gaataaaaaa gttatactaa taacaaacag caacaattat aagaaaatga     4380
aaataaaagg gaaagagcac tcacataaac tagaaactgt agagttggca agtaccaggt     4440
atatatgtcc ttgaatgttt tttacgagga attgagtaaa acgctagcta tttcaacaca     4500
tatataaaaa gcatcaatac caattttatg gtttctctta ggtgttgata gattctcttt     4560
tgtcagcaaa gttcttgcat taactatatg aaatttataa taaaaatgct gctctttaa     4620 ttgagtatac atgcagtctc ctaacatata cattctccgt cccgatatat acttgatttg     4680
```

| | | | | |
|---|---|---|---|---|
| atgcatttca | aaaattaaat | gtttgagtgt | tttggtgaat | tgtgcttgat | atagaagtat | 4740 |
| ttaaaataag | aaagaaatgt | aacggcagaa | tcttaagtcg | aaagtcaaat | taaatttgaa | 4800 |
| aaataaaaaa | taatactctt | gatacttact | agtactagtc | aatgggcagc | tctttcggga | 4860 |
| ctaaccaaaa | gcattattct | tattgttttcc | ggcatagtat | taaaatgtaa | caatgcttaa | 4920 |
| ttatgttaca | aaattaatgt | ttttgtggac | ttcggaataa | tttatttctg | aattcgccgg | 4980 |
| tgttatcgaa | aacatgggga | | | | | 5000 |

<210> SEQ ID NO 100
<211> LENGTH: 5007
<212> TYPE: DNA
<213> ORGANISM: Nicotiana tabacum

<400> SEQUENCE: 100

| | | | | | | |
|---|---|---|---|---|---|---|
| tgggggccct | ccgcacaagg | gaggagctag | gggaggcaag | aaaattacat | gtgtatataa | 60 |
| gattaaattt | tcttcttctt | ttttgtgtat | aggataaata | tttaattttc | ttaattttt | 120 |
| tgcgtagtta | ctcttttaat | tatttttaac | tcctctgaac | gcaagtctta | cctccgccgc | 180 |
| tgactcctct | agagaggagg | ggtctaaatg | catgcaactc | aaacgacgaa | agggtctttg | 240 |
| cctaactaaa | ggttccttat | tctaatatat | ccttctagaa | aaggtaatag | aagttgattc | 300 |
| gaatatcaaa | gagagataca | tgtcggttac | aaaaataatt | ctcaagataa | tcaatagaca | 360 |
| tctctagatt | ctcggactta | aagatccat | ttagacacat | aatcatattt | tttttccaaa | 420 |
| caatcgtcga | aggcagcttg | ttgcacaaaa | tatttcgtat | ttacataagg | tttaaggaaa | 480 |
| aatcgtactt | caaagagtat | gatgtagata | atacattcta | attagggtcg | gctctatagg | 540 |
| tgtaaggcaa | gtgtcttagg | ccccaatttt | gggaggcccc | attttttagt | aatactatat | 600 |
| attttagagg | tttataattt | ttttttaaat | aattaaataa | tatatatagt | atttttttac | 660 |
| ttttcatata | taaaaaagaa | aaactttaaa | tatattaata | aagtaaagat | taaaatagta | 720 |
| ctaaaaaata | gttgtcactt | tgatttgatt | tgacaacttt | acttttgct | cttcttccca | 780 |
| aataattcct | agacccaatc | caacatttca | attttcatat | agaaggatga | gacatagtaa | 840 |
| catccttct | tcctttcttt | tgattcgtgc | tcatttgtt | tctactagat | ttctttcttt | 900 |
| ctccaaaact | ccaacaagcc | aacaactaca | tattttgaaa | tcaaagtctt | caaatttttt | 960 |
| gaatcagtta | gtcgggtaat | atcattctaa | cttttagta | ttatttttat | ttattattta | 1020 |
| ttatttttatt | aatttaccca | tgtacatatt | gtttaatttt | tttagaatat | aaatatgtct | 1080 |
| acaagaaaat | atgcatccgg | atattcaaaa | atccaaaaga | aaagaaagt | tgaaaattta | 1140 |
| ataaaatctc | aaaaggagt | tctcgagaat | tttgacaaa | taataaaaaa | actaaatcgc | 1200 |
| aaaatgtagg | agaatattct | gtagatgaac | aagtcactaa | ctttgagtca | gatgataaca | 1260 |
| aaattcaaat | tgaagaagat | gtttatgaga | atctgacga | agaaacaaac | tttagcctta | 1320 |
| ggccctatat | taaactttgg | ccctaggcct | catatgagct | tgagtcgccc | ctaattctaa | 1380 |
| tacaagtatt | agtggctact | ttcacggctt | gtgacttatg | gattacaaac | aactttacag | 1440 |
| ttacgtcaag | gctccacgta | gttctcaatt | tatggagcat | atattagatg | attaacgcag | 1500 |
| ggaaagattc | tgctctcctc | tgatacatgg | ctattattcc | tcgtttagtt | caaaaggaa | 1560 |
| aagagggta | gtcttgttat | attattgggg | aatgaattat | ggtttcaaac | ttttcaaact | 1620 |
| taaggattt | tgtacatggt | aaaacctaaa | ttgacacgta | acttggtact | ttcaagaca | 1680 |
| cgatcttttta | cgcgatattt | taaataaaga | aaagatcaag | tcaaacatg | ggccaaaaag | 1740 |

```
aaaaaccccca tgattttttc tgataaaaag ctgctaactt ttagtttgtt ttatccaata    1800 aaacatctttt aacggtctgc ctgctttagt ttaatcctct ttttaagatg taattaagca    1860
taaaatagaa aagggaaaaa aaaggtccat tggattttgg aagaaatttt aagaaagtac    1920
aagaactagt aaagtcattt tgtatagagt atgttaaaaa ggtgagtgac aattcgaaaa    1980
agaaagcatt gataagtcaa tcactaaata aaaaagcaca cctaataatc attcattcaa    2040
aaaaacaaat ttctatgaaa gataatcatt atcataagtc actgcagaaa tcccatatac    2100
agtagagtac caggatttta cgataaggtg ttagcaaact atctattcat ttttgacaa     2160 gcattttatg tttggtcatt tgttgggaaa aattagggag aaatttaaaa atagttagat    2220
ttacaactgg tcattaaaaa tagcccaatt tcaaagtaa tcgaaattta gccacttttc     2280
atgtaaagat aaatctgagc gaaaatattg ttcaaaaccc ggaaaatacg cccgtatatt    2340
atactggagt tccagcataa gtatgcttga actccagcat attatacggg agttctagga    2400
taactatgtt ggaactccag cataatatgt tggagttcca gcataagtac actagaactc    2460
cagcatatta tacgggagtt ccaacaagta taactgtccc gtataatata ttggagtttg    2520
gagcaccggt gctccagtct cccgtatatt atacaggagt cagcaaagta taccggtcca    2580
gcataatatg ctggagttcg tacacagatg caccgaactc acgtatatta tgcggaaccg    2640
gtctctgttg cagcaaaata gtggctattt tcattgact tcgtaaacgg tggctatttt     2700
tgaatgacca gtccgaaaac tggctatacc gtgctatttt gacgaaaaat tatccccccca   2760 cccacccacc cacccaaacg caccttacac acattagtgc acatctttta actagttttt    2820 ggttatttttt ttatttgatg cccgatattc gtatatggat ttcgattaat tagaattcac   2880
accgaaacat tctttcttag gattttgtac atacttaata tgcgaataca aaacctatgc    2940
ggaaaggtaa gggaacctat tcatccctct acagtacttg tgataatgtt atactttttt    3000
gaatttaatt tgggagacat gtcaatcttt attttgaaaa aaaatagaa taaaaccata     3060 gggaaatgaa caatttatct ttcactccta tctcatttta tttgtcttga attttttcaaa   3120 attttgaatt atattttgaa acttcttcaa tttatttttct tggaatcttc agaattcaat   3180
ttaaaattcc aaaattccaa ggatttagct cccgtttggc cacagatttt ggcttcattt    3240
ttttaaaaaa aattttgaaa acattctttg tttatgcaat atgatcatgt tttagggga    3300 aaaaattaaa aaaaataaaa aaaatcaaa ttcccaaaaa ctggttaggc aattttggga    3360
tgatattttt tcttccactc acaaaacttt aacatgtcca aacacaactt caacttcaaa    3420
aattattttc aacacaattt taaaaactct tttttcaagt ttcaatcaaa tctatatcca    3480
aatgttagct tagtatcaaa taagtgattg aaatcaaatt aaaatcgagt ggtaaataaa    3540
atagaggaga gctcggtaaa ttacaagagt gcggtaaatc ttttctcctt tactctcact    3600
gtagcctatt ctatctgttg taactaataa gtaactgagc tacggaaaaa gtgcctagac    3660
ttttaacttc acaagtataa taaatagaag tcaattcttt cataatattg tttccatcct    3720
atcaaacaga ctttgtctca ctgaccttcc ttctgagtgt gtcttttata tgtcattttt    3780
agtgaatcca tatgatttag agactctaat attccacatg cgggtcttaa tttggtgtat    3840
atgtatatgg taataatttt tgttaggtag ctgtagtatt ctattattgt tatgtattga    3900
ctcatcatgt aaataaagcc ggttagataa ggctagaaaa atatgagtat acctagaaat    3960
tattagcata ttgtttggaa catgtcaaaa atttcaatga cctagctaga gctgtcaatt    4020
agtcaaataa ctttattaat atttacttat gaaaacactt tgaaattctt ggagtttaag    4080
ggaaagacta ctgactaaaa aacaaagcaa aagtctatgc attactatac tatacacagc    4140
```

| | |
|---|---|
| acagcatttt ccaatagtat ttgagatgaa tctccaatca gctactgttg ttcttttctt | 4200 |
| ttctttattt agtttaagtt ttatgtgttg atggtataca aattatttgc acaatcaaat | 4260 |
| ggcttatctg gataatatag gtaaacctct tgtaatcact aattggtaat ctggtaaaaa | 4320 |
| taacactatt tctattccaa tttatgtgat caatttcact agacaaaaat ttaagaaga | 4380 |
| ataaattttt ttagaacttg tagtcataaa caagttgtaa catttgtatg gctataattt | 4440 |
| ttttaacttg tgatgttaaa catgtcagat tgtttgtgta gctataaaag ttttttcatta | 4500 |
| ggcgtaaaat taaaaattta gattaaatta ttattaaatt tagaaagagg tcattttttt | 4560 |
| tagcgaagta aaaagaaat cggttcacat aaaccgaaac atagagtaag taatctgtta | 4620 |
| tgacaaatta aaaattactt gtagtgtaaa aaaatctta caacattcgt gtatatactt | 4680 |
| aaatcttttt tatttttgg caagagatag ttgttcagca aaagtaagtt agaaataggt | 4740 |
| ctgtccttct gactttgtaa ctctgaaatg aaaatttcaa aatcccttct attttctt | 4800 |
| tcccccccc ccccctcac aaaccccaac tcactcttat ttaataaaaa gctctactta | 4860 |
| gaaaagacac ccttgtccat ctgtctatat aggtagaatg agagtaaagg agaaaacata | 4920 |
| tcctcctctc catttctgta gacaaagatt ctcaaagaga aacaaattaa acactagaga | 4980 |
| gtgagagagt gctataagaa aaagaat | 5007 |

<210> SEQ ID NO 101
<211> LENGTH: 5000
<212> TYPE: DNA
<213> ORGANISM: Nicotiana tabacum

<400> SEQUENCE: 101

| | |
|---|---|
| agaagaaatg actgttgaaa agaaaacaaa tgcaagtacc attaggaaga tttgaaaggg | 60 |
| cgtttgggta tgggggttgc caagaagatt cagactttt ttggggtttt gtgtagttgt | 120 |
| ggtagaatta ttattgaatg aaaaaaaaaa acttcctgta ctttaattcg tcagtacata | 180 |
| ctacatacta ctacaaagta gttaaaagcc tattctattt gtgcttttt tttcactcga | 240 |
| tgttcaataa ttatattggt ttttgattaa atttgaattt gagcaaggaa gatcaacatt | 300 |
| ggagggataa attgtttcct aacgaaggcg attacatact tagaacttga actcaatatc | 360 |
| tctaattaaa aatgaagtaa tacttataat aactccacca caattcttat tgttgtgcat | 420 |
| ttctttataa aatatgtaaa taatgggtca tatatattgt ttacctttc tattcatata | 480 |
| catagatttt aaattaatta tacacatata tataatacat taattattca tatattatat | 540 |
| ttttgctagc tattttagt ttaagcgatt tggtaggcga ctacttgggt taattctttt | 600 |
| ttttaatat atatatcaaa ataatgaagc tgtataatac acttaaaaat catatttgaa | 660 |
| aggtattaaa tacgacttag gagagttctt aaaccatttt ggaaccttgt ctacgtactt | 720 |
| ttatgcaata gctgttttg tttgtctctg ctaaaaccta tgctccccaa ccgtgcacca | 780 |
| atcaacttag aagttagaac tcagaaataa atgtaactat actccacaga agttaaaaa | 840 |
| gttttactgt taccattcac tcaaggatca gaaactgaaa gacaaatgaa tcagtgcttc | 900 |
| actgttcttc actaaaagaa atactgtta cattagtttc aaaagagttt aatcataaaa | 960 |
| acaaatgtac cataaaaagg ggagattatc aacctgaaaa tgaaacagaa catacgttat | 1020 |
| atatcaatct atatacggtc gagatcggac tcgtctatta cacgacagat cgggattgaa | 1080 |
| acgtaacagt tttgaagatc aaccccgggt tccgtcggac cgaggtacaa ggtcagaatg | 1140 |
| cccgttctcg agaacatcga gtccatgacc ccagaatcaa ccctgacccc aaatgagctc | 1200 |

```
gaggaaacat ccggataacg gaaggcgaaa tatccgtaac cggtcgggta tcacggcatg   1260
aatttcggca cgtaacaatg agaaaccggc taattagcaa atcatggaat tttttacctt   1320
ttatagaatt gtaactaaag tgggattccc ctactatgta aaggggtct  gactatttgt   1380 acgggacatt cattaaacgc atcccaaagt aatataatat tattttcttt ttgtaagcta   1440
ttgttctcct gtatctgata ctatttgaat tgcatcaagt tcaagtgaga ctcattttt t  1500 caaggctata attgttcaag tcgcacggtt tgaatttatt cgatcattgt tcgctttaat   1560
tacaattcaa ttcatcgctt tatgtcaaat taatccacat atccttaaaa ccacttacaa   1620
atttaattgt tatcaaattt taagggtaaa cagtttggcg ctcaccgtgg agctaaggat   1680
aatagtggtt gtttgatata gattttcata acacacacta ttttacaatt gttcttcgaa   1740
gtgtctctca tttcaggttt aagctcaaaa tgtcaaactc acaattggca ccctacctg   1800 cacacaatga gtctggtcac catggtgaaa ataacaacat agcacctggt aacgaggtac   1860
cgcccgctga tcccatcaga atttcaatcg cggacccgtt ggacgctaac tcgcatgtgg   1920
ctatcgacat gttacagtct caacaggcga cgatagctca gttacaaaac caaagccgca   1980
caccgagcag agttgaactc gatccgtccc ggaaaatcac ctgcagggaa gaaccgtccg   2040
cggagaggtc aaatggagat gagtcgggga ctaaccccga gatcataaaa atgcttgagg   2100
aaccgatgat acggattgaa tcaggggaaa agaaaatcga ggcaaatgac aagaaggtaa   2160
aaacttacaa tttcacggtc aaccaaatcc cgggagcacc gccggtactg aaaagcttgg   2220
attccaagaa gttcgtgcaa aaacatttcc ctccgagtgt ggccccgaaa tcgatcccaa   2280
aaacatttat atgcccgaga ttcttaagta taatgggaca accgacccaa acgagtatgt   2340
cacttcttac acatgcccta tcaaagggaa caacttagag gttgatgaga tcgagtctgt   2400
tttgttgaag aaattcggag agaccctgtc aaatggagct atgatatggt atcacttacc   2460
tcctaattct attgactcat ttgcaatgct tgcaaactct ttcgtgaaag cacacgccag   2520
ggctatcaag gtcgagaccc agaagtcgga cctcttcaaa gtaagacaga aggataatga   2580
gatgctcaaa gagtccgtgt cctagtttca aatgaaacag aaggacctac caccggtcgc   2640
tgatgattgg gccgttcaag ctttcaccca aggactcaat gttcgaagct cggtggcttc   2700
acagcagttg aagcaaaatc tgataaagta cccaactgtt atttgggcca atgtgcataa   2760
ccgctatcaa tcaaaaatca agtcgaaga  tgatcaactt gaggctcttt ccgggtcggt   2820
ttaccctgtc agactcgtcg acagaatcaa gagagatatc gaccgtgaac caaggtcaaa   2880
cgtagatcat tactagccat atgatggaga ttggaaaagc aataggtctg ggtgaagttc   2940
tacacagaat gaaaagagaa atgatccagg tcagagcact cgaggactcg caagcaagaa   3000
cgacttcgac aggcctatca ggcctaaaga agcaccaagg ttatcgaaat ataactttaa   3060
tattgatgcg gctgccatcg tatcagctat cagacgcatc aaagatacca aatggcctcg   3120
acctttacaa tccgatccag cccaaaggga tcctaaccaa atgtgcaaat tcatggcac    3180 ttctggccac agaataaagg attgtcgacg gttaagagag gaagtagccc ggttgttcaa   3240
taacgggcac cttcaagaat ttctgagcga ccgagccaag aatcatttta gaaataggga   3300
ttctaacaaa tagaccgaac cagaagaacc tcaacacgtc attaacatga tcatcggtgg   3360
agtcgatgcc cctcaagtgc tgatgttgaa gcgcaccaaa gtgtccatta caagggaaaa   3420
acggactcga gattacatat tagaaggaac cttgtctttc aacgacgagg atgcagaagg   3480
gatcgtgcag cctcacaatg atgcattggt aatatctgta ctcataaata aatctcgagt   3540
taagcgtgtg ttaattgatc caggtagctc aaccaacatc atccgattga gggtcctaga   3600
```

```
atggcttggc ctacaagatc aaatcatgcc tgcagtccga gttctaaatg gattcaacat    3660
agcatgcaaa accactaagg gagaaataac attgccggtg aataccacca gaaccatcca    3720
ggaaaccaag ttttatgtga tcgaaggaga catgaggtac aacgctctgt tcgggaggct    3780
aaggatctac agcatgaggg cagcaccctc gactcttcac caagtgttaa agttcccaac    3840
gtcgggaggg atcaaaacaa tctacgggga caaccggcc gcaaaagaaa tatttgcagt    3900
cgaagaagag atcccggtat agacactagc aacatcaaag gaaccgagtt cggataagaa    3960
ataataggct aaatagcaat tatcgacacc agccacgacc caatcggata aaaaggggac    4020
tgatgaagat gatgattatg gggttcccag atcttttata gtccctgatg attctgacgc    4080
caccaaatca atggtcgagg agctggaaca ggtcacatta atcgaacgtc tacccaatca    4140
gaaggtatac ctgggcacga ggttaacccc cgagcttagg aaaaactcat tcaatttctt    4200
atagctaaca tagactattt tgcttggtcc catattgata tgacagggat cccaccggag    4260
ataatcattc aaaagctgag cctggacttg aaattctacc cagtcaagca gaaaaggaga    4320
ccccagtcaa aaatcaaaca tgctttcatc aaggacgagt atttgcacaa aactttcaac    4380
atattgaaga agtacaatat gaagctaaac ccggagaaat gtgcattcag agtcggatca    4440
ggtaaattcc tcggattcat ggtatccaat cggggaattg agatcaaccc cgacaagatc    4500
aaatccatca agatatcac gatcgtggac aacgtgaagg ccgtgcaaag attaatcggc    4560
cgcatagccg ccttggggca attttatctcg agattctcag ataaaagtca ccggttcatt    4620
tcgctactaa agaagaagca caacttttcg tggaccccgg agtgtcaccg ggacttggag    4680
gaactcaagc ggagatagct gcttcacaca acaaaggcaa acgaacaact ataccctatc    4740
ttggcagtat cggagatagc ggtaagtgga gtcttggtcc gggaagaaca aggtacacaa    4800
tttccaattt actatgttag caggacccta ggtgaggccg aaactaggta ccctcaccta    4860
gaaatattgg cattcacttt gctaagcgcg tctaggaaac tgaaaccata tttctagtga    4920
catcccatat gtgttgtgat taccaaccaa ttgtggaata taatgtataa acggctactc    4980
tcgggatgat tggccaaatg                                                5000
```

<210> SEQ ID NO 102
<211> LENGTH: 5002
<212> TYPE: DNA
<213> ORGANISM: Nicotiana tabacum

<400> SEQUENCE: 102

```
aatgcagcct cagtcttcaa cataaaaaat cacatgagta tataagatta atttttttt      60 ttttgtatat atgttagatg ttgaatttct tagttgtttt gcgtgtgttt tttttttttt    120 tttttgaccct ccctcggtaa aagtcttacc tccggcaact gtctccgcga gagagaggg    180 gtctaaacgc atgtaattat tcaatgattg aaggatggtc tttgcctaaa tactaaaggt    240
tccttattgt ataggtcata ggtgttgatt cgaatatcaa agagagattc ctgtgggtta    300
taaaagtaat tctaagataa taaatactct ttttagaggt gttgttttac tgtaaaatac    360
gtatttggtt aaagtgatag acatatctag attctcagac ataaaagatc catttagaca    420
cataatcata ttttttgccag atagttgttg cagctgaaaa ttggagcata tacttaga     480 agtagcataa cactttactt ccatatagtc ggatggaaaa ttggagtatc atatcttctt    540
ttaattcaca gttaaatctt taaacatatt taataaattt tttaatacaa atataaagtc    600
tatgcaaaag ttattgggtt ggtccaagcc cttaatttcg atctctagct ccgtccccgc    660
```

```
atataattct aaaacttctg cttctcctat gatacatggc taatgtttat cgtttagttc    720
aacaagaaaa agagggtagt cttattatat tatgaacggc aaaggtccaa atatgccctt    780
gtactatacg aaattgagta catttgccat ttgttaatac tttagctcaa atatacccct    840
accgtcacgt agttggtcca tatacactac tagaaatccg gtaaaaccga ccaaaaaaac    900
cgaccaactt tggtcggtaa tggccaataa ccgtccaaaa cacgaccatt acgtgtggac    960
ggtattttag gggtcggaaa ggcataccga ccaaagttgg tgtaaattac cgaccaattt   1020
tggtcggtca attaaattaa aaaaaaaccg accaaagttg atcggtattt taattatgta   1080
atcaaaagat tgaccatctg ggaatcgaac cggggtttgt attgtggcag gatactattc   1140
taccactagg ccattagtgc attttgtttt aagactgttt tttatttgat ttatactctt   1200
taattgtatt ttcgcacgaa ataaccgat caaagttagt cgattttatt aaaaaataaa    1260
attaccgacc aaagttggtc ggttttttaa aatgaccggc cgaattaacc gaccaatttt   1320
ggtcggtttt ttaatattaa tttttattta ttttaattaa aactgaccaa aattggtcgg   1380
tttcttgaaa aaaatttccg ggactcgaaa atagtttttc gcattttcct ccaaagaaaa   1440
ccgaccaaag ttggtcgatt tcgtaaaaaa aaattaaaaa taaatatttt taaaaaaccg   1500
accaactttt gtcggttttt tggtcggtgt tttgaccgac caaagttggt cggtcgacct   1560
tggtcggttt ttgccgaatt tctagtagtg atataccctt agagttacac aattggcaca   1620
tatatgccct tctcaaaacg aaattcaccc aaaaattatg gtttaaactt taaaataata   1680
aaaacatctc aaactttaac aatactcaaa agaccaaaat atttaaatta tttctaaaaa   1740
gataatttaa tgattaaaag cctagagttc aagttgtagt gttataaatt tgagttgtta   1800 gtcttttttca tcttttttcag ctggacattt tctatttttt ttattaacta tgtaaattag   1860
gggtgtacat ggaacgggtt ggatcgattt ttatcaaaac taaccaaac cgattatatc    1920 ggtttgaatt gttcggtttt attggttttt tcagattttt tgttacataa atattatttc   1980
aatcttgctt tgttaaattt tttagaacta aatatatgtt cagtaaaact taaaaaattg   2040
acaaacatat gatctatctt gattacctta tgggagaatt ttcttagtaa ttggaattca   2100
tgagttttgt caagtgaaat tggtgacgaa aatagagaag acatcagtaa ttgaggaaat   2160
cggataaggg agaaagaaaa agaaaaaaag aaaaaaagaa gaaagaaaag agaaaggtaa   2220
agaaaaaagc actaataaaa aggaaatagt atttgtaata tactttaata caattaacgt   2280
aagagctaat tagtttgagt ggattccgtt ttgaaaaggg catacatgtg ccaattatat   2340
aactctaagg gcatatatgg accaactatc tgacggtaag ggcatatttg agttaatata   2400
ttaacgaatg acaaatgtgc tcaatttcgt ataatacaag gacatattac atttccccta   2460
ttatgaaatg gttcaaactt aaggattttg tacatggtaa aacctaaatt gacatgtaac   2520
ttggtacttt ccattgggca aagacacgat cttttacgtg atattttaaa tcaagtaaag   2580
atcaagtcgg gccaaaaaga aaaaaaccca tgattttttta agataaaaag ctgctaactt   2640
ttagtttgtt tcatccaata aaacatcttt aacgatctgt ctgctttagt ttaatcctct   2700
ttttaagatg taactaagca tgaaatagaa aaggggaaaa aaaaggacca ttggatttg    2760 gaagaagttt taagaaagta caagaactag taaagtcatt ttgtatagag tatgttaaaa   2820
aggtgagtga caattcgaaa aagagagagc attgataagt caatcaataa aataaaagca   2880
cacctgataa tcattcattc agaaaacaaa tttctatgaa tgataatcat tatcataagt   2940
cactgcagaa atcccatata cagtagagta ccaggatttt acgataaggt gttagcagac   3000
tatctattca ttttttgaca accattttac gtttggtcat ttttttgggaa acgaactctc   3060
```

```
ccaacattct tccaaattac cccacgcacc ttactgtgca catcttttaa ccaacttctg    3120
gttatttttt cttttgatgt ccgatattcg tatatgaatt cccattaatt ctaagttgca    3180
ccgaaatggt ttttatcaag attttgtata tatttaatat tcgaattcaa aactaatggt    3240
cgaaggtgga agatcgtatc catcccatca taatatttgg ttggtaatat cacacctttt    3300
tgaatttggg agacttgtca attttttattt tgaaaaaaga aaaaaaaaag aaatagaaac    3360
taaaaccata gggaaatgaa caattttatt ttcactccta cctcatttta tttgtcttga    3420 attttttcaat tttgttttga aacttcttca gtttattttc ttggaatctt cagaatttaa    3480
tttgaaattc caaattcca aggatttagt gtcaaatcag tgcttgaaat taaatttaaa    3540
acgagtggta aataaaatag aggagaactc ggtaaattac aggagtgcgg taaatctttt    3600
ctccttttct ctctttggag cctactctat tctattgtaa ctaagtaact taactacgaa    3660
aaacgtgcct agacttttaa cttcacaagt ataataaata gaagtcaaat tctttcataa    3720 tattgttttcc atcctatcaa acagactttg cctcactgac tctccttctg agtgtgtctt    3780
ttttatgtca tttttagtga atccaattga tttagagact caaatattcc acatgcgtgt    3840
cttaatttgg tgtatatatg gtaataattt ttgttaggta gctgtagtat tctattattg    3900
ttatgtatta actcatgtaa ataaaagccg gttagataag actagaaaaa atagagtcta    3960
cttagaaatt attagcctat tgtttggaac atgtcaaaaa ttcagtgact cagctagagc    4020
tgtcaattag tcaaataact ttattaatat taacttatga aaacacttgg ggattcttgt    4080
agtttaaggg aaagactact gactgaaaaa caaagcaaaa gtctatgcat tactatatta    4140
tacacaatac agcattttcc aatagtattt tagataaatc tccaatcagc tactgttgtt    4200
cttttctttt cttttttagt ttaagttgta tgtgttgacg gtatacaaat tatttgcaca    4260
attagatggc ttatctagat aatacgtgta aatctattga taatcattaa ttagtaatct    4320
ggtaaaaata atattgcttt tgttctaata taatgtgata tatttgactg ggtacgaaat    4380
ttaaaaaaaa ataagacata tagaacttgt tgtcttaaac aattcataac atttgtgtgg    4440
ctataattct tttgaaactt atggtgttaa acatgtctaa ttgtttgtgt atgtataaaa    4500
gattctcatt aagcgtagga aaatttgaat taaattattt ttttaattta aaagagatc    4560 actccttttta gagctgactt aaaaagaaat tgattcacat aaactcgcac ggagggaata    4620
agtaatatac tatcaaaaat taaaaatcac ttgtagtgta aaaaaatctt tacaccaatc    4680
gtgtatattc tcaattttttt tttttttttt ggcgagaggt agttgttcag caaaagtaag    4740
ttagaaatag gtctgtactt ttgactttgt aactctgaaa tgaaaaattc aaaatctctt    4800 ctttttttact gttttaaaaa ctccaactca ctcttattaa tataaagctc tagttagcaa    4860 agacacccctt gtccacttgt ctatatagca agaaagagag taaggagaa aacatattct    4920 cctctccatt tctgtagaca agattctcaa aaagaaacaa attaaacact agagagtgag    4980
agagaactat aagaaaaaga at                                            5002
```

<210> SEQ ID NO 103
<211> LENGTH: 5000
<212> TYPE: DNA
<213> ORGANISM: Nicotiana tabacum

<400> SEQUENCE: 103

```
agaagaaatg actagctgtt gaaaagagaa aacaaatgta agtacaccat taggaagatt      60
tgaaagggcg tttgggtatg ggggttggca agaagattca aacttttttct ggggttttgt    120
```

```
gtaattgtgg tggaattatt attattgaaa cttctttact tcaatttaaa tcgtcggtac    180
atattacgta gttgtagtaa aagccttttc cttttgtgc tttttttttt ttttcgtgtt    240
cgtattaaga cttcattaaa tccaaatttg catagggacg gtcaacatta gaggaataaa    300
ttgcttccta acaaagacga ttttatactc aagagttcga gcccgaaaaa cgacctctgg    360
ttaagggtaa aaatagtaat tacaataact ccaccacaat ccttattggt gtgcatttct    420
tcattaaata ctccctccaa tccactttaa ttgatttgtt tttggctatt tttatatata    480
ttaaggaatt atcttttagc attaatcaat aatgaaattg accatattaa ccttttagtt    540
cattggaaat ataacaaata ctcctaggct ttttaattca agagcaactt ttaaatccga    600
atttgggcta agaatacaag cttgttcttt tttatctgtt tttcactcgg tgtacgagga    660
ctcaattaaa tccgaatttg agctaagaat acagacatta gaggtaatat gctttctaac    720
aaatgtgact caatgttcag actcagaact cgatatctct ggtaaggatg acatagtact    780
tacaataact ccatcataat ctttataggt atgtatttct ttataaaata tgtaaatagt    840
gttatgattt tttgtatcaa aaatgatgaa gtataatact cttaaaaatc atactccatc    900
cgtttcaatt tatgtgaacg tattttcttt ttagtctgtg ccaaaagaa tgacctattt    960 ccttatttgg aaataattta cctttatgca atgatttata gtcacacaaa atatatgtgt   1020 ctcatttta accacaagtt caaaagtctt ctatcttttt ttaaactctg tgcccagtca   1080
aatgagttca cataaattaa aacggaggga ataataaaaa tgtattaaag actacttagg   1140
agagttctta aaaaccatt ttggaaccctt gtctacgtac ttttatgcaa taactgctta   1200
agtttgtctc tgctaaaacc tatgctcccc aaccgtgcac caatcagctt agaaatttga   1260
actcaggaat aaatgtaact acactccaca gaaacttaaa aagttttact gttaccattc   1320
actcaaggat cagaactgaa aaacaaaaga atcagtgctt cactaaaaga aatactgttt   1380
acattatttt caaaagagtt taatcattaa aatagatgta ccatcagatt agctaaaaga   1440
taaataatcg ttaaaaaaag gagattatca acttgaaaat gaaacaaatt atatgttata   1500
atatgtcaaa atatactgac agtataaaaa ctcgttaaat gtgttaaatc ctatgaaaaa   1560
actgcccaaa taaatatttg agcttaggtg tcaaatgttg tactcaacaa caataacaac   1620
aacgcattag gatcctacta gtggggtgtc caatgttgta ctattgaaca ttattcaact   1680
aacttttgtt aggtgttcct gtagtttagt gaaattaaag tccactgttc ccctatatat   1740
taatcccaaa ttaattaatc aagtgcagat aaaaattct cattttctat taatttatta   1800
agtgtaacaa actaaagaaa ttcaagaatc ttgaatgatg agaaagagtc atgcatgtag   1860
aaaaatagat aataatacat ggaaatatat atgtatttgg ggatttgcat ggtagctcaa   1920
agattattgg aaagtgacag gaagataaat caaaatctca gtgttatttc aaaaataaaa   1980
ggcacagatt atttaaataa ttgacagcca gttttataat actatgtggg aggggacaga   2040
gatcaatcca tgtacgtgca tggctaatat taaagtaagg gagaaaaaaa tattaagtta   2100
attgatgatt aaaaatagta aaatttcaga cgtatatcac ggcaatgaag agtttgatct   2160
ttaatatctg tataatggtc cataatatga tggataggcg ttgtttatga tatgattgat   2220
tgatcattga tcattgacta ttgtttcttg aataattaat cagtatggga aagggtccca   2280
ttaaagttga ccatttgctt agcaatatta tcttaggtaa gctccatatt agtttaatcc   2340
acttgcgaat atattccgtc ctcgcaaatc aatatttaca attcttttt ttcagttttc   2400 tatccggtat ctgatacttg cattggtgtt cgacaaaatc tgtattcgcg tcaaaaaatt   2460
tcatattatg gggcaaaatg ctccataata aaagcgactc aatattaggg ctcgaaccaa   2520
```

```
tggcggaaac aagatttta ctaagggaat tcaaaaaata aaaacgaaaa cacatgaaga    2580
acctcaggga attcaacatc taatataaat atatgaaata aaaatttgat tctattgtaa    2640
tttgatatac agtgtaattt acaccgtagg ggatttggct aaacctcctt ccgcgtacct    2700
agctccgtcc ctgactcgaa tccgaggtat ttggttaaaa atgaaagagt acttctcata    2760
acctcgtcgg tttttgtttc taatcaatct ttatattgtt aaaacataaa acgtttactt    2820
cctttcttct tcttttaagt tttgaaaatg ataactactt ttgtttgact aatattttgt    2880 agttttgat  gctaatcaat tttgtaaaaa ttactgtact tcaactagcg tttactaccc     2940
cacctcactt taaaaaattc cctaaagaga taacttttg  attaattcat aaactaaatt    3000
gaagaacttt tcaaatgaga gtaagttgaa aatgcatatt atattgtagt atataattgc    3060
aattttgcat aacttaccgt aaaatgttct tccttttaat gatttgttaa tatgggaaat    3120
ttgaactttt ctttctttga aattgtattc ttgtcccatg gtttctatgc aatctcaatc    3180
atcaaattgc aattattttt ttttgttttt tgttggcaaa ttcaggagag cttaggtcag    3240
tgatatatga aaaactattt tttactctta tttattttac cctttactta ttaaagaata    3300
aagtccaaga cgaatagacg atgtacaacg caaatgtaaa aatacaaaaa aatgtttacg    3360
acttcttctc tatttatttt ctacttaatt tacttattaa acaagtactt acttgttaaa    3420
ctagctaatc tgaccaacaa tgtgaaaatg tttgacatta tacatcttga ctttttattt    3480
ctctattatt ttctcgatgg ttacttcaaa tcatagattt gctaatctga ccaatatcgt    3540
ttaacttcaa gtagaacgaa atgaacattt caaggtttta gaaaacagtt gaaattggac    3600
cctaaaataa ataaaatgaa gttattaata ggtttacacc ccaatcttat ctaatgctta    3660
aaacacatag tgtggagcgg aattcattgt cttcacatta ttgtacatta atcatatttt    3720
cttaactaat tctgacgatt atttgtgttc atctaataga aaatgcaaaa gtcattttcc    3780
ttaatacttg gcatctttat agtcaaaata taactcatat ccaatgcaaa agtacagtca    3840
tgcacaacaa tttaaagtat taggagcatt tattagtttc acttgtttat taatgtaaaa    3900
gtacgtagta aaatgaaagg taaactcaaa aatatcacat acatatttta atttgatcga    3960
tcaagtcagc ttgagttctt gaactttgtg aaagcaatat atataatg  aatgaaacac     4020 ttatgcattg cgacattgag agttaattta agaaaatttt accccacaag ttctagcttt    4080
gattgacagg cctagccaca aagtaagata tgcacaattt atcttagtgc ttctatgttg    4140
tgtatcaaaa ctcaacaagt tatgtttagt actcctatga tgtttatcct aatttaaaag    4200
tcaatattaa gtaaataaaa ataaaaataa attaaagtct atgtatgtat tctcttacca    4260
atgcctatag tttaggccca gaacctacca tctccctgcc aacccactac tcttactggt    4320
tttgcagaaa tagttgctga tcaaatcatt tatccaaaga tctagtttca accttaaaga    4380
tggaaggttc gagtcacttg attttgaagt attgacttaa tgatgtactt tctttaacat    4440
aaggtgaaat tagttgtgga cttcatcgat aatctgtcgt taaatcgttt gtagctaact    4500
aaaaatctat cgcgaaatag gattaacgac gaattttct  gtttaactag agaattttt     4560 cgtcgctaat taattttt   tttttgtagt gagtacatat tagaaagaaa aaaaaaaa      4620 aaaaggaaag tgttgaagtc gtaatgtgta caacatatga agtccataac ctgccaggta    4680
caattcttta aagaattaaa atggaagaag aaaggtaaaa gcaaagattg acaacaattt    4740
ttttgtggct cgatgaaaat tattagtgtc aagaaagaa  ataaaggtaa aaatggcag     4800 aggaaagaat caccctttggg aaatagcccc ttcacaaaga ctagagtcca aaattacaaa    4860
```

| | |
|---|---|
| catcaaaaga tctttggtcg gttctactgt ttgcatctct tgttgttgct ttcgtcttgt | 4920 |
| gaaaaatcat tgaggtacta tgtaaattta taatcagttt tttaatctta ttgaaagttt | 4980 |
| catagtgaga aggaatttat | 5000 |

<210> SEQ ID NO 104
<211> LENGTH: 5000
<212> TYPE: DNA
<213> ORGANISM: Nicotiana tabacum

<400> SEQUENCE: 104

| | |
|---|---|
| gtactatcag aaaagattta aatctaacct tcgttataat ttgagtccaa atatacccct | 60 |
| gatgctatac tattggttca aatatattct tttccattaa gtttgtccaa agtggacatc | 120 |
| caatcctacg ttgcactgac atttgatgat gtgggtgtca catggcttgc cacctcagcg | 180 |
| ccccaaatcc atatattaga gactaaaatt tgaaatacaa taattttcg taatggtggc | 240 |
| aatagtgatg aagggaaga aaattttagt ggtggaaaaa aaaatagaa ggaagggta | 300 |
| aaataggtta tgagcgctga ggtggcatgt cacctcatca aacgtcagtt tttcgtagga | 360 |
| ttggatgtcc accttggaca aacttaacag aagatgggta tatttaaacc aatagtatta | 420 |
| cggcaatgat atattttgac ccaaagtata acgaaagata tttactcata gtacaacgat | 480 |
| acatttcgtc atttaccgaa tttcgaattt acattctcaa agaactcata actttgatgt | 540 |
| taactaatta agtttaaact ttagatcacc ctacaattgt tgggagacat atcaaaccca | 600 |
| taccattgat atatataaga actttgtaaa actcttttta atatgttagg gtatgtacta | 660 |
| gctagcacca tggatagtgc gtgtcaccat tttacagcaa ataatatgcc tcatgaattg | 720 |
| gtagggaaag ggtcttttaaa gttgaagtgt ttttttcttt tttcttggtag gtagtggggg | 780 |
| aggggaaaat aaggggacaa aacacaaaat caatttgagt acaatttaca caagtctcca | 840 |
| tatattgata tagtgctgaa agaaatata atgttctaag gcaaagggga taacacttag | 900 |
| aaattagcca acctcatgtt tcttacaagt ggatgagggt tcgactttgc atttagcatc | 960 |
| accttattct ctctaatttt caacaggaca tgttaataaa aggatgacaa tccagattga | 1020 |
| caaagttatg aaagtgaaag cactgtaaca tttcattcaa tcatgcaagc atctcccgtt | 1080 |
| aatttttcta tcttttggaa tattacgaaa atcaaaccaa ccttttacg tataagtttc | 1140 |
| taatgacatc aggggactc ctgagaaata ttctcactca aggtcgaaaa ggacccttta | 1200 |
| ataatgatca atataaattt ttttataat ggtccttta tattcgaatc agctcgtaca | 1260 |
| catctcaatt tttgtaatga gtacatgtta tccccgacaa tatatatata agataacttt | 1320 |
| gccctcaaga atttatatcg acagataaga gatcacataa tatttttgtc tttgttggaa | 1380 |
| tgtaaactct acttttatga aattttatta actggtaggt cacatcctac agagctttta | 1440 |
| gtcaatgtta ctattattaa gaaggaaaaa aagaagaagc aaaaggaaga tattaacaat | 1500 |
| agtataacaa cattcataaa cgtgatttag gaaataaagt atggaaaaat gaatagtgaa | 1560 |
| aaaaagtcaa gtactagga gttaaggttc gtaagttgat gggacagatc gcggtggaaa | 1620 |
| aggaagataa gcttcaaaga tacaaaagca aagggggtt gggttgagat tctgagttgt | 1680 |
| gattaatacc actcatgaac aaaaagttat gtcatggcac cattcatgag attaagacaa | 1740 |
| cggtggaatt aagaattta ttaaagggag tcaaatttta aaaaataaa ttcatcaaaa | 1800 |
| agttaaagag tatcaatata tatcaatata tatatatata tatatatata tatatatata | 1860 |
| tatatattta tattaaatta tctaattaca cagtataatt tttaacgaaa gggtgtcgat | 1920 |
| cgacacccct gaatgcatgt ggccccgcca ctgcattcag agccaactct cccccaaaag | 1980 |

```
aaaaggcgca aaacaaaagg atttgaaaca gtagttgtgg aggtgattca gccatgcttt    2040
catgactcat caatacctac tttttatgtt tttcttttc cttttatttt tcaggatata    2100
aattttgttg taaactgata taagaaata aatttactct cttcaaccta ttaagctttt    2160
aggtgaaatt agtaagtcgt acaatttaac atggtgtaga attgatagaa gtcgtagaca    2220
ctcataggtg cactttgtag tgaaaattag gagaaattag ggttcaaaat ccaactaaga    2280
taaaagatgc ttggtaattt cttcacatct gcttagaaat aatctgctta aatttggatg    2340
agcaaagtta tccaatacaa gtgttgctga gaaataatcg gtatctaata gaatagtcga    2400
gatgcacgca aataagtttt gactctactt taacaaaaaa aacaataggc agatgtatcc    2460
aaaattcata tcttatggtc actcgtcaac aaaaatattc cttatgttta gtccaagaaa    2520
aataaccata cccaaatata agggtttgtt gaagacggaa atatataaac aaataaacaa    2580
atatcatcat atctccgata gtttaaaatt ttagattgga tatttcacac aatttatcaa    2640
aattttcaaa aaaaattct acttttctt gcttggaact tggaagggga aggggtggtg    2700
gtggagatag ggcggggcat cttctatcta gtctatgtga ttaatataac aaaacaaaaa    2760
gggcgaggca aaaacatgga tgaatggtgg tccttttcta tatttatatg gattgttacg    2820
atacgtcgat ttcactttgc aaaataccaa ttagattcat ttagttatct ttttgatcac    2880
tctgctttta ctatcatata tatataggag tccttccacg tttcgcatgt gtcattgttt    2940
atattttcca tggtcttcct tccaaatggc taaaaaaatt tgacacagtg gtcccaaaag    3000
tttatagaaa tagaattcaa cagtgaggca tacctatg aattctattt tacatcttca    3060
tcgtataaaa tagaatgtgt tataaacttt acctcgtgat gcttacaagg ggtgaaaata    3120
taaaagcact ttatagattt acaagagtca caccttgatt tatcctaaga ttttattttt    3180
ttacatgcca aacaatgaag tatgggagat ccaattggaa taacatcaaa tttaataaaa    3240
ttcgaaatag tcagagagct gtctactgag gtatattgaa acttattttt ttttaataga    3300
aaatatcaaa tacttagcaa tatattaaaa tgtttcataa attacattgt ttaaaccaag    3360
cgttgaaaca tatgctgata cgaggtaggc ttattgatga atttataagg gcctcattgg    3420
aaaagacgat ccaaagcaat gggctaaaaa ttggcccatt ttctgccacc cagtgtatgg    3480
ttattactag tttcacccac acagatttgc acttcattag aggacaatgt tgctgaattt    3540
gaaacataag tccatttatc tccactgtac agtccttcct ggagtccaat cctgaccata    3600
tcttcatgat tttatgtaat gtggtgaata agcaaagttt catgttatgc tttgtctcat    3660
tttatagcaa attcatttcc tcataaaatt tacttcaaaa aagtttcgtt tgattttcag    3720
aaatcaaaat atgcttttcg gtaaccaaat ggttttcaat tttgtttacg aagaacttaa    3780
aactttccaa caccctacat ctatgattgc aagttaaaat tgcagaaata tgacactttt    3840
tggagtggtc tttatcgttt aacttcactt gcactttaag ggcaaaagtt aaaagtgttt    3900
ccatgaagca agcgagggat aacacttatt aaacttgaaa ttctactcat agaccaaaac    3960
aaggacaaaa attcaagact atctatgtgg gtaaacgtac gaaaattggg cttctccaga    4020
ttagagccgg accttgtgga aagacagaga aattcgaggc ccacttccag tttctaagga    4080
gattaagcct atcaaacgat ggtccagaac gaaatatgtc tttctttatt ctctactata    4140
tagctgactc agaatcgtta gaatttgcaa tttcctcata ataaaatgtg aggcagtata    4200
gattcgaaaa cctttgttga agattattga ctcagctacg cgaaacaaac tgtagtatcc    4260
aatgtaccga ttaacaagcg actggttaac tatgaatttg ttagctcgac aaaatcaccg    4320
```

| | |
|---|---|
| gttaataatg agtttgtgag ttcgataaaa tctaattttc tgatagaaat tttatatatt | 4380 |
| atgcagaaat ttaataaaag tagacttaac ttatatattt tagcattgac tcttttgaag | 4440 |
| taaaatccat tccatctaaa ttatgacttc cctacatcga gtaagtaagt tgcgtctgta | 4500 |
| tcctcatttt acccactttt cgctatgcaa ttattcaagg atcttacac aaatagcaag | 4560 |
| ccaatattaa ttatttattt tttttagtca tatatataaa ttatacatat attatatacc | 4620 |
| cattaattat ttttaattta agtgatagat tggacgacta tttggattaa ttcttcgtta | 4680 |
| ttcaagataa tagatgtcgt ctctaataca tgagctagaa gataataagg attactaggc | 4740 |
| cgaaaggctg atggaaatga acaagaagat aagctcctaa atggaaacag tacggaaaaa | 4800 |
| gtcaaagagc agtgcatggg aggaatcatc agtcagaaaa ggaagccacg tgtcaagtag | 4860 |
| aaacaagcac gtgtccatgc aaaagccacg taactcccctt ccatcacatc ttccttcttc | 4920 |
| aaaacctcgt gttttactct ctcttttctc actgccagtg atcgtcagga ctgtgcatgt | 4980 |
| ttgtttaaaa actaaaggca | 5000 |

<210> SEQ ID NO 105
<211> LENGTH: 5000
<212> TYPE: DNA
<213> ORGANISM: Nicotiana tabacum

<400> SEQUENCE: 105

| | |
|---|---|
| acatgacccg gttgtctcct tgtggtgtc tttcagaaca tcgccagtag ttcgttgatg | 60 |
| tggtgttgag tgaatacttt ttcaatatat aagcaatttc gtgcctttt tggttcattt | 120 |
| tgaggcttat gtaatatatt tgatcatgta atcgtgaata cttcaataaa aggtaactct | 180 |
| tcctcagata atgtaaccaa gaataatttc attgaaggga agcggtataa gcataaaggt | 240 |
| aactttccct gtgatgaaga atgatgtat caagtaggcg ttgttgatca actttccaaa | 300 |
| tgggtggagg gtaagctact tcactgcctt acttcctcta agttcaagtt gggggaggta | 360 |
| tgatcgggga ttctctatct tcttgttgaa caagaaaaca gtactactac ttagcatata | 420 |
| tagttttcaat caataaatag gaactgtact aacaatcaga gcccttattt tcacttagca | 480 |
| tagttgtata ccagttagaa ctcatactgt ggaaacagag actcgtggac tagcaatgcc | 540 |
| cttattaaaa actatcatgg atgctctact cattgtctct ccaaacaaca gcactctttc | 600 |
| ataaaaggt acttcatgcg acatccatta atacaagaag ttcaagatac ataacatgca | 660 |
| gtaacagaac tcgactcaac ttagacttat cccacatcta gcttgatttt ccatcaaacc | 720 |
| agtgtgcgta aaagtaaaac ataactatag aattgatccc atggttaatc acattcacat | 780 |
| aacaagcggt tgggataaaa agatggtcag ttctaaggct tcaaaattaa tatagccaat | 840 |
| tagtcgaacg gacggtgtgc aatcctagat gacttctatg aaagtgagac gaatcaatct | 900 |
| cccaaaagtt tagtacaaag aaataacagc aaccgttcaa acaatctaat acggctacac | 960 |
| atattaatct tcacaaatta acattacaa caaaagcata ctaaattctg aactcagtaa | 1020 |
| agattcaaat caacagcacc atattataga cataacaaca ctagtgaatt ggtcatcaaa | 1080 |
| gcaacgaaga gcacagaaaa gttcgaaatt taaccaatca cgaacctgat cgaagctctt | 1140 |
| gtggaacatc tacacgcttc ctgacttgtg gagacaagag tctcgagtag attcggaaac | 1200 |
| tgcccagtct aattttgata cgtattctac aatttcctta ctaaagagaa aaagagaaag | 1260 |
| tgtgtgagaa tataaaattg gcgccttctt tcttttggcg ctatttatct agttttagcg | 1320 |
| accagttatc atgattttta aagatatttt tagattgcca attttcgctg agaaaaaaag | 1380 |
| gaggtaaaag gggtggtagt taaaagtgat aatcaacttt atataagact agtcttaata | 1440 |

```
tacgtgcgtt gcgcgtgtca taaaaaatat tttaaaaaat atatttgtgt tataatataa    1500
aaattaatac aaatttgcaa gcttcaaaat aatgaattaa tcatatttag gagtttgatc    1560
cactctagtg gttttttggtt catcttgctt cattgtacaa aaaatttgag tatacttcca   1620
attctaagtc gttctattgt tcaaaggaaa aaaagtgtcc taattgctct tcaacttcta    1680
aaatattgcc tatctcttac cttaaatatg aattatcatt tctgcgtcca tattttttt    1740 ttaaatcaaa attgtctttt tcgtttttt tttttagaa aactatactc tatagcccac     1800
aaaattttaa tagctcatgt ctttctcac ttacacgaaa tggcccttg gcccaaacat     1860 aatagaccga aatgtctatt ttgtatattt tttgtatagt gacagtctat tttgaatatt   1920
tttttatata atgacagtct attttgtata tatattgtat agtgacggtg gggagtgggt   1980
tgctctagtg gtaagcaccc tccacttcca accaagaggt tgtgagttcg agtcacccca   2040
agagcaaggt ggggagttct tggagggagg gagccgaggg tctatcagaa aagcctctct   2100
accccagggt agaggtaagg tctgcgtaca cactaccctc cacataccct actagtggga   2160
ttatactgga tcgttgttgt tgttgttgtt gtattgtata gtgacggtct atttagtata   2220
taattgtata gtgtttgtat atttttttgta tagtgacagt ctattgtata taaattgtac  2280
agtgacagac tattttatat attttttgta tactgacagt ctattttgta tatatgttgt   2340
atagtgacaa tctatttat actccctccg ttccaattta tgtgaacatg tttgactggg    2400
catgaaattt aagaaaaaat aaagactttt ggaatttgtg gtcctaaaca agtcaaaagg   2460
aggtccagag tatttgtggg gttataaaag cttctcatta agggtacaat tgtaagttta   2520
agctaaatta ttatcaaatt tagaaaaggg tcattctttt tggaacagac caaaaaggaa   2580
ataggttcac ataaactgga acaaatggag tatatttttt gtatagtgag agtctatttt   2640
tcatacttct atgctaagta ttgactttaa acactgttca aacttaaacg tgtctctttc   2700
gcgtgaaatt actctatatt gaactactac aactatttgt gccggatttt gtcaaaaaat   2760 tcaatttttcc ggccaagttc gttctgcttc ctcctcccat ccttccaatc ttattctttc  2820
tgccactttt cagcaatagt gatacaacta agatatgttt taaggttttg aactatttgt   2880
gtggaagagt tttatggcat atacttttc tttggtcgtt gagaagagag gtcgacgtcg    2940
ctcatgaaga cattctgccg ccgacgaaac agatcttata gctagccgct agaattattt   3000
taggctataa aatgtatatt ataattttgg actactggat gatatatgtt ttgggccgat   3060
gggctataaa tgaattttgc tcattttttt aacgtgttct ttattagcat aaaaattgca   3120
ggatgagttt gttactttaa tttcattaat ttactctttt tttgcagaat atacatacat   3180
gaaaagtaac atgtagtaaa tattattatg ttacatatat agtttaaata aaggaaaaag   3240
ttaatgtaag gtagaatttt aattgacttt aaattcctaa attttaggac ttctcaccta   3300
gttcaaataa gtaaatattt aataatcagc atcttagtta atttcaaagt actaaatatt   3360
atgataataa ttaaatgact attttgtcta gtcgaaatct attttttaag ggtaaaaaaa   3420
gcgaacgata tttcgctaag aaccttcgtg cttttaatat aatactagtt tctatgtacg   3480
tgcgttgcac gtaaatcttt agtttatcat ttatatgaaa aaacaataca ttaaatttac   3540
tggaaaatca tatacaaaaa gaccgaataa agccattaat gtgggaacaa tgcaaatgta   3600
tcgtcaatgg gaacatgcat tgcacatata ttccgtgtca atagttatct ttgtgaaata   3660
aaaaatgata catgtaattt tatactatca ttcatattat gaataaactt gtttgatttt   3720
taaaatagaa aataataaag agcacgaaaa gttactgcta gtcattaaaa tttgttatga   3780
```

```
acattgactc tattatagaa taactcatca agaagaattt taagtgcaat attgaaggat    3840
ttgctttagt ttctaatagt ataaatcgat gtctcttatc ggatcataaa accaaaagaa    3900
ctataatgtc catacaactc cctatgtatg tttacaattt gctttgtgtg tgtaaacatt    3960
agaacttttc acctaaatat ctcatacctc ttaagaaaga atccttgctg gatacttttc    4020
ttttggagct tcacaattat aagttaccaa ttaactaatc tctccaagcc tctatttaac    4080
atatacacgt ttatctctgg acgaacaaac aatagatggc gtcgaagatc cactcttcat    4140
cttcctgatt ttcatcaact tccttatgcc tatttatttc ttgttttcag ttaattcgac    4200
aaattaaatt agaacaaaat ccattactgc tggttatcag acaaagaaaa actaaagtaa    4260
ctccttttgc caacaccaat gtagaacata ataagctta aaggtaattt cttttaaatt     4320
ttaggcaaaa cctttatgta aacgaacatt taagccgtgg ctttgccatt ggagttctaa    4380
tacaaatagg acctttagtt ttcaatgact tgaattctac aactaatgaa ctgttttttac   4440 gtttttggat attaatgttg aagacatgat ttaaatatga agggtaaaaa agtcggtcaa    4500
tatttcaggg acatttttgt cgttcaatat ttagcgtgta acattcgtgt ttttataata    4560
atatagatat agatatagat ttctctcccc aaccccgaga ttttttaaaa gtattttaaa    4620
atagggttac tgtgcacata taagaatcag aaatttccag gaccatagca atgagcatta    4680
ttgaacagta gtagtacgta tgtcctttct ggtataggat atgtagcttc attaaaagat    4740
agaaaatgaa aagcgtataa agtttgtgat acatttacta ataaatccaa cgaataaaag    4800
aaatactcgt atataaaagt agaaagtaa gtgtttgtac ttttttataaa aacacaatag    4860 gtggagttga gagggatatg gaaattgcct tggatattat gtaggcatca tgaaccaatt    4920
aatgggacct acaagattaa tgttttggct atccttatct tttattgaca ggcccttcaa    4980
tttaaatcgt tgctgcccaa                                                5000
```

<210> SEQ ID NO 106
<211> LENGTH: 5000
<212> TYPE: DNA
<213> ORGANISM: Nicotiana tabacum

<400> SEQUENCE: 106

```
ccgactaaca aaggagtcaa acaatggcga aactagaaat ttacccaagg gtattcaaat      60
ttaaaaaaag tgaaaacaaa ttcctacaaa gggtgtttaa tatgtgttat atacttctaa     120
aacgtaatat ttatctataa acacaatgca attttcaac gaagagtgat caactgacca     180
ccttataacc gccactggag tcaaacccta gttttctttt ttagcttctt tgtattattg     240
gtagaggtga accattttat acaaacatac atacatatat gtgtgtgtga gagagaaact    300
ttataaaaat agtactatga atattgaata tcgaatttcc attctcaaat aactcataac    360
tttaatgtta actcattgta aaaccttttt tttacatgtt agggtctgta ctagctagca    420
ccatggatag tgcgtgtcac cattttacag caaataatat gcctcatgaa ttggtagggg   480
aagggtcttt aaagttagtg tgtttttttt tcttttttctt ggtaggtggt ggggagggg    540 aaaatgaggg gacaaaaaaa atcaattgga gtacaattta cacaagactc cattgtatag    600
tgctgaaaag aaatataatg ttgtaaggca aagaggataa cactttagaa attatagcca    660
acctcatgtt tcttacaagt ggatgagggt tcgactttgc atttagcatc accttattcc    720
ctctaatttt caacaggaca tgttaataaa aggatgacaa tccagattga caaagttatg    780
aaagtgaaag cactgtaaca tttcattcaa tcatgaaaag catctcccat taattttctct   840 atcttttgga atattacgaa atcaaaacca acttttttac gtataaattt ctaatgatgt    900
```

```
cagggggaact cctgagaaat attctcactc aagttcgaaa aggacccttt aataatgatc       960 aataatttt  tttaatggtc gtgtaatatt cgaatcagct cgtacacatt tcaattattg      1020
taacaagtac cttttatccc ccaacaatac atatataagg taacttatca cgtaatattt      1080
ttgtctttgt tggaatgtaa atcctgttt  tataatttt  atccacttta ttgaccgcta      1140
ggtcacatct tatggagctt ttttagtcat gataaatatt actattatta agaagggaga      1200
aaaaagcaaa aggaagatat taacattagt ataacaccat tcataaacgt gatttaggaa      1260
ataaagtatg aagaaatgaa tagtgaaaaa agtcaagtac ttaggagtta aggttcgtaa      1320
gtagatggga cagatcgcgg tggaaaagga agagaagctt gaaagataca aaagcaaagg      1380
ggggttgggt tgagattctg agttgtgatt aataccactc atgaagaaaa agatatgtca      1440
tggcaccatt caggacatac agagccaact ctcccccaa  agaaaaggc  gcaaaacaaa      1500 aggtttgaaa cagtacttgt ggaggtgatt cagccatgct ttcatgactc atcaatgcct      1560 acttttttt  ctgtttttgt ttttcctttt tattttcagg atataaagtt tgttgttaac      1620
ttaaataaag aaataaaatt actctcttca acctattaag ctttaggtga aattagtaac      1680
tcataaaatt taacatggta tgaattgata gaagtcgtag acacccatag gtgcgctttg      1740
tagtgaaaat tagggttcaa ataagataaa acatgcttga tgatttcttc tcatcggttt      1800
aagtttggat gagcaaagtt atccaataca agtattgccg gtacctaata aaatactcga      1860
gatgcacgca aacaaatttt gacactactg ttaacaataa acaatatgca gctgtccaaa      1920
attaatacta tatcttattg tcactcagtc aacaaaaata ttccttatgt ttagtccaag      1980
aaaaataacc atacccaatt ataagggttt gttgaagaca gaaatatata aataaatgaa      2040
tcatcatatc tccaatagtt taaaatttca aatgggggta tttcacacaa tttatcaaaa      2100
ttttaaataa ttttatact  ttttcttgct tggaagggga aggggtggtg gtggagatag      2160
ggcggggcat cttctatcta gtctatgtga ttaatataac taaacaaaaa gggcaaggca      2220
aaaacatgga tgaatggtgg tcctttcta  tatttatatg gattgttacg atacgtcgat      2280
ttcactttgc aaaatacccca ctagattcat ttagttttct ttttgatcac tctgcttttt      2340
ctatcatata tataggaagt ccttccacgt ttcgcatgtg tcattgttta tattttccat      2400
ggtcttcctt ccaaatggct aaataatttt gacacagtgg tcccgaaagt ttatagaaat      2460
agaattcaac agtgaggcat atacgtatga attatatttt acatcttcat cgtataaaat      2520
agaatgtgct ataaacttta cctcgtgatg cttacaaggg gtgaaaatat aaaagcactt      2580
tatagattta caagagtcac accttcttga tttatcctaa gattgtattt ttttacatgc      2640
caagcaatga agtatgggag atccaattgg aataacatca aaattaataa gattcgaaat      2700
tgtcagagag ctgtctactg agatacattg aaacttattt cttttgtaca acagaaaata      2760
tcaaatattt agcaacatat taaaatcttc ataaattaca ttgtttaaat cttacgctgt      2820
aacatatgtt gataggaggt aggcctattg atgaatttat aaggtgaaaa tacatggact      2880
agccagtttt cgaactagta attgaaaaaa ggtatattat cacttttagc ccgcgccaga      2940
aattatttat atttggtagt tgaaaaagtg tataaatttg taattttttg tatataacac      3000
acataatgtg tgtgtgagtg tatatatata cacacacaaa aactatatat attttttcta      3060 ttatttttgag agtggttata cagtgtcatc tttctaatcg aaaatagcca gcgtttgcaa      3120
tgttattaaa aaaaaatagc cactattta  gctgaaacac ggaaagttcc agcataatat      3180
atcggatttc agagctcctg catataaact tccagcacat tatgaaattc catcacatta      3240
```

```
tgctgaaatt tttccggatt cttaaggtgt tttcattcag attttatctt tacataaaaa   3300
aatggctaaa tttcgattac ttttgaaatt atagctcttt ttcaattact aattataaat   3360
ctgactattt ctgattttt gcctctggtc aaaatggcat ggcatagtca tttttagggg    3420
tggttattga aaatagcta gtattcacaa agttattgaa atagtcatt atttacggcg     3480 aagattaaat cttaacaaat gtacctgagt taaaacacaa aaagttacaa cataatatgt   3540
tggatcatgg aactccttca tgtatgcttc tagcatatta tgttgaaact ccagcacatt   3600
atgaattcca acacattatg tcgaaatctc atatgtaaaa aattcgaact ctggcatatt   3660
atgctggaat ttttcgtat tttttatcag attttatttt cacataacaa agtgactaga    3720
tttcaataac ttttgaaact atgaccaatt ttcaattaat tgtaaatcaa attatttctg   3780 attttttttcc tccagggcaa taatgggact caactttagg caacaaaaaa ctgtttatgt  3840
aggtaaacgc acgaaaattg ggcttctcca gattagagcc gggccttgtg gaaagacaag   3900
aaattcgagg cccacttcta gtttctaagg agattaagcg taaaaatagc actggctagc   3960
cagttttcgg actgatcatt caaaaatagc cagtatttgc aaagtcattg aaaaatagcc   4020 attagtatt tgctgcaaca cgaaaagttc caacataata tattggagat cagtgcacct    4080
atgtatgaac ttcagcata ttatgctgga actccaacac gcggaaagtt ccactataat    4140
atactggaga ttggagcacc ggtgtcaaca aatctatcat ttaataggat ttatggctat   4200
ttttaaatga ccacttgtaa atctgattat tttttaattt ctcccgctta agcctaacca   4260
acgatggtca tgaacgaaat gtctgttttt actctctact atatagctga cccagaatca   4320
ttacaatttg caatttcctc ataataaaat gtgatgtagt atagatttga aaaccettga   4380 agattattaa tttatctttc gcgaaacaaa ctgtagtatc caaggtaccg aatagtaagc   4440
gattggctca caatgagtct gtttgttcga taaaatcatt ggttaataat gagtctctga   4500
gttccataca atctaatgct ctgatagaaa ttttatatat atgcagaaag taataaaaat   4560
agactatgac ttactatatt ttaacattca ctcttttgaa gtaaaatccc ttccgtcaaa   4620
attatgactt cattacacca aattgcgcct gtatactcat tttaccttct cttcactatg   4680
caattattga gataaaaaat ttcgtctcta agacatagct agaggataag gatcttaggc   4740
cgaaacactg atggaactga acaagaagat aatcacctaa atgggaacag tacggaaaaa   4800
gtcaaagagc agtgcatggg aggaatcatc agtcagagaa ggtagccacg tgtcaagtag   4860
aaacaagcac gtgtccatgc aaaagccacg taactccact ccctcatatc ttccttcttc   4920
aaaacctcgt gttttactcc ccctttcctc actgccggtg atcgtcagga ctgtgcatgt   4980
ttgtttaaaa attaaaggcg                                               5000
```

<210> SEQ ID NO 107
<211> LENGTH: 5000
<212> TYPE: DNA
<213> ORGANISM: Nicotiana tabacum

<400> SEQUENCE: 107

```
acatgacccg gttgtctcct tggtggtgtc attcaaaaaa tcgccagtag ttcgttgatg     60
tggtgttgag tgcatacttt ttcaatataa gcaatttcgt gccttttgtt tttccatttt    120
gaggcttatg tagtatattt gatcatgtaa tcgtgaatat ttcaataaaa ggtaacttt     180 ccttagataa tgtgaccaat gatgatctca ttgaagggta acttttcct gtgaagaaga     240 atgatgatac tccatcatg taggcgttgt tgatcaactt tcccaatggg tgaagggtaa     300
gctacttcac tgccttactt tttctaagtt caagttggtg gaggtgtgat tggggatcct    360
```

```
ttatcttctt gttgaacaag aaaacgctac taattagcaa tgaataggaa ctgtactaac      420
aatcagagcc cttattttca cttagtatag ttgtatgtat accagttaga acctatactc      480
tggaaacagg gactcgtcaa caataaccag aagggtggat tagaaactat catgaattcc      540
ctactcattg tctctccaaa caacaacact cttttataaa aagtgtactg caagaatcat      600
gttatgcttt taaggaatgt gcatcaagat tgaagtatca tgcgacatcc attaacacga      660
gaagttcaag atgcacaacg tgcactaact gaagtcgact caacgtagac ttattccaca      720
tctaacttga tctttcataa aaccggtgtg cgtaaaacat tactatagaa ttgatcccac      780
ggttactcat attcacacaa caagcaattg gacaaaaag atggtcagtt ctaaggcttc       840
aaaattcata cagccaatta gtcgaacatg cggtgtgcaa tcctagatga cttctatgaa      900
aatgagacca atcaatcttc caaaagttca gtacaaagaa ataacagcaa cccttcaaac      960
aatctaatac aacgacacat attaatcttc acaaattaaa cacaacatca aaagcgtact     1020
agattttgaa ctcggtaaag aatccaaatc aacagcaccg aattatcgac ataataccac     1080
tagtgaatta gtcatcaaag caacgaagag cacagaaaaa gttaagaaat ttaaccaata     1140
acaaacctga tcgaagatct cttagaacat ctacacgctt cccgacttgt ggcgacaaga     1200
gtctcaagta gactcggaag ctgctcagtc taattttaaa tatatattct cactttcct      1260
cgcaaaagag aaaagagag tgtatgagaa tattaaattg gcgccttttt cttttggcgg      1320
aattgttcta gttttagcga ccagttatca tgattttact actatgtaaa tcgcaagcat     1380
taaagttata gcaagaaatg agaccgagtg acctaaaaac aatcacattt gtatgtttcg     1440
gttccacgag cagctctggg cggacctagt aggagctcct ttgcactgtt gcaggagtgc     1500
tcaagtacct ttactctctt ggtgactcag acactactgc catatcaatg agaaaaaagg     1560
aggtaaagtg gtagttaaaa gtgataatcc attttatata aaatccctcc ccccgccccc     1620
ataccccgg aattgtaaaa atatttttaa atagtgttac tatgcgcata tactagtcag      1680
aaatttgtag gattacggga ggtagtacgt gcgggtgtac aaaccaaatc ggaaaatcgc     1740
accaaaccga aaagtcaaat caaaaccgat taaaagattc gactagattt ggtttggtat     1800
tgagtaaaac aacccgaatt aaaccgacat ataaatataa attttatgt atactttaa       1860
gatttttata tagaattttc tttaagaaaa tatctaaaaa tatttgggat tctcttacgg     1920
gatataatat ttaataaaat atgaagtgct ccatatttat taaccttaaa caatgggtcg     1980
tatgatcact ttcttatcaa gtgttactga aatgcgtcaa tctctttgtt cttccatagt     2040
caagatctat taaattctta tatcttttc gaatttgaag tggttattat tatttaagta     2100
tcatattgac ttttacgttt aattactaaa ttcggttaac cttgaaagtg tatatcaaca     2160
aaaattattg tcgacgact aaaagactaa ctatcatgtg ttattaagta aattcacgca      2220
taagaatatt taatagataa tatttttc taattttaa aattttact aaatatattt         2280
acttataaaa aatttaacaa agtaagattg aaataatatt taagtaacga aaaccagcc      2340
aaaaccgata tagtttgtgt agtttgattt aaataaaagt cgaacccaac ccgatccatg     2400
tacacccta atagtacgta tgtcctttct ggcatactgg taggatttgt agctgcatta     2460
aagatagaaa gcgaaaatcg tacaaagttt gtaatactag tacattacta ataaatccaa     2520
cggataaaag aaatatataa aagtagaaaa gtaattggtc tagattttat gaaacacaat     2580
aggtggagtt gagagggta tggaaattgg cttggatatt atgtaggcat catgaaccat      2640
taatgggacc tacaagatta atgttttgga tatccatatc ttttgttgac aggcccttca     2700
```

```
attgaaatct tgttgccca aaatgattcc actgtcaacc aattataagt tttttgttaa   2760
aaggtttatt gcaccattgc tccactaact tcatgtgcat ttgcaactta ccacacaaga   2820
gagaagaaaa gtttccagta cacaggatta acatttgcta agttgattcg agttttagt   2880
tagcaaagtt gaaattatca aagacagatt ttgaaactat aagccagtgg atcgctaagg   2940
ggttcctcgt tgataaatac ttattttcat ctggtgttta tactaatcca ataaatatat   3000
aatatatgtc tttacaaata tggttataat taaatcataa ttaattagta cacattgtta   3060
cctcacgtta tcactttacc atgataagag tttggtataa atactggtgg gactaagttt   3120
tttaccttcc tcgtttagtg tctacaagcc taattaggtg aagatggtgc tggatttttt   3180
ttttttttg ttacaagtgt agactacaga aattaaatta ctggtcctat tgtgcaaaat   3240
ttgaattcaa atcttcgtgc atttcagtat gttatttggt acaaaaaaca tggcatttat   3300
ggcttcgcat tgaggaagaa cttgtatata gcttgaatgc tcttgttaca tccaccctcc   3360
ttaaataccc ctagttgatc aacaggcacc aaaaatgtct agacacaaac atgaaccagt   3420
tttatttcta ttctctttat tgtaggtaat tgtttgctgt catcatataa tataagctag   3480
gaagaaaata agtaaaaatc atcagatgtg ataggtcttg aatagagaag caaacctaat   3540
gtagcataat aagaaaggaa gattaggtgg gagaccatta tttatgacct catcccaatt   3600
ttaatcatat ttcattattc caggttacta ctaccaaaca aaaataaacg acaagaataa   3660
tgcataaact tccacaatag ctcattattt atttatcagc cggagtgtat taaagtaatg   3720
atataattag aagacaattg agttgctact taaactgatg ctaacctgac gcgttttcgt   3780
tttccaggta cagtcttcca acatcagatg tcccaattgg agttccaagt caaagtggaa   3840
ttggaaaatg gtaagaaaac tctcagcctt agctgtgaca tagacatcaa taaagtagaa   3900
aaaaatcata agatttcaat gtttgaatgc taagcgacac aaaaatcact aaataatttt   3960
tttcatttct gactaagtct ttatgagcaa aactatttat tacttacaat tttgtgatga   4020
taggagatat caaatactcg tggaatactt gaggtaccca caaagtgatt gagaagttgc   4080
tgttaattaa aaaatccttg catcagatcc cttcagtttg aggtcaaaag cacaatcatg   4140
aaaagccctc tcacagcaca ttcacttgat ccattctatt ttacgtctt tctctaacta   4200
cgacttaagt tcttctaact tttaatcatt accaccctat taaaacttat ctaaagactg   4260
ttttttctctg cttttctcca tatttacctc aacgtctcct tccatatcca agctttggta   4320
cttttttcccc ttgtggtatt gattcaggca tggtcccttc tccaatctta tcaatcaaac   4380
atatactaat aaagtataat ataccaccga ctttggtgtc aaccacgagt tcgggagctt   4440
gtgaaatatg gtggtattta gccaatttt ttcttttaa taaaattgac aattaggaac   4500
caacttgccg gcttcataat aaagtatata gttgaaatgg ttcagaaata ttaaattcaa   4560
ttctataaat tacttggatt cggtccatcc taaaggtggt cacttctagg atcaagcccc   4620
attgttggct aaattttggt tttaaataga ttaattagct tggagtcgaa cagcaagcat   4680
taagtttacc aggtctatga tttagttagg catgaattgt aatacaaaga tgatttatgc   4740
agtgattaat gatatcagga tatatatata taagtattgt tatactataa ataacaacaa   4800
caacaacgac ccagtaaagt cccactaagt ggggtttggg gaaggtagtg tgtacgcaga   4860
ccttatcctt accctgatag ggcagagagg ttgtttccga tagatcctca gctcaggaag   4920
atgaaaataa aacaagaaaa caagaaaaga cagtaaccat agaaataatg acagcatcct   4980
aaaaaccata aaatagatga                                               5000
```

<210> SEQ ID NO 108
<211> LENGTH: 5000
<212> TYPE: DNA
<213> ORGANISM: Nicotiana tabacum

<400> SEQUENCE: 108

| | | | | | |
|---|---|---|---|---|---|
| aagctagcac | catagatagt | gggtgtcacc | attttacagc | aaataatatg | cctcaattgg | 60 |
| tggagaaagg | gtctttaaag | ttgaagtgtt | tttcttttt | tctctttctt | tttcttggta | 120 |
| ggtggtgggg | aagggaaaa | tgagggaca | aaacacgaaa | aatcaattt | gatgtataat | 180 |
| ttacacaaga | ctcaagctaa | gtgatagagt | tgataaaagg | ataacaataa | tatgggacac | 240 |
| ataaattcat | gacgtctccg | tttatcggat | attttctcaa | attgatgtaa | catatgtttc | 300 |
| aagaagttca | ataatgtgt | atatagattt | attttctataa | aatattattt | cgaattataa | 360 |
| atcttcgact | caagaaaaaa | taaaaatgtt | agatatggca | aagggatag | cacttagaca | 420 |
| attaggcaac | ctcatatttg | ttacaagtgg | gggtgagggt | tcaactttgc | attatttagc | 480 |
| atcactttgt | tatttatttt | ttttatataa | aatttataga | acaggagatg | ttaatataag | 540 |
| gatgacaatc | cagattgaca | aagttgtgat | agtgatacta | ctgtaacatc | ttattcaatc | 600 |
| atgcaaagca | tctcccatta | atttgtccat | cttttcgaat | attacgaaaa | tcagacctac | 660 |
| ttttttaca | tataattttc | tctaatgaca | tcacaggaac | tactcctgag | agaaatattc | 720 |
| tcactcaagt | ttgaaaacga | ctcttaaatt | atgataaagt | gataactaca | atgaccggct | 780 |
| aactcttgcg | tgcattatga | gtgtatatag | ttatatgtta | tttactctcg | tcgtaaatat | 840 |
| caagtgcgaa | taatatgtat | gaaatttaga | gaaatgagag | taaattagtc | gatgttttta | 900 |
| atttacgttg | tgatttattc | gttactttt | gctttctcta | aagtcaattt | cagtagttcg | 960 |
| tggagataca | ttagattaaa | ttaatctaat | ctgttaaata | ctacacggta | aaaataaaa | 1020 |
| aatatttaaa | acgacataaa | attttattat | caaaataagt | aaatcacaaa | ttgggggggg | 1080 |
| gtttggcttt | tttttttttt | gtccgaaaat | tattatcatc | ggtatatata | actatgcttc | 1140 |
| ttatattata | ttttttagt | gaaaattcta | attttcgtag | gcatacattt | aattaagata | 1200 |
| agtaaatatg | atgaataaga | acagattgat | aaacgtgatt | taagaaaaat | aaagaaagga | 1260 |
| gaaatgaata | gtagttccaa | tttataaaaa | aaagtcaagt | acttaggagt | taaggttcgt | 1320 |
| gagtagatgg | gacatatcac | ggtggaaaag | gtagaagaag | cttcaaagat | acaaagaaa | 1380 |
| aagagggtt | gagattctgt | gttgtgatta | atacaattca | atcaaagaaa | aagatgtgtc | 1440 |
| attttggaca | tacaactctc | cctaaaataa | aatgccaata | aacacagtac | ttgtggacat | 1500 |
| catccaccca | tcctttatg | actcatcaca | caaaaaaaac | acttttttcc | ttcttatttt | 1560 |
| tgaagatatt | ctatgaagtt | tgttgtaaac | ttaaacaaaa | taaatcaaca | aaattgtcct | 1620 |
| atctctaaat | agaggagttt | ttaaaagtta | aaatcaata | gaatagatac | atgaagtagt | 1680 |
| cgaaggagat | ttgacatttt | attatgtata | tatataaaat | tattttaatc | atatataaaa | 1740 |
| aatataattt | tctatcaaaa | agtgaatcct | ttcatatttg | tatctccgcc | ctatctccaa | 1800 |
| atattaagct | cacacatgaa | aagagcgaga | gacgaatgta | gcctattggc | tatgggttcc | 1860 |
| ctcactttcg | atatgatgtg | tataaaaaaa | ttaattgaaa | tctcaataaa | tattagattt | 1920 |
| taacaataag | ttaaaaattc | aaatcattaa | gtggggtctt | gatttatttt | cttttgtttt | 1980 |
| ctttctcaaa | ctgatgtttt | tattaaggat | ttattagaaa | aatatttcta | tctctcgggg | 2040 |
| taggaattaa | atttgctatg | tgtatatcct | accttttgtt | aaatttagtt | tacagaatta | 2100 |
| tcggttaaat | atgttagata | tgttattatt | gttgttacgt | ccgaatagac | acccataggt | 2160 |

```
gtagtgtagt caaattaata aaaccatgga atacgatggg atatcaaagt tgataatttt      2220
taactaaaaa aaaatgtcac tagatgattt tttttctct caattgtcta atcttgacag       2280
aaagatgtac ctaatgaaat aataaaagtg caacaaaaaa gaatagacaa atttccaaaa      2340
attgaatctt ttgttggtac tcgtcaacaa gttattcttc atgtctaaat cctaaaaaaa      2400
atatctcctc gtgtaaagac tggtatattg aaaatttaaa ataaattaat acatctaaac      2460
gtatcatatc ttctatataa tataaaattt ttagtgactc gtttcttaca attcaataat      2520
ttagtataaa taatttgtcg attgcgcgga tgaaagaaag gggtggtggt ggagatataa      2580
agtgtgatcg atagggtatc ttgtatgtga ttaatatagc taaacaaaaa ggtgaaaggc      2640
aaaaacatat atgaatggtg gtcctattcc atatttaaat ggattattag gatacgtcga      2700
tttcactttg caaaataccc tctatagatt catatatttt cttttctcat caacttttt      2760 ttctatcata taactagcct tactctggct tctcacgttt cacatgtctc aatgtttatt      2820
tgtttttttt ccactcttgg gcgtctaaag ggtttagaaa aatttgacaa tgtggaccac      2880
ccaaagttta taaaattaga attaaacagt catgaaggca tatacctagg agttccattt      2940
acatcttcac gtataaaatg tgtactttat attaattta tttatctcat gattcttatt       3000
agagatgata aatgtaacat ttttttttg tttttattaa atttagaag ataaccttt         3060 cttgattaat tctatgattt tcctttttta ttacgaaact gaaacttaac aattaactga      3120
gacataacaa acatgaatgt agttcatatc taaattaaca tcaaagccat catatctaac      3180
tcaactaagt tagtcatggt actcttgtga ttgacataaa ttttacaata aactttctta     3240
gctagaacgg actcaccaac aaatataaaa ccacagaaaa aattatatcg aactcaatac    3300
taaacaaaga agtatggaag actaaatatg ttgatacgag gtaggcttat tggtgatttt    3360
acaagggctt atatagcaaa agttgataca aacaatggg ctaaaaagta aatggcccat    3420 ttatttatt tattttttcc attatcaata cacagatttg cacttcgtta gcggacaatt    3480
ttgggtaaat tatgaaaatt gggcctcttc acaatttaga tcccgaccgt gtggatggat   3540
ggacaaggaa attttaggtc cagttccagt tatattgggg agataaaagg aaaaattacg  3600
tggttaagta atatatatat tagttaatta gttattataa taattatttt agttaattat    3660
tattcgcgat taacattagt gataattatg taggctgaga ttttgagttt gtataatttg   3720
aaattttaag atataatttc tataactttt atatagtaca attttataaa atattatttg   3780
tataattgat aaaatttaga tgtttgtgtt tgtataaatt tatattttag atttatcaaa  3840
atataactca attattcaaa ctaaccataa tacgtacgaa ttcactcaca aattatacaa    3900
acaatacaat ttgaaccata gctgcaaccc ctaataatgc gagctacgac tataaagtat    3960
aattaaattt atttactata acggatattt gcaaaaattc tccttaggca taaccaataa    4020
tggcccctga acgagttgct cgaaaaagct aattaaagat cattcatttt tggaaaacta    4080
tataaatcag aagactaaaa tatagctttt agcttttcac ttgaaataag ttatttttta    4140
tttaaataaa ttatttttgat aattattaaa cactctaata aattaaaaag atgattttta    4200
agtcagattg atcagctttt aagtccatct aaagatgctt taattacatc ttatttttta    4260
aaaaaaatta attattaaaa tttcaaagtt ttcattgctc tcgaagacat ttttttaaat    4320
gtccggtaca ttgtaataat atattattta atggaaggaa agtatagaag gatttttaa    4380 aaaaaataat taagtgataa acttttttag aaattataat atgttgtata tttacgttaa    4440
atttcttaat tttttaattt aacatttccc aaaaattttg tgttatccaa atgtccgaat    4500
aacaaccaat taactgacac tgaatttgtg aattttacga gacaaatgtt cttgttaaaa    4560
```

```
tttcatatta ggtttcaact gtgagttatt tttggaaatt taaattatgt gtgttgatca    4620
aaatacttta aatatttttt tttcattata tcatgaattt taaatagata tcatatattt    4680
ttaaaagatt tagatttaaa ttttactatt aatatactaa accgacatag ccttaagttg    4740
aaaaaatatc aaattcatcg agggaaaacg aaaattgcaa gtatatttgg ccaaacgaag    4800
cacctgtcca tgaaatgcca cgtaaaaatt ctaagcaaaa atactacaat aagtgcatgg    4860
aatgagacga gcacgtgtca agttgaaaga agcacctgtc catgaaatgc cacgtaactc    4920
acaccttcaa aacctctcca ttgctacaaa tctccatatt tttgtttttt tttttttaaga    4980 aaaagataaa agtactagca                                                5000

<210> SEQ ID NO 109
<211> LENGTH: 2400
<212> TYPE: DNA
<213> ORGANISM: Nicotiana tabacum

<400> SEQUENCE: 109
ttagcactta aaaaacatag gtttacatgc tctcattgtc acgccaggcc gctaattaaa      60
tggtacattt catcatcccc atttttggc ctcatagtta attatcacaa tttctgaaag      120
caacatcaga acaaccccac atttcttgtg gtcctataat tactgctaga tagtccaaac    180
ccatctgcct atttagggct tgtgaatgag gattgaaaat ggtagagaat atttgcaaag    240
gcatcatgca tatatggaaa agactaaaga gagagttagt gccttgcaaa gcggattctc    300
acagttgtag aaaaggactc accattttca agaatactcc cggcatgaag atggacaatt    360
taatataaaa aacaaagaaa atagtaatta agtgcgttga gatgaatgaa atttatccgc    420
tcttaattga atatggggaa ttgaaagaaa tttctgataa taaattaatg agtcttacat    480
gacgtggatc cgacttaatc tagtctattt aaactaagaa tagataagaa tagagaatat    540
agacaaaaga gaggctcatt ggctagggtt tcaaggggagt tccttgaaca taagtggcaa    600
gtacaagcac aaagccaatt tccatggact aaagatgaat aagatgtgtc gtgtggtatg    660
gtgggaaggt gaggaggtat ggggtaattg gagatgctaa acctctctaa aagctctttt    720
gctccaaata tctaaatcca tctctatcac ttttggcgac tgccccaaaa tttgcaactt    780
atgaattaaa gttttaatat ttttaagtta ataaattctg aattaataat ttaacatatt    840
caataaactt tttaaaacaa attacgtata taccatcaaa ctggctgcac catgatcact    900
ttctaaactc acaatgacat atggatttaa tcaggcacaa agtcatgttg atagaaagag    960
atagtacgga gaatgaagaa aaaggtaggg gagagagatg gggtgagtgg ggaaaagata    1020
gggttctctt tttagtgaaa gcgacagggt ctgagaaccc taggtcaaaa gttgcataaa    1080
cctctataca ggcttcttca ctcccttact actaatatac tctcattaag gcttgaggtt    1140
taattcatta aaattgtggt ttaattattg tatcccctca aacgaaataa ttgtccttgt    1200
cgaggttaga caatgttgcg tactattttc aaacgcagtc agccattatt ctcctatcct    1260
ttacagtcga gattcaaaga cagaaagtag catgcaagct gttattaatt tactttgatt    1320
aggactttgc caagaaaatg aagaaccttt tcttttttct tttaatttag ttatcttaca    1380
acatgtaatt tttcctagca agcaaatacg gtaacttttt tttttattct catttaattt    1440
gttggagcta ttgctacttt gatgacttca accaaatcct ggttggtagg cggagggtgc    1500
tgacgatgga aactacccct cttgtccaaa tacgataacc taaaaaatag aataatagct    1560 tatttgtactg tgctgcaaaa attgcattgt cagtatacat aattaaaatc tattttgaat    1620
```

```
gtgtggaggg caaagagggg tgactggtct agggttgtag aaatcaggtg ggagagagaa    1680
tggtatttgt ctctgtgtca gctgatatca cgtgaagagg cacaataaga agtccttcgt    1740
atccattcac ttcccaaaaa taccggcatt actacaaata tagtactagc acttgctttc    1800
tctatcccca tctttgctat ttcctttccc tttccaactt tttggcttta gaattgcaaa    1860
gatggaggga attgtggttc tttgtatctg taaaatttt cctccaagct ccagttgtag    1920
ctagcttaat gcgtggacgc gcgcgcgcac acactagaaa tctgcaatct atatatatat    1980
tcacaaggca ctcacatatc aaaaaccaca tagacattgt atagagagag ctgtcgttct    2040
caagcagaaa aaatgatatg atttcatcag catgtggtca accaaatagt tcaattctag    2100
tctttgcttc ctctttctaa ttactgtata aatagagcca caggacata gaattgagaa    2160 aataaaagac aataaaaaca aatctagcta cttaagcgaa tgatgatgac tctctctcag    2220
tagtcttaac tcttaatacc cttgttttcc ttcttgtgct gcagtttgat tggttaatta    2280
acctaatcaa aagatgtttt aactgtgttt tatccgtctt tctcaagatc tatcttagtc    2340
ccaccacata gctccctcaa gctacagctg caaaatatat actatatata tatataacaa    2400
```

<210> SEQ ID NO 110
<211> LENGTH: 7
<212> TYPE: PRT
<213> ORGANISM: Unknown
<220> FEATURE:
<223> OTHER INFORMATION: Description of Unknown:
      WRKY transcription factor core domain sequence

<400> SEQUENCE: 110

Trp Arg Lys Tyr Gly Gln Lys
1               5

<210> SEQ ID NO 111
<211> LENGTH: 7
<212> TYPE: PRT
<213> ORGANISM: Unknown
<220> FEATURE:
<223> OTHER INFORMATION: Description of Unknown:
      WRKY transcription factor core domain sequence

<400> SEQUENCE: 111

Trp Arg Lys Tyr Gly Lys Lys
1               5

<210> SEQ ID NO 112
<211> LENGTH: 5
<212> TYPE: PRT
<213> ORGANISM: Unknown
<220> FEATURE:
<223> OTHER INFORMATION: Description of Unknown:
      WRKY transcription factor "PRSYY" motif sequence

<400> SEQUENCE: 112

Pro Arg Ser Tyr Tyr
1               5

<210> SEQ ID NO 113
<211> LENGTH: 777
<212> TYPE: DNA
<213> ORGANISM: Nicotiana tabacum

<400> SEQUENCE: 113
atggatacaa gttctcggga caagtctttt gctattgacc ttaacacaaa cccttcaccg      60
caaaacgtca atagtattcc gcatgagatg ttggatgaag agttgatcag gatgaaagag     120

```
gagaataaga agctaacgac aacgttaaca actttgtgtg agaactacaa ttacttgcaa    180
actcacctaa ttgaattgct gcaaaaacac aactctgagg agcagaattc caaattatta    240
tctagaaaaa gaaaggctga agatgatcac tgttgtgaaa attcagaaat cataattgaa    300
gaagcatcac ctaagaagcc aagggaaatc agaaccaacg tttcaactgt ttgtgtaaaa    360
actactccct ccgatcaaag cgcagtggtg aagatggat atcactggag aaaatatggt     420
caaaaagtca caagagataa tccttcacct agagcctact ataagtgttc ttttgcacca    480
tcatgcccag tcaagaagaa ggtgcaaaga agtgttgaag atccatcagt tttagtagct    540
acatatgagg gggagcacaa ccatcctctc ccatcccaag ctcaagtaac agtcccatta    600
attaaccaaa atgttacaac aaatcctagt tttctgaaca aattcatgca agacattgac    660
acaacttcgc tacagcaagt tttagtcgca caaatggcgt cttccttgac caagaaccct    720
agtttcacag ctgcagttgc tgcagccatc tccggaaaat tctttgaata tgattaa      777
```

<210> SEQ ID NO 114
<211> LENGTH: 258
<212> TYPE: PRT
<213> ORGANISM: Nicotiana tabacum

<400> SEQUENCE: 114

```
Met Asp Thr Ser Ser Arg Asp Lys Ser Phe Ala Ile Asp Leu Asn Thr
1               5                   10                  15

Asn Pro Ser Pro Gln Asn Val Asn Ser Ile Pro His Glu Met Leu Asp
            20                  25                  30

Glu Glu Leu Ile Arg Met Lys Glu Glu Asn Lys Lys Leu Thr Thr Thr
        35                  40                  45

Leu Thr Thr Leu Cys Glu Asn Tyr Asn Tyr Leu Gln Thr His Leu Ile
    50                  55                  60

Glu Leu Leu Gln Lys His Asn Ser Glu Glu Gln Asn Ser Lys Leu Leu
65                  70                  75                  80

Ser Arg Lys Arg Lys Ala Glu Asp Asp His Cys Cys Glu Asn Ser Glu
                85                  90                  95

Ile Ile Ile Glu Glu Ala Ser Pro Lys Lys Pro Arg Glu Ile Arg Thr
            100                 105                 110

Asn Val Ser Thr Val Cys Val Lys Thr Thr Pro Ser Asp Gln Ser Ala
        115                 120                 125

Val Val Lys Asp Gly Tyr His Trp Arg Lys Tyr Gly Gln Lys Val Thr
    130                 135                 140

Arg Asp Asn Pro Ser Pro Arg Ala Tyr Tyr Lys Cys Ser Phe Ala Pro
145                 150                 155                 160

Ser Cys Pro Val Lys Lys Lys Val Gln Arg Ser Val Glu Asp Pro Ser
                165                 170                 175

Val Leu Val Ala Thr Tyr Glu Gly Glu His Asn His Pro Leu Pro Ser
            180                 185                 190

Gln Ala Gln Val Thr Val Pro Leu Ile Asn Gln Asn Val Thr Thr Asn
        195                 200                 205

Pro Ser Phe Leu Asn Lys Phe Met Gln Asp Ile Asp Thr Thr Ser Leu
    210                 215                 220

Gln Gln Val Leu Val Ala Gln Met Ala Ser Ser Leu Thr Lys Asn Pro
225                 230                 235                 240
```

Ser Phe Thr Ala Ala Val Ala Ala Ala Ile Ser Gly Lys Phe Phe Glu
                245                 250                 255

Tyr Asp

<210> SEQ ID NO 115
<211> LENGTH: 33
<212> TYPE: PRT
<213> ORGANISM: Unknown
<220> FEATURE:
<223> OTHER INFORMATION: Description of Unknown:
      WRKY transcription factor zinc finger region sequence
<220> FEATURE:
<221> NAME/KEY: MOD_RES
<222> LOCATION: (2)..(6)
<223> OTHER INFORMATION: Any amino acid
<220> FEATURE:
<221> NAME/KEY: MISC_FEATURE
<222> LOCATION: (2)..(6)
<223> OTHER INFORMATION: This region may encompass 4-5 residues
<220> FEATURE:
<221> NAME/KEY: MOD_RES
<222> LOCATION: (8)..(30)
<223> OTHER INFORMATION: Any amino acid
<220> FEATURE:
<221> NAME/KEY: MISC_FEATURE
<222> LOCATION: (8)..(30)
<223> OTHER INFORMATION: This region may encompass 22-23 residues
<220> FEATURE:
<221> NAME/KEY: MOD_RES
<222> LOCATION: (32)..(32)
<223> OTHER INFORMATION: Any amino acid

<400> SEQUENCE: 115

Cys Xaa Xaa Xaa Xaa Xaa Cys Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa His Xaa
            20                  25                  30

His

<210> SEQ ID NO 116
<211> LENGTH: 35
<212> TYPE: PRT
<213> ORGANISM: Unknown
<220> FEATURE:
<223> OTHER INFORMATION: Description of Unknown:
      WRKY transcription factor zinc finger region sequence
<220> FEATURE:
<221> NAME/KEY: MOD_RES
<222> LOCATION: (2)..(8)
<223> OTHER INFORMATION: Any amino acid
<220> FEATURE:
<221> NAME/KEY: MOD_RES
<222> LOCATION: (10)..(32)
<223> OTHER INFORMATION: Any amino acid
<220> FEATURE:
<221> NAME/KEY: MOD_RES
<222> LOCATION: (34)..(34)
<223> OTHER INFORMATION: Any amino acid

<400> SEQUENCE: 116

Cys Xaa Xaa Xaa Xaa Xaa Xaa Xaa Cys Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

His Xaa Cys
        35

<210> SEQ ID NO 117
<211> LENGTH: 4
<212> TYPE: PRT
<213> ORGANISM: Unknown
<220> FEATURE:
<223> OTHER INFORMATION: Description of Unknown:
     WRKY transcription factor "WRKY" motif sequence

<400> SEQUENCE: 117

Trp Arg Lys Tyr
1

<210> SEQ ID NO 118
<211> LENGTH: 204
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 118
cctcttcctg gcataccagc agttgctaac atctatgttt tgttgttct attttgcaca        60 tttgtccact aataggtcct gtgttcttac acttcatcac tatagtgtgt gtacagagaa     120
acaggacctt ttagtggaca aatgcctaaa atagggcaaa ggatggtcac gtcttaatgt     180
tatattaata tgatggtcag gttt                                            204

<210> SEQ ID NO 119
<211> LENGTH: 204
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 119
cctcttcctg gcataccagc agttgctaac atctatgttt tgttgttct attttgcaca        60 tcatttgcgc ggaaactacg atgttcttac acttcatcac tatagtgtgt gtacagagaa     120
atcgtagtta ccgcgcaaat gatgcctaaa ataggcaaa ggatggtcac gtcttaatgt      180
tatattaata tgatggtcag gttt                                            204

<210> SEQ ID NO 120
<211> LENGTH: 204
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 120
cctcttcctg gcataccagc agttgctaac atctatgttt tgttgttct attttgcaca        60 tacattcgtc ttacggtcca gtgttcttac acttcatcac tatagtgtgt gtacagagaa     120
actggaccga aagacgaatg tatgcctaaa ataggcaaa ggatggtcac gtcttaatgt      180
tatattaata tgatggtcag gttt                                            204

<210> SEQ ID NO 121
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 121
tttgtccact aataggtcct g                                           21

<210> SEQ ID NO 122
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
tcatttgcgc ggaaactacg a                                           21

<210> SEQ ID NO 123
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
tacattcgtc ttacggtcca g                                           21

<210> SEQ ID NO 124
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
caggaccttt tagtggacaa a                                           21

<210> SEQ ID NO 125
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
tcgtagttac cgcgcaaatg a                                           21

<210> SEQ ID NO 126
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
ctggaccgaa agacgaatgt a                                           21
```